US009447177B2

(12) United States Patent
Bradley et al.

(10) Patent No.: US 9,447,177 B2
(45) **Date of Patent: *Sep. 20, 2016**

(54) TRANSGENIC MOUSE HOMOZYGOUS FOR CHIMERIC IGH LOCUS

(75) Inventors: Allan Bradley, Cambridge (GB); E-Chiang Lee, Cambridge (GB); Qi Liang, Cambridge (GB); Wei Wang, Cambridge (GB); Glenn Friedrich, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/416,684

(22) Filed: Mar. 9, 2012

(65) Prior Publication Data

US 2012/0167237 A1 Jun. 28, 2012
US 2013/0042331 A2 Feb. 14, 2013

Related U.S. Application Data

(60) Division of application No. 13/310,431, filed on Dec. 2, 2011, which is a continuation-in-part of application No. PCT/GB2010/051122, filed on Jul. 7, 2010, and a continuation-in-part of application No. PCT/GB2011/050019, filed on Jan. 7, 2011.

(60) Provisional application No. 61/223,960, filed on Jul. 8, 2009, provisional application No. 61/355,666, filed on Jun. 17, 2010.

(30) Foreign Application Priority Data

Jul. 8, 2009 (GB) .................................. 0911846.4
Jul. 28, 2009 (GB) .................................. 0913102.0

(51) Int. Cl.

| | |
|---|---|
| ***A01K 67/027*** | (2006.01) |
| ***C07K 16/00*** | (2006.01) |
| ***C12N 15/85*** | (2006.01) |
| ***C07K 16/18*** | (2006.01) |
| ***C07K 16/12*** | (2006.01) |
| ***C07K 16/46*** | (2006.01) |
| ***A61K 39/02*** | (2006.01) |
| ***A61K 39/35*** | (2006.01) |

(52) U.S. Cl.

CPC .......... *C07K 16/18* (2013.01); *A01K 67/0275* (2013.01); *A01K 67/0278* (2013.01); *A61K 39/107* (2013.01); *A61K 39/35* (2013.01); *C07K 16/00* (2013.01); *C07K 16/1203* (2013.01); *C07K 16/1239* (2013.01); *C07K 16/462* (2013.01); *A01K 2227/105* (2013.01); *A01K 2267/01* (2013.01); *C07K 2317/24* (2013.01)

(58) Field of Classification Search

CPC .. C07K 16/00; C07K 16/1239; C07K 16/18; C07K 16/1203; C07K 2317/24; A01K 67/0275; A01K 67/0278

See application file for complete search history.

(56) References Cited

U.S. PATENT DOCUMENTS

| | | | | |
|---|---|---|---|---|
| 4,720,449 | A | 1/1988 | Borror et al. | 430/338 |
| 5,169,939 | A | 12/1992 | Gefter et al. | 530/387.3 |
| 5,545,807 | A | 8/1996 | Surani et al. | 800/2 |
| 5,633,425 | A | 5/1997 | Lonberg et al. | |
| 5,770,429 | A | 6/1998 | Lonberg et al. | 435/240.2 |
| 5,789,215 | A | 8/1998 | Berns et al. | 435/172.3 |
| 5,939,598 | A | 8/1999 | Kucherlapati et al. | 800/25 |
| 5,948,600 | A | 9/1999 | Roschger et al. | 430/348 |
| 6,162,963 | A | 12/2000 | Kucherlapati et al. | 800/18 |
| 6,395,487 | B1 | 5/2002 | Bradley et al. | |
| 6,461,818 | B1 | 10/2002 | Bradley et al. | |
| 6,596,541 | B2 | 7/2003 | Murphy et al. | 435/463 |
| 6,673,986 | B1 | 1/2004 | Kucherlapati et al. | 800/18 |
| 6,713,610 | B1 | 3/2004 | Kucherlapati et al. | 530/388.23 |
| 6,833,268 | B1 | 12/2004 | Green et al. | 435/320.1 |
| 6,914,128 | B1 | 7/2005 | Salfeld et al. | 530/387.3 |
| 6,998,514 | B2 | 2/2006 | Brüggemann | 800/18 |
| 7,119,248 | B1 | 10/2006 | Rajewsky et al. | 800/6 |
| 7,205,148 | B2 | 4/2007 | Economides et al. | |
| 7,435,871 | B2 | 10/2008 | Green et al. | 800/18 |
| 7,501,552 | B2 | 3/2009 | Lonberg et al. | 800/6 |
| 7,605,237 | B2 | 10/2009 | Stevens et al. | 530/387.3 |
| 7,910,798 | B2 | 3/2011 | Tanamachi et al. | 800/18 |
| 7,932,431 | B2 | 4/2011 | Brüggemann | 800/18 |
| 8,158,419 | B2 | 4/2012 | Lonberg et al. | 435/328 |
| 8,502,018 | B2 | 8/2013 | Murphy et al. | 800/18 |
| 8,642,835 | B2 | 2/2014 | MacDonald | 800/16 |
| 9,253,965 | B2 | 2/2016 | Bradley et al. | |

(Continued)

FOREIGN PATENT DOCUMENTS

| | | | | |
|---|---|---|---|---|
| CA | 2 307 503 A1 | 11/2001 | | A61K 39/42 |
| EP | 1780272 A1 | 5/2007 | | C12N 15/00 |

(Continued)

OTHER PUBLICATIONS

Clark et al (Nature Reviews: Genetics. 2003, 825-833.*

(Continued)

*Primary Examiner* — Anoop Singh

(74) *Attorney, Agent, or Firm* — Sunstein Kann Murphy & Timbers LLP

(57) ABSTRACT

The invention discloses methods for the generation of chimaeric human—non-human antibodies and chimaeric antibody chains, antibodies and antibody chains so produced, and derivatives thereof including fully humanized antibodies; compositions comprising said antibodies, antibody chains and derivatives, as well as cells, non-human mammals and vectors, suitable for use in said methods.

6 Claims, 57 Drawing Sheets

(56) References Cited

U.S. PATENT DOCUMENTS

| | | | | |
|---|---|---|---|---|
| 2002/0088016 | A1 | 7/2002 | Bruggemann | 800/18 |
| 2003/0108925 | A1 | 6/2003 | Dix et al. | 435/6 |
| 2003/0217373 | A1 | 11/2003 | Green et al. | 800/6 |
| 2004/0231012 | A1 | 11/2004 | Bruggemann | |
| 2005/0048621 | A1 | 3/2005 | Grasso et al. | 435/69.1 |
| 2006/0015949 | A1 | 1/2006 | Lonberg et al. | 800/5 |
| 2006/0015957 | A1* | 1/2006 | Lonberg et al. | 800/18 |
| 2006/0021074 | A1 | 1/2006 | Kellermann et al. | 800/18 |
| 2006/0199204 | A1 | 9/2006 | Dix et al. | 800/16 |
| 2007/0280945 | A1 | 12/2007 | Stevens et al. | 424/145.1 |
| 2008/0098490 | A1 | 4/2008 | Jakobovits et al. | 800/13 |
| 2009/0083870 | A1 | 3/2009 | Horn et al. | 800/13 |
| 2009/0196112 | A1 | 8/2009 | Cho | 365/200 |
| 2009/0209036 | A1 | 8/2009 | Reynaud et al. | 435/455 |
| 2010/0011450 | A1 | 1/2010 | Garcia et al. | |
| 2010/0069614 | A1 | 3/2010 | Houtzager et al. | 530/387.1 |
| 2010/0146647 | A1 | 6/2010 | Logtenberg et al. | 800/4 |
| 2010/0196367 | A1 | 8/2010 | Day | 424/130.1 |
| 2011/0138489 | A1 | 6/2011 | Tanamachi et al. | 800/6 |
| 2011/0145937 | A1 | 6/2011 | MacDonald et al. | 800/6 |
| 2011/0195454 | A1 | 8/2011 | McWhirter et al. | 435/69.6 |
| 2011/0236378 | A1 | 9/2011 | Green et al. | 424/133.1 |
| 2011/0283376 | A1 | 11/2011 | Murphy et al. | |
| 2012/0070861 | A1 | 3/2012 | Macdonald et al. | 435/91.1 |
| 2012/0073004 | A1 | 3/2012 | Macdonald et al. | 800/18 |
| 2012/0167237 | A1 | 6/2012 | Bradley et al. | 800/9 |
| 2012/0204278 | A1 | 8/2012 | Bradley et al. | 800/18 |
| 2012/0233715 | A1 | 9/2012 | Kuroiwa et al. | 800/3 |
| 2012/0322108 | A1 | 12/2012 | Macdonald et al. | 435/69.6 |
| 2013/0039850 | A1 | 2/2013 | Lonberg et al. | 424/1.49 |
| 2013/0102031 | A1 | 4/2013 | King et al. | 435/69.6 |
| 2013/0160153 | A1 | 6/2013 | Macdonald et al. | 800/18 |
| 2013/0212719 | A1 | 8/2013 | Macdonald et al. | 800/6 |
| 2013/0254911 | A1 | 9/2013 | Macdonald et al. | 800/18 |
| 2013/0263293 | A1 | 10/2013 | Bradley et al. | 800/6 |
| 2013/0323790 | A1 | 12/2013 | Macdonald et al. | 435/70.2 |
| 2013/0323890 | A1 | 12/2013 | Duong et al. | 435/70.2 |
| 2013/0326647 | A1 | 12/2013 | Macdonald et al. | 800/18 |
| 2013/0333057 | A1 | 12/2013 | Macdonald et al. | 800/6 |
| 2014/0017228 | A1 | 1/2014 | Macdonald et al. | 424/132.1 |
| 2014/0130193 | A1 | 5/2014 | Macdonald et al. | 800/18 |
| 2014/0130194 | A1 | 5/2014 | Macdonald et al. | 800/18 |
| 2014/0137275 | A1 | 5/2014 | Macdonald et al. | 800/18 |
| 2014/0213773 | A1 | 7/2014 | Macdonald et al. | 530/387.3 |
| 2014/0331344 | A1 | 11/2014 | Friedrich et al. | 800/18 |

FOREIGN PATENT DOCUMENTS

| | | | | |
|---|---|---|---|---|
| EP | 2550363 | | 10/2012 | C12N 15/85 |
| EP | 2421357 | | 1/2013 | A01K 67/027 |
| GB | 2398784 | | 9/2004 | A01K 67/027 |
| KR | 1020050042792 | A | 5/2005 | A01K 67/027 |
| WO | WO 90/04036 | | 4/1990 | C12P 21/08 |
| WO | WO 91/00906 | | 1/1991 | C12N 15/00 |
| WO | WO 91/10741 | | 7/1991 | C12P 21/06 |
| WO | WO 93/12227 | | 6/1993 | C12N 15/00 |
| WO | WO 94/02602 | | 2/1994 | C12N 15/00 |
| WO | WO 94/04667 | | 3/1994 | C12N 15/00 |
| WO | WO 96/30498 | | 10/1996 | C12N 15/00 |
| WO | WO 98/24884 | | 6/1998 | C12N 5/00 |
| WO | WO 98/24893 | | 6/1998 | C12N 15/00 |
| WO | WO 99/45962 | | 9/1999 | A61K 39/295 |
| WO | WO 02/08409 | A2 | 1/2002 | C12N 15/00 |
| WO | WO 02/36789 | A2 | 5/2002 | C12N 15/85 |
| WO | WO 02/43478 | | 6/2002 | A01K 67/027 |
| WO | WO 02/053596 | A2 | 7/2002 | C07K 16/28 |
| WO | WO 02/059263 | A2 | 8/2002 | |
| WO | WO-02066630 | A1 | 8/2002 | |
| WO | WO 02/070648 | | 9/2002 | |
| WO | WO 03/006639 | A1 | 1/2003 | C12N 5/10 |
| WO | WO 03/047336 | A2 | 6/2003 | |
| WO | WO 03/061363 | A2 | 7/2003 | |
| WO | WO 2004/050838 | A2 | 6/2004 | |
| WO | WO 2005/003364 | A2 | 1/2005 | C12N 15/90 |
| WO | WO-2005004592 | A2 | 1/2005 | |
| WO | WO 2005/019463 | A1 | 3/2005 | C12N 15/85 |
| WO | WO-2005058815 | A2 | 6/2005 | |
| WO | WO 2006/044492 | | 4/2006 | C12N 15/52 |
| WO | WO-2006055704 | A2 | 5/2006 | |
| WO | WO-2006068953 | A2 | 6/2006 | |
| WO | WO 2006/122442 | A1 | 11/2006 | C12N 9/22 |
| WO | WO 2007/096779 | A2 | 8/2007 | |
| WO | WO 2007/117410 | * | 10/2007 | |
| WO | WO 2007/117410 | A2 | 10/2007 | A01K 67/027 |
| WO | WO-2007117410 | A2 | 10/2007 | |
| WO | WO-2007143168 | A2 | 12/2007 | |
| WO | WO 2008/022391 | A1 | 2/2008 | C07K 16/28 |
| WO | WO 2008/054606 | | 5/2008 | C07K 16/00 |
| WO | WO 2008/070367 | A2 | 6/2008 | C12N 15/09 |
| WO | WO/2008/076379 | * | 6/2008 | |
| WO | WO 2008/076379 | A2 | 6/2008 | C07K 16/18 |
| WO | WO-2008076379 | A2 | 6/2008 | |
| WO | WO 2008/094178 | A2 | 8/2008 | C12Q 1/68 |
| WO | WO 2008/103474 | A1 | 8/2008 | C12N 15/13 |
| WO | WO 2008/118970 | A2 | 10/2008 | A61K 48/00 |
| WO | WO 2008/122886 | | 10/2008 | C12N 15/85 |
| WO | WO 2008/151081 | A1 | 12/2008 | C12N 15/13 |
| WO | WO 2009/013620 | | 1/2009 | |
| WO | WO-2009013620 | A2 | 1/2009 | |
| WO | WO 2009/018411 | | 2/2009 | C07K 16/28 |
| WO | WO 2009/023540 | | 2/2009 | A61K 39/395 |
| WO | WO-2009076464 | A2 | 6/2009 | |
| WO | WO 2009/080254 | A1 | 7/2009 | C07K 16/46 |
| WO | WO 2009/094178 | A2 | 7/2009 | C09B 67/08 |
| WO | WO 2009/118524 | A2 | 10/2009 | C12N 5/00 |
| WO | WO 2009/129247 | A2 | 10/2009 | C12N 15/13 |
| WO | WO 2009/143472 | A2 | 11/2009 | C07K 16/46 |
| WO | WO-2009143472 | A2 | 11/2009 | |
| WO | WO 2009/157771 | | 12/2009 | A01K 67/027 |
| WO | WO-2010039900 | A2 | 4/2010 | |
| WO | WO 2010/070263 | | 6/2010 | C12N 15/85 |
| WO | WO 2010/070263 | A1 | 6/2010 | C12N 15/85 |
| WO | WO-2010077854 | A1 | 7/2010 | |
| WO | WO 2010/097385 | A1 | 9/2010 | C07K 16/24 |
| WO | WO 2010/113039 | A1 | 10/2010 | C12N 5/00 |
| WO | WO 2011/004192 | A1 | 1/2011 | A01K 67/027 |
| WO | WO 2011/008093 | | 1/2011 | C07K 16/00 |
| WO | WO 2011/008093 | A1 | 1/2011 | C07K 16/00 |
| WO | WO 2011/056864 | A1 | 5/2011 | C12P 21/06 |
| WO | WO 2011/062206 | A1 | 5/2011 | C12N 15/09 |
| WO | WO-2011062207 | A1 | 5/2011 | |
| WO | WO-2011-071957 | A1 | 6/2011 | |
| WO | WO 2011/097603 | | 8/2011 | C12N 15/85 |
| WO | WO-2011146121 | A1 | 11/2011 | |
| WO | WO 2011/158009 | | 12/2011 | A01K 67/027 |
| WO | WO 2011/163311 | | 12/2011 | C12N 15/85 |
| WO | WO 2011/163314 | | 12/2011 | C12N 15/85 |
| WO | WO 2012/018764 | | 2/2012 | C12N 15/85 |
| WO | WO 2012/023053 | | 2/2012 | |
| WO | WO 2012/141798 | | 10/2012 | C12N 15/85 |
| WO | WO 2012/148873 | A2 | 11/2012 | A01K 67/027 |
| WO | WO 2013/022782 | | 2/2013 | C12N 15/85 |
| WO | WO 2013/022782 | A1 | 2/2013 | C12N 15/85 |
| WO | WO 2013/041844 | | 3/2013 | C12N 15/85 |
| WO | WO 2013/041844 | A2 | 3/2013 | C12N 15/85 |
| WO | WO 2013/041845 | A2 | 3/2013 | C12N 15/85 |
| WO | WO 2013/059230 | A1 | 4/2013 | C12N 15/85 |
| WO | WO 2013/061098 | A2 | 5/2013 | C12N 15/85 |
| WO | WO 2013/096142 | | 6/2013 | A01K 67/027 |
| WO | WO 2013/116609 | | 8/2013 | A01K 67/027 |
| WO | WO-2013176772 | A1 | 11/2013 | |
| WO | WO-2014093622 | A2 | 6/2014 | |

OTHER PUBLICATIONS

Niemann et al (Rev. Sci, Tech. Off. Int. Spiz. 2005, (24), 285-298.*
Smith Journal of Biotechnology 99 (2002) 1-22.*
Ristevski et al (Molecular Biotechnology, 2005, 153-163.*
Qi et al Hypertension. 2005, 45:1004-1011.*
Gama Sosa et al Brain Struct Funct, 2010, 214:91-109.*
Wagner et al abstract Nucleic Acids Res. 1994; 22(8):1389-93.*
Butler Rev Scientifique et Technique Office International Des Epizooties. 1998, 17, 1, 43-70.*
NCBI accession No. AC111740, dated Nov. 9, 2202, pp. 1-3.*

(56) References Cited

OTHER PUBLICATIONS

Janeway et al, Immunobiology: The Immune System in Health and Disease, 5th edition. New York: Garland Science; 2001, 1-5.*
Taki, et al Science, 1993, 262 (5137) 1268-1271.*
Nicholson et al (The Journal of Immunology, 1999, 163: 6898-6906)).*
Jackson Laboratory Recourse Manual, 2007, 1-29.*
Lonberg et al (Nature Biotech, 2005, 23, 1117-1125).*
Sen and Baltimore Cell, 1986, 46, 705-716.*
Adams Genomics. Dec. 2005; 86 (6):753-8.*
Briney, et al., "Human Peripheral Blood Antibodies with Long HCDR3s Are Established Primarily at Original Recombination Using a Limited Subset of Germline Genes," PLoS One, May 2012, vol. 7, Issue 5, e36750, 13 pages.
Brüggemann, et al., "Human Antibody Production in Transgenic Mice: Expression from 100 kb of the Human IgH Locus," European Journal of Immunology, May 1991, vol. 21, Issue 5, pp. 1323-1326.
Feeney, "Genetic and Epigenetic Control of V Gene Rearrangement Frequency," V(D)J Recombination Advances in Experimental Medicine and Biology, 2009, vol. 650, 2009, pp. 73-81.
Green, "Antibody Engineering via Genetic Engineering of the Mouse: XenoMouse Strains are a Vehicle for the Facile Generation of Therapeutic Human Monoclonal Antibodies," Journal of Immunological Methods, Dec. 10, 1999, vol. 231, Issues 1-2, pp. 11-23.
Huang, et al., "Structural Basis of Tyrosine Sulfation and VH-Gene Usage in Antibodies that Recognize the HIV Type 1 Coreceptor-Binding Site on gp120," PSNA, Mar. 2, 2004, vol. 101, No. 9, pp. 2706-2711.
Jung, et al., "Mechanism and Control of V(D)J Recombination at the Immunoglobulin Heavy Chain Locus," Annual Review of Immunology, Apr. 2006, vol. 24, pp. 541-570.
Liu, et al., "Potent and Broad Anti-HIV-1 Activity Exhibited by a Glycosyl-Phosphatidylinositol-Anchored Peptide Derived from the CDR H3 of Broadly Neutralizing Antibody PG16," Journal of Virology, Sep. 2011, vol. 85, No. 17, pp. 8467-8476.
Mendez, et al., "Functional Transplant of Megabase Human Immunoglobulin Loci Recapitulates Human Antibody Response in Mice," Nature Genetics, Feb. 1997, vol. 15, pp. 146-156.
Nadel, et al., "Sequence of the Spacer in the Recombination Signal Sequence Affects V(D)J Rearrangement Frequency and Correlates with Nonrandom Vκ Usage In Vivo," J. Exp. Med., May 4, 1998, vol. 187, No. 9, pp. 1495-1503.
Nicholson, et al., "Antibody Repertoires of Four- and Five-Feature Translocus Mice Carrying Human Immunoglobulin Heavy Chain and κ and λ Light Chain Yeast Artificial Chromosomes1," The Journal of Immunology, Dec. 15, 1999, vol. 163, No. 12, pp. 6898-6906.
Schroeder, et al., "Preferential utilization of conserved immunoglobulin heavy chain variable gene segments during human fetal life," Proceeding of the National Academy of Sciences of the United States of America, Aug. 1990, vol. 87, pp. 6146-6150.
Yu, et al., Differential Usage of VH Gene Segments is Mediated by cis Elements, The Journal of Immunology, Oct. 1, 1998, vol. 161, No. 7, pp. 3444-3454.
International Search Report and Written Opinion, International Application No. PCT/GB2012/052298, Jun. 13, 2013, 22 pages.
ISR issued Sep. 29, 2010 in PCT/GB2010/051122.
IPEA Examiner's Report regarding allowability of claims in PCT/GB2010/051122.
Auerbach, et al., "Establishment and chimera analysis of 129/SvEv- and C57BL/6-derived mouse embryonic stem cell lines," Biotechniques 29: pp. 1024-1032 (Nov. 2000).
Beard, et al., "Efficient method to generate single-copy transgenic mice by site-specific integration in embryonic stem cells," Genesis (2006), vol. 44, pp. 23-28.
Billiard, et al., "Ongoing D114-Notch signaling is required for T-cell homeostasis in the adult thymus," European Journal of Immunology, Aug. 4, 2011, vol. 41, pp. 2207-2216.
Brüggemann, et al., "Human antibody production in transgenic mice: expression from 100 kb of the human 1gH locus," European Journal of Immunology, May 1991, vol. 21, Issue 5, pp. 1323-1326.
Carstea, et al., "Germline competence of mouse ES and iPS cell lines: Chimera technologies and genetic background," World Journal of Stem Cells, Dec. 31, 2009; 1(1): pp. 22-29.
Ding, et al., "Generation of high-affinity fully human anti-interleukin-8 antibodies from its cDNA by two-hybrid screening and affinity maturation in yeast," Protein Science, Oct. 2010; vol. 19, pp. 1957-1966.
Doyle, et al., "The construction of transgenic and gene knockout/knockin mouse models of human disease," Transgenic Research, Apr. 2012; 21(2): pp. 327-349.
Hagiwara, Transgenic expression of VpreB-3 under the control of the immunoglobulin heavy chain enhancer and SV40 promoter, Kobe Journal of Medical Sciences, Feb. 1996, vol. 42, No. 1, pp. 43-59 (English Abstract).
Iglesias-Ussel, et al, "Forced expression of AID facilitates the isolation of class switch variants from hybridoma cells," Journal of Immunological Methods, Oct. 2006; 316(1-2), pp. 59-66.
Jakobovits, et al., "From XenoMouse technology to panitumumab, the first fully human antibody product from transgenic mice," Nature Biotechnology, vol. 25, No. 10, pp. 1134-1143, Oct. 2007.
Janssens, et al., "Generation of heavy-chain-only antibodies in mice," Proceedings of the National Academy of Sciences (USA), Oct. 10, 2006, vol. 103, No. 41, pp. 15130-15135.
Laventie, et al., "Heavy chain-only antibodies and tetravalent bispecific antibody neutralizing *Staphylococcus aureus* leukotoxins," Proceedings of the National Academy of Sciences (USA), Sep. 27, 2011; vol. 108, No. 39, pp. 16404-16409.
Luby, et al., "The μ switch region tandem repeats are important, but not required, for antibody class switch recombination," The Journal of Experimental Medicine, Jan. 15, 2001; 193(2): pp. 159-168.
Murphy, "VelocImmune: immunoglobulin variable region humanized mice," Recombinant Antibodies for Immunotherapy. 1st ed. Cambridge: Cambridge University Press, pp. 100-108, 2009.
Shultz, et al., "Humanized mice in translational biomedical research," The Journal of Immunology, Feb. 2007, vol. 7, No. 2, pp. 118-130.
Te Riele, et al., "Highly efficient gene targeting in embryonic stem cells through homologous recombination with isogenic DNA constructs," Proceedings of the National Academy of Sciences (USA), vol. 89, pp. 5128-5132, Jun. 1992.
Tomizuka, et al., "Double trans-chromosomic mice: Maintenance of two individual human chromosome fragments containing Ig heavy and k loci and expression of fully human antibodies," Proceedings of the National Academy of Sciences (USA), Jan. 18, 2000, vol. 97, No. 2, pp. 722-727.
Valenzuela, et al., "High-throughput engineering of the mouse genome coupled with high-resolution expression analysis," Nature Biotechnology vol. 21, No. 6, p. 652-659 and vol. 21, No. 7, p. 822, (2003).
Xu, et al., "Combinatorial surrobody libraries," Proceedings of the National Academy of Sciences (USA), (2008) vol. 105, No. 31, pp. 10756-10761.
Kaminski, et al., "Antibody class switching differs among SJL, C57BL/6 and 129 mice," International Immunology, vol. 19, No. 4, pp. 545-556 (2007).
Kellermann, et al., "Developing the XENOMOUSE® technology for evaluating immunogenicity," AntibOZ 2: An International Forum to Predict the Next Wave of Protein-based Therapies and Immunodiagnostics, AntibOZ 2 Conference, Australia, p. 1 (2004).
Scott, "Mice with a human touch," Nature Biotechnology, vol. 25, No. 10, pp. 1075-1077, Oct. 2007.
European Patent Office, Authorized Officer, Gaby Brouns, International Search Report—International Application No. PCT/GB2013/050682, dated Sep. 25, 2013, 4 pages.
Intellectual Property Office, United Kingdom, International Search Report, Application No. GB1116122.1, dated Feb. 2, 2012, 1 page.
Intellectual Property Office, United Kingdom, Corrected International Search Report and Opinion, Application No. GB1122047.2, dated Apr. 20, 2012, 5 pages.

(56) References Cited

OTHER PUBLICATIONS

European Patent Office, Munich, Germany, International Search Report, Application No. EP 12194977, dated Jul. 5, 2013, 4 pages.
European Patent Office, Munich, Germany, International Search Report, Application No. EP 12195041, dated Nov. 8, 2013, 3 pages.
Adams et al., "A genome-wide, end-sequenced 129Sv BAC library resource for targeting vector construction", Genomics 86, pp. 753-759, 2005.
Askew et al., Site-Directed Point Mutations in Embryonic Stem Cells: a Gene-Targeting Tag-and-Exchange Strategy, Molecular and Cellular Biology, vol. 13, No. 7, pp. 4115-4124, Jul. 1993.
Baker et al., "Homologous Recombination between Transferred and Chromosomal Immunoglobulin k Genes", Mol. Cell. Biology, pp. 4041-4047, Oct. 1988.
Barreto et al., "AID from bony fish catalyzes class switch recombination", Journal of Experimental Medicine, pp. 1-6, Sep. 12, 2005.
Beck et al., "Nucleotide sequence and exact localization of the neomycin phosphotransferase gene from transposon Tn5". Gene, vol. 19, pp. 327-336, Oct. 1982.
Berg et al., "Inverted repeats of Tn5 are transposable elements". PNAC USA, Genetics, Vo. 79, pp. 2632-2635, Apr. 1982.
Betke et al., "Segmental genomic replacement by Cre-mediated recombination: genotoxic stress activation of the p53 promoter in single-copy transformants", Nucleic Acids Research, vol. 25, No. 14, pp. 2828-2834, 1997.
Bolland et al., "Antisense Intergenic Transcription Precedes IghD-to-J Recombination and is Controlled by the Intronic Enhancer Eμ", Mol. Cell. Biology, vol. 27, No. 15, pp. 5523-5533, Aug. 2007.
Bonin et al., "Isolation, Microinjection, and Transfer of Mouse Blastocysts" Methods in Molecular Biology, vol. 158, Gene Knockout Protocols, pp. 121-134.
Bottaro et al., "Deletion of the IgH intronic enhancer and associated matrix-attachment regions decreases, but does not abolish, class switching at the μ locus", Int. Immunol. Vo. 10, No. 6, pp. 799-806, 1998.
Bradley et al., "Formation of germ-line chimaeras from embryo-derived teratocarcinoma cell lines", Nature Publishing Group, pp. 255-256, vol. 309, 1984.
Breden et al., "Comparison of Antibody Repertoires Produced by HIV-1 Infection, Other Chronic and Acute Infections, and Systemic Autoimmune Disease", PLoS One. vol. 6, Issue 3, pp. 1-11, Mar. 2011.
Brocker et al., "Evolutionary divergence and functions of the ADAM and ADAMTS gene families" Human Genomics, vol. 4, No. 2, pp. 43-55, Oct. 2009.
Bruggemann et al., "Immunoglobulin heavy chain locus of the rat: Striking homology to mouse antibody genes", Proc. Natl. Acad. Sci. USA, Immunology, vol. 83, pp. 6075-6079, Aug. 1986.
Bruggemann et al., "A repertoire of monoclonal antibodies with human heavy chains from transgenic mice", Proc. Natl. Acad. Sci. USA, Immunology, vol. 86, pp. 6709-6713, Sep. 1989.
Buehr et al., "Capture of Authentic Embryonic Stem Cells from Rat Blastocysts", Cell, vol. 135, pp. 1287-1298, Dec. 26, 2008.
Cadinanos et al., "Generation of an inducible and optimized piggyBac transposon system", Nucleic Acids Research, vol. 35, No. 12, Jun. 18, 2007.
Chen et al., "B cell development in mice that lack one or both immunoglobulin χ light chain genes", The EMBO Journal, Vo. 12, No. 3, pp. 821-830, 1993.
Chen et al., "Immunoglobulin Heavy Chain Gene Replacement: A Mechanism of Receptor Editing" Immunity, vol. 3, pp. 747-755, Dec. 1995.
Cho, "Testicular and epididymal ADAMs: expression and function during fertilization", Nature, vol. 9, pp. 550-560, Oct. 2012.
Choi et al., "Characterization and comparative genomic analysis of intronless Adams with testicular gene expression", Genomics 83, pp. 636-646, Aug. 2003.
Clark et al., "Trends in Antibody Sequence Changes During the Somatic Hypermutation Process", The Journal of Immunology, vol. 177, pp. 333-340, 2006.
Colbere_Garapin et al., "A New Dominant Hybrid Selective Marker for Higher Eukaryotic Cells". J Mol. Biol., vol. 150, No. 1, pp. 1-14, Jul. 25, 1981.
Copeland et al., "Recombineering: A Powerful New Tool for Mouse Functional Genomic", Nature Reviews, Genetics, vol. 2, pp. 769-869, Oct. 2001(10):769-79.
Corti et al. "A Neutralizing Antibody Selected from Plasma Cells That Binds to Group 1 and Group 2 Influenza A Hemagglutinins" Science, vol. 333, pp. 850-856, 2011.
Cuesta et al., "Multivalent antibodies: when design surpasses evolution", Trends Biotechnology, vol. 28, pp. 355-362, 2010.
De Saint Vincent et al., "Homologous recombination in mammalian cells mediates formation of a functional gene from two overlapping gene fragments", Proc. Natl. Acad. Sci., USA, Genetics, vol. 80, pp. 2002-2006, Apr. 1983.
DeChiara et al. "Producing Fully ES Cell-Derived Mice From Eight-Cell Stage Embryo Injections", Methods in Enzymology, vol. 476, Chapter 16, pp. 285-294.
DeChiara et al. "VelociMouse: Fully ES Cell-Derived FO-Generation Mice Obtained from the Injection of ES Cells into Eight-Cell-Stage Embryos", Gene Knockout Protocols: Second Edition, vol. 530, pp. 311-324, 2009.
Denome et al. "Patterns of polyadenylation site selection in gene constructs containing multiple polyadenylation signals", Mol. Cell Biol., vol. 8, No. 11, pp. 4829-4839, Nov. 1988.
Diez-Roux et al., "A High-Resolution Anatomical Atlas of the Transcriptome in the Mouse Embryo", PLoS Biology, vol. 9, Issue 1, pp. 1-13, Jan. 2011.
DiNoia et al., "Molecular Mechanism of Antibody Somatic Hypermutation", Annu. Rev. Biochem, vol. 76, No. 1, pp. 1-22, 2007.
Doetschman et al., "Establishment of Hamster Blastocyst-Derived Embryonic Stem (ES) Cells", Developmental Biology, vol. 127, pp. 224-227, 1988.
Doetschman et al., "Targeted mutation of the H*prt* gene in mouse embryonic stem cells" Proc. Natl. Acad. Sci., vol. 85, pp. 8583-8587, Nov. 1988.
Durbin, "A map of human genome variation from population-scale sequencing", Nature, vol. 467, pp. 1061-1074, Oct. 28, 2012.
Durdik et al., "Isotype switching by a microinjected μ immunoglobulin heavy chain gene in transgenic mice", PNAS USA Immunol, vol. 86, pp. 2346-2350, Apr. 1989.
Ekiert et al., "A Highly Conserved Neutralizing Epitope on Group 2 Influenza A Viruses", Science, vol. 333, pp. 843-850, Aug. 12, 2011.
Evans, "Fertilin B and other ADAMs as integrin ligands: insights into cell adhesion and fertilization", BioEssays 23.7, pp. 628-639, 2001.
Featherstone et al., "The Mouse Immunoglobulin heavy Chain V-D Intergenic Sequence Contains Insulators That May Regulate Ordered V(D)J Recombination", The Journal of Biological Chemistry, vol. 285, No. 13, pp. 9327-9338, Mar. 26, 2010.
Fell et al., "Homologous recombination in hybridoma cells: heavy chain chimeric antibody produced by gene targeting", PNAS USA Immunology, vol. 86, pp. 8507-8511, Nov. 1989.
Feschotte et al., "DNA Transposons and the Evolution of Eukaryotic Genomes.", Annu Rev Genet., vol. 41, pp. 331-368, 2007.
Folger et al., "Patterns of Integration of DNA Microinjected into Cultured Mammalian Cells: Evidence for Homologous Recombination Between Injected Plasmid DNA Molecules", Mol. Cell Biol., vol. 2, No. 11, pp. 1372-1387, 1982.
Forconi et al., "The normal IGHV1-69-derived B-cell repertoire contains stereotypic patterns characteristic of unmutated CLL", vol. 115, pp. 71-77, 2010.
Fukita et al., "Somatic Hypermutation in the Heavy Chain Locus Correlates with Transcription", Immunity, vol. 9, pp. 106-114, Jul. 1998.
Gefter et al., "Expression of a VHC kappa chimaeric protein in mouse myeloma cells", Nature, pp. 364-367, May 24-30, 1984 (Abstract only).

(56) References Cited

OTHER PUBLICATIONS

Gerdes et al., "Physical Map of the mouse λ light chain and related loci", Immunogenetics, vol. 54, pp. 62-65, 2002.
Geurts et al., "Knockout Rats via Embryo Microinjection of Zinc-Finger Nucleases", Science, vol. 325, p. 433, Jul. 24, 2009.
Gluzman, "SV40-Transformed Simian Cells Support the Replication of Early SV40 Mutants". Cell, vol. 23, pp. 175-182, Jan. 1981.
Gorman et al., "The Igκ 3' enhancer influences the ratio of Ig? versus Ig? B lymphocytes" Immunity, vol. 5, pp. 241-252, Sep. 1996.
Gorny et al., "Human Anti-V3 HIV-1 Monoclonal Antibodies Encoded by the VH5-51/VL Lambda Genes Define a Conserved Antigenic Structure", PLoSone, vol. 6, Issue 12, pp. 1-10, Dec. 2011.
Goyenechea et al., "Cells strongly expressing Ig(kappa) transgenes show clonal recruitment of hypermutation: a role for both MAR and the enhancers" The EMBO Journal, vol. 16, No. 13., pp. 3987-3994, 1997.
Gu et al., Independent Control of Immunoglobulin Switch Recombination at Individual Switch Regions Evidenced through Cre-loxP-Mediated Gene Targeting. Cell, vol. 73, pp. 1155-1164, Jun. 18, 1993.
Guerrero et al., "The bleomycin resistance gene of transposon Tn5 is an excellent marker for transformation of corynebacteria", Applied Microbiology Biotechnology, vol. 36, pp. 759-762, 1992.
Guntaka, "Transcription Termination and Polyadenylation in Retroviruses" Microbiological Reviews, vol. 57, No. 3, pp. 511-521, Sep. 1993.
Han et al., "Comprehensive Analysis of Reproductive ADAMs: Relationship of ADAM4 and ADAM6 with an ADAM Complex Required for Fertilization in Mice", Biology of Reproduction 80, pp. 1001-1008, Jan. 7, 2009.
Hasty et al., "Target frequency and integration pattern for insertion and replacement vectors in embryonic stem cells", Molecular Cellular Biology, vol. 11, No. 9, pp. 4509-4517, Sep. 1991.
Houvila et al., "Shedding light on ADAM metalloproteinases", Trends in Biochemical Sciences, vol. 30, No. 7, pages, Jul. 2005.
Hudziak et al., "Establishment of Mammalian Cell Lines Containing Multiple Nonsense Mutations and Functional Suppressor tRNA Genes", Cell, vol. 31, pp. 137-146, Nov. 1982.
Ivics et al., "The expanding universe of transposon technologies for gene and cell engineering", Mobile DNA, pp. 1-25, 2010.
Ivics et al., "The Sleeping Beauty Transposable Element: Evolution, Regulation and Genetic Applications", Curr. Issues Mol. Biol., vol. 6, pp. 43-56, 2004.
Izsvak et al., "Sleeping Beauty Transposition: Biology and Applications for Molecular Therapy", Molecular Therapy, vol. 9, No. 2, pp. 147-156, Feb. 2, 2004.
Jacob et al., "Gene targeting in the rat: advances and opportunities", Trends in Genetics, vol. 26, No. 12, pp. 510-518, Dec. 2010.
Jakobovits, "From XenoMouse Technology to Panitumumab, the First Fully Human Antibody Product from Transgenic Mice", Nature Biotechnology, vol. 25, No. 10, pp. 1134-1143, Oct. 2007.
Kim et al. "CHO cells in biotechnology for production of recombinant proteins: current state and further potential" Appl. Microbiology Biotechnology, vol. 93, pp. 917-930, Dec. 9, 2011.
Kohrer et al. "Import of amber and ochre suppressor tRNAs into mammalian cells: A general approach to site-specific insertion of amino acid analogues into proteins", PNAS USA, vol. 98, No. 25, pp. 214310-214315, Dec. 4, 2001.
Kotzamaris et al. Recombining overlapping BACs into a single larger BAC, BMC Biotechnology, pp. 1-10, 2004.
Krause, Epitope-Specific Human Influenza Antibody Repertoires Diversify by B Cell Intraclonal Sequence Divergence and Interclonal Convergence, The Journal of Immunology, pp. 3704-3711, Aug. 31, 2011.
Kruif et al., "Human Immunoglobulin Repertoires against Tetanus Toxoid Contain a Large and Diverse Fraction of High-Affinity Promiscuous Vh Genes", Journal of Molecular Biology, vol. 387, pp. 548-558, Feb. 11, 2009.
Krutskikh et al., "Epididymal protein Rnase10 is required for post-testicular sperm maturation and male fertility", The FASEB Journal, pp. 4198-4209, 2012.
Kucherlapati et al., "Homologous recombination between plasmids in mammalian cells can be enhanced by treatment of input DNA", PNAS USA Genetics, vol. 81, pp. 3135-3157, May 1984.
Li et al., "Transgenic mice with a diverse human T cell antigen receptor repertoire", Nature Medicine, vol. 16, No. 9, pp. 1029-1035, Sep. 2010.
Li et al. "The minimum Internal and external sequence requirements for transposition of the eukaryotic transformation vector piggyBAC", Mol. Genet. Genomics, vol. 266, pp. 190-198, 2001.
Li et al., "Crafting rat genomes with zinc fingers", Nature Biotechnology, vol. 29, No. 1, pp. 39-41, Jan. 2011.
Li et al., "Germline Competent Embryonic Stem Cells Derived from Rat Blastocysts", Cell, vol. 135, pp. 1299-1310, Dec. 26, 2008.
Liao et al., "Generation of Induced Pluripotent Stem Cell Lines from Adult Rat Cells", Cell Stem Cell Brief Report, vol. 4, pp. 11-15, Jan. 9, 2009.
Luciw et al., "Location and Function of Retroviral and SV40 Sequences that Enhance Biochemical Transformation after Microinjection of DNA", Cell., vol. 33, pp. 705-176, Jul. 1983.
Luo et al., "Chromosomal transposition of a Tc1/mariner-like element in mouse embryonic stem cells", Proc. Natl. Acad. Sci. USA, Genetics, vol. 95, pp. 10769-10773, Sep. 1998.
Mack et al., "A small bispecific antibody construct expressed as a functional single-chain molecule with high tumor cell cytotoxicity", Proc. Natl. Acad. Sci. USA, Immunology, vol. 92, pp. 7021-7025, Jul. 1995.
Makris et al., "Mutational analysis of insertion sequence 50 (IS50) and transposon 5 (Tn5) ends", Proc. Natl. Acad. Sci. USA, Genetics, vol. 85, pp. 2224-2228, Apr. 1988 1998.
Mallender et al., "Construction, Expression, and Activity of a Bivalent Bispecific Single-chain Antibody", The Journal of Biological Chemistry, vol. 269, No. 1, pp. 199-206, 1994.
Marcello et al., Lack of Tyrosylprotein Sulfotransferase-2 Activity Results in Altered Sperm-Egg Interactions and Loss of ADAM3 and ADAM6 in Epididymal Sperm, The Journal of Biological Chemistry, vol. 286, No. 15, pp. 13060-13070, Apr. 15, 2011.
Martensson et al., "Role of the surrogate light chain and the pre-B-cell receptor in mouse B-cell development", Immunology, vol. 101, pp. 435-441, 2000.
Maul et al., "Aid and Somatic Hypermutation", Advances in Immunology, vol. 105, pp. 159-191, 2010.
McCreath et al., "Production of gene-targeted sheep by nuclear transfer from cultured somatic cells", Nature, vol. 405, pp. 1066-1070, Jul. 29, 2000.
Mejia et al., "The Assembly of Large BACs by in Vivo Recombination", Genomics, vol. 70, pp. 165-170, 2000.
Mir, "Sequencing Genomes: From Individuals to Populations", Briefings in Functional Genomics Proteomics, vol. 8, No. 5, pp. 367-378, 2009.
Moreau et al., "The SV40 72 base repair repeat has a striking effect on gene expression both in SV40 and other chimeric recombinants", Nuclear Acids Research, vol. 9, No. 22, pp. 6047-6068, 1981.
Moreno et al., "The emerging role of matrix metalloproteases of the ADAM family in male germ cell apoptosis", Spermatogenesis, vol. 1, No. 3, pp. 195-208, Jul./Aug./Sep. 2011.
Mouellic et al., "Pattern of transcription of the homeo gene Hox-3.1 in the mouse embryo", Denes Dev., vol. 2, pp. 125-135, 1988.
Murphy, "VelocImmune: Immunoglobulin Variable Region Humanized Mice", Recombinant Antibodies for Immunotherapy. 1st ed. Cambridge: Cambridge University Press, pp. 100-108, 2009.
Nandi et al., "Regulated expression of genes inserted at the human chromosomal B-globin locus by homologous recombination", Proc. Natl. Sci. USA, Cell Biology, vol. 85, pp. 3845-3849, Jun. 1998.
Narayanan et al., "Bacterial Artificial Chromosome Mutagenesis Using Recombineering" Journal of Biomedicine and Biotechnology, vol. 2011, Article ID 971296, 10 pages, Dec. 9, 2010.
Nelson et al., "Development trends for human monoclonal antibody therapeutics", Nature Reviews, Drug Discovery, vol. 9, pp. 767-774, Oct. 2010.

(56) References Cited

OTHER PUBLICATIONS

Neuberger et al., "Somatic hypermutation", Current Opinion in Immunology, vol. 7, pp. 248-254, 1995.
Oancea et al., "Expression of the (Recombinant) Endogenous Immunoglobulin Heavy-Chain Locus requires the Intronic Matrix Attachment Regions", Molecular and Cellular Biology, vol. 17, No. 5, pp. 2658-2668, May 1997.
Osborn et al. "High-Affinity IgG Antibodies Develop Naturally in Ig-Knockout Rats Carrying Germline Human IgH/Ig k/Ig? Loci Bearing the Rat Ch Region", The Journal of Immunology, pp. 1481-1491.
Osoegawa et al., "Bacterial Artificial Chromosome Libraries for Mouse Sequencing and Functional Analysis", Genome Research, pp. 16-28, 2000.
Pavlicek et al., "Ancient Transposable Elements, Processed Pseudogenes, and Endogenous Retroviruses", Genomic Disorders, pp. 57-72, 2006.
Pelham et al., "Expression of a *Drosophila* Heat Shock Protein in Mammalian Cells: Transient Association with Nucleoli after Heat Shock", Philosophical Transactions of the Royal Society, pp. 301-307, 1984.
Perlot et al., "Antisense transcripts from immunoglobulin heavy-chain locus V(D)J and switch regions", PNAS, vol. 105, No. 10, pp. 3843-3848, Mar. 11, 2008.
Perlot et al., "Cis-Regulatory Elements and Epigenetic Changes Control Genomic Rearrangements of the IgH Locus", Advances in Immunology, vol. 99, pp. 1-32, 2008.
Plasterk et al., "Resident aliens: The Tc1/mariner superfamily of transposable elements", YIG, vol. 15, No. 8, pp. 326-333, Aug. 1999.
Popov et al., "A Human Immunoglobulin λ Locus is Similarly Well Expressed in Mice and Humans", Journal of Experimental Medicine, vol. 189, No. 10, pp. 1611-1619, May 17, 1999.
Primakoff et al., "Penetration, Adhesion, and Fusion in Mammalian Sperm-Egg Interaction", Science, vol. 296, pp. 2183-2185, Jun. 21, 2002.
Primakoff et al., "The ADAM Gene Family: surface proteins with adhesion and protease activity", Trends in Genetics, vol. 16, No. 2, pp. 83-87, Feb. 2000.
Puente et al., "Comparative genomic analysis of human and chimpanzee proteases", Genomics, vol. 86, pp. 638-647, 2005.
Raynard et al., "Cis-acting regulatory sequences promote high-frequency gene conversion between repeated sequences in mammalian cells", Nucleic Acids Research, vol. 32, No. 19, pp. 5916-5927, Nov. 4, 2004.
Reddy et al., "Monoclonal antibodies isolated without screening by analyzing the variable-gene repertoire of plasma cells", Nature Biotechnology, vol. 28, No. 9, pp. 965-971, Sep. 2010.
Retter, "Sequence and Characterization of the Ig Heavy Chain Constant and Partial Variable Region of the Mouse Strain 129S1", The Journal of Immunology, vol. 179, pp. 2419-2427, 2007.
Rogozin et al., "Cutting Edge: DGYW/WRCH Is a Better Predictor of Mutability at G:c Bases in Ig Hypermutation Than the Widely Accepted RGYW/WRCY Motif and Probably Reflects a Two-Step Activation-Induced Cytidine Deaminase-Triggered Process", Journal of Immunology, vol. 172, pp. 3382-3384, 2004.
Sakai et al., "Recombination and transcription of the endogenous Ig heavy chain locus is effected by the Ig heavy chain intronic enhancer core region in the absence of the matrix attachment regions", Proc. Natl. Acad. Sci., vol. 96, pp. 1526-1531, Feb. 1999.
Sarkar et al., "Molecular evolutionary analysis of the widespread *piggyBac* transposon family and related "domesticated" sequences", Mol. Gen. Genomics, vol. 270, pp. 173-180, 2003.
Sasso et al., "Expression of the Immunoglobulin Vh Gene 51p1 is Proportional to Its Germline Gene Copy Number", J. Clin. Invest., vol. 97, No. 9, pp. 2074-2080, May 1996.
Sauer, "Functional Expression of the cre-lox Site-Specific Recombination System in the Yeast Saccharomyces cerevisiae", Molecular and Cellular Biology, vol. 7, No. 6, pp. 2087-2096, Jun. 1987.
Sauer et al. "Cre-stimulated recombination at loxP-containing DNA sequences placed into the mammalian genome", Nucleic Acids Research, vol. 17, No. 1, pp. 147-161, 1989.
Sauer et al., "Site-specific DNA recombination in mammalian cells by the Cre recombinase of bacteriophage P1", Proc. Natl. Acad. Sci. USA, Genetics, vol. 85, pp. 5166-5170, 1988.
Schlake et al., "Use of Mutated FLP Recognition Target (FRT) Sites for the Exchange of Expression Cassettes at Defined Chromosomal Loci", Biochemistry, vol. 33, pp. 12746-12751, 1994.
Schrock et al. "Comparative Genomic Hybridization (CGH)-Detection of Unbalanced Genetic Aberrations Using Conventional MicroArray Techniques", Molecular Cytogenetics, Unit 8.12.1, Supplement 18, 30 pages, 2001.
Schweinfest et al., "A heat-shock-inducible eukaryotic expression vector", Gene. 71, pp. 207-210, 1988.
Seed et al., "Purification of genomic sequences from bacteriophage libraries by recombination and selection in vivo", Nucleic Acids Research, vol. 11, No. 8, pp. 2427-2445, 1983.
Serwe et al., "V(D)J recombination in B cells is impaired but not blocked by targeted deletion of the immunoglobulin heavy chain intron enhancer", The EMBO Journal, vol. 12, No. 6, pp. 2321-2327, 1993.
Shaul et al., "Homologous recombination between a virus and a chromosomal sequence in mammalian cells", PNAS, Genetics, vol. 82, pp. 3781-3784, Jun. 1985.
Shimizu et al. "Immunoglobulin double-isotype expression by trans-mRNA in a human immunoglobulin transgenic mouse", Proc. Natl. Acad. Sci. USA, Immunology, vol. 86, pp. 8020-8023, Oct. 1989.
Simpson et al., "Gene variation among 129 substrains and its importance for targeted mutagenesis in mice", Nature Genetics, vol. 16, pp. 19-27, May 16, 1997.
Skoultchi et al., "Expression of Genes Inserted at the Human B-Globin Locus by Homologous Recombination", Developmental Control of Globin Gene Expression, pp. 581-594, 1987.
Smithies, "Direct Alteration of a Gene in the Human Genome" J. inher. Metab., Dis. 9, Suppl. 1, pp. 92-97, 1986.
Smithies et al., "Insertion of DNA sequences into the human chromosomal B-globin locus by homologous recombination", Nature, vol. 317, No. 19, pp. 230-234, Sep. 1985.
Sohn et al., "Somatic Hypermutation of an Immunoglobulinμ Heavy Chain Transgene", J. Exp. Med., vol. 177, pp. 493-504, Feb. 1993.
Song et al., "Accurate modification of a chromosomal plasmid by homologous recombination in human cells", Proc. Natl. Acad. Sci. USA, Genetics, vol. 84, pp. 6820-6824, Oct. 1987.
Sonoda et al., "B Cell Development under the Condition of Allelic Inclusion", Immunology, vol. 6, pp. 225-233, Mar. 1997.
Taki et al., "Targeted Insertion of a Variable Region Gene into the Immunoglobulin Heavy Chain Locus", Science, vol. 262, pp. 1268-1271, Nov. 19, 1993.
Talbot et al., "Cell Adhesion and Fertilization: Steps in Oocyte Transport, Sperm-Zona Pellucida Interactions, and Sperm-Egg Fusion", Biology of Reproduction 68, pp. 1-9, 2003.
Thomas et al., "High Frequency Targeting of Genes to Specific Sites in the Mammalian Genome", Cell, vol. 44, pp. 419-428, Feb. 14, 1986.
Thomas et al., "Introduction of homologous DNA sequences into mammalian cells induces mutations in the cognate gene" Nature, vol. 324, Nov. 1986.
Thomas et al., "Site-Directed Mutagenesis by Gene Targeting in Mouse Embryo-Derived Stem Cells", Cell, vol. 51, pp. 503-512, Nov. 6, 1987.
Vassilieva et al. "Establishment of SSEA-1- and Oct-4 Expressing Rat Embryonic Stem-like Cell Lines and Effects of Cytokines of the IL-6 Family on Clonal Growth", Experimental Cell Research, vol. 258, pp. 361-373, 2000.
Vora et al., "Altering the Antibody Repertoire via Transgene Homologous Recombination: Evidence for Global and Clone-autonomous Regulation of Antigen-driven B Cell Differentiation", J. Exp. Med., vol. 181, pp. 271-281, Jan. 1995.

(56) References Cited

OTHER PUBLICATIONS

Wang et al., "AID upmutants isolated using a high-throughput screen highlight the immunity/cancer balance limiting DNA deaminase activity", Nature Structural & Molecular Biology, vol. 16, No. 7, Jul. 2009.
Wang et al., "Altering the spectrum of immunoglobulin V gene somatic hypermutation by modifying the active site of AID", J. Exp. Med., vol. 207, No. 1, pp. 141-153, 2010.
Wang et al., "Catching a Moving Target", Science, Biochemistry, vol. 333, pp. 834-835, Aug. 21, 2011.
Wilkie et al., "Analysis of the Integrant in MyK-103 Transgenic Mice in which Males Fail to Transmit the Integrant", Molecular and Cellular Biology, pp. 1646-1655, May 1987.
Zou et al. "Cre-loxP-mediated gene replacement: a mouse strain producing humanized antibodies", Current Biology, vol. 4, No. 12, pp. 1099-1104, 1994.
Yancopoulous et al., "Preferential utilization of the most $J_H$-proximal $V_H$ gene segments in pre-B-cell lines", Nature, vol. 311, pp. 727-733, 1984.
Sen et al., "Multiple Nuclear Factors Interact with the Immunoglobulin Enhancer Sequences", Cell, vol. 46, pp. 705-716, Aug. 29, 1986.
Storb et al., "Physical Linkage of Mouse Genes by Pulsed-Field Gel Electrophoresis Suggests that the Rearrangement Process Favors Proximate Target Sequences", Molecular and Cellular Biology, vol. 9, No. 2, pp. 711-718, Feb. 1989.
Gerstein et al., Isotype Switching of an Immunoglobulin Heavy Chain Transgene Occurs by DNA Recombination between Different Chromosomes, Cell, vol. 63, pp. 537-548, Nov. 2, 1990.
Kitamura et al. "A B cell-deficient mouse by targeted disruption of the membrane exon of the immunoglobulin chain gene", Nature, vol. 350, pp. 423-426, Apr. 1991.
Torres et al., "Laboratory Protocols for Conditional Gene Targeting", Institute for Genetics, University of Cologne, pp. 37-40, 1997.
Kingzette et al., "Trans-chromosomal recombination within the Ig heavy chain switch region in B lymphocytes", Proc. Natl. Acad. Sci., vol. 95, pp. 11840-11845, Sep. 1998.
Williams et al., "Unequal $V_H$ Gene Rearrangement Frequency Within the Large Vh7183 Gene Family is not Due to Recombination Signal Sequence Variation, and Mapping of the Genes Shows a Bias of Rearrangement Base on Chromosomal Location", The Journal of Immunology, pp. 257-263, 2001.
Bruggemann, "Human Antibody Expression in Transgenic Mice", Archivum Immunologiae et Therapiae Experimentalis, vol. 49, pp. 203-208, 2001.
Mortuza et al., "Immunoglobulin heavy-chain gene rearrangement in adult acute lymphoblastic leukemia reveals preferential usage of $J_H$-proximal variable gene segments", Blood, vol. 97, No. 9, pp. 2716-2726, May 2001.
Clark et al., "A Future for Transgenic Livestock", Nature Reviews, Genetics, vol. 4, pp. 825-833, Oct. 2003.
Oberdoerffer et al., "Unidirectional Cre-mediated genetic inversion in mice using the mutant loxP pair lox66/1ox71", Nucleic Acids Research, vol. 31, No. 22, pp. 1-7, 2003.
Kuroiwa et al., "Sequential targeting of the genes encoding immunoglobulin and prion protein in cattle", Nature Genetics, vol. 36, No. 7, pp. 775-780, Jul. 2004.
Niemann et al., "Transgenic farm animals: present and future", Rev. Sci Tech Off. Int Epiz., vol. 24, pp. 285-298, 2005.
Lonberg, "Human antibodies from transgenic animals", Nature Biotechnology, vol. 23, No. 9, pp. 1117-1125, Sep. 2005.
Venken et al., "P[acman]: A BAC Transgenic Platform for Targeted Insertion of Large DNA Fragments in *D. melanogaster*", Science, vol. 314, pp. 1747-1751, Dec. 15, 2006.
Qu et al., "Gene Targeting of ErbB3 Using a Cre-Mediated Unidirectional DNA Inversion Strategy", Technology Report, Genesis, vol. 44, pp. 477-486, 2006.
Ungrin et al., "Strict control of telomerase activation using Cre-mediated inversion", BMC Biotechnology, vol. 6, pp. 1-9, 2006.
Wallace et al., "Manipulating the Mouse Genome to Engineer Precise Functional Syntenic Replacements with Human Sequence", Cell, vol. 18, pp. 197-209, Jan. 12, 2007.
"News in Brief", Nature Biotechnology, vol. 25, No. 6, p. 613, Jun. 2007.
Nagle, "Regeneron helps make Sanofi VelocImmune to its 'weak' pipeline", Outsourcing-Pharmac.com, 2 pages, Dec. 3, 2007.
Bates et al., "Chromosomal position of a $V_H$ gene segment determines its activation and inactivation as a substrate for V(D)J recombination", The Journal of Experimental Medicine, vol. 204, No. 13, pp. 3247-3256, Dec. 24, 2007.
Stevens et al., "Human Antibody Discovery, VelocImmune—A novel platform", Pharma Focus Asia, Clinical Trials Issue 8, pp. 1-5, 2008.
Statement of Fact and Arguments in Support of Opposition pertaining to Application No. 10734546.4, 41 pages, dated Oct. 22, 2013.
Declaration of Andrew J. Murphy, dated Oct. 6, 2014, including Slide Presentation dated Nov. 3, 2009, at Wellcome Trust Advanced Course: Genetic Manipulation of ES Cells, in Hinxton, UK, entitled "BAC-based Modifications of the Mouse Genome: The Big and the Backward", cited in an IDS in U.S. Appl. No. 14/192,051 of MacDonald et al. 62 pages.
Excerpts from U.S. Appl. No. 14/682,859, filed Apr. 9, 2015, including Applicant Initiated Interview Summary; Amendments to the Claims,; and Information Disclosure Statement, 14 pages.
Butler, "Immunoglobulin Diversity, B-Cell and Antibody Repertoire Development in Large Farm Animals," Revue Scientifique et Technique (Paris), vol. 17, No. 1, pp. 43-70, Apr. 1998.
Davies, et al, "Creation of Mice Expressing Human Antibody Light Chains by Introduction of a Yeast Artificial Chromosome Containing the Core Region of the Human Immunoglobulin λ Locus," Nature Biotechnology, vol. 11, pp. 911-914, 1993.
Gama Sosa, et al., Animal Transgenesis: An Overview, Brain Structure & Function, vol. 214, No. 2-3, pp. 91-109, Mar. 2010.
Green, et al, "Antigen-Specific Human Monoclonal Antibodies From Mice Engineered With Human *lg* Heavy and Light Chain YACs," Nature Genetics, vol. 7, No. 1, pp. 13-21, May 1994.
Green, et al, "Regulation of B Cell Development by Variable Gene Complexity in Mice Reconstituted with Human Immunoglobulin Yeast Artificial Chromosomes," The Journal of Experimental Medicine, vol. 188, No. 3, pp. 483-495, Aug. 3, 1998.
Huber, et al, "Distinct Contributions of Vaccine-Induced Immunoglobulin G1 (IgG1) and IgG2a Antibodies to Protective Immunity against Influenza," Clinical and Vaccine Immunology, vol. 13, No. 9, pp. 981-009, Sep. 2006.
Jacob et al., "Gene Targeting in the Rat: Advances and Opportunities," Trends in Genetics, vol. 26, No. 12, pp. 510-518, Dec. 2010.
The Jackson Laboratory, "Breeding Strategies for Maintaining Colonies of Laboratory Mice," A Jackson Laboratory Resource Manual, pp. 1-29, 2007.
Janeway et al., "Structural Variation in Immunoglobulin Constant Regions," Immunobiology: The Immune System in Health and Disease. 5th Edition, New York: Garland Science, 2001.
Janeway, et al., "The rearrangement of antigen-receptor gene segments controls lymphocyte development", In Immunobiology, 5th edition (retrieved online at <http://www.ncbi.nlm.nih.gov/books/NBK27113/>).
Kaushik, et al., "Novel Insight Into Antibody Diversification From Cattle," Veterinary Immunology and Immunopathology, vol. 87, No. 3-4, pp. 347-350, Sep. 10, 2002.
Little et al "Generation of a Large Complex Antibody Library From Multiple Donors," Journal of Immunology Methods, vol. 231, No. 1-2, pp. 3-9, Dec. 10, 1999.
Macdonald, et al., "Velocigene Technology Extended to Humanization of Several Megabases of Complex Gene Loci," (Abstract) $1^{st}$ International MUGEN Conference on Animal Models for Human Immunological Dissease, Athens Greece, Sep. 10-13, 2006, 1 page.
Oberdoerffer et al., "Unidirectional Cre-mediated Genetic Inversion in Mice Using the Mutant Loxp Pair Lox66/Lox71," Nucleic Acids Research, vol. 31, No. 22, pp. 1-7, 2003.
Parng, et al., "Gene Conversion Contributes to Ig Light Chain Diversity in Cattle," The Journal of Immunology, vol. 157, No. 12, pp. 5478-5486, Dec. 15, 1996.

(56) References Cited

OTHER PUBLICATIONS

Qi, et al., "A New Transgenic Rat Model of Hepatic Steatosis and the Metabolic Syndrome, Hypertension," vol. 45, No. 5, pp. 1004-1011, May 2005.
Ramirez-Solis, et al, "Chromosome Engineering in Mice," Nature, vol. 378, No. 6558, pp. 720-724, Dec. 14, 1995.
Ramsden, et al, "Conservation of Sequence in Recombination Signal Sequence Spacers," Nucleic Acids Research, vol. 22, No. 10, pp. 1785-1796, Apr. 13, 1994.
Ristevski, "Making Better Transgenic Models," Molecular Biotechnology, vol. 29, No. 2, pp. 153-163, Feb. 2005.
Shi, et al., "The Mapping of Transgenes by Fluorescence In Situ Hybridization on G-Banded Mouse Chromosomes," Mammalian Genome, vol. 5, No. 6, pp. 337-341, Jun. 1994.
Smith, Kevin R., "Gene Transfer in Higher Animals: Theoretical Considerations and Key Concepts," Journal of Biotechnology, vol. 99, No. 1, pp. 1-22, Oct. 9, 2002.
Stevens, et al., "Velocimmune: Humanization of Immunoglobulin Loci Using Velocigene Technology", (Abstract) Presented at 1st International MUGEN Conference on Animal Models for Human Immunological Disease, Athens, Greece, 1 page, Sep. 10-13, 2006.
Tonegawa, "Somatic Generation of Antibody Diversity," Nature, vol. 302, No. 14, pp. 575-581, Apr. 14, 1983.
Van Snick, et al., "Genetic Control of Rheumatoid Factor Production in the Mouse Role of Genes Linked to the Immunoglobulin Heavy Chain Locus and to the Major Histocompatibility Complex," Arthritis & Rheumatism, vol. 24, No. 9, pp. 1085-1090, Sep. 1983.
Wagner, et al, "Antibodies Generated From Human Immunoglobulin Miniloci in Transgenic Mice," Nucleic Acids Research, vol. 22, No. 8, pp. 1389-1393, Apr. 25, 1994.
Wuerffel, et al., "S-S Synapsis during Class Switch Recombination Is Promoted by Distantly Located Transcriptional Elements and Activation-Induced Deaminase," Immunity, vol. 27, Issue 5, pp. 711-722, Nov. 26, 2007.
Zheng et al., Engineering Mouse Chromosomes with Cre-loxP: Range, Efficiency, and Somatic Applications, Molecular and Cellular Biology, vol. 20, No. 2, pp. 648-655, Jan. 2000.
Atlas of Genetics and Cytogenetics in Oncology and Hematology: VPREB1. Accessed online: <http://atlasgeneticsoncology.org/Genes/GC_VPREB1.html> on May 25, 2015 All References.
Bode et al., "The Transgeneticist's Toolbox: Novel Methods for the Targeted Modification of Eukaryotic Genomes," *Biol. Chem.*, vol. 381, pp. 801-813 (Sep./Oct. 2000).
Bono et al., "$V_H$ Gene Segments in the Mouse and Human Genomes," *J. Mol. Biol.*, vol. 342, pp. 131-143 (2004).
Feng et al., "Site-specific Chromosomal Integration in Mammalian Cells: Highly Efficient CRE Recombinase-mediated Cassette Exchange," *J. Mol. Biol.*, vol. 292, pp. 779-785 (1999).
Matthews et al., "A locus affecting immunoglobulin isotype selection (*Igis1*) maps to the MHC region in C57BL, BALB/c and NOD mice," *Immunology and Cell Biol.*, vol. 79, pp. 576-582 (2001).
Nature Publishing Group, "Making mice at high speed," *Nature Methods*, vol. 4, No. 3, pp. 196-197 (Mar. 2007).
European Patent Office, Communication pursuant to Article 94(3) EPC—Application No. 12 194 970.5-1410, dated Sep. 23, 2013 (6 pages).
Kevin J. Pobursky, Attorney for Applicant, Third-Party Pre-Issuance Submission Under 37 CFR 1.290 in U.S. Appl. No. 13/843,528, dated Mar. 18, 2014 (14 pages).
Charles E. Lyon, Attorney for Applicant, Third-Party Pre-Issuance Submission Under 37 CFR 1.290 in U.S. Appl. No. 13/875,892, dated May 5, 2015 (32 pages).
Brenda Hershbach Jarrell, Attorney for Applicant, Third-Party Pre-Issuance Submission Under 37 CFR 1.290 in U.S. Appl. No. 14/052,259, dated Aug. 6, 2014 (7 pages).
Charles E. Lyon, Attorney for Applicant, Third-Party Pre-Issuance Submission Under 37 CFR 1.290 in U.S. Appl. No. 14/226,698, dated Jun. 5, 2015 (53 pages).
Sean Avery, Attorney for Applicant, Third-Party Pre-Issuance Submission Under 37 CFR 1.290 in U.S. Appl. No. 14/517,755, dated Jun. 26, 2015 (16 pages).
Dr. Martin Grund, European Patent Attorney Grund Intellectual Property Group, Observations according to Article 115 EPC regarding EP 12 171 791.2, dated Dec. 19, 2014 (7 pages).
Dr. Martin Grund, European Patent Attorney Grund Intellectual Property Group, Observations according to Article 115 EPC regarding EP 12 194 970.5, dated Apr. 25, 2014 (6 pages).
Dr. Martin Grund, European Patent Attorney Grund Intellectual Property Group, Observations according to Article 115 EPC regarding EP 12 194 970.5, dated Nov. 15, 2013 (6 pages).
Dr. Martin Grund, European Patent Attorney Grund Intellectual Property Group, Observations according to Article 115 EPC regarding EP 12 772 122.3, dated Mar. 12, 2015 (5 pages).
Dr. Martin Grund, European Patent Attorney Grund Intellectual Property Group, Observations according to Article 115 EPC regarding EP 14 176 740.0, dated Aug. 10, 2015 (13 pages).
Dr. Martin Grund, European Patent Attorney Grund Intellectual Property Group, Third-Party Observation—Appl. No. PCT/US2012/026416, dated Jun. 7, 2013 (2 pages).
Dr. Martin Grund, European Patent Attorney Grund Intellectual Property Group, Third-Party Observation—Appl. No. PCT/GB2012/052297, dated Jan. 17, 2014 (3 pages).
Dr. Martin Grund, European Patent Attorney Grund Intellectual Property Group, Third-Party Observation—Appl. No. PCT/GB2012/052298, dated Jan. 17, 2014 (4 pages).
Dr. Martin Grund, European Patent Attorney Grund Intellectual Property Group, Third-Party Observation—Appl. No. PCT/GB2012/050682, dated Jul. 28, 2014 (3 pages).
Dr. Martin Grund, European Patent Attorney Grund Intellectual Property Group, Third-Party Observation—Appl. No. PCT/GB2012/050683, dated Jul. 28, 2014 (2 pages).
Dr. Martin Grund, European Patent Attorney Grund Intellectual Property Group, Third-Party Observation—Appl. No. PCT/GB2012/052380, dated Jan. 24, 2014 (4 pages).
Baker, et al, "Adaptation of TCR Expression Vectors for the Construction of Mouse-Human Chimeric MBP-Specific TCR Transgenes," Journal of Neuroscience Research, vol. 45, No. 4, pp. 487-491, Aug. 15, 1996.
Bhattacharya, et al., "Switch Region Identity Plays an Important Role in Ig Class Switch Recombination," Journal of Immunology, vol. 184, pp. 6242-6248, Apr. 28, 2010.
Blankenstein, et al., "Immunoglobulin Vh Region Genes of the Mouse are Organized in Overlapping Clusters," European Journal of Immunology, vol. 17, No. 9, pp. 1351-1357, Jul. 13, 1987.
Bogen, et al., "A Rearranged λ2 Light Gene Chain Retards But Does Not Exclude χ and λ1 Expression," vol. 21, No. 10, pp. 2391-2395, Oct. 1991.
Bradley et al. "Formation of Germ-Line Chimaeras From Embryo-Derived Teratocarcinoma Cell Lines," Nature Publishing Group, vol. 309, pp. 255-256, May 17, 1984.
Brezinchek, et al., "Analysis of the Human $V_H$ Gene Repertoire," The American Society for Clinical Investigations, Inc., vol. 99, No. 10, pp. 2488-2501, May 1997.
Briney, et al., "Human Peripheral Blood Antibodies with Long HCDR3s Are Established Primarily at Original Recombination Using a Limited Subset of Germline Genes," Public Library of Science One, vol. 7, No. 5, e36750, 13 pages, May 9, 2012.
Brüggemann, et al., "Strategies for Expressing Human Antibody Repertories in Transgenic Mice," Immunology Today, vol. 17, No. 8, pp. 391-397, Aug. 1996.
Brüggemann et al., "Immunoglobulin heavy chain locus of the rat: Striking homology to mouse antibody genes," Proceedings of the National Academy of Sciences USA, Immunology, vol. 83, pp. 6075-6079, Aug. 1986.
Brüggemann, et al, "Immunogenicity of Chimeric Antibodies," The Journal of Experimental Medicine, Volume, 170, No. 6, pp. 2153-2157, Dec. 1, 1989.
Cadinanos et al., "Generation of an Inducible and Optimized Piggyback Transposon System," Nucleic Acids Research, vol. 35, No. 12, Jun. 18, 2007.

(56) References Cited

OTHER PUBLICATIONS

Cho, "Testicular and Epididymal Adams: Expression and Function During Fertilization," Nature Reviews Urology, vol. 9, No. 10, pp. 550-560, Oct. 2012.
Clark, Michael R., "IgG Effector Mechanisms," Chemical Immunology, vol. 65, pp. 88-110, 1997.
Collins, et al., "A Mouse for All Reasons," Cell, vol. 128, Issue 1, pp. 9-13, Jan. 2007.
Combriato, et al., "Regulation of Human Igλ Light Chain Gene Expression by NF-κB1," Journal of Immunology, Issue 168, vol. 3, pp. 1259-1266, Feb. 1, 2002.
Conrath, et al., "Camel Single-domain Antibodies as Modular Building Units in Bispecific and Bivalent Antibody Constructs," The Journal of Biological Chemistry, vol. 276, No. 10, pp. 7346-7350, Mar. 9, 2001.
Copeland et al., "Recombineering: A Powerful New Tool for Mouse Functional Genomic," Nature Reviews Genetics, vol. 2, No. 10, pp. 769-869, Oct. 2001.
Corbett, et al., "Sequence of the Human Immunoglobulin Diversity (D) Segment Locus: A Systematic Analysis Provides no. Evidence for the Use of Dir Segments, Inverted D Segments, "Minor" D Segments or D-D Recombination," Journal of Molecular Biology, vol. 270, No. 4, pp. 587-597, Jul. 25, 1997.
Deng, et al., "Reexamination of Gene Targeting Frequency as a Function of the Extent of Homology between the Targeting Vector and the Target Locus," Molecular and Cellular Biology, vol. 12, No. 8, pp. 3365-3371, Aug. 1992.
Edwards, et al., "The ADAM Metalloproteinases," Molecular Aspects of Medicine, vol. 29, No. 5, pp. 258-289, Oct. 2008.
Eisener-Dorman, et al., "Cautionary Insights on Knockout Mouse Studies: The Gene or Not the Gene?," Brain, Behavior, and Immunity, vol. 23, No. 3, pp. 318-324, Sep. 2009.
Fleischer, et al., "Reactivity of Mouse T-Cell Hybridomas Expressing Human Vbeta Gene Segments With Staphylococcal and Streptococcal Superantigens," Infection and Immunity, vol. 64, No. 3, pp. 987-994, Mar. 1996.
Folger et al., "Patterns of Integration of DNA Microinjected into Cultured Mammalian Cells: Evidence for Homologous Recombination Between Injected Plasmid DNA Molecules," Molecular and Cellular Biology, vol. 2, No. 11, pp. 1372-1387, Nov. 1982.
Fujieda, et al., "Multiple Types of Chimeric Germ-Line Ig Heavy Chain Transcripts in Human B Cells: Evidence for Trans-Splicing of Human Ig RNA," The Journal of Immunology, vol. 157, No. 8, pp. 3450-3459, Oct. 15, 1996.
Gallo, et al., "The Human Immunoglobulin Loci Introduced Into Mice: V (D) and J Gene Segment Usage Similar to That of Adult Humans," European Journal of Immunology, vol. 30, pp. 534-540, Aug. 28, 2000.
Gavilondo, et al, "Antibody Engineering at the Millennium," BioTechniques, vol. 29, No. 1, pp. 128-145, Jul. 2000.
Giallourakis, et al., "Elements Between the *Igh* Variable (V) and Diversity (D) Clusters Influence Antisense Transcription and Lineage-Specific V(D)J Recombination," Proceedings of the National Academy of Science USA, vol. 107, No. 51, pp. 22207-22212, Dec. 2010.
Giraldo, et al., Size Matters: Use of YACs, BACs and PACs in Transgenic Animals, Transgenic Research, vol. 10, No. 2, pp. 83-103, Apr. 2001.
Giusti, et al., "Hypermutation is Observed Only in Antibody H Chain V Region Transgenes That Have Recombined with Endogenous Immunoglobulin H DNA: Implications for the Location of *cis*-acting Elements Required for Somatic Mutation," The Journal of Experimental Medicine, vol. 177, pp. 797-809, Mar. 1, 1993.
Glanville, et al., "Naïve Antibody Gene-Segment Frequencies Are Heritable and Unaltered by Chronic Lymphocyte Ablation," Proceedings of the National Academy of Sciences, USA, vol. 108, No. 50, pp. 20066-20071, Dec. 13, 2011.
Goodhart, et al., "Rearrangement and Expression of Rabbit Immunoglobulin Kappa Light Chain Gene in Transgenic Mice," Proceedings of the National Academy of Sciences, USA, vol. 84, No. 12, pp. 4229-4233, Jun. 1987.
Green, et al, Antigen-Specific Human Monoclonal Antibodies From Mice Engineered With Human *Ig* Heavy and Light Chain YACs, Nature Genetics, vol. 7, No. 1, pp. 13-21, May 1994.
Green, et al, Regulation of B Cell Development by Variable Gene Complexity in Mice Reconstituted with Human Immunoglobulin Yeast Artificial Chromosomes, The Journal of Experimental Medicine, vol. 188, No. 3, pp. 483-495, Aug. 3, 1998.
Guerrero et al., "The Bleomycin Resistance Gene of Transposon Tn5 Is an Excellent Marker for Transformation of Corynebacteria," Applied Microbiology Biotechnology, vol. 36, No. 6, pp. 759-762, Mar. 1992.
Hendricks, et al, "Organization of the Variable Region of the Immunoglobulin Heavy-Chain Gene Locus of the Rat," Immunogenetics, vol. 62, No. 7, pp. 479-486, Jul. 2010.
Houldsworth, et al, "Comparative Genomic Hybridization: an Overview," American Journal of Pathology, vol. 145, No. 6, pp. 1253-1260, Dec. 1994.
Huang, et al., "Structural Basis of Tyrosine Sulfation and VH-Gene Usage in Antibodies that Recognize the HIV Type 1 Coreceptor-Binding Site on gp120," PSNA, vol. 101, No. 9, pp. 2706-2711, Mar. 2, 2004.
Jakobovits, et al, "Production of Fully Human Antibodies by Transgenic Mice," Biotechnology, vol. 6, No. 5, pp. 561-566, Oct. 1995.
Jakobovits, "The Long-Awaited Magic Bullets: Therapeutic Human Monoclonal Antibodies from Transgenic Mice," Expert Opinion on Investigational Drugs, vol. 7, No. 4, pp. 607-614, Apr. 1998.
Jendreyko, et al., "Intradiabodies, Bispecific, Tetravalent Antibodies for the Simultaneous Functional Knockout of Two Cell Surface Receptors," The Journal of Biological Chemistry, vol. 278, pp. 47812-47819, Nov. 28, 2003.
Jessen, et al., "Molecular Analysis of Metastasis in a Polyomavirus Middle T Mouse Model: The Role of Osteopontin," Breast Cancer Research, vol. 6, No. 3, pp. R157-R169, Feb. 25, 2004.
Johnston, et al., "Complete Sequence Assembly and Characterization of the C57BL/6 Mouse Ig Heavy Chain V Region," The Journal of Immunology, vol. 176, No. 7, pp. 4221-4234, Apr. 1, 2006.
Jung, et al., "Mechanism and Control of V(D)J Recombination at the Immunoglobulin Heavy Chain Locus," Annual Review of Immunology, vol. 24, pp. 541-570, Apr. 2006.
Karu, et al, "Recombinant Antibody Technology," Institute for Laboratory Animal Research, vol. 37, No. 3, pp. 132-141, 1995.
Kellerman, et al, "Developing the Xenomouse Technology for Evaluating Immunogenicity ," AntibOZ 2 Conference, Australia, 2004.
Kenter, et al., "Three Dimensional Architecture of the IgH Locus Facilitates Class Switch Recombination," Annals of the New York Academy of Sciences, vol. 1267, No. 1, pp. 86-94, Sep. 1, 2012.
Kingzette et al., "Trans-Chromosomal Recombination Within the Ig Heavy Chain Switch Region in B Lymphocytes," Proceeding of the National Academy of Science USA, vol. 95, pp. 11840-11845, Sep. 1998.
Kim, et al., "Expression and Relationship of Male Reproductive Adams in Mouse," Biology of Reproduction, vol. 74, No. 4, pp. 744-750, Apr. 2006.
Kostenuik, et al., "Denosumab, a Fully Human Monoclonal Antibody to RANKL, Inhibits Bone Resorption and Increases BMD in Knock-In Mice that Express Chimeric (Murine/Human) RANKL," Journal of Bone and Mineral Research, vol. 24, No. 2, pp. 182-195, Feb. 2009.
Kotzamaris et al., "Recombining Overlapping Bacs Into a Single Larger BAC," BMC Biotechnology, vol. 4, No. 1, pp. 1-10, Jan. 6, 2004.
Kouskoff, et al, "Cassette Vectors Directing Expression of T Cell Receptor Genes in Transgenic Mice," Journal of Immunology Methods, vol. 180, pp. 273-280, Mar. 27, 1995.
Laventie, et al. "Heavy Chain-Only Antibodies and Tetravalent Bispecific Antibody Neutralizing *Staphylococcus aureus*

(56) References Cited

OTHER PUBLICATIONS

Leukotoxins," Proceedings of the National Academy of Sciences, USA, vol. 108, No. 39, pp. 16404-16409, Sep. 27, 2011.
Lee et al, "Human C5ar Knock-In Mice Facilitate the Production and Assessment of Anti-Inflammatory Monoclonal Antibodies," Nature Biotechnology, vol. 24, No. 10, pp. 1279-1284, Oct. 2006.
Lee, et al., "Complete Humanization of the Mouse Immunoglobulin Loci Enables Efficient Therapeutic Antibody Discovery," Nature Biotechnology, vol. 32, No. 4, pp. 356-363, Mar. 16, 2014.
Lefranc, Marie-Paule, "Nomenclature of the Human Immunoglobulin Heavy (IGH) Genes," Experimental and Clinical Immunogenetics, vol. 18, pp. 100-1116, Aug. 31, 2000.
Lefranc, Marie-Paule, "Nomenclature of the Human Immunoglobulin lambda (IGL) Genes," Experimental and Clinical Immunogenetics, Mar. 17, 2001.
Liu, et al., "Potent and Broad Anti-HIV-1 Activity Exhibited by a Glycosyl-Phosphatidylinositol-Anchored Peptide Derived from the CDR H3 of Broadly Neutralizing Antibody PG16," Journal of Virology, vol. 85, No. 17, pp. 8467-8476, Sep. 2011.
Loveslati, et al., "A Study of Gm Allotypes and Immunoglobulin Heavy Gamma IGHG Genes in Berbers, Arabs and Sub-Saharan Africans From Jerba Island, Tunisia" Blackwell Science Ltd., European Journal of Immunogenetics, vol. 28, No. 5, pp. 531-538, Oct. 2001.
Ma, et al "Human Antibody Expression in Transgenic Rats: Comparison of Chimeric IgH Loci With Human VH, D and JH but Bearing Different Rat C-Gene Regions," Journal of Immunological Methods, vol. 400-401, pp. 78-86, Dec. 31, 2013.
Manis, et al., "Mechanism and Control of Class-Switch Recombination," Trends in Immunology, vol. 23, Issue 1, pp. 31-39, Jan. 2002.
Macdonald, et al., "Precise and In Situ Genetic Humanization of 6Mb of Mouse Immunoglobulin Genes," Proceedings of the National Academy of Sciences, USA, vol. 111, No. 14, pp. 5147-5152, Apr. 8, 2014.
Maitta, et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," Infection and Immunity, vol. 72, No. 1, pp. 196-208, Jan. 2004.
Mattila, P.S., et al., "Extensive Allelic Sequence Variation in the J Region of the Human Immunoglobulin Heavy Chain Gene Locus," European Journal of Immunology, vol. 25, No. 9, pp. 2578-2582, Sep. 1995.
McMurry, et al, "Enhancer Control of Local Accessibility of V(D)J Recombinase," Molecular and Cellular Biology, vol. 17, No. 8, pp. 45533-4561, Aug. 1997.
Mendez, et al., "Functional Transplant of Megabase Human Immunoglobulin Loci Recapitulates Human Antibody Response in Mice," Nature Genetics, vol. 15, pp. 146-156, Feb. 1997.
Milner, et al, "Polymorphism and utilization of Human $V_h$ Genes," Annals of the New York Academy of Sciences, vol. 764,, pp. 50-61, Sep. 1995.
Monaco, et al., YACs, Bas, OPACs and MACs: Artificial Chromosomes as Research Tools, Tends in Biotechnology, vol. 12, No. 7, pp. 280-286, Jul. 1994.
Moran, Nuala, "Mouse Platforms Jostle for Slice of Humanized Antibody Market," Nature Biotechnology, vol. 31, pp. 267-268, 2013.
Mortuza et al., "Immunoglobulin Heavy-Chain Gene Rearrangement in Adult Acute Lymphoblastic Leukemia Reveals Preferential Usage of JH-Proximal Variable Gene Segments," Blood, vol. 97, No. 9, pp. 2716-2726, May 2001.
Müller, Ulrike, "Ten Years of Gene Targeting: Targeted Mouse Mutants, From Vector Design to Phenotype Analysis," Mechanisms of Development, vol. 82, Issues 1-2, pp. 3-21, Apr. 1999.
Murphy, et al., "Mice With Megabase Humanization of Their Immunoglobulin Genes Generate Antibodies as Efficiently as Normal Mice," Proceedings of the National Academy of Sciences, vol. 111, No. 14, pp. 5153-5158, Apr. 8, 2014.
Muyrers, et al, "Rapid Modification of Bacterial Artificial Chromosomes by ET-Recombination," Nucleic Acids Research, vol. 27, No. 6, pp. 1555-1557, Feb. 2, 1999.
Nadel, et al., "Sequence of the Spacer in the Recombination Signal Sequence Affects V(D)J Rearrangement Frequency and Correlates with Nonrandom Vκ Usage In Vivo," Journal of Experimental Medicine, vol. 187, No. 9, pp. 1495-1503, May 4, 1998.
Narayanan, et al., "Efficient and Precise Engineering of a 200 Kb β-Globin Human/Bacterial Artificial Chromosome in *E. coli* Dh10b Using an Inducible Homologous Recombination System," Gene Therapy, vol. 6, No. 3, pp. 442-447, Mar. 1999.
Neuberger et al., "Somatic hypermutation," Current Opinion in Immunology, vol. 7, pp. 248-254, 1995.
Neuberger, et al, "Isotype Exclusion and Transgene Down-Regulation in Immunoglobulin-Lambda Transgenic Mice," Nature, vol. 338, No. 5213, pp. 350-352, Mar. 23, 1989.
Nicholson, et al., "Antibody Repertoires of Four- and Five-Feature Translocus Mice Carrying Human Immunoglobulin Heavy Chain and κ and λ Light Chain Yeast Artificial Chromosomes," The Journal of Immunology, vol. 163, No. 12, pp. 6898-6906, Dec. 15, 1999.
Ohlin, et al., "The Human Antibody Repertoire to Infectious Agents: Implications for Disease Pathogenesis," Molecular Immunology, vol. 40, Issue 1, pp. 1-11, Sep. 2003.
Ohm-Laursen, et al., "Identification of Two New Alleles, IGHV3-23*04 and IGHJ6*04, and the Complete Sequence of the IGHV3-H Pseudogene in the Human Immunoglobulin Locus and Their Prevalences in Danish Caucasians," Immunogenetics, vol. 57, No. 9, pp. 621-627, Oct. 2005.
Pettitt, et al., "Agouti C57BL/6N Embryonic Stem Cells for Mouse Genetic Resources," Nature Methods, vol. 6, No. 7, pp. 493-495 (Jul. 2009).
Ponsel, et al., "High Affinity, Developability and Functional Size: The Holy Grail of Combinatorial Antibody Library Generation," Molecules, vol. 16, No. 5, pp. 3675-3700, 2011.
Pramanik, et al., Segmental Duplication as One of the Driving Forces Underlying the Diversity of the Human Immunoglobulin Heavy Chain Variable Gene Region, BMC Genomics, vol. 12, No. 78, 2011.
Prosser, et al., "Mosaic Complementation Demonstrates a Regulatory Role for Myosin Viia in Actin Dynamics of Stereocilia," Molecular and Cellular Biology, Mar. 2008, vol. 28, No. 5, pp. 1702-1712.
Prosser, et al., "A Resource of Vectors and ES Cells for Targeted Deletion of Micrornas in Mice," Nature Biotechnology, vol. 29, No. 9, pp. 840-845, Sep. 2011.
Pruzina, et al., "Human Monoclonal Antibodies to HIV-1 Gp140 From Mice Bearing YAC-Based Human Immunoglobulin Transloci," Protein Engineering, Design & Selection, vol. 24, No. 10, pp. 791-799, Aug. 2011.
Puente et al., "Comparative Genomic Analysis of Human and Chimpanzee Proteases," Genomics, vol. 86, No. 6, pp. 638-647, Dec. 2005.
Ray, et al., "Ectopic Expression of a C-Kitw42 Minigene in Transgenic Mice: Recapitulation of W Phenotypes and Evidence for C-Kit Function in Melanoblast Progenitors," Genes & Development, vol. 5, pp. 2265-2273, 1991.
Regeneron, "Big Pharma Vies for Mice," Nature Biotechnology, Jun. 2007,vol. 25, No. 6, p. 613.
Ren, et al, "Targeted Insertion Results in a Rhombomere 2-Specific Hoxa2 Knockdown and Ectopic Activation of Hoxal Expression," Developmental Dynamics, vol. 225, No. 3, pp. 305-315, Nov. 2002.
Rivera, et al., "Genetic Background and the Dilemma of Translating Mouse Studies to Humans," Immunity, vol. 28, No. 1, pp. 1-4, Jan. 28, 2008.
Rodriguez, et al., "High-efficiency Deleter Mice Show That Flpe Is an Alternative to Cre-Loxp," Nature Genetics, vol. 25, pp. 139-140, Jun. 2000.
Sasso, et al., "Ethnic differences in Polymorphism of an Immunoglobulin $V_h3$ gene," Journal of Clinical Investigation, vol. 96, No. 3, pp. 1591-1600, Sep. 1995.

(56) References Cited

OTHER PUBLICATIONS

Scapini, et al., "Myeloid Cells, BAFF, and IFN-γ Establish an Inflammatory Loop That Exacerbates Autoimmunity in Lyn-Deficient Mice," The Journal of Experimental Medicine, vol. 207, No. 8, pp. 1757-1773, Jul. 12, 2010.
Schnutgen et al., "A Directional Strategy for Monitoring Cre-Mediated Recombination at the Cellular Level in the Mouse", Nature Biotechnology, vol. 21, pp. 562-565, May 2003.
Schroeder, et al., "Preferential Utilization of Conserved Immunoglobulin Heavy Chain Variable Gene Segments During Human Fetal Life," Proc. Natl. Acad. Science USA, vol. 87, pp. 6146-6150, Aug. 1990.
Scott, "Mice With a Human Touch," Nature Biotechnology, vol. 25, pp. 1075-1077, Dec. 2007.
Seals, et al., "The Adams Family of Metalloproteases: Multidomain Proteins With Multiple Functions," Genes & Development, vol. 17, No. 1, pp. 7-30, Jan. 2003.
Seidl, et al, "An Expressed Neo® Cassette Provides Required Functions of the 1gamma2b Exon for Class Switching," International Immunology, vol. 10, No. 11, pp. 1683-1692, Nov. 1998.
Seidl, et al., "Position-Dependent Inhibition of Class-Switch Recombination by PGK-neo$^r$ Cassettes Inserted Into the Immunoglobulin Heavy Chain Constant Region Locus," Proceedings of the National Academy of Sciences,USA, vol. 96, No. 6, pp. 3000-3005, Mar. 16, 1999.
Seong, et al., "To knockout in 129 or in C57BL/6: that is the question," Trends in Genetics, vol. 20, No. 2, pp. 59-62, Feb. 2004.
Shi, et al., "Comparative Analysis of Human and Mouse Immunoglobulin Variable Heavy Regions from IMGT/LIGM-DB with IMGT/HighV-QUEST," Theoretical Biology and Medical Modelling, vol. 11, pp. 1-11, Nov. 2014.
Shih, Heather H., "Discovery Process for Antibody-Based Therapeutics," Development of Antibody-Based Therapeutics, Chapter 2, pp. 9-32, Apr. 24, 2012.
Sirac, et al., "Role of the Monoclonal κ Chain V Domain and Reversibility of Renal Damage in a Transgenic Model of Acquired Fanconi Syndrome," Blood, Jul. 15, 2006, vol. 108, No. 2, pp. 536-543.
Skarnes, et al., "A Conditional Knockout Resource for the Genome-Wide Study of Mouse Gene Function," Nature, vol. 474, pp. 337-342, Jun. 16, 2011.
Soukharev, et al., "Segmental Genomic Replacement in Embryonic Stem Cells by Double *lox* Targeting," Nucleic Acids Research, vol. 27, No. 18, pp., e21-i to e21-viii, Jun. 1, 1999.
Spanopoulou, et al., "Functional Immunoglobulin Transgenes Guide Ordered B-Cell Differentiation in Rag-1 -Deficient Mice," Genes & Development, vol. 8, No. 9, pp. 1030-1042, May 1, 1994.
Stavnezer, et al., "Mechanism and Regulation of Class Switch Recombination," Annual Review of Immunology, vol. 26, pp. 261-292, Apr. 2008.
Suárez, et al., "Rearrangement of Only One Human IGHV Gene is Sufficient to Generate a Wide Repertoire of Antigen Specific Antibody Responses in Transgenic Mice," Molecular Immunology, vol. 43, No. 11, pp. 1827-2835, Dec. 2006.
Takeda et al., Construction of chimaeric processed immunoglobulin genes containing mouse variable and human constant region sequences, Nature, 314, 452-252, Apr. 4, 1985.
Tan, et al., "A Human-Mouse Chimeric Immunoglobulin Gene With a Human Variable Region Is Expressed in Mouse Myeloma Cells," The Journal of Immunology vol. 135, No. 5, pp. 3564-3567, Nov. 1, 1985.
Taylor, et al., "Human Immunoglobulin Transgenes Undergo Rearrangement, Somatic Mutation and Class Switching in Mice That Lack Endogenous IgM," International Immunology, vol. 6, No. 4, pp. 579-591, Apr. 1994.
Thykhaer, et al., "Gene Targeting Approaches Using Positive-Negative Selection and Large Flanking Regions," Plant molecular Biology, vol. 35, No. 4, pp. 523-530, Nov. 1997.
Tucker, et al., "Mouse IgA Heavy Chain Gene Sequence: Implications for Evolution of Immunoglobulin Hinge Axons," Proceedings of the National Academy of Sciences, USA, vol. 78, No. 12, pp. 7684-7688, Dec. 2008.
Van Spriel, et al., "Immunotherapeutic Perspective for Bispecific Antibodies," Immunology Today, vol. 21, No. 8, pp. 391-397, Aug. 1, 2000.
Vasicek, et al., Structure and Expression of the Human Immunoglobulin λ Genes, Journal of Experimental Medicine, vol. 172, pp. 609-620, Aug. 1990.
Vollmer, et al., "Antigen Contacts by Ni-Reactive TCR: Typical αβ Chain Cooperation Versus a Chain-Dominated Specificity," International Immunity, vol. 12, No. 12, pp. 1723-1731, May 31, 2000.
Wang, et al., "Chromosomal Transposition of piggyBac in Mouse Embryonic Stem Cells," Proceedings of the National Academy of Sciences, USA, vol. 105, No. 27, pp. 9290-9295, 2008.
Wang, et al., "Many Human Immunoglobulin Heavy-Chain IGHV Gene Polymorphisms Have Been Reported in Error," Immunology and Cell Biology, vol. 86, No. 2, pp. 111-115, Feb. 2008.
Waterson, et al., "Initial Sequencing and Comparative Analysis of the Mouse Genome," Nature, vol. 420, No. 6915, pp. 520-562, Dec. 2002.
Waterhouse, et al., "Combinatorial Infection and In Vivo Recombination: A Strategy for Making Large Phage Antibody Repertories," Nucleic Acids Research, vol. 21, No. 9, pp. 2265-2266. May 11, 1993.
White, et al, "Genome-Wide Generation and Systematic Phenotyping of Knockout Mice Revels New Roles for Many Genes," Cell, vol. 154, Issue 2: pp. 452-464, Jul. 18, 2013.
Wilke, et al. "Diagnosis of Haploidy and Triploidy Based on Measurement of Gene Copy Number by Real-Time PCR," Human Mutation vol. 16, Issue 5, pp. 431-436, Nov. 2000.
Williams et al., "Unequal VH Gene Rearrangement Frequency Within the Large Vh7183 Gene Family is not Due to Recombination Signal Sequence Variation, and Mapping of the Genes Shows a Bias of Rearrangement Base on Chromosomal Location," The Journal of Immunology, pp. 257-263, 2001.
Xu, et al., "Deletion of the Igκ Light Chain Intronic Enhancer/Matrix Attachment Region Impairs but Does Not Abolish VκJκ Rearrangement," Immunity, vol. 4, pp. 377-385, Apr. 1, 1996.
Yang, et al., "Homologous Recombination Based Modification in *Esherichia coli* and Germline Transmission in Transgenic Mice of a Bacterial Artificial Chromosome," Nature Biotechnology, vol. 15, No. 9, pp. 859-865, Sep. 1997.
Yu, et al., Differential Usage of VH Gene Segments Is Mediated by cis Elements, The Journal of Immunology, vol. 161, No. 7, pp. 3444-3454, Oct. 1, 1998.
Yu, et al., "Engineering Chromosomal Rearrangements in Mice," Nature Reviews Genetics, vol. 2, No. 10, pp. 780-790, Oct. 2001.
Zhang, et al., "A New Logic for DNA Engineering Using Recombination in *Escherichia coli*," Nature Genetics, vol. 20, No. 2, pp. 123-128, Oct. 1998.
Zhao, Shaving, "A Comprehensive BAC Resource," Nucleic Acids Research, vol. 29, No. 1, Jan. 2001.
Zou et al., "Cre-loxP-mediated Gene Replacement: A Mouse Strain Producing Humanized Antibodies," Current Biology, vol. 4, No. 12, pp. 1099-1104, 1994.
Arnaout et al, "High-resolution description of antibody heavy-chain repertoires in humans," PloS ONE,. vol. 6, Issue 8, pp. 1-8, Aug. 2011.
Harding, et al, "Class Switching in Human Immunoglobulin Transgenic Mice," Annals of New York Academy of Science, vol. 764, pp. 536-546, Sep. 29, 1995.
Lefranc, et al., "The Immunoglobulin Facts Book," Academic Press, May 2001, ISBN:978-0-08-057447-9.
Zemlin et al, "Expressed Murine and Human CDR-H3 Intervals of Equal Length Exhibit Distinct Repertoires that Differ in their Amino Acid Composition and Predicted Range of Structures," Journal of Molecular Biology, vol. 334, No. 5 pp. 733-749, Dec. 2003.
Rosner, et al., "Third Complementarity-Determining Region of Mutated VH Immunoglobulin Genes Contains Shorter V, D, J, P, and N Components Than Non-Mutated Genes," Immunology, vol. 103, No. 2, pp. 179-187, Jun. 2001.

(56) References Cited

OTHER PUBLICATIONS

Schultz, et al., "Humanized Mice in Translational Biomedical Research," Nature Reviews Immunology, vol. 7, No. 2, pp. 118-130, Feb. 2007.
Stevens, Sean, Regeneron Pharmaceuticals, "Human Antibody Discovery," Veloclmmune —A novel Platform, Pharma Focus Asia, Issue 8, p. 72-74, 2008.
Third Party Observation in PCT/GB2012/052960 dated Apr. 2, 2014, 3 pages.
Charles Lyon, Attorney for Applicant, Third Party Pre-Issuance Submission Under 37 C.F.R. §1.290 in U.S. Appl. No. 14/056,700, Nov. 28, 2014, 6 pages.
Charles Lyon, Attorney for Applicant, Third Party Pre-Issuance Submission Under 37 C.F.R. §1.290 in U.S. Appl. No. 14/056,434, Filed Dec. 15, 2014, 6 pages.
Charles Lyon, Attorney for Applicant, Third Party Pre-Issuance Submission Under 37 C.F.R. §1.290 in U.S. Appl. No. 14/040,405, Filed Jan. 16, 2015, 18 pages.
Charles Lyon, Attorney for Applicant, Third Party Pre-Issuance Submission Under 37 C.F.R. §1.290 in U.S. Appl. No. 14/056,707, Nov. 28, 2014, 13 pages.
Charles Lyon, Attorney for Applicant, Third Party Pre-Issuance Submission Under 37 C.F.R. §1.290 in U.S. Appl. No. 14/137,902, Nov. 13, 2014 12 pages.
European Patent Office, Munich, Dr. Martin Grund, Third Party Observations according to Article 115 EPC regarding EP12171791.2, dated Feb. 26, 2014, 9 pages.
European Patent Office, Munich, Dr. Martin Grund, Third Party Observations according to Article 115 EPC regarding EP 12194970.5, dated Mar. 5, 2014, 9 pages.
European Patent Office, Munich, Dr. Martin Grund, Third Party Observations according to Article 115 EPC regarding EP 12194977.0 dated Mar. 26, 2014, 4 pages.
European Patent Office, Munich, Dr. Martin Grund, Third Party Observations according to Article 115 EPC regarding EP 12171793.8 dated Jun. 25, 2014, 7 pages.
European Patent Office, Munich, Dr. Martin Grund, Third Party Observations according to Article 114(2) EPC regarding EP12 195041.4 dated Jul. 30, 2014,5 pages.
European Patent Office, Munich, Dr. Martin Grund, Third Party Observations according to Article 114(2) EPC regarding EP12171791.2 dated Aug. 4, 2014,6 pages.
European Patent Office, Munich, Dr. Martin Grund, Third Party Observations according to Article 114(2) EPC regarding EP12194970.5 dated Aug. 12, 2014, 5 pages.
European Patent Office, Munich, Dr. Martin Grund, Third Party Observations according to Article 115 EPC regarding EP 11705964.2 dated Oct. 9, 2013, 8 pages.
European Patent Office, Munich, Dr. Martin Grund, Third Party Observations according to Article 115 EPC regarding EP 11705964.2 dated Apr. 30, 2014, 4 pages.
European Patent Office, Munich, Dr. Martin Grund, Third Party Observations according to Article 115 EPC regarding EP 11705964.2 dated Feb. 26, 2015, 5 pages.
European Patent Office, Munich, Dr. Martin Grund, Third Party Observations according to Article 115 EPC regarding EP12795606.8, dated Feb. 26, 2014, 6 pages.
European Patent Office, Munich, Dr. Martin Grund, Third Party Observations according to Article 115 EPC regarding EP 12 795606.8 dated Mar. 26, 2015, 4 pages.
Mouse Genome Sequencing Consortium, "Initial sequencing and comparative analysis of the mouse genome," Nature, vol. 420, pp. 520-562, Dec. 5, 2002.
Kling, "News in Brief," Nature Biotechnology, vol. 25, No. 6, p. 613, Jun. 2007.
"Statement of Fact and Arguments in Support of Opposition pertaining to Application No. 10734546.4", 41 pages, dated Oct. 22, 2013.
Opposition against EP2421357 Animal Models and Therapeutic Molecules in the name of Kymab Limited pertaining to Application No. 10734546.4, 44 pages, dated Oct. 23, 2013.
Opposition against EP2421357 B1 in the name of Kymab Limited Statement of Facts and Arguments pertaining to Application No. 10734546.4, 29 pages, dated Oct. 23, 2013.
Opposition against EP2421357 Animal Models and Therapeutic Molecules in the name of Kymab Limited pertaining to Application No. EP10734546.4, 41 pages, dated Jan. 23, 2013.
GenBank Accession No. AC111740.4 GI:24818723, accessed Nov. 9, 2002, 42 pages.
GenBank Accession No. X97051 S64822, accessed Aug. 6, 2014, 29 pages.
Nucleotide Sequence RID Y55HBK1W114, accessed Aug. 6, 2014, 2 pages.
GenBank, Accession No. X97051 S64822, accessed Nov. 14, 2006, 26 pages.
Grunecker, Kinkeldey, Stockmair & Schwanhausser, Notice of Opposition to a European Patent, Patent No. EP2421357, dated Oct. 23, 2013, 44 pages.
European Patent Office Munich, Germany, Extended European Search Report, Application No. 12194977.0, dated Jul. 17, 2013, 8 pages.
European Patent Office Munich, Germany, Extended European Search Report, Application No. 12171791.2, dated Jun. 18, 2013, 5 pages.
European Patent Office Munich, Germany, Extended European Search Report, Application No. 12195041.4, dated Nov. 18, 2013,8 pages.
European Patent Office Munich, Germany, Extended European Search Report, Application No. 12171793.8 dated Jun. 21, 2013, 8 pages.
European Patent Office Munich, Germany, Extended European Search Report, Application No. 14176740.0, dated Oct. 15, 2014, 7 pages.
Intellectual Property Office United Kingdom, Combined Search and Examination Report under Sections 17 and 18(3), Application No. GB1317410.7, dated Nov. 21, 2013, 8 pages.
European Patent Office Munich, Germany, Extended European Search Report, Application No. 14196645.7, dated Jun. 26, 2015, 12 pages.
Intellectual Property Office United Kingdom, Combined Search and Examination Report under Sections 17 and 18(3), Application No. GB1317447.9, dated Jan. 14, 2014, 7 pages.
International Searching Authority, International Search Report—International Application No. PCT/GB2013/051280, dated Nov. 15, 2013, together with the Written Opinion of the International Searching Authority, 20 pages.
International Searching Authority, International Search Report—International Application No. PCT/GB2012/052296, dated May 17, 2013, together with the Written Opinion of the International Searching Authority, 31 pages.
International Searching Authority, International Search Report—International Application No. PCT/GB2012/052956, dated Mar. 1, 2013, 8 pages.
International Searching Authority, Invitation to Pay Additional Fees, Application No. PCT/GB2012/052296, dated Jan. 24, 2013, 9 pages.
INPI—France, International Search Report—France Patent Application No. 1359518, dated Mar. 4, 2014, 3 pages.
Dr. Martin Grund, Third-Party Observations according to Article115 EPC regarding EP12194977.0, dated May 12, 2015, 6 pages.
Macdonald et al., Poster: "VelociGene® Technology Extended to Humanization of Several Megabases of Complex," Exhibit IJR-47 to Jeffrey rourke Declaration, 1 page (2006).
Jeffrey Rourke, Declaratin of Jeffrey Rourke, Registered Patent Attorney for Regeneron Pharmaceuticals, Inc.—In the matter of Patent Acceptance 2011266843 in the Name of Kymab Limited and In the Matter of Opposition thereto by Regeneron Pharmaceuticals, Inc., 5 pages, dated Jan. 29, 2016.

(56) References Cited

OTHER PUBLICATIONS

Stevens et al., Poster: "VelocImmune™: Humanization of immunoglobulin loci using VelociGene® technology," Exhibit IHR-46 to Jeffrey Rourke Declaration, 1 page (2006).
U.S. Appl. No. 13/310,431, filed Dec. 2, 2011.
U.S. Appl. No. 13/433,084, filed Mar. 28, 2012.
U.S. Appl. No. 13/740,727, filed Jan. 14, 2013.
U.S. Appl. No. 13/846,672, filed Mar. 18, 2013.
U.S. Appl. No. 13/843,528, filed Mar. 15, 2013.
U.S. Appl. No. 13/875,892, filed May 2, 2013.
U.S. Appl. No. 13/886,511, filed May 3, 2013.
U.S. Appl. No. 13/890,147, filed May 8, 2013.
U.S. Appl. No. 14/040,427, filed Sep. 27, 2013.
U.S. Appl. No. 14/040,405, filed Sep. 27, 2013.
U.S. Appl. No. 14/052,259, filed Oct. 11, 2013.
U.S. Appl. No. 14/056,434, filed Oct. 17, 2013.
U.S. Appl. No. 14/056,700, filed Oct. 17, 2013.
U.S. Appl. No. 14/056,707, filed Oct. 17, 2013.
U.S. Appl. No. 14/080,630, filed Nov. 14, 2013.
U.S. Appl. No. 14/137,902, filed Dec. 20, 2013.
U.S. Appl. No. 14/543,359, filed Nov. 17, 2013.
U.S. Appl. No. 14/220,074, filed Mar. 19, 2014.
U.S. Appl. No. 14/220,095, filed Mar. 19, 2014.
U.S. Appl. No. 14/220,099, filed Mar. 19, 2014.
U.S. Appl. No. 14/220,080, filed Mar. 19, 2014.
U.S. Appl. No. 14/226,698, filed Mar. 26, 2014.
U.S. Appl. No. 14/226,706, filed Mar. 26, 2014.
U.S. Appl. No. 14/263,158, filed Apr. 28, 2014.
U.S. Appl. No. 14/263,176, filed Apr. 28, 2014.
U.S. Appl. No. 14/498,685, filed Sep. 26, 2014.
U.S. Appl. No. 14/497,054, filed Sep. 25, 2014.
U.S. Appl. No. 14/516,461, filed Oct. 16, 2014.
U.S. Appl. No. 14/750,870, filed Jun. 25, 2015.
U.S. Appl. No. 14/818,162, filed Aug. 4, 2015.
U.S. Appl. No. 14/935,010, filed Nov. 6, 2015.
U.S. Appl. No. 15/016,211, filed Feb. 4, 2016.
U.S. Appl. No. 15/018,670, filed Feb. 8, 2016.
U.S. Appl. No. 15/095,315, filed Apr. 11, 2016.
Ahmed, "Sanofi-aventis and Regeneron Extend Therapeutic Antibody Agreement," *PharmaDeals Review*, vol. 2009, Issue No. 11, p. 115, Nov. 2009.
Beerli, R. et al., "Mining Human Antibody Repertoires," *MAbs*, vol. 2, Issue No. 4, pp. 365-378, Jul./Aug. 2010.
Bransteitter R., et al., "Activation-Induced Cytidine Deaminase Deaminates Deoxycytidine on Single-Stranded DNA but Requires the Action of RNase," *Proceedings of the National Academy of Sciences*, vol. 100, Issue No., pp. 4102-4107, 2003.
Brüggemann M., et al., "Human Monoclonal Antibodies from Translocus Mice," *Molecular Biology of B Cells*, Chapter 34, pp. 547-561, 2003.
Casrouge, A., et al., "Size Estimage of the αβ TCR Repertoire of Naïve Mouse Splenocytes," *Journal of Immunology*, vol. 164, Issue No. 11, pp. 5782-5787, 2000.
Chan A. et al., "Therapeutic Antibodies for Autoimmunity and Inflammation," *Nature Reviews Immunology*, vol. 10, Issue No. 5, pp. 301-316, 2010.
Chen, Y. et al., "PiggyBac Transposon-Mediated, Reversible Gene Transfer in Human Embryonic Stem Cells," *Stem Cells and Development*, vol. 19, Issue No. 6, pp. 763-771, Sep. 2009.
Crouch, E. et al., "Regulation of AID expression in the immune response," *Journal of Experimental Medicine*, vol. 204, Issue No. 5, pp. 1145-1156, Apr. 2007.
Ebert, A. et al., "The Distal V(H) Gene Cluster of the *IgH* Locus Contains Distinct Regulatory Elements with Pax5 Transcription Factor-Dependent Activity in Pro-B Cells," *Immunity*, vol. 34, Issue No. 2, pp. 175-187, 2011.
Friedrich, G., Declaration of Glenn Friedrich, 4 pages, dated Mar. 3, 2016.
GenBank, Accession No. KF698731.1, 1 page, accessed Nov. 18, 2013.
GenBank, Accession No. NT 114985, "Mus Musculus Strain 129S1/SvlmJ Chromosome 12 Genomic Sca Locus Group 129S1/SVIMJ_MMCHR12_CTG1," 1 page, Dec. 27, 2013.
GenBank, Accession No. x97051.1 S64822, DNA Sequence of the Human Immunoglobulin D Segment Locus, 26 pages, Mar. 3, 2015.
Goldman, I. et al., "Transgenic animals in medicine: Integration and expression of foreign genes, theoretical and applies aspects," *Medical Science Monitor*, vol. 10, Issue No. 11, pp. RA274-RA285, 2004.
Guirouilh-Barbat J. et al., "Is homologous recombination really an error-free process?," *Frontiers in Genetics*, vol. 5, Issue No. 175, 15 pages, Jun. 2014.
Hewitt, S. et al., "Association Between the *Igk* and *Igh* immunoglobulin loci mediated by the 3' *Igk* enhancer induces 'decontraction' of the *Igh* locus in pre-B cells," *Nature Immunology*, vol. 9 Issue No. 4, pp. 396-404, 2008.
Houdebine, L., "The methods to generate transgenic animals and to control transgene expression," *Journal of Biotechnology*, vol. 98, Issue Nos. 2-3, pp. 145-160, 2002.
Houdebine, L., "Transgenic Animal Models in Biomedical Research," Chapter 10, *Methods in Molecular Biology*, vol. 360, pp. 163-202, 2007.
Kondo, S. et al., "Highly Improved Gene Targeting by Germline-Specific Cas9 Expression in *Drosophila,*" *Genetics*, vol. 195, pp. 715-721, Nov. 2013.
Kondo, S. et al., "Highly Improved Gene Targeting by Germline-Specific Cas9 Expression in *Drosphila,*" *Genetics*, vol. 195, pp. 715-721, Nov. 2013 (Abstract—1 page).
Kuraoka M., et al., "AID expression during B-cell development: searching for answers," *Immunologic Research*, vol. 49, Issue Nos. 1-3, pp. 3-13, 2011.
Laffleur, B. et al., Chapter 9, "Production of Human or Humanized Antibodies in Mice," *Methods in Molecular Biology*, vol. 901, pp. 149-159, 2012.
Lee, E. et al., Chapter 8, "The Application of Transgenic Mice for Therapeutic Antibody Discovery," *Methods in Molecular Biology*, vol. 901, pp. 137-148, 2012.
Lefranc, M., "Nomenclature of the Human Immunoglobulin Kappa (IGK) Genes," *Experimental and Clinical Immunogenetics*, vol. 18, Issue No. 3, pp. 161-174, 2001.
Li, H. et al., "Genetic diversity of the human immunoglobulin heavy chain V(H) region," *Immunological Reviews*, vol. 190, pp. 53-68, 2002.
Lonberg, N., "Fully human antibodies from transgenic mouse and phage display platforms," *Current Opinion in Immunology*, vol. 20, Issue No. 4, pp. 450-459, 2008.
MacDonald, L. et al., Expanded Poster: "VelociGene® Technology Extended to Humanization of Several Megabases of Complex," Exhibit IJR-49 to Jeffrey Rourke Declaration, 6 pages, 2006.
MacDonald, Lynn E., "Declaration of Lynn E. MacDonald," (with Exhibits) dated Feb. 3, 2015, relating to International Application No. PCT/US02/04500, 13 pages (published as WO 02/066630 A1).
MacDonald, Lynn E., "Curriculum Vitae of Lynn E. MacDonald, Ph.D.," 3 pages.
Magadán, S. et al., "Production of Antigen-Specific Human Monoclonal Antibodies: Comparison of Mice Carrying IgH/kappa or IgH/kappa/lambda Transloci," *BioTechniques*, vol. 33, Issue No. 3, pp. 680, 682, 684 passim, Sep. 2002.
Martinez-Jean, C. et al., "Nomenclature and Overview of the Mouse (*Mus musculus* and *Mus*. sp.) Immunoglobulin Kappa (IGK) Genes," *Experimental and Clinical Immunogenetics*, vol. 18, pp. 255-279, 2001.
Pear, W. et al., "Localization of the Rat Immunoglobulin Heavy Chain Locus to Chromosone 6," *Immunogenetics*, vol. 23, Issue No. 6, pp. 393-395, 1986.
Regeneron Pharmaceuticals, Inc., "AstraZeneca Licenses Regeneron's VelocImmune® Technology for Discovering Human Monoclonal Antibodies—AstraZeneca Is First Licensee of Novel VelocImmune Technology License Fees Total up to $120 Million Over Six Years," 2 pages, Feb. 5, 2007.
Regeneron Pharmaceuticals, Inc., "Astellas Licenses Regeneron's Velocimmune® Technology for Discovering Human Monoclonal Antibodies," 2 pages, Mar. 30, 2007.

(56) References Cited

OTHER PUBLICATIONS

Regeneron Pharmaceuticals, Inc., "Regeneron Initiates Major Global Collaboration with Sanofi-aventis to Develop and Commercialize Fully-Human Therapeutic Antibodies," 2 pages, Nov. 29, 2007.
Sekiguchi, J. et al., "The Mechanism of V(D)J Recombination," Chapter 5, *Molecular Biology of B Cells*, pp. 61-82, 2004.
Sigmund C., "Viewpoint: Are Studies in Genetically Altered Mice Out of Control?", *Arteriosclerosis, Thrombosis and Vascular Biology*, vol. 20, Issue No. 6, pp. 1425-1429, 2000.
Stevens, S. et al., Expanded Poster: "VelocImmune™: Humanization of immunoglobulin loci using VelociGene® technology," Exhibit IJR-48 to Jeffrey Rourke Declaration, 1 page, 2006.
Tuaillon, N. et al., "Human immunoglobulin heavy-chain minilocus recombination in transgenic mice: Gene-segment use in μ and γ transcripts," *Proceedings of the National Academy of Sciences USA*, vol. 90, pp. 3720-3724, 1993.
Wasserman, R. et al., "The Pattern of Joining ($J_H$) Gene Usage in the Human IgH Chain Is Established Predominantly at the B Precursor Cell Stage[1]," *The Journal of Immunology*, vol. 149, pp. 511-516, Jul. 1992.
Weichhold, G. et al., "Megabase inversions in the human genome as physiological events," *Nature*, vol. 347, Issue No. 6288, pp. 90-92, Sep. 1990.
Weichhold, G. et al., "The Human Immunoglobulin Kappa Locus Consists of Two Copies That Are Organized in Opposite Polarity," *Genomics*, vol. 16 (2), pp. 503-511, 1993.
Weiner, L., "fully Human Therapeutic Monoclonal Antibodies," *Journal of Immunology*, vol. 29, Issue No. 1, pp. 1-9, Jan/Feb. 2006.
Yamada, M. et al., "Preferential Utilization of Specific Immunoglobulin Heavy Chain Diversity and Joining Segments in Adult Human Peripheral Blood B Lymphocytes," *Journal of Experimental Medicine*, vol. 173, pp. 395-407, Feb. 1991.
Zheng, J. et al., "Immunoglobulin Gene Transcripts Have Distinct $V_HDJ_H$ Recombination Characteristics in Human Epithelial Cancer Cells," *Journal of Biological Chemistry*, vol. 284, Issue No. 20, pp. 13610-13619, May 2009.
Zou, X. et al., "Removal of the BiP-retention domain in Cμ permits surface deposition and developmental progression without L-chain," *Molecular Immunology*, vol. 45, Issue No. 13, pp. 3573-3579, 2008.
Chinese Patent Office, First Office Action for Chinese Application No. 201180039668.1, 6 pages, dated Jan. 3, 2014.
Chinese Patent Office, First Office Action for Chinese Application No. 201180039668.1, 6 pages, dated Jan. 3, 2014 (English Translation).
Chinese Patent Office, Search Report, Chinese Application No. 201180039668.1, 2 pages, dated Jan. 3, 2014.
Chinese Patent Office, Search Report, Chinese Application No. 201180039668.1, 1 page, dated Jan. 3, 2014 (English Translation).
European Patent Office, Laurent Deleu, Authorized Officer, International Preliminary Report on Patentability Chapter II for Application No. PCT/GB2010/051122, 33 pages, mailed Nov. 2, 2011.
European Patent Office, Laurent Deleu, Authorized Officer, International Search Report and Written Opinion of the International Searching Authority for Application No. PCT/GB2011/050019, 12 pages, mailed May 16, 2011.
European Patent Office, Alessandro Brero, Authorized Officer, International Search Report and Written Opinion of the International Searching Authority for Application No. PCT/GB2012/052297, 24 pages, mailed Jun. 19, 2013.
European Patent Office, International Search Report and Written Opinion of the International Searching Authority for Application No. PCT/GB2012/052960, 19 pages, mailed Apr. 29, 2013.
European Patent Office, Gaby Brouns, Authorized Officer, Written Opinion for the International Searching Authority for Application No. PCT/GB2013/050682, 9 pages, mailed Sep. 25, 2013.
European Patent Office, International Search Report and Written Opinion of the International Searching Authority for Application No. PCT/GB2013/050683, 11 pages, mailed Jul. 9, 2013.
European Patent Office, Statement of Fact and Arguments in Support of Opposition against EP2421357, pertaining to Application No. 10734546.4, 41 pages, Dated Jan. 23, 2013.
European Patent Office, Laurent Deleu, Authorized Officer, Extended European Search for Application No. EP12194970, 9 pages, mailed Jan. 23, 2013.
European Patent Office, Gaby Brouns, Authorized Officer, Examination Report for Application No. EP 12795841.1, 5 pages, mailed Feb. 12, 2016.
European Patent Office, Gaby Brouns, Authorized Officer, Examination Report for Application No. EP 13711119.1, 6 pages, mailed Dec. 17, 2015.
European Patent Office, Laurent Deleu, Authorized Officer, Extended European Search Report for Application No. EP14170196, 8 pages, mailed Oct. 8, 2014.
European Patent Office, Laurent Deleu, Authorized Officer, Communications pursuant to Article 94(3) EPC for Application No. 14176740.0, 5 pages, mailed Oct. 23, 2015.
European Patent Office, Extended European Search Report for Application No. 15188522.5, 15 pages, mailed Feb. 2, 2016.
Grund, Martin, European Patent Attorney, Grund Intellectual Property Group, Third-Party Observations according to Article 115 EPC regarding EP1215041.4, 5 pages, dated Jul. 30, 2014.
Grund, Martin, European Patent Attorney, Grund Intellectual Property Group, Third-Party Observations according to Article 115 EPC regarding 12762377.5, 7 pages, dated May 22, 2015.
Grund, Martin, European Patent Attorney, Grund Intellectual Property Group, Third-Party Observations according to Article 115 EPC regarding 12762377.5, 8 pages, dated Feb. 12, 2016.
Grund, Martin, European Patent Attorney, Grund Intellectual Property Group, Third-Party Observations according to Article 115 EPC regarding 13711119.1, 7 pages, dated Dec. 9, 2015.
Grund, Martin, European Patent Attorney Grund Intellectual Property Group, Third-Party Observation for Application No. PCT/GB2012/052956, 2 pages, dated Mar. 26, 2014.
Lyon, Charles E., Attorney for Applicant, Third Party Pre-Issuance Submission Under 37 CFR 1.290 in U.S. Appl. No. 13/846,672, 32 pages, dated Mar. 17, 2015.
Lyon, Charles E., Attorney for Applicant, Third Party Pre-Issuance Submission Under 37 CFR 1.290 in U.S. Appl. No. 13/886,511, 18 pages, dated May 5, 2015.
Lyon, Charles E., Attorney for Applicant, Third Party Pre-Issuance Submission Under 37 CFR 1.290 in U.S. Appl. No. 14/040,427, 20 pages, dated Jan. 16, 2015.
Lyon, Charles E., Attorney for Applicant, Third Party Pre-Issuance Submission Under 37 CFR 1.290 in U.S. Appl. No. 14/080,630, 8 pages, dated Oct. 31, 2014.
Lyon, Charles E., Attorney for Applicant, Third Party Pre-Issuance Submission Under 37 CFR 1.290 in U.S. Appl. No. 14/220,080, 28 pages, dated Jul. 28, 2015.
Lyon, Charles E., Attorney for Applicant, Third Party Pre-Issuance Submission Under 37 CFR 1.290 in U.S. Appl. No. 14/220,095, 19 pages, dated Aug. 4, 2015.
Lyon, Charles E., Attorney for Applicant, Third Party Pre-Issuance Submission Under 37 CFR 1.290 in U.S. Appl. No. 14/220,099, 43 pages, dated Apr. 29, 2015.
Lyon, Charles E., Attorney for Applicant, Third Party Pre-Issuance Submission Under 37 CFR 1.290 in U.S. Appl. No. 14/226,706, 53 pages, dated Jul. 28, 2015.
Lyon, Charles E., Attorney for Applicant, Third Party Pre-Issurance Submission Under 37 CFR 1.290 in U.S. Appl. No. 14/263,158, 16 pages, dated Apr. 29, 2015.
Lyon, Charles E., Attorney for Applicant, Third Party Pre-Issurance Submission Under 37 CFR 1.290 in U.S. Appl. No. 14/263,176, 16 pages, dated Apr. 29, 2015.
Lyon, Charles E., Attorney for Applicant, Third Party Pre-Issurance Submission Under 37 CFR 1.290 in U.S. Appl. No. 14/497,054, 81 pages, dated Oct. 21, 2015.
Lyon, Charles E., Attorney for Applicant, Third Party Pre-Issurance Submission Under 37 CFR 1.290 in U.S. Appl. No. 14/498,685, 37 pages, dated Sep. 18, 2015.

(56) References Cited

OTHER PUBLICATIONS

Lyon, Charles E., Attorney for Applicant, Third Party Pre-Issurance Submission Under 37 CFR 1.290 in U.S. Appl. No. 14/516,461, 27 pages, dated Aug. 4, 2015.
New Zealand Patent Office, Simon Maguire, Authorized Officer, Further Examination Report for Patent No. 623756, 3 pages, mailed Sep. 9, 2015.
Pobursky, Kevin J, Attory for Applicant, Third-Party Pre-Issuance Submission Under 37 CFR 1.290 in U.S. Appl. No. 13/433,084, 15 pages, dated Apr. 1, 2014.
Pobursky, Kevin J, Attorney for Applicant, Third-Party Pre-Issuance Submission Under 37 CFR 1.290 in U.S. Appl. No. 13/434,361, 15 pages, dated Apr. 1, 2014.
Pobursky, Kevin J, Attorney for Applicant, Third-Party Pre-Issuance Submission Under 37 CFR 1.290 in U.S. Appl. No. 13/740,727, 25 pages, dated May 27, 2014.
Stephen, Robert, Olswang, LLP, Kymab Limited Statement of Facts and Evidence in Opposition to EP2550363, 22 pages, dated Sep. 10, 2015.
Urquhart-Dykes & Lord LLP, Third-Party Observation for Appl. No. EP20140772198, 8 pages, dated Dec. 14, 2015.
Williams, Kathleen M., Attorney for Applicant, Third-Party Pre-Issuance Submission Under 37 CFR 1.290 in U.S. Appl. No. 14/600,829, 18 pages, dated Apr. 1, 2016.
Williams, Kathleen M., Attorney for Applicant, Third-Party Pre-Issuance Submission Under 37 CFR 1.290 in U.S. Appl. No. 14/679,949, 18 pages, dated Apr. 1, 2016.
Mills F. et al., "Enhancer Complexes Located Downstream of Both Human Immunoglobulin Cα Genes," *The Journal of Experimental Medicine*, vol. 186, Issue No. 6, pp. 845-858, Sep. 1997.
Neuberger, M., "Expression and regulation of immunoglobulin heavy chain gene transfected into lymphoid cells," *The EMBO Journal*, vol. 2, Issue No. 8, pp. 1373-1378, 1983.
Pettersson, S. et al., "A second B cell-specific enhancer 3' of the immunoglobulin heavy-chain locus," *Nature*, vol. 344, pp. 165-168, Mar. 1990.
Tanimoto, Y. et al., "Embryonic Stem Cells Derived from C57BL/6J and C57BL/6N Mice," *Comparative Medicine*, vol. 58, Issue No. 4, pp. 347-352, Aug. 2008.

* cited by examiner

Entry / Initiation vector: Step 1

*Validation:*

1. Standard gene-targeting LR-PCR/Southern
2. Make chimaeras & breed in parallel with next step

Confirmation of Successful Insertion into Landing Pad
*Colonies : 6-TG and Puro - Resistant*
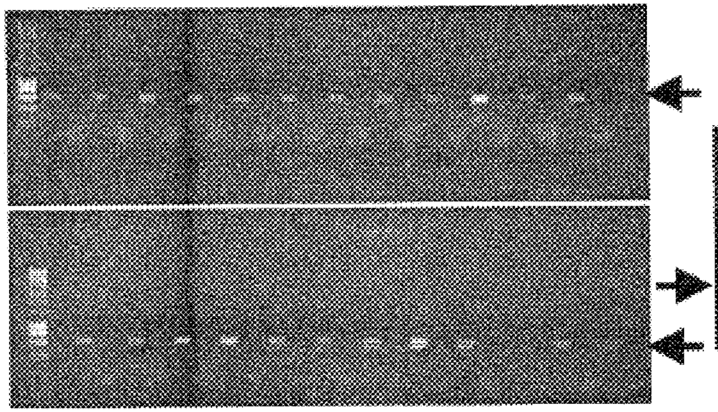
5' Primer set (①) – 23 of 24 correct
3' Primer set (②) – 20 of 24 correct
*Summary:*
| | Puro + 6TG | | Puro | | G418 + 6TG | | G418 | |
|---|---|---|---|---|---|---|---|---|
| Colony # | 220 | | 239 | | 198 | | 360 | |
| Junction PCR | 5' | 3' | 5' | 3' | 5' | 3' | 5' | 3' |
| | 23/24 | 20/24 | 22/24 | 19/24 | 22/24 | 22/24 | 11/24 | 11/24 |
Fig. 31

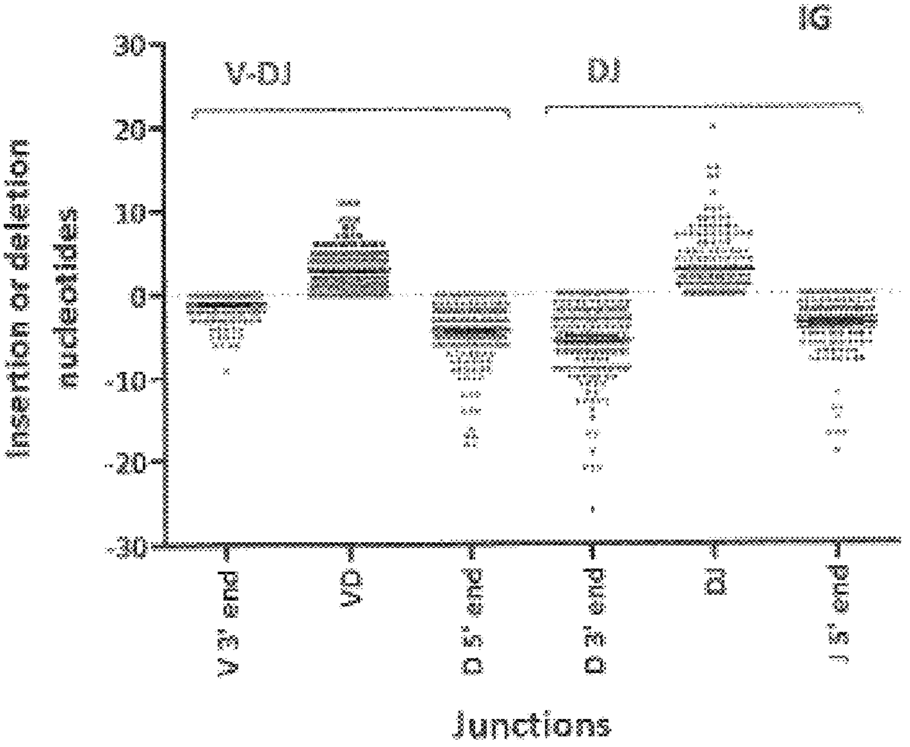
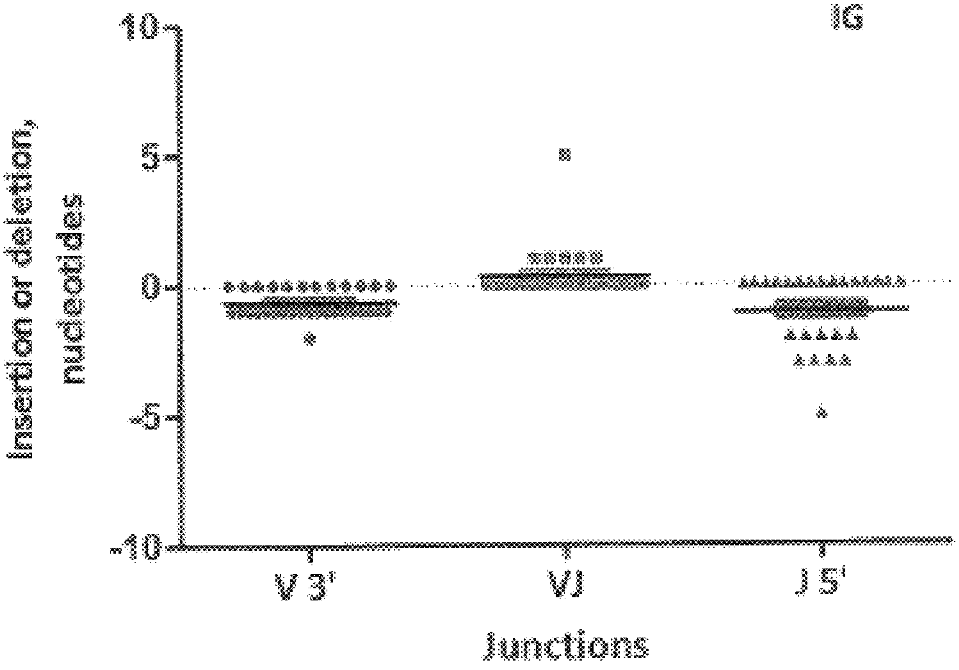
Fig. 38

Distribution of JH Usage Within Each VHs

| | JH1 | JH2 | JH3 | JH4 | JH5 | JH6 |
|---|---|---|---|---|---|---|
| V2-5 | | 1 | 5 | 5 | 2 | 1 |
| V4-4 | | 1 | 1 | 1 | | 8 |
| V1-3 | 1 | 6 | 6 | 49 | 13 | 40 |
| V1-2 | 1 | | | 1 | | 1 |
| V6-1 | | 1 | 4 | 18 | 1 | 29 |
| Total | 2 | 9 | 16 | 74 | 16 | 79 |

The data includes 196 independent sequences.

Fig. 39

Distribution of DH Usage Within Each VHs

| [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] |
|---|---|---|---|---|---|---|---|---|---|---|---|---|---|---|---|---|---|---|---|---|---|---|---|---|---|---|---|---|---|
| V 7-3 | | | | | | | | | 1 | 3 | | | | | | 3 | | | 2 | | | | 1 | | | 1 | 3 | | 14 |
| V 4-4 | | | | | | | | | | 5 | | | | | 1 | | | | 3 | | | | | | | 1 | 1 | | 11 |
| V 1-3 | 1 | 5 | 1 | 1 | 2 | | | 1 | 13 | 25 | | 1 | 12 | | | | 2 | | 18 | | 1 | 3 | | 1 | | 7 | 8 | 13 | 115 |
| V 3-2 | | | | | | | | | | 1 | | | | | | | | | 1 | | | | | 1 | | | | | 3 |
| V 6-1 | | | 2 | | 1 | | | | 3 | 10 | | 1 | 4 | | | 1 | 2 | | 10 | 1 | | 2 | | 1 | | 8 | 7 | | 53 |
| T | 1 | 5 | 3 | 1 | 3 | 0 | 0 | 1 | 17 | 44 | 0 | 2 | 16 | 0 | 1 | 4 | 4 | 0 | 34 | 1 | 1 | 5 | 1 | 3 | 0 | 17 | 19 | 13 | 196 |

The data includes 196 independent sequences.

Fig. 40

Nucleotide Gain or Loss at VJ Joints Generates IGK Variants

Joint Diversity Produces Functional CDS

V1-8_J1_Ck

VAQWPQISRNQGKPLSS Stop SIRRLV Stop KVGSHQGSAAVDLGQNSLSPSAAC
SL Met ILQLITANSIIVILLTFGQGTKVEIKRADAAPTVSIFPPSSEQLTSGGASVV
CFLNNFYPKDINVKWKIDGSERQNGV

#12

SSWLAWYQQKPGKAPKLLIYKASSLESGVPSRFSGSGSGTEFTLTISSLQPDD
FATYYCQQYNSYSTFGQGTKVEIKRADAAPTVSIFPPSSEQLTSGGASVVCFL
NNFYPKDINVKWKIDGSERQNGV

V1-8_J4_Ck

AQWPGISRNQGKPLSS Stop SIRRLV Stop KVGSHQGSAAVDLGQNSLSPSAACS
L Met ILQLITANSIIVILWTFGGGTKVEIKRADAAPTVSIFPPSSEQLTSGGASVV
CFLNNFYPKDINVKWKIDGSERQNGV

E1

SWLAWYQQKPGKAPKLLIYKASSLESGVPSRFSGSGSGTEFTLTISSLQPDDF
ATYYCQQYNSYSWTFGQGTKVEIKRADAAPTVSIFPPSSEQLTSGGASVVCFL
NNFYPKDINVKWKIDGSERQNGV

E3

SWLAWYQQKPGKAPKLLIYKASSLESGVPSRFSGSGSGTEFTLTISSLQPDDF
ATYYCQQYNSYSTFGQGTKVEIKRADAAPTVSIFPPSSEQLTSGGASVVCFLN
NFYPKDINVKWKIDGSERQNGV

E8

SSWLAWYQQKPGKAPKLLIYKASSLESGVPSRFSGSGSGTEFTLTISSLQPDD
FATYYCQQYNSYSWTFGQGTKVEIKRADAAPTVSIFPPSSEQLTSGGASVVCF
LNNFYPKDINVKWKIDGSERQNGV

Fig. 43

SEQUENCE LISTING

<160> NUMBER OF SEQ ID NOS: 68

<210> SEQ ID NO 1
<211> LENGTH: 4272
<212> TYPE: DNA
<213> ORGANISM: Rattus norvegicus

<400> SEQUENCE: 1

```
agatctgccc atctcaggct agttaaatta gttcatccca gtttggccca acttacccca     60
tctagagtag cgaaactaat ctgagcctag ctaagtccag tttagtttaa tgtagcccag    120
cttggcacag gctaatacat actgctacag tttggtctag cctaccctaa ttaagctgat    180
ccaggcctgg gtagacctag ctcatctcag cccagttaag gttatccagt acatctcttt    240
ccagttcagc tcaggttacc ataccttatc tcaattcagc tcagctagtg taattcatct    300
tagttcatcc cctacccctc tagactccct gttgatctta actcagttta gacatggcca    360
acaaagcctg gcccaactca ggccaggtta gtgtagctca gcataagcag tctagccttg    420
ctcagtctag ctcacccttc ctcatctaaa ttcaactcag ctatgccggc cctgcagcag    480
gtcccctcag ctcacccaag tccaaccagt tcagtctggc tcatttaagt cttgacaatc    540
cccaattcat cccagctcag cttagcataa ctcaggcagt ccattcttag cccaacccag    600
tttagcccag tttatcccag ttcatcctgg ctgtactcag tgcaactcga ttcatgttct    660
cccaggccac ctcagcccag ttcatggtag ctcatctgag cccaacttat cccagctcat    720
cccaaaccac ctcacctaag ccctgctcag cctagctcat ctgagcctag ttcaacctct    780
ctcatcctgc cagctagccc agtttagtcc acatcatctt gcaaagctca accagcccaa    840
```

-continued

```
gtcagccggg tccagctcat tcatgtccaa accagctcag tcatgctcat cctaactcag    900
cctcaccatc atccacatca gctagcccag ttcagctgag ctcatcccag cccacttcaa    960
tcacagctca tttaagtaca gctcacccca gctctattta gctcaagcta gcttatttag   1020
cctacttcat cccagctcag cccagccaac tcaactcatc ctagctcagc taaaccctgc   1080
tcagctcacc caagcaaagc tgactccaac ccagatcctt tcagctcagc tcacccagct   1140
caggccagct cacccatccc agctcaccca gcttagctca cccagcccag ctcagcccag   1200
ctcacccagc ccagctcagc ccagctcacc cagcccagct cagcccagct cagctcagct   1260
cagctcagct cagctcagct cacccagctc agctcagcca gctcagctca ccccagctca   1320
gtccagctca gttcagctca ccccagctca gctcacccaa ctcagctcac tcaactcagc   1380
tcacccaact cagctcagct cagttcaccc agctcagctc acccagccca gcacagctca   1440
tctcacccag ctcagctcac ccagcccagc tcaccccagc tcaccccagc tcagctcagc   1500
tcaccccagc tcagcccagc tcagctcacc cagctcagct cacccaactc agctcagctc   1560
agttcaccca gctcagctca cccagcccag cacagctcat ctcacccagc ccagctcacc   1620
ccagctcacc ccagctcagc tcagctcagc ccagctcacc cagctcagct cagctcaccc   1680
cagctcagct cacccagctc agctcaccca gcccagctca gctcagctca ccccagctca   1740
gcccagctca gctcacccag ctcagctcac ccagcccagc tcaccccagc tcaccccagc   1800
tcagtccagc tcagttcagc tcacccagct cagctcaccc aactcaactc agctcagttc   1860
acccagctca gctcagctca ccccagctca ccccagctca cccagctcag ttcagctcac   1920
cccagctcag ttcacccagc tcagctcacc cagcccagct cagcccagct caccccagct   1980
cagctcaacc agatcagctc agcccagctc accctagttt agttcaccca gcccagctca   2040
ccccagctca gctcacccca actcagctca cccagctcat cccagctcag ccagctaatc   2100
ccagctcagc tcaccccagc tcagctcacc cagctcagct cacccaactc agctcacccc   2160
agctcacccc agctcatccc agctcatccc agttcagacc tgttcagctc atctcacccc   2220
agctcagctc accccagttc agctcaccta gcccaactca ccccagctca gtccagctca   2280
gttcagctca ccccaactca tctcacccag ctcagctcac cccagctcat cccagctcag   2340
ctcaccccag ttcagccctg ttcagctcat ctcacccagc tcagctcatc cagcccagct   2400
caccccagct caccccagct cagtccagct cagttcagct cacccagctc agctcaccca   2460
actcaactca gctcagttca cccagctcag ctcagctcac cccagctcac ccagctcagt   2520
tcagctcacc ccagctcagt tcacccagct cagctcaccc agcccagctc aaccagatca   2580
gctcagccca gctcacccta gtttagttca cccagcccag ctcaccccag ctcagctcac   2640
cccaactcag ctcacctagc tcatcccagc tcagctcacc ccagctcagc tcaccccagc   2700
tcatctcacc ccagctcagc tcacccagct catcccagct cagctcagcc cagctcatcc   2760
cagccctgct catcccagct cagctcagct cagcccagct cagcccagct cagcccagct   2820
cagcccagct cagcccagct cagctcaacc cagctcagct cacccagccc agctcagccc   2880
agctcaccca gctcagctca ccccagctca gctcacccca gctcatctca cccagctcag   2940
ctcacccagc tcagcccagc tcagctcagc tcacccagct catctcaccc agctcagctc   3000
accccagctc atcccagctc agctcacccc agttcagccc tgttcagctc atctcacccc   3060
agctcagctc acccagttca gctcatccca gcccatccca gctcagctca gcccagctca   3120
gcccagctca gcccagccca gcccagccca gctcagctca gcccagctca gcccagctca   3180
gtccagctca gcttagccca gcccagctca gctcagccca gctcagccca gctcagccca   3240
```

```
gctcagctca cccagctcac cccagctcag cccagctcag cccagctcag ctcacccagc   3300
tcaccccacc ccagctcacc ccagttcagc ccagctcagc ccagctcagc ccagcccagc   3360
ccagcccagc ccagcccagc tcagcccagc tcagctcagc ccagcccagc tcagctcagc   3420
ccagctcagc ccagctcatc ccagctcagc tcaccccagc tcagcccagc tcagcccagc   3480
tcagctcacc cagctcaccc caccccagct caccccagtt cagcccagct catccagctc   3540
agctcacccc cagctctgct cacccagctc agctcagctt acccagctca gctcaactca   3600
cccagctcag ctcacccagc tcagctcagc tcaccccagc ccagctcagc tcagctcacc   3660
ccagctctgc tcacccagct cagctcagct cacctcagct ctgctcaccc agctcagctc   3720
aaccacctca ggtcagccca gctcacccca gcttacccca gctcacccag ctcagctcag   3780
ctcacccagc tcagctcacc cagctcagct caccccagct taccccagct caccccagct   3840
cagctaaccc agctcagctc acccagctca gctcacccag ctcagctcat cccagctcac   3900
cccagctacc acagagtagc tcatgctagc tcagctcacc ccagcacaac acagcccaac   3960
acagctcagt tcagagcagt ccagtagagt ttagctccaa tcagcccaga tcaagacaat   4020
tcattccaat ttggctatct tggttaagtc agcctagttt agcttagccg gcctagctca   4080
attcagctca ttgcagtcta cctcgttcct gctcaagtcc agctttggct acctcagagt   4140
aatcatctca gcttagcaca tttttgaagg gctcagggaa gcctacacat ctcagtccaa   4200
ctgtgcttaa ctagagccta gcttcctagc caggctgtca accttgttca ctaaattttg   4260
ctcagcaagc tt                                                       4272
```

```
<210> SEQ ID NO 2
<211> LENGTH: 22190
<212> TYPE: DNA
<213> ORGANISM: Artificial Sequence
<220> FEATURE:
<223> OTHER INFORMATION: Tragetting Vector (long version)

<400> SEQUENCE: 2

gcggccgcaa cctgggcaaa tgggagctta gcaacaatgt aggggggctgg acctagactt     60
cctacacatt tgtagcagat gtgcagcttg gtcttcatgt gtgtattacc ctaacatttg    120
gagcaggagc tgtctctgac tctgttgcct gccattggat ccccttcccc tgcttgggct    180
gccttgtttg gccttagtag gaaaggatgt gcttagtcct gctgtgactt gatgtcccta    240
ggcagaatga taccccaggg gggctcccca tctctgagga gatgggcaaa gggtaatggt    300
tggagggact tgtgaggctg ggactgggag gagagaaagg agacagctgt aactggaatg    360
atgttaagtg aacaaatgaa tggatagatt agatagacag atagacagac agacagacag    420
acagacagac agacagacag acagatagaa agatagatag ataaggggaa aaagaaacgt    480
agctgagcaa gccagagaga gcaagccaaa taagcagcat tcctccatga cttttccttc    540
agctcctgcc tatgagtctg ccttgacttc cctcagtgat tggttgtaag ttaaaaggtg    600
aaataaaccc tttctttgac aagttgcttt tggttctgat ttttatcaca gcaagagaaa    660
atcaaactag aacaaacatg tatttttcct ggcacatgtc catagtaagg cagaaatgat    720
cttcagacct agaccataga tactacagag agcagaagtg tagataggtg gacttactgt    780
atgattgtaa tccaagtaaa tctacatagc tagagagcta gaggaaaggc caaagcttcc    840
tctgggaggt cagatcctgt cgcactgtag ccaataaggc atattgcatc acaggaaagg    900
actaagaccc aggctggcaa tagtgtctgt atcttaacta gacctctcta gtgagtgagg    960
```

```
aaggaagttt gtgagagccc agactgtggg ctcggaaggt acctgccatg cccctgttag   1020
taactgagta ctacagcagg agcaggtgtt ctctagaaag cctgagacaa ctctacttct   1080
tctctcaaga gaccacctaa tacaggcctg agagaacaga ctctggaaat agatgggact   1140
taaggagcta agatctagag ctcatctaca gagcagaatc ccagccaaga gaacaaagaa   1200
tactggctct ctctcctgtt ccctactcct agagttctaa aacacactat agggaaggga   1260
gcctctagac ctccgtccat tccccatctt gctcattcca tcttcccatg tccccaggtc   1320
tccaagccac agacactacc tttcctattc acccaccttt ctgtgtccct aggtccccag   1380
gccatagtca cctcccccca cacacacccc actcaccctg ccccatctat gcccctagat   1440
gcttacttac cagagtcttt tgtctgacgt ggggctacaa gcatctatgc tccctaagca   1500
cctactgctg acctgtagga cccagctctg aaccaactca tataagtaaa tacagactct   1560
cccctgtctt aggatggcct cctggatcag gaggagacca ctgccaaaga accttctctc   1620
agagcactga actcctcccc tgtaccactt aggacagacc tgagacctat tattactgat   1680
taccagagct ctggcagtga ccacggagga gataggtcca ccctggacac aggaaacaca   1740
gcagcagaga tactgctcca tcacaacagt agagtgacac tttagacttt aatttgggtc   1800
actttcctgc tgcagaggtg ggatcagaaa gcaaagagca gtatgagtgc ctgataggca   1860
cccaagtaca ctatagagta ctcatggtga ataaggtacc tccatggctt cccagggagg   1920
ggcactgccc cacccccacc atcacagacc tttctccata gttgataact cagacacaag   1980
tgaatgacag atggacctcc atctactctt attttaaaaa gaagacaaac cccacaggct   2040
cgagaacttt agcgactgtt ttgagagaaa tcattggtcc ctgactcaag agatgactgg   2100
cagattgggg atcagaatac ccatactctg tggctagtgt gaggtttaag cctcagagtc   2160
cctgtggtct ctgactggtg caaggttttg actaagcgga gcaccacagt gctaactggg   2220
accacggtga cacgtggctc aacaaaaacc ttctgtttgg agctctccag ggcagcctg   2280
agctatgagg aagtagagag gcttgagaaa tctgaggaag aaaagagtag atctgagagg   2340
aaaggtagct ttctggaggt caggagacag tgcagagaag aacgagttac tgtggacagg   2400
tcttagatgg ggaaagaatg agcaaatgca agcatcagaa gggtggatgc aatgtcctgc   2460
caaggactta ccaagaggat ccccggacag agcaggcagg tggagttgac tgagaggaca   2520
gggtaggtgc aggtccctct ctcgtttcct ttctccttct cctgtttcct tcctctcttg   2580
tcacaggtct cactatgcta gccaaggcta gcctgaaaga ttaccatcct acagatgggc   2640
ccatccagtt gagttaaggt ggagatctct ccaaacatct gagtttctga ggcttggatg   2700
ccactgggga cgccaaggga ctttggctg ggtttggttg gccccagatg aagggctact   2760
tcactgggtc tataattact ctgatgtcta ggaccagggg gctcaggtca ctcaggtcag   2820
gtgagtcctg catctgggga ctgtggggtt caggtgtcct aaggcaggat gtggagagag   2880
ttttagtata ggaacagagg cagaacagag actgtgctac tggtacttcg atgtctgggg   2940
cgcagggacc acggtcaccg tctcctcagg taagctggct tttttctttc tgcacattcc   3000
attctgaaat gggaaaagat attctcagat ctccccatgt caggccatct gccacactct   3060
gcatgctgca gaagcttttc tgtaaggata gggtcttcac tcccaggaaa agaggcagtc   3120
agaggctagc tgcctgtgga acagtgacaa tcatggaaaa taggcattta cattgttagg   3180
ctacatgggt agatgggttt ttgtacaccc actaaagggg tctatgatag tgtgactact   3240
ttgactactg gggccaaggc accactctca cagtctcctc aggtgagtcc ttacaacctc   3300
tctcttctat tcagcttaaa tagattttac tgcatttgtt ggggggggaaa tgtgtgtatc   3360
```

```
tgaatttcag gtcatgaagg actagggaca ccttgggagt cagaaagggt cattgggagc   3420
cctggctgat gcagacagac atcctcagct cccagacttc atggccagag atttataggg   3480
atcctggcca gcattgccgc taggtccctc tcttctatgc tttctttgtc cctcactggc   3540
ctccatctga gatcatcctg gagccctagc caaggatcat ttattgtcag ggtctaatc    3600
attgttgtca caatgtgcct ggtttgctta ctggggccaa gggactctgg tcactgtctc   3660
tgcaggtgag tcctaacttc tcccattcta aatgcatgtt ggggggattc tgagccttca   3720
ggaccaagat tctctgcaaa cgggaatcaa gattcaaccc ctttgtccca aagttgagac   3780
atgggtctgg gtcagggact ctctgcctgc tggtctgtgg tgacattaga actgaagtat   3840
gatgaaggat ctgccagaac tgaagcttga agtctgaggc agaatcttgt ccagggtcta   3900
tcggactctt gtgagaatta ggggctgaca gttgatggtg acaatttcag ggtcagtgac   3960
tgtctggttt ctctgaggtg aggctggaat ataggtcacc ttgaagacta aagaggggtc   4020
caggggcttc tgcacaggca gggaacagaa tgtggaacaa tgacttgaat ggttgattct   4080
tgtgtgacac caggaattgg cataatgtct gagttgccca ggggtgattc tagtcagact   4140
ctggggtttt tgtcgggtat agaggaaaaa tccactattg tgattactat gctatggact   4200
actggggtca aggaacctca gtcaccgtct cctcaggtaa gaatggcctc tccaggtctt   4260
tatttttaac ctttgttatg gagttttctg agcattgcag actaatcttg gatatttgtc   4320
cctgagggag ccggctgaga gaagttggga aataaactgt ctagggatct cagagccttt   4380
aggacagatt atctccacat ctttgaaaaa ctaagaatct gtgtgatggt gttggtggag   4440
tccctggatg atgggatagg gactttggag gctcatttga gggagatgct aaaacaatcc   4500
tatggctgga gggatagttg gggctacgcg tttttaaccc tagaaagata gtctgcgtaa   4560
aattgacgca tgcattcttg aaatattgct ctctctttct aaatagcgcg aatccgtcgc   4620
tgtgcattta ggacatctca gtcgccgctt ggagctcccg tgaggcgtgc ttgtcaatgc   4680
ggtaagtgtc actgattttg aactataacg accgcgtgag tcaaaatgac gcatgattat   4740
cttttacgtg acttttaaga tttaactcat acgataatta tattgttatt tcatgttcta   4800
cttacgtgat aacttattat atatatattt tcttgttata gatatcgcta gtggatccgg   4860
ctggttcttt ccgcctcaga aggtactttt tttttttttt tttttttttt tttttttttt   4920
tttttttttt tttttttttt ttttttaaat ttttgggaat ttattgattt gcatttaaaa   4980
gggaactgct gacaaagatt cactggtaat aatttgaaca agttggaaaa tacagtcaac   5040
attactgaaa cactactaaa ataattccag gacagaacaa aacttcttag atgctgtctt   5100
tgatgtgaaa attgactgct tcttactttt ctaacacacg gtggtataat taacaatatt   5160
caatcacttc tattctttcc tgcatatata aaaattaaaa taccaattaa aaaactaata   5220
tatcttctct ttatttctta cagatatgag ttcaatgttt cactcaatag tgctgtggtt   5280
taagagaatt ttttcattta caagttaaac aacaatccgc ccaaagggaa ctgatagtct   5340
ataggctcat agtgcaaata aacagtttag gaatgcagca actgacattt ctaaagtaca   5400
aaacagataa aattcttaga agatacatgc aaaaagctct actaagcaga tggccacaga   5460
actagaacat tgataatttt actggcgatg tcaataggac tccagatgtt tccaaactca   5520
acttgaactc tcatcttagg ctttgtattt tgcttttcca gtttcactaa tgacacaaac   5580
atgattcaaa tccctgaagt attcattata gtcaagggca tatcctacaa caaacttgtc   5640
tggaatttca aatccaacaa agtctggctt atatccaaca cttcgtgggg tcctttttcac  5700
```

-continued

```
cagcaagctt gcgaccttga ccatctttgg attatactgc ctgaccaagg aaagcaaagt   5760
ctgcattgtt ttgccagtgt caattatatc ttccacaatc aagacattct ttccagttaa   5820
agttgagaga tcatctccac caattacttt tatgtcccct gttgactggt cattacaata   5880
gctcttcagt ctgataaaat ctacagtcat aggaatggat ctatcactat ttctattcag   5940
tgctttgatg taatccagca ggtcagcaaa gaatttatag ccccccttga gcacacagag   6000
ggctacaatg tgatggcctc ccatctcctt catcacatct cgagcaagac gttcagtcct   6060
acagaaataa aatcaggaat ttaatagaaa gtttcataca ttaaacttta taacaaacac   6120
ctcttagtca ttaaacttcc acaccaacct gggcaatata gtgagacccc atgcctgcaa   6180
aaaaaaaaaa attagccagg catggtagca tgtacctgta gtcccagcta cttgagaggt   6240
gaggtgggaa aatcacttta gtgcaggatg ttgaggctgg agtgaactgt gattgtgcca   6300
ctgcactcca gcctggacaa tagagcaaga ccttgtctca aaaaaatgca ttaaaaattt   6360
tttttaaatc ttccacgtaa cacatccttt gccctcatgt ttcataaggt aaaaaatttg   6420
ataccttcaa aaaaaccaag cataccacta tcataatttt ttttaaatgc aaataaaaac   6480
aagataccat tttcacctat cagactggca ggttctgatt aaatgaaatt tcttggataa   6540
tatacaatat taagagagac tgtagaaact gggccagtgg ctcatgcctg taatcccagc   6600
actttgggag gctgggtaac atggcgaacc ctgtttctac aaaataaaaa tattagctgg   6660
gagtggtggc gcacacctat agtcccagct actcaggagg ctgaggtgga aggatcgctt   6720
gaacccagga ggttgagact gcagtgaact gtgatcattc tgctgcactg caccccagcc   6780
tgggcaacag agaccttgtc tcaaaaaaaa aaaaaaaaga gacaaattgt gaagagaaag   6840
gtactctcat ataacatcag gagtataaaa tgattcaact tcttagagga aaatttggca   6900
ataccaaaat attcaataaa ctctttcccc ttgacccaga aattccactt gaataaagct   6960
gaacaagtac caaacatgta aaagaatgtt tcttctagta cagtcggtaa gaacaaaata   7020
gtgtctatca atagtggact ggttaaatca gttatggtat ctccataaga cagaatgcta   7080
tgcaaccttt aaaatatatt agatagctct agacagtgga tcccctcgag ggacctaata   7140
acttcgtata gcatacatta tacgaagtta tattaagggt tattgaatat gtcgactaga   7200
cacactaata ttaaaagtgt ccaataacat ttaaaactat actcatacgt taaaatataa   7260
atgtatatat gtacttttgc atatagtata catgcatagc cagtgcttga gaagaaatgt   7320
gtacagaagg ctgaaaggag agaactttag tcttcttgtt tatggcctcc atagttagaa   7380
tattttataa cacaaatatt ttgatattat aattttaaaa taaaaacaca gaatagccag   7440
acatacaatg caagcattca ataccaggta aggtttttca ctgtaattga cttaacagaa   7500
aattttcaag ctagatgtgc ataataataa aaatctgacc ttgccttcat gtgattcagc   7560
cccagtccat taccctgttt aggactgaga aatgcaagac tctggctaga gttccttctt   7620
ccatctccct tcaatgttta ctttgttctg gtccctacag agtcccacta taccacaact   7680
gatactaagt aattagtaag gccctcctct tttattttta ataaagaaga ttttagaaag   7740
catcagttat ttaataagtt ggcctagttt atgttcaaat agcaagtact cagaacagct   7800
gctgatgttt gaaattaaca caagaaaaag taaaaaacct cattttaaga tcttacttac   7860
ctgtccataa ttagtccatg gggaataaac accctttcca aatcctcagc ataatgatta   7920
ggtatgcaaa ataaatcaag gtcataacct ggttcatcat cactaatcac gacgccaggg   7980
ctgcgggtcg ccataacgga gccggccggc gcgcgggctg aataacttcg tataatgtgt   8040
actatacgaa gttatttgtt caggaggagg aagccggtgg cggagcagag gaggaggcgg   8100
```

```
aggcgcagca agaccccccc cccccctgcag gtcgaaaggc ccggagatga ggaagaggag   8160
aacagcgcgg cagacgtgcg cttttgaagc gtgcagaatg ccgggcctcc ggaggacctt   8220
cgggcgcccg ccccgcccct gagcccgccc ctgagcccgc ccccggaccc accccttccc   8280
agcctctgag cccagaaagc gaaggagcaa agctgctatt ggccgctgcc ccaaaggcct   8340
acccgcttcc attgctcagc ggtgctgtcc atctgcacga gactagtgag acgtgctact   8400
tccatttgtc acgtcctgca cgacgcgagc tgcggggcgg gggggaactt cctgactagg   8460
ggaggagtag aaggtggcgc gaaggggcca ccaaagaacg gagccggttg gcgcctaccg   8520
gtggatgtgg aatgtgtgcg aggccagagg ccacttgtgt agcgccaagt gcccagcggg   8580
gctgctaaag cgcatgctcc agactgcctt gggaaaagcg cctcccctac ccggtagata   8640
tctataacaa gaaaatatat atataataag ttatcacgta agtagaacat gaaataacaa   8700
tataattatc gtatgagtta aatcttaaaa gtcacgtaaa agataatcat gcgtcatttt   8760
gactcacgcg gtcgttatag ttcaaaatca gtgacactta ccgcattgac aagcacgcct   8820
cacgggagct ccaagcggcg actgagatgt cctaaatgca cagcgacgga ttcgcgctat   8880
ttagaaagag agagcaatat ttcaagaatg catgcgtcaa ttttacgcag actatctttc   8940
tagggttaaa agaattcgat atcaagctta tcgatgtagt tggagatttt cagtttttag   9000
aataaaagta ttagttgtgg aatatacttc aggaccacct ctgtgacagc atttatacag   9060
tatccgatgc atagggacaa agagtggagt ggggcacttt ctttagattt gtgaggaatg   9120
ttccgcacta gattgtttaa aacttcattt gttggaagga gagctgtctt agtgattgag   9180
tcaagggaga aaggcatcta gcctcggtct caaaagggta gttgctgtct agagaggtct   9240
ggtggagcct gcaaaagtcc agctttcaaa ggaacacaga agtatgtgta tggaatatta   9300
gaagatgttg cttttactct taagttggtt cctaggaaaa atagttaaat actgtgactt   9360
taaaatgtga gagggttttc aagtactcat ttttttaaat gtccaaaatt tttgtcaatc   9420
aatttgaggt cttgtttgtg tagaactgac attacttaaa gtttaaccga ggaatgggag   9480
tgaggctctc tcataccccta ttcagaactg acttttaaca ataataaatt aagtttaaaa   9540
tatttttaaa tgaattgagc aatgttgagt tggagtcaag atggccgatc agaaccagaa   9600
cacctgcagc agctggcagg aagcaggtca tgtggcaagg ctatttgggg aagggaaaat   9660
aaaaccacta ggtaaacttg tagctgtggt ttgaagaagt ggttttgaaa cactctgtcc   9720
agccccacca aaccgaaagt ccaggctgag caaaacacca cctgggtaat ttgcatttct   9780
aaaataagtt gaggattcag ccgaaactgg agaggtcctc ttttaactta ttgagttcaa   9840
ccttttaatt ttagcttgag tagttctagt ttccccaaac ttaagtttat cgacttctaa   9900
aatgtattta gaattcattt tcaaaattag gttatgtaag aaattgaagg actttagtgt   9960
ctttaatttc taatatattt agaaaacttc ttaaaattac tctattattc ttccctctga  10020
ttattggtct ccattcaatt cttttccaat acccgaagca tttacagtga ctttgttcat  10080
gatctttttt agttgtttgt tttgccttac tattaagact ttgacattct ggtcaaaacg  10140
gcttcacaaa tctttttcaa gaccactttc tgagtattca ttttaggaga aatacttttt  10200
ttttaaatga atgcaattat ctagacttat ttcagttgaa catgctggtt ggtggttgag  10260
aggacactca gtcagtcagt gacgtgaagg gcttctaagc cagtccacat gctctgtgtg  10320
aactccctct ggccctgctt attgttgaat gggccaaagg tctgagacca ggctgctgct  10380
gggtaggcct ggactttggg tctcccaccc agacctggga atgtatggtt gtggcttctg  10440
```

-continued

```
ccacccatcc acctggctgc tcatggacca gccagcctcg gtggctttga aggaacaatt  10500
ccacacaaag actctggacc tctccgaaac caggcaccgc aaatggtaag ccagaggcag  10560
ccacagctgt ggctgctgct cttaaagctt gtaaactgtt tctgcttaag agggactgag  10620
tcttcagtca ttgctttagg gggagaaaga gacatttgtg tgtcttttga gtaccgttgt  10680
ctgggtcact cacatttaac tttccttgaa aaactagtaa aagaaaaatg ttgcctgtta  10740
accaataatc atagagctca tggtattttg aggaaatctt agaaaacgtg tatacaattg  10800
tctggaatta tttcagttaa gtgtattagt tgaggtactg atgctgtctc tacttcagtt  10860
atacatgtgg gtttgaattt tgaatctatt ctggctcttc ttaagcagaa aatttagata  10920
aaatggatac ctcagtggtt tttaatggtg ggtttaatat agaaggaatt taaattggaa  10980
gctaatttag aatcagtaag gagggaccca ggctaagaag gcaatcctgg gattctggaa  11040
gaaaagatgt ttttagtttt tatagaaaac actactacat tcttgatcta caactcaatg  11100
tggtttaatg aatttgaagt tgccagtaaa tgtacttcct ggttgttaaa gaatggtatc  11160
aaaggacagt gcttagatcc aaggtgagtg tgagaggaca ggggctgggg tatggatacg  11220
cagaaggaag gccacagctg tacagaattg agaaagaata gagacctgca gttgaggcca  11280
gcaggtcggc tggactaact ctccagccac agtaatgacc cagacagaga aagccagact  11340
cataaagctt gctgagcaaa atttagtgaa caaggttgac agcctggcta ggaagctagg  11400
ctctagttaa gcacagttgg actgagatgt gtaggcttcc ctgagccctt caaaaatgtg  11460
ctaagctgag atgattactc tgaggtagcc aaagctggac ttgagcagga acgaggtaga  11520
ctgcaatgag ctgaattgag ctaggccggc taagctaaac taggctgact taaccaagat  11580
agccaaattg gaatgaattg tcttgatctg ggctgattgg agctaaactc tactggactg  11640
ctctgaactg agctgtgttg ggctgtgttg tgctggggtg agctgagcta gcatgagcta  11700
ctctgtggta gctggggtga gctgggatga gctgagctgg gtgagctgag ctgggtgagc  11760
tgagctgggt tagctgagct ggggtgagct ggggtaagct ggggtgagct gagctgggtg  11820
agctgagctg ggtgagctga gctgagctgg gtgagctggg gtaagctggg gtgagctggg  11880
ctgacctgag gtggttgagc tgagctgggt gagcagagct gaggtgagct gagctgagct  11940
gggtgagcag agctggggtg agctgagctg agctgggctg gggtgagctg agctgagctg  12000
ggtgagctga gctgggtgag ttgagctgag ctgggtaagc tgagctgagc tgggtgagca  12060
gagctggggg tgagctgagc tggatgagct gggctgaact ggggtgagct ggggtggggt  12120
gagctgggtg agctgagctg ggctgagctg ggctgagctg gggtgagctg agctgggatg  12180
agctgggctg agctgggctg agctgagctg ggctgggctg agctgagctg ggctgagctg  12240
ggctgggctg ggctgggctg ggctgggctg agctgggctg agctgggctg aactggggtg  12300
agctggggtg gggtgagctg ggtgagctga gctgggctga gctgggctga gctggggtga  12360
gctgggtgag ctgagctggg ctgagctggg ctgagctggg ctgagctgag ctgggctggg  12420
ctaagctgag ctggactgag ctgggctgag ctgggctgag ctgagctggg ctgggctggg  12480
ctgggctgag ctgggctgag ctgggctgag ctgagctggg atgggctggg atgagctgaa  12540
ctgggtgagc tgagctgggg tgagatgagc tgaacagggc tgaactgggg tgagctgagc  12600
tgggatgagc tggggtgagc tgagctgggt gagatgagct gggtgagctg agctgagctg  12660
ggctgagctg ggtgagctga gctgggtgag atgagctggg gtgagctgag ctggggtgag  12720
ctgagctggg tgagctgggc tgagctgggc tgggtgagct gagctgggtt gagctgagct  12780
gggctgagct gggctgagct gggctgagct gggctgagct gggctgagct gagctgagct  12840
```

gggatgagca gggctgggat gagctgggct gagctgagct gggatgagct gggtgagctg 12900
agctggggtg agatgagctg gggtgagctg agctggggtg agctgagctg ggatgagcta 12960
ggtgagctga gttggggtga gctgagctgg ggtgagctgg gctgggtgaa ctaaactagg 13020
gtgagctggg ctgagctgat ctggttgagc tgggctgggt gagctgagct gggtgaactg 13080
agctggggtg agctgaactg agctgggtga gctggggtga gctgagctga gctgggtgaa 13140
ctgagctgag ttgagttggg tgagctgagc tgggtgagct gaactgagct ggactgagct 13200
ggggtgagct ggggtgagct gggctggatg agctgagctg ggtgagatga gctgaacagg 13260
gctgaactgg ggtgagctga gctgggatga gctggggtga gctgagctgg gtgagatgag 13320
ttggggtgag ctgaactgag ctggactgag ctggggtgag ttgggctagg tgagctgaac 13380
tggggtgagc tgagctgggg tgagatgagc tgaacaggtc tgaactggga tgagctggga 13440
tgagctgggg tgagctgggg tgagctgagt tgggtgagct gagctgggtg agctgagctg 13500
gggtgagctg agctgggatt agctggctga gctgggatga gctgggtgag ctgagttggg 13560
gtgagctgag ctggggtgag ctgggctggg tgaactaaac tagggtgagc tgggctgagc 13620
tgatctggtt gagctgagct ggggtgagct gggctgagct gggctgggtg agctgagctg 13680
ggtgaactga gctggggtga gctgaactga gctgggtgag ctggggtgag ctggggtgag 13740
ctgagctgag ctgggtgaac tgagctgagt tgagttgggt gagctgagct gggtgagctg 13800
aactgagctg gactgagctg gggtgagctg gggtgagctg ggctgggtga gctgagctgg 13860
gtgagctgag ctgggctgag ctggggtgag ctgagctgag ctgggctggg tgagctgagc 13920
tgggtgagct gagctggggt gagctgagct gagctgggtg agctgggctg agctgagctg 13980
agctggggtg agctggggtg agctgggctg ggtgagatga gctgtgctgg gctgggtgag 14040
ctgagctggg tgaactgagc tgagctgagt tgggtgagct gagctgggtg agctgagctg 14100
ggctgagctg gggtgagctg agctgagctg gggtgagctg gggtgagctg ggctgggtga 14160
gctgagctgg gtgagatgag ctgtgctggg ctgggtgagc tgagctgggt gaactgagct 14220
gagctgagtt gggtgagctg agttgagtga gctgagttgg gtgagctgag ctggggtgag 14280
ctgaactgag ctggactgag ctggggtgag ctgagctggc tgagctgagc tgggtgagct 14340
gagctgagct gagctgagct gagctgagct gggctgagct gggctgggtg agctgggctg 14400
agctgggctg ggtgagctgg gctgagctgg gctgggtgag ctaagctggg tgagctggga 14460
tgggtgagct ggcctgagct gggtgagctg agctgaaagg atctgggttg gagtcagctt 14520
tgcttgggtg agctgagcag ggtttagctg agctaggatg agttgagttg gctgggctga 14580
gctgggatga agtaggctaa ataagctagc ttgagctaaa tagagctggg gtgagctgta 14640
cttaaatgag ctgtgattga agtgggctgg gatgagctca gctgaactgg gctagctgat 14700
gtggatgatg gtgaggctga gttaggatga gcatgactga gctggtttgg acatgaatga 14760
gctggacccg gctgacttgg gctggttgag ctttgcaaga tgatgtggac taaactgggc 14820
tagctggcag gatgagagag gttgaactag gctcagatga gctaggctga gcagggctta 14880
ggtgaggtgg tttgggatga gctgggataa gttgggctca gatgagctac catgaactgg 14940
gctgaggtgg cctgggagaa catgaatcga gttgcactga gtacagccag gatgaactgg 15000
gataaactgg gctaaactgg gttgggctaa gaatggactg cctgagttat gctaagctga 15060
gctgggatga attggggatt gtcaagactt aaatgagcca gactgaactg gttggacttg 15120
ggtgagctga ggggacctgc tgcagggccg gcatagctga gttgaattta gatgaggaag 15180

-continued

```
ggtgagctag actgagcaag gctagactgc ttatgctgag ctacactaac ctggcctgag  15240
ttgggccagg ctttgttggc catgtctaaa ctgagttaag atcaacaggg agtctagagg  15300
ggtaggggat gaactaagat gaattacact agctgagctg aattgagata aggtatggta  15360
acctgagctg aactggaaag agatgtactg gataacctta actgggctga gatgagctag  15420
gtctacccag gcctggatca gcttaattag ggtaggctag accaaactgt agcagtatgt  15480
attagcctgt gccaagctgg gctacattaa actaaactgg acttagctag gctcagatta  15540
gtttcgctac tctagatggg gtaagttggg ccaaactggg atgaactaat ttaactagcc  15600
tgagatgggc agatctgaat gagcagagct gggatgaact gaatgagttt caccaggcct  15660
ggaccagtta ggctaggacc tcgttctata gaggcagact gtgtgctaca gtggagtttc  15720
aagatgattc catgagtcct ccccgccccc aacataaccc accttcctcc taccctacaa  15780
gcctgtctgg tgtgtaaatc ccagctttgt gtgctgatac agaagcctga gcccctcccc  15840
cacctccacc tacctattac tttgggatga gaatagttct cccagccagt gtctcagagg  15900
gaagccaagc aggacaggcc caaggctact tgagaagcca ggatctaggc ctctccctga  15960
gaacgggtgt tcatgcccct agagttggct gaagggccag atccacctac tctagaggca  16020
tctctccctg tctgtgaagg cttccaaagt cacgttcctg tggctagaag gcagctccat  16080
agccctgctg cagtttcgtc ctgtatacca ggttcaccta ctaccatatc tagccctgcc  16140
tgccttaaga gtagcaacaa ggaaatagca gggtgtagag ggatctcctg tctgacagga  16200
ggcaagaaga cagattctta cccctccatt tctcttttat ccctctctgg tcctcagaga  16260
gtcagtcctt cccaaatgtc ttccccctcg tctcctgcga gagcccccctg tctgataaga  16320
atctggtggc catgggctgc ctggcccggg acttcctgcc cagcaccatt tccttcacct  16380
ggaactacca gaacaacact gaagtcatcc agggtatcag aaccttccca acactgagga  16440
cagggggcaa gtacctagcc acctcgcagg tgttgctgtc tcccaagagc atccttgaag  16500
gttcagatga atacctggta tgcaaaatcc actacggagg caaaaacaaa gatctgcatg  16560
tgcccattcc aggtaagaac caaaccctcc cagcaggggt gcccaggccc aggcatggcc  16620
cagagggagc agcggggtgg ggcttaggcc aagctgagct cacaccttga cctttcattc  16680
cagctgtcgc agagatgaac cccaatgtaa atgtgttcgt cccaccacgg gatggcttct  16740
ctggccctgc accacgcaag tctaaactca tctgcgaggc cacgaacttc actccaaaac  16800
cgatcacagt atcctggcta aaggatggga agctcgtgga atctggcttc accacagatc  16860
cggtgaccat cgagaacaaa ggatccacac cccaaaccta caaggtcata agcacactta  16920
ccatctctga aatcgactgg ctgaacctga atgtgtacac ctgccgtgtg gatcacaggg  16980
gtctcacctt cttgaagaac gtgtcctcca catgtgctgc cagtgagtgg cctgggataa  17040
gcccaatgcc tagccctccc agattaggga agtcctccta caattatggc caatgccacc  17100
cagacatggt catttgctcc ttgaactttg gctccccaga gtggccaagg acaagaatga  17160
gcaataggca gtagaggggt gagaatcagc tggaaggacc agcatcttcc cttaagtagg  17220
tttgggggat ggagactaag ctttttttcca acttcacaac tagatatgtc ataacctgac  17280
acagtgttct cttgactgca ggtccctcca cagacatcct aaccttcacc atcccccccct  17340
cctttgccga catcttcctc agcaagtccg ctaacctgac ctgtctggtc tcaaacctgg  17400
caacctatga aaccctgaat atctcctggg cttctcaaag tggtgaacca ctggaaacca  17460
aaattaaaat catggaaagc catcccaatg gcaccttcag tgctaagggt gtggctagtg  17520
tttgtgtgga agactggaat aacaggaagg aatttgtgtg tactgtgact cacagggatc  17580
```

-continued

```
tgccttcacc acagaagaaa ttcatctcaa aacccaatgg taggtatccc cccttccctt  17640
cccctccaat tgcaggaccc ttcctgtacc tcatagggag ggcaggtcct cttccacccct  17700
atcctcacta ctgtcttcat ttacagaggt gcacaaacat ccacctgctg tgtacctgct  17760
gccaccagct cgtgagcaac tgaacctgag ggagtcagcc acagtcacct gcctggtgaa  17820
gggcttctct cctgcagaca tcagtgtgca gtggcttcag agagggcaac tcttgcccca  17880
agagaagtat gtgaccagtg ccccgatgcc agagcctggg gccccaggct tctactttac  17940
ccacagcatc ctgactgtga cagaggagga atggaactcc ggagagacct atacctgtgt  18000
tgtaggccac gaggccctgc cacacctggt gaccgagagg accgtggaca agtccactgg  18060
taaacccaca ctgtacaatg tctccctgat catgtctgac acaggcggca cctgctattg  18120
accatgctag cgctcaacca ggcaggccct gggtgtccag ttgctctgtg tatgcaaact  18180
aaccatgtca gagtgagatg ttgcatttta taaaaattag aaataaaaaa aatccattca  18240
aacgtcactg gttttgatta tacaatgctc atgcctgctg agacagttgt gttttgcttg  18300
ctctgcacac accctgcata cttgcctcca ccctggccct tcctctacct tgccagtttc  18360
ctccttgtgt gtgaactcag tcaggcttac aacagacaga gtatgaacat gcgattcctc  18420
cagctacttc tagatatatg gctgaaagct tgcctaacct ggtgcaggca gcattcaggc  18480
acatatatag acacacatgc atttatacat agatatatag gtacacatgt gtagacacat  18540
acatgaatgt gtattcatgg acacacagac aaaggtacac atatatacac atgagttcat  18600
gcgcacacac atgcatggac acttacaaac gccttcagag acaaataggc atagacacac  18660
aaccactcac agaaacagat accaatatgc atggtcctgt gtacacagaa acagactata  18720
ggcaaatata cacaaataaa ctatatagat acaaagatat gcatatacac acatgtacag  18780
aaacatcttc acatgtgtac actaacatgt ggacaggtat agcacacaga tacacctgga  18840
ctctgaccag ggctgtaatc tccaaggctc acggctcaga gagcctacac taggctgggt  18900
cactgatact cctcaggagc ccactctatg attgggagag ataaccccag gtacaaagta  18960
tgcctatctg tctcaacacc atggggcaga agatactcca ctaaccaccc atgacagaaa  19020
gttagccttg gctgtgtctc cattaataga acacctcaga agaccaatgt gaaattgcct  19080
aacccactca cacccaccct gatctccagt tcaaaatgca gaaaacataa tgcagttgtc  19140
caaaagatgc cccaaccaca cacacacaca cacacacaca cacacacaca cacacacaca  19200
cacacataca cacacacaca ccatcaagga gcctctgtaa ggagtcacca cccaataaca  19260
ctgcctcttt gggctcatat cctggacatt cttcatattc atatccattt ggggcctagg  19320
ctttagatat ccccaagggc tcatctttac agggatcaga gatcccaata aatgccctgg  19380
tcccacagcc tccctcaggt atctgtctgt ttatctcttg gtacctttct tagacgttag  19440
gtggcacttt tcggggaaat gtgcgcggaa cccctatttg tttatttttc taaatacatt  19500
caaatatgta tccgctcatg agacaataac cctgataaat gcttcaataa tattgaaaaa  19560
ggaagagtat gagtattcaa catttccgtg tcgcccttat tccctttttt gcggcatttt  19620
gccttcctgt ttttgctcac ccagaaacgc tggtgaaagt aaaagatgct gaagatcagt  19680
tgggtgcacg agtgggttac atcgaactgg atctcaacag cggtaagatc cttgagagtt  19740
ttcgccccga agaacgtttt ccaatgatga gcacttttaa agttctgcta tgtggcgcgg  19800
tattatcccg tgttgacgcc gggcaagagc aactcggtcg ccgcatacac tattctcaga  19860
atgacttggt tgagtactca ccagtcacag aaaagcatct tacggatggc atgacagtaa  19920
```

-continued

```
gagaattatg cagtgctgcc ataaccatga gtgataacac tgcggccaac ttacttctga  19980
caacgatcgg aggaccgaag gagctaaccg cttttttgca caacatgggg gatcatgtaa  20040
ctcgccttga tcgttgggaa ccggagctga atgaagccat accaaacgac gagcgtgaca  20100
ccacgatgcc tgcagcaatg gcaacaacgt tgcgcaaact attaactggc gaactactta  20160
ctctagcttc ccggcaacaa ttaatagact ggatggaggc ggataaagtt gcaggaccac  20220
ttctgcgctc ggcccttccg gctggctggt ttattgctga taaatctgga gccggtgagc  20280
gtgggtctcg cggtatcatt gcagcactgg ggccagatgg taagccctcc cgtatcgtag  20340
ttatctacac gacggggagt caggcaacta tggatgaacg aaatagacag atcgctgaga  20400
taggtgcctc actgattaag cattggtaac tgtcagacca agtttactca tatatacttt  20460
agattgattt aaaacttcat ttttaattta aaaggatcta ggtgaagatc ctttttgata  20520
atctcatgac caaaatccct taacgtgagt tttcgttcca ctgagcgtca gaccccgtag  20580
aaaagatcaa aggatcttct tgagatcctt tttttctgcg cgtaatctgc tgcttgcaaa  20640
caaaaaaacc accgctacca gcggtggttt gtttgccgga tcaagagcta ccaactcttt  20700
ttccgaaggt aactggcttc agcagagcgc agataccaaa tactgtcctt ctagtgtagc  20760
cgtagttagg ccaccacttc aagaactctg tagcaccgcc tacatacctc gctctgctaa  20820
tcctgttacc agtggctgct gccagtggcg ataagtcgtg tcttaccggg ttggactcaa  20880
gacgatagtt accggataag gcgcagcggt cgggctgaac ggggggttcg tgcacacagc  20940
ccagcttgga gcgaacgacc tacaccgaac tgagatacct acagcgtgag ctatgagaaa  21000
gcgccacgct tcccgaaggg agaaaggcgg acaggtatcc ggtaagcggc agggtcggaa  21060
caggagagcg cacgagggag cttccagggg gaaacgcctg gtatctttat agtcctgtcg  21120
ggtttcgcca cctctgactt gagcgtcgat ttttgtgatg ctcgtcaggg gggcggagcc  21180
tatggaaaaa cgccagcaac gcggcctttt tacggttcct ggccttttgc tggccttttg  21240
ctcacatgtt ctttcctgcg ttatcccctg attctgtgga taaccgtatt accgcctttg  21300
agtgagctga taccgctcgc cgcagccgaa cgaccgagcg cagcgagtca gtgagcgagg  21360
aagcggaaga gcgcctgatg cggtattttc tccttacgca tctgtgcggt atttcacacc  21420
gcatatggtg cactctcagt acaatctgct ctgatgccgc atagttaagc cagtatacac  21480
tccgctatcg ctacgtgact gggtcatggc tgcgccccga cacccgccaa cacccgctga  21540
cgcgccctga cgggcttgtc tgctcccggc atccgcttac agacaagctg tgaccgtctc  21600
cgggagctgc atgtgtcaga ggttttcacc gtcatcaccg aaacgcgcga ggcagctgcg  21660
gtaaagctca tcagcgtggt cgtgaagcga ttcacagatg tctgcctgtt catccgcgtc  21720
cagctcgttg agtttctcca gaagcgttaa tgtctggctt ctgataaagc gggccatgtt  21780
aagggcggtt ttttcctgtt tggtcactga tgcctccgtg taagggggat ttctgttcat  21840
gggggtaatg ataccgatga aacgagagag gatgctcacg atacgggtta ctgatgatga  21900
acatgcccgg ttactggaac gttgtgaggg taaacaactg gcggtatgga tgcggcggga  21960
ccagagaaaa atcactcagg gtcaatgcca gcgcttcgtt aatacagatg taggtgttcc  22020
acagggtagc cagcagcatc ctgcgatgca gatccggaac ataatggtgc agggcgctga  22080
cttccgcgtt tccagacttt acgaaacacg gaaaccgaag accattcatg ttgttgctca  22140
ggtcgcagac gttttgcagc agcagtcgct tcacgttcgc tcgcgtatcg             22190
```

<210> SEQ ID NO 3
<211> LENGTH: 14130

<212> TYPE: DNA
<213> ORGANISM: Artificial Sequence
<220> FEATURE:
<223> OTHER INFORMATION: Targetting vector (short version)

<400> SEQUENCE: 3
gcggccgcaa cctgggcaaa tgggagctta gcaacaatgt agggggctgg acctagactt 60
cctacacatg tgtaacagat gtgcagcttg gtcttcatgt gtgtattacc ctaacatttg 120
gagcaggagc tgtctctgac tctgttgcct gccattggat ccccttcccc tgcttgggct 180
gccttgtttg gccttagtag gaaaggatgt gcttagtcct gctgtgactt gatgtcccta 240
ggcagaatga taccccaggg gggctcccca tctctgagga gatgggcaaa gggtaatggt 300
tggagggact tgtgaggctg ggactgggag gagagaaagg agacagctgt aactggaatg 360
atgttaagtg aacaaatgaa tggatagatt agatagacag atagacagac agacagacag 420
acagacagac agacagacag acagacagat agaaagatag atagataagg ggaaaaagaa 480
acgtagctga gcaagccaga gagagcaagc caaataagca gcattcctcc atgacttttc 540
cttcagctcc tgcctatgag tctgccttga cttccctcag tgattggttg taagttaaaa 600
ggtgaaataa accctttctt tgacaagttg cttttggttc tgatttttat cacagcaaga 660
gaaaatcaaa ctagaacaaa catgtatttt tcctggcaca tgtccatagt aaggcagaaa 720
tgatcttcag acctagacca tagatactac agagagcaga agtgtagata ggtggactta 780
ctgtatgatt gtaatccaag taaatctaca tagctagaga gctagaggaa aggccaaagc 840
ttcctctggg aggtcagatc ctgtcgcact gtagccaata aggcatattg catcacagga 900
aaggactaag acccaggctg gcaatagtgt ctgtatctta actagatctc tctagtgagt 960
gaggaagtaa atttgtgaga gcccagactg tgggctcgga aggtacctgc catgcccctg 1020
ttagtaactg agtactacag caggagcagg tgttctctag aaagcctgag acaactctac 1080
ttcttctctc aagagaccac ctaatacagg cctgagagaa cagactctgg aaatagatgg 1140
gacttacgga gctaagatct agagctcatc tacagagcag aatcccagcc aagagaacaa 1200
agaatactga ctctctcctg ttccctactc ctagagttct aaaacacact atagggaagg 1260
gagcctctag acctccgtcc attccccatc ttgctcattc catcttccca tgtccccagg 1320
tctccaagcc acagacacca cctttcctat tcacccacct ttctgtgtcc ctaggtcccc 1380
aggccatagt cacctccccc cacaccccgc tcaccctgcc ccatctatgc ccctagatgc 1440
ttacttacca gagtcttttg tctgacgtgg ggctacaagc atctatgctc cctaagcacc 1500
tactgctgac ctgtaggacc cagctctgaa ccaactcata taagtaaata cagactctcc 1560
cctgtcttag gatggccccc tgggtcagga ggagaccact gccaaggaac cttctcttag 1620
agcactgaac tcctcccctg taccacttag gacagacctg agacctatta ttactgatta 1680
ccagagctct ggcagtgacc acggaggaga tagatccacc ctggacacag gaaacacagc 1740
accagagata ctgcttcatc acaacagtag agtgacactt tagactttaa tttgggtcac 1800
tttcctgctg tagaggtggg atcagaaagc aaagagcagt atgagtgcct gataggcacc 1860
caagtacact atagagtact catggtgaat aaggtacctc catggcttcc cagggagggg 1920
cactgcccca cccccaccat cacagacctt tctccatagt tgataactca gacacaagtg 1980
aatgacagat ggacctccat ctgctcttat tttaaaaaga agacaaaccc cacaggctcg 2040
agaactttag cgactgtttt gagagaaatc attggtccct gactcaagag atgactggca 2100
gattggggat cagaataccc atactctgtg gctagtgtga ggtttaagcc tcagagtccc 2160

-continued

```
tgtggtctct gactggtgca aggttttgac taagcggagc accacagtgc taactgggac   2220
cacggtgaca cgtggctcaa caaaaacctt ctgtttggag ctctccaggg gcagcctgag   2280
ctatgaggaa gtagagaggc ttgagaaatc tgaggaagaa aagagtagat ctgagaggaa   2340
aggtagcttt ctggaggtca ggagacagtg cagagaagaa cgagttactg tggacaggtc   2400
ttagatgggg aaagaatgag caaatgcaag catcagaagg gtggatgcaa tgtcctgcca   2460
aggacttacc aagaggatcc ccggacagag caggcaggtg gagttgactg agaggacagg   2520
ataggtgcag gtccctctct tgtttccttt ctccttctcc tgtttccttc ttctcttgtc   2580
acaggtctca ctatgctagc caaggctagc ctgaaagatt accatcctac agatgggccc   2640
atccagttga attaaggtgg agatctctcc aaacatctga gtttctgagg cttggatgcc   2700
actggggacg ccaagggact ttgggatggg tttggttggc cccagatgaa gggctacttc   2760
actgggtcta taattactct gatgtctagg accagggggc tcaggtcact caggtcaggt   2820
gagtcctgca tctggggact gtggggttca ggtggcctaa ggcaggatgt ggagagagtt   2880
ttagtatagg aacagaggca gaacagagac tgtgctactg gtacttcgat gtctggggca   2940
cagggaccac ggtcaccgtc tcctcaggta agctggcttt tttctttctg cacattccat   3000
tctgaaacgg gaaaagatat tctcagatct ccccatgtca ggccatctgc cacactctgc   3060
atgctgcaga agcttttctg taaggatagg gtcttcactc ccaggaaaag aggcagtcag   3120
aggctagctg cctgtggaac agtgacaatc atggaaaata ggcatttaca ttgttaggct   3180
acatgggtag atgggttttt gtacacccac taaaggggtc tatgatagtg tgactacttt   3240
gactactggg gccaaggcac cactctcaca gtctcctcag gtgagtcctt acaacctctc   3300
tcttctattc agcttaaata gattttactg catttgttgg gggggaaatg tgtgtatctg   3360
aatttcaggt catgaaggac tagggacacc ttgggagtca gaaagggtca ttgggagccc   3420
tggctgacgc agacagacat cctcagctcc catacttcat ggccagagat ttatagggat   3480
cctggccagc attgccgcta ggtccctctc ttctatgctt tctttgtccc tcactggcct   3540
ccatctgaga tcatcctgga gccctagcca aggatcattt attgtcaggg gtctaatcat   3600
tgttgtcaca atgtgcctgg tttgcttact ggggccaagg gactctggtc actgtctctg   3660
caggtgagtc ctaacttctc ccattctaaa tgcatgttgg ggggattctg ggccttcagg   3720
accaagattc tctgcaaacg ggaatcaaga ttcaacccct ttgtcccaaa gttgagacat   3780
gggtctgggt cagggactct ctgcctgctg gtctgtggtg acattagaac tgaagtatga   3840
tgaaggatct gccagaactg aagcttgaag tctgaggcag aatcttgtcc agggtctatc   3900
ggactcttgt gagaattagg ggctgacagt tgatggtgac aatttcaggg tcagtgactg   3960
tctggtttct ctgaggtgag gctggaatat aggtcacctt gaagactaaa gaggggtcca   4020
ggggcttctg cacaggcagg gaacagaatg tggaacaatg acttgaatgg ttgattcttg   4080
tgtgacacca ggaattggca taatgtctga gttgcccagg ggtgattcta gtcagactct   4140
ggggtttttg tcgggtatag aggaaaaatc cactattgtg attactatgc tatggactac   4200
tggggtcaag gaacctcagt caccgtctcc tcaggtaaga atggcctctc caggtcttta   4260
tttttaacct ttgttatgga gttttctgag cattgcagac taatcttgga tatttgtccc   4320
tgagggagcc ggctgagaga agttgggaaa taaactgtct agggatctca gagcctttag   4380
gacagattat ctccacatct ttgaaaaact aagaatctgt gtgatggtgt tggtggagtc   4440
cctggatgat gggataggga ctttggaggc tcatttgaag aagatgctaa aacaatccta   4500
tggctggagg gatagttggg gctacgcgtt tttaacccta gaaagatagt ctgcgtaaaa   4560
```

-continued

```
ttgacgcatg cattcttgaa atattgctct ctctttctaa atagcgcgaa tccgtcgctg   4620
tgcatttagg acatctcagt cgccgcttgg agctcccgtg aggcgtgctt gtcaatgcgg   4680
taagtgtcac tgattttgaa ctataacgac cgcgtgagtc aaaatgacgc atgattatct   4740
tttacgtgac ttttaagatt taactcatac gataattata ttgttatttc atgttctact   4800
tacgtgataa cttattatat atatattttc ttgttataga tatcgctagt ggatcctggt   4860
tctttccgcc tcagaaggta cttttttttt ttttttttt ttttttttt ttttttttt   4920
ttttttttt ttttttttt taaatttttg ggaatttatt gatttgcatt taaaagggaa   4980
ctgctgacaa agattcactg gtaataattt gaacaagttg gaaaatacag tcaacattac   5040
tgaaacacta ctaaaataat tccaggacag aacaaaactt cttagatgct gtctttgatg   5100
tgaaaattga ctgcttctta cttttctaac acacggtggt ataattaaca atattcaatc   5160
acttctattc tttcctgcat atataaaaat taaaatacca attaaaaaac taatatatct   5220
tctctttatt tcttacagat atgagttcaa tgtttcactc aatagtgctg tggtttaaga   5280
gaatttttc atttacaagt taaacaacaa tccgcccaaa gggaactgat agtctatagg   5340
ctcatagtgc aaataaacag tttaggaatg cagcaactga catttctaaa gtacaaaaca   5400
gataaaattc ttagaagata catgcaaaaa gctctactaa gcagatggcc acagaactag   5460
aacattgata attttactgg cgatgtcaat aggactccag atgtttccaa actcaacttg   5520
aactctcatc ttaggctttg tattttgctt ttccagtttc actaatgaca caaacatgat   5580
tcaaatccct gaagtattca ttatagtcaa gggcatatcc tacaacaaac ttgtctggaa   5640
tttcaaatcc aacaaagtct ggcttatatc caacacttcg tggggtcctt ttcaccagca   5700
agcttgcgac cttgaccatc tttggattat actgcctgac caaggaaagc aaagtctgca   5760
ttgttttgcc agtgtcaatt atatcttcca caatcaagac attctttcca gttaaagttg   5820
agagatcatc tccaccaatt acttttatgt cccctgttga ctggtcatta caatagctct   5880
tcagtctgat aaaatctaca gtcataggaa tggatctatc actatttcta ttcagtgctt   5940
tgatgtaatc cagcaggtca gcaaagaatt tatagccccc cttgagcaca cagagggcta   6000
caatgtgatg gcctcccatc tccttcatca catctcgagc aagacgttca gtcctacaga   6060
aataaaatca ggaatttaat agaaagtttc atacattaaa ctttataaca aacacctctt   6120
agtcattaaa cttccacacc aacctgggca atatagtgag accccatgcc tgcaaaaaaa   6180
aaaaaattag ccaggcatgg tagcatgtac ctgtagtccc agctacttga gaggtgaggt   6240
gggaaaatca ctttagtgca ggatgttgag gctggagtga actgtgattg tgccactgca   6300
ctccagcctg gacaatagag caagaccttg tctcaaaaaa atgcattaaa aattttttt   6360
aaatcttcca cgtaacacat cctttgccct catgtttcat aaggtaaaaa atttgatacc   6420
ttcaaaaaaa ccaagcatac cactatcata attttttta aatgcaaata aaaacaagat   6480
accattttca cctatcagac tggcaggttc tgattaaatg aaatttcttg gataatatac   6540
aatattaaga gagactgtag aaactgggcc agtggctcat gcctgtaatc ccagcacttt   6600
gggaggctgg gtaacatggc gaaccctgtt tctacaaaat aaaaatatta gctgggagtg   6660
gtggcgcaca cctatagtcc cagctactca ggaggctgag gtggaaggat cgcttgaacc   6720
caggaggttg agactgcagt gaactgtgat cattctgctg cactgcaccc cagcctgggc   6780
aacagagacc ttgtctcaaa aaaaaaaaaa aaagagacaa attgtgaaga gaaaggtact   6840
ctcatataac atcaggagta taaaatgatt caacttctta gaggaaaatt tggcaatacc   6900
```

-continued

```
aaaatattca ataaactctt tcccccttgac ccagaaattc cacttgaata aagctgaaca   6960
agtaccaaac atgtaaaaga atgtttcttc tagtacagtc ggtaagaaca aaatagtgtc   7020
tatcaatagt ggactggtta aatcagttat ggtatctcca taagacagaa tgctatgcaa   7080
cctttaaaat atattagata gctctagaca gtggatcccc tcgagggacc taataacttc   7140
gtatagcata cattatacga agttatatta agggttattg aatatgtcga ctagacacac   7200
taatattaaa agtgtccaat aacatttaaa actatactca tacgttaaaa tataaatgta   7260
tatatgtact tttgcatata gtatacatgc atagccagtg cttgagaaga aatgtgtaca   7320
gaaggctgaa aggagagaac tttagtcttc ttgtttatgg cctccatagt tagaatattt   7380
tataacacaa atattttgat attataattt taaaataaaa acacagaata gccagacata   7440
caatgcaagc attcaatacc aggtaaggtt tttcactgta attgacttaa cagaaaattt   7500
tcaagctaga tgtgcataat aataaaaatc tgaccttgcc ttcatgtgat tcagccccag   7560
tccattaccc tgtttaggac tgagaaatgc aagactctgg ctagagttcc ttcttccatc   7620
tcccttcaat gtttactttg ttctggtccc tacagagtcc cactatacca caactgatac   7680
taagtaatta gtaaggccct cctcttttat ttttaataaa gaagatttta gaaagcatca   7740
gttatttaat aagttggcct agtttatgtt caaatagcaa gtactcagaa cagctgctga   7800
tgtttgaaat taacacaaga aaaagtaaaa aacctcattt taagatctta cttacctgtc   7860
cataattagt ccatggggaa taaacaccct ttccaaatcc tcagcataat gattaggtat   7920
gcaaaataaa tcaaggtcat aacctggttc atcatcacta atcacgacgc cagggctgcg   7980
ggtcgccata acggagccgg ccggcgcgcg ggctgaataa cttcgtataa tgtgtactat   8040
acgaagttat ttgttcagga ggaggaagcc ggtggcggag cagaggagga ggcggaggcg   8100
cagcaagacc cccccccccc tgcaggtcga aaggcccgga gatgaggaag aggagaacag   8160
cgcggcagac gtgcgctttt gaagcgtgca gaatgccggg cctccggagg accttcgggc   8220
gcccgccccg cccctgagcc cgcccctgag cccgcccccg gacccacccc ttcccagcct   8280
ctgagcccag aaagcgaagg agccaaagct gctattggcc gctgccccaa aggcctaccc   8340
gcttccattg ctcagcggtg ctgtccatct gcacgagact agtgagacgt gctacttcca   8400
tttgtcacgt cctgcacgac gcgagctgcg gggcgggggg gaacttcctg actaggggag   8460
gagtagaagg tggcgcgaag gggccaccaa agaacggagc cggttggcgc ctaccggtgg   8520
atgtggaatg tgtgcgaggc cagaggccac ttgtgtagcg ccaagtgccc agcggggctg   8580
ctaaagcgca tgctccagac tgccttggga aaagcgcctc ccctacccgg tagatatcta   8640
taacaagaaa atatatatat aataagttat cacgtaagta gaacatgaaa taacaatata   8700
attatcgtat gagttaaatc ttaaaagtca cgtaaaagat aatcatgcgt cattttgact   8760
cacgcggtcg ttatagttca aaatcagtga cacttaccgc attgacaagc acgcctcacg   8820
ggagctccaa gcggcgactg agatgtccta aatgcacagc gacggattcg cgctatttag   8880
aaagagagag caatatttca agaatgcatg cgtcaatttt acgcagacta tctttctagg   8940
gttaaaagaa ttcgtagttg gagattttca gtttttagaa taaaagtatt agctgcggaa   9000
tatacttcag gaccacctct gtgacagcat ttatacagta tccgatgcat agggacaaag   9060
agtggagtgg ggcactttct ttagatttgt gaggaatgtt ccacactaga ttgtttaaaa   9120
cttcatttgt tggaaggaga gctgtcttag tgattgagtc aagggagaaa ggcatctagc   9180
ctcggtctca aaagggtagt tgctgtctag agaggtctgg tggagcctgc aaaagtccag   9240
ctttcaaagg aacacagaag tatgtgtatg gaatattaga agatgttgct tttactctta   9300
```

-continued

```
agttggttcc taggaaaaat agttaaatac tgtgacttta aaatgtgaga gggttttcaa   9360
gtactcattt ttttaaatgt ccaaaatttt tgtcaatcaa tttgaggtct tgtttgtgta   9420
gaactgacat tacttaaagt ttaaccgagg aatgggagtg aggctctctc ataccctatt   9480
cagaactgac ttttaacaat aataaattaa gtttaaaata tttttaaatg aattgagcaa   9540
tgttgagttg gagtcaagat ggccgatcag aaccagaaca cctgcagcag ctggcaggaa   9600
gcaggtcatg tggcaaggct atttggggaa gggaaaataa aaccactagg taaacttgta   9660
gctgtggttt gaagaagtgg ttttgaaaca ctctgtccag ccccaccaaa ccgaaagtcc   9720
aggctgagca aaacaccacc tgggtaattt gcatttctaa aataagttga ggattcagcc   9780
gaaactggag aggtcctctt ttaacttatt gagttcaacc ttttaatttt agcttgagta   9840
gttctagttt ccccaaactt aagtttatcg acttctaaaa tgtatttaga attcattttc   9900
aaaattaggt tatgtaagaa attgaaggac tttagtgtct ttaatttcta atatatttag   9960
aaaacttctt aaaattactc tattattctt ccctctgatt attggtctcc attcaattct  10020
tttccaatac ccgaagcatt tacagtgact ttgttcatga tctttttttag ttgtttgttt  10080
tgccttacta ttaagacttt gacattctgg tcaaaacggc ttcacaaatc tttttcaaga  10140
ccactttctg agtattcatt ttaggagaaa tacttttttt ttaaatgaat gcaattatct  10200
agacttattt cggttgaaca tgctggttgg tggttgagag gacactcagt cagtcagtgg  10260
cgtgaagggc ttctaagcca gtccacatgc tctgtgtgaa ctccctctgg ccctgcttat  10320
tgttgaatgg gccaaaggtc tgagaccagg ctgctgctgg gtaggcctgg actttgggtc  10380
tcccacccag acctgggaat gtatggttgt ggcttctgcc acccatccac ctggctgctc  10440
atggaccagc cagcctcggt ggctttgaag gaacaattcc acacaaagac tctggacctc  10500
tccgaaacca ggcaccgcaa atggtaagcc agaggcagcc acagctgtgg ctgctgctct  10560
taaagcttgt aaactgtttc tgcttaagag ggactgagtc ttcagtcatt gctttagggg  10620
gagaaagaga catttgtgtg tcttttgagt accgttgtct gggtcactca catttaactt  10680
tccttgaaaa actagtaaaa gaaaaatgtt gcctgttaac caataatcat agagctcatg  10740
gtattttgag gaaatcttag aaaacgtgta tacaattgtc tggaattatt tcagttaagt  10800
gtattagttg aggtactgat gctgtctcta cttcagttat acatgtgggt ttgaattttg  10860
aatctattct ggctcttctt aagcagaaaa tttagataaa atggatacct cagtggtttt  10920
taatggtggg tttaatatag aaggaattta aattggaagc taatttagaa tcagtaagga  10980
gggacccagg ctaagaaggc aatcctggga ttctggaaga aaagatgttt ttagttttta  11040
tagaaaacac tactacattc ttgatctaca actcaatgtg gtttaatgaa tttgaagttg  11100
ccagtaaatg tacttcctgg ttgttaaaga atggtatcaa aggacagtgc ttagatccaa  11160
ggtgagtgtg agaggacagg ggctggggta tggatacgca gaaggaaggc cacagctgta  11220
cagaattgag aaagaataga gacctgcagt tgaggccagc aggtcggctg gactaactct  11280
ccagccacag taatgaccca gacagagaag gccagactca taaagcttta tcgataccgt  11340
cgacctcgag ggggggcccg gtacctttct tagacgtcag gtggcacttt tcggggaaat  11400
gtgcgcggaa cccctatttg tttatttttc taaatacatt caaatatgta tccgctcatg  11460
agacaataac cctgataaat gcttcaataa tattgaaaaa ggaagagtat gagtattcaa  11520
catttccgtg tcgcccttat tccctttttt gcggcatttt gccttcctgt ttttgctcac  11580
ccagaaacgc tggtgaaagt aaaagatgct gaagatcagt tgggtgcacg agtgggttac  11640
```

-continued

```
atcgaactgg atctcaacag cggtaagatc cttgagagtt ttcgccccga agaacgtttt  11700
ccaatgatga gcacttttaa agttctgcta tgtggcgcgg tattatcccg tgttgacgcc  11760
gggcaagagc aactcggtcg ccgcatacac tattctcaga atgacttggt tgagtactca  11820
ccagtcacag aaaagcatct tacggatggc atgacagtaa gagaattatg cagtgctgcc  11880
ataaccatga gtgataacac tgcggccaac ttacttctga caacgatcgg aggaccgaag  11940
gagctaaccg cttttttgca caacatgggg gatcatgtaa ctcgccttga tcgttgggaa  12000
ccggagctga atgaagccat accaaacgac gagcgtgaca ccacgatgcc tgcagcaatg  12060
gcaacaacgt tgcgcaaact attaactggc gaactactta ctctagcttc ccggcaacaa  12120
ttaatagact ggatggaggc ggataaagtt gcaggaccac ttctgcgctc ggcccttccg  12180
gctggctggt ttattgctga taaatctgga gccggtgagc gtgggtctcg cggtatcatt  12240
gcagcactgg ggccagatgg taagccctcc cgtatcgtag ttatctacac gacggggagt  12300
caggcaacta tggatgaacg aaatagacag atcgctgaga taggtgcctc actgattaag  12360
cattggtaac tgtcagacca agtttactca tatatacttt agattgattt aaaacttcat  12420
ttttaattta aaaggatcta ggtgaagatc ctttttgata atctcatgac caaaatccct  12480
taacgtgagt tttcgttcca ctgagcgtca gaccccgtag aaaagatcaa aggatcttct  12540
tgagatcctt tttttctgcg cgtaatctgc tgcttgcaaa caaaaaaacc accgctacca  12600
gcggtggttt gtttgccgga tcaagagcta ccaactcttt ttccgaaggt aactggcttc  12660
agcagagcgc agataccaaa tactgtcctt ctagtgtagc cgtagttagg ccaccacttc  12720
aagaactctg tagcaccgcc tacatacctc gctctgctaa tcctgttacc agtggctgct  12780
gccagtggcg ataagtcgtg tcttaccggg ttggactcaa gacgatagtt accggataag  12840
gcgcagcggt cgggctgaac ggggggttcg tgcacacagc ccagcttgga gcgaacgacc  12900
tacaccgaac tgagatacct acagcgtgag ctatgagaaa gcgccacgct tcccgaaggg  12960
agaaaggcgg acaggtatcc ggtaagcggc agggtcggaa caggagagcg cacgagggag  13020
cttccagggg gaaacgcctg gtatctttat agtcctgtcg ggtttcgcca cctctgactt  13080
gagcgtcgat ttttgtgatg ctcgtcaggg gggcggagcc tatggaaaaa cgccagcaac  13140
gcggcctttt tacggttcct ggccttttgc tggccttttg ctcacatgtt ctttcctgcg  13200
ttatcccctg attctgtgga taaccgtatt accgcctttg agtgagctga taccgctcgc  13260
cgcagccgaa cgaccgagcg cagcgagtca gtgagcgagg aagcggaaga gcgcctgatg  13320
cggtattttc tccttacgca tctgtgcggt atttcacacc gcatatggtg cactctcagt  13380
acaatctgct ctgatgccgc atagttaagc cagtatacac tccgctatcg ctacgtgact  13440
gggtcatggc tgcgccccga cacccgccaa cacccgctga cgcgccctga cgggcttgtc  13500
tgctcccggc atccgcttac agacaagctg tgaccgtctc cgggagctgc atgtgtcaga  13560
ggttttcacc gtcatcaccg aaacgcgcga ggcagctgcg gtaaagctca tcagcgtggt  13620
cgtgaagcga ttcacagatg tctgcctgtt catccgcgtc cagctcgttg agtttctcca  13680
gaagcgttaa tgtctggctt ctgataaagc gggccatgtt aagggcggtt ttttcctgtt  13740
tggtcactga tgcctccgtg taagggggat ttctgttcat gggggtaatg ataccgatga  13800
aacgagagag gatgctcacg atacgggtta ctgatgatga acatgcccgg ttactggaac  13860
gttgtgaggg taaacaactg gcggtatgga tgcggcggga ccagagaaaa atcactcagg  13920
gtcaatgcca gcgcttcgtt aatacagatg taggtgttcc acagggtagc cagcagcatc  13980
ctgcgatgca gatccggaac ataatggtgc agggcgctga cttccgcgtt tccagacttt  14040
```

acgaaacacg gaaaccgaag accattcatg ttgttgctca ggtcgcagac gttttgcagc 14100
agcagtcgct tcacgttcgc tcgcgtatcg 14130

<210> SEQ ID NO 4
<211> LENGTH: 3551
<212> TYPE: DNA
<213> ORGANISM: Mus musculus
<220> FEATURE:
<221> NAME/KEY: misc_feature
<222> LOCATION: (1399)..(1498)
<223> OTHER INFORMATION: n is a, c, g, or t

<400> SEQUENCE: 4
aagcttgctg agcaaaatta agggaacaag gttgagagcc ctagtaagcg aggctctaaa 60
aagcatggct gagctgagat gggtgggctt ctctgagcgc ttctaaaatg cgctaaactg 120
aggtgattac tctgaggtaa gcaaagctgg gcttgagcca aaatgaagta gactgtaatg 180
aactggaatg agctgggccg ctaagctaaa ctaggctggc ttaaccgaga tgagccaaac 240
tggaatgaac ttcattaatc taggttgaat agagctaaac tctactgcct acactggact 300
gttctgagct gagatgagct ggggtgagct cagctatgct acgctgtgtt ggggtgagct 360
gatctgaaat gagctactct ggagtagctg agatggggtg agatggggtg agctgagctg 420
ggctgagctg gactgagctg agctagggtg agctgagctg ggtgagctga gctaagctgg 480
ggtgagctga gctgagcttg actgagctag ggtgagctgg actgagctgg ggtgagctga 540
gctgagctgg ggtaagctgg gatgagctgg ggtgagctga gctgagctgg agtgagctga 600
gctgggctga gctggggtga gctgggctgg gctgagctgg ggtgagctgg gctgagctgg 660
ggtgagctga gctggggtga gctgagctga gctggggtga gctgagctga gctggggtga 720
gctgagctgg ggtgagctga gctgagctgg gctgagctga ggtgagctga gctggggtga 780
gctgagctgg ggtgagctga gctgagctgg ggtaagctgg gatgagctgg ggtgagctga 840
gctgagctgg agtgagctga gctgggctga gctgggctga gctggggtga gctgagctgg 900
ggtgagctga gctgagctgg gctgagctga ggtgagctga gctggggtga gctgagctga 960
gctggggtga gctgagctga gctggggtga gctgagctgg ggtgagctga gctggggtga 1020
gctgagctga gctggggtga gctgagctgg ggtgagctga gctgagctgg ggtgagctga 1080
gctgagctgg ggtgagctga gctgagctga gctggggtga gctgagctga gctggggtga 1140
gctgagctga gctggggtga gctgagctgg ggtgagctgg gctgagctga gctgggctga 1200
gctgagctga gctgagctga gctggggtga gctgagctgg gctgagctgg ggtgagctgg 1260
gctgagctgg ggtgagctga gctggggtga gctgagctga gctggggtga gctgagctga 1320
gctggggtga gctgagctgg ggtgagctga gctgagctgg gctgagctga gctgagctgg 1380
ggtgagctga gctgagctnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnag 1500
ctgagctgag ctgagctgag ctgagctggg gtgagctggg gtgagctgag ctggggtgag 1560
ctgagctgag ctggggtgag ctgagctgag ctgagctgag ctgagctgag ctgggtgagc 1620
tgagctgagc tgagctgggg tgagctgagc tggggtgagc tgagctgagc tggggtgagc 1680
tgagctgggg tgagctgagc tgagctgggg tgagctgggg tgagctgggg tgagctgggg 1740
tgagctgagc tgaactgggg tgagctgggc tgagctgggg tgagctgagc tgagctgggc 1800
tgagctgggg tgagctgggg tgagctgggg tgagctgagc tgagctaggg tgagctgagc 1860

-continued

```
tgagctaggg tgagctgagc tgagctgggg tgagctgagc tgagctgggg tgagctgagc   1920

tgagctgggg tgagctgagc tgagctgggg tgagctgagc tgagctgggg tgagcttggc   1980

tgagctgggg tgagctgggg tgagctgagc tggggtgagc tggggtaagc tgagctgagc   2040

tggggtgagc tgagctgagc tggggtgagc tggggtgagc tgagctgagc tgagctgggt   2100

gatctgagct gagctgagct gggtgagctg agctgagctg agctgggtga gctgagctga   2160

gctgagctga gctgggtgag ctgagctgag ctgagctgag ctgagctgag ctggggtgag   2220

ctgggctgag ctgagctgag ctggggtgag ctgagctgag ctgagctgag ctggggtgag   2280

ctgggctgag ctggggtgag ctgggctgag ctgagctggg tgagctgagc tgaactgagc   2340

tgagctgggt gagctgagct gagctgagct gggtgagctg agctgggctg agctgagctg   2400

ggtgagctga gctgaactga gctgagctgg gtgagctgag ctgagctgag ctgggtgagc   2460

tgagctgggg tgagctgagc tgagctgggg tgagctgagc tgagctgagc tgggtgagct   2520

gagctggggt gagctgagct gagctggggt gagctgagct gagctggggt gagctgagct   2580

gagctggggt gagctgagct gagctggggt gagctgagct agggtgaact gggctgggtg   2640

agctggagtg agctgagctg aggtgaactg gggtgagccg ggatgttttg agttgagctg   2700

gggtaagatg agctgaactg gggtaagatg ggatgagctg tggtgagggg agctggattg   2760

aactgagctg tgtgagctga gctggggtca gctgagcaag agtgagtaga gctggctggc   2820

cagaaccaga atcaattagg ctaagtgagc cagattgcgc tgggatcagc tgtactcaga   2880

tgagctggga tgaggtaggc tgggatgagc tgggctagct gacatggatt atgtgaggct   2940

gagctagcat gggctggcct agctgatgag ctaagcttga atgaacgggg ctgagctgga   3000

ctcagatgtg ctagactgag ctgtactgga tgatctggtg tagggtgatc tggactcaac   3060

tgggctggct gatgggatgc cccaggttga actaggctca gataagttag gctgagtagg   3120

gcctggttga gatggttcgg gatgagctgg gaaaagatgg actgggacca tgaactgggc   3180

tgagctgggt tgggagacca tgaattgagc tgaactgagt gcagctggga taaactgggt   3240

tgagctaaga atagactacc tgaattgtgc caaactgggc tgggatcaat tggaaattat   3300

caggatttag atgagccgga ctaaactatg ctgagctgga ctggttggat gtgttgaact   3360

ggcctgctgc tgggctggca tagctgagtt gaacttaaat gaggaaggat gagcaaggct   3420

agcctgcttg catagagctg aactttagcc tagcctgagc tggaccagcc tgagctgagt   3480

aggtctaaac tgagttaaaa atcaacaggg ataatttaac agctaattta acaagcctga   3540

ggtctgagat t                                                        3551
```

```
<210> SEQ ID NO 5
<211> LENGTH: 2484
<212> TYPE: DNA
<213> ORGANISM: Mus musculus

<400> SEQUENCE: 5

aagcttgctg agcaaaatta agggaacaag gttgagagcc ctagtaagcg aggctctaaa     60

aagcacagct gagctgagat gggtgggctt ctctgagtgc ttctaaaatg cgctaaactg    120

aggtgattac tctgaggtaa gcaaagctgg gcttgagcca aaatgaagta gactgtaatg    180

aactggaatg agctgggccg ctaagctaaa ctaggctggc ttaaccgaga tgagccaaac    240

tggaatgaac ttcattaatc taggttgaat agagctaaac tctactgcct acactggact    300

gttctgagct gagatgagct ggggtgagct cagctatgct acgctgtgtt ggggtgagct    360

gatctgaaat gagatactct ggagtagctg agatggggtg agatggggtg agctgagctg    420
```

```
ggctgagcta gactgagctg agctagggtg agctgagctg ggtgagctga gctaagctgg    480
ggtgagctga gctgagcttg gctgagctag ggtgagctgg gctgagctgg ggtgagctga    540
gctgagctgg ggtaagctgg gatgagctgg ggtgagctga gctgagctgg agtgagctga    600
gctgggctga gctggggtga gctgggctga gctgggctga gctgggctga gctggggtga    660
gctgagctgg ggtgagctga gctgagctgg ggtgagctga gctgagctgg ggtgagctgg    720
ggtgagctga gctggggtga gctgagctga gctggggtga gctgagctgg ggtgagctga    780
gctgagctgg ggtgagctga gctgagctga gctgagctga gctggggtga gctgagctga    840
gctgagctgg ggtgagctgg ggtgagctga gctgagctgg agtgagctga gctgggctga    900
gctggggtga gctgggctga gctggggtga gctgagctga gctgagctga gctggggtga    960
gctgagctga gctggggtga gctgagctgg ggtgagctgg gctgagctga gctgagctga   1020
gctgagctga gctgagctga gctgagctga gctgagctga gctgagctga gctgagctga   1080
gctgagctgg ggtgagctga gctgagctgg gctgagctgg ggtgagctgg gctgagctgg   1140
gctgagctgg gctgagctgg ggtgagctga gctggggtga gctgagctga gctgggctga   1200
gctgagctga gctggggtga gctgagctga gctggggtga gctgagctga gctgagctgg   1260
ggtgagctga gctgggctga gcagggctga gctggggtga gctgagctga gctggggtga   1320
gctgggctga gctgggctga gctgagctga gctgggctga gctgggctga gctgggctga   1380
gctgggctga gctgggctga gctggggtga gctgagctga gctggggtga gctggggtga   1440
gctgagctgg ggtgagctga gctggggtga gctgagctga gctggggtga gctgagctgg   1500
ggtgagctga gctgagctgg ggtgagctga gctgagctgg ggtgagctga gctagggtga   1560
actgggctgg gtgagctgga gtgagctgag ctgaggtgaa ctggggtgag ccgggatgtt   1620
ttgagttgag ctggggtaag atgagctgaa ctggggtaaa ctgggatgag ctgtggtgag   1680
cggagctgga ttgaactgag ctgtgtgagc tgagctgggg tcagctgagc aagagtgagt   1740
agagctggct ggccagaacc agaatcaatt aggctaagtg agccagattg tgctgggatc   1800
agctgtactc agatgagctg ggatgaggta ggctgggatg agctgggcta gctgacatgg   1860
attatgtgag gctgagctag catgggctgg cctagctgat gagctaagct tgaatgagcg   1920
gggctgagct ggactcagat gtgctagact gagctgtact ggatgatctg gtgtagggtg   1980
atctggactc aactgggctg gctgatggga tgcgccaggt tgaactaggc tcagataagt   2040
taggctgagt agggcctggt tgagatggtt cgggatgagc tgggaaaaga tggactcgga   2100
ccatgaactg ggctgagctg ggttgggaga ccatgaattg agctgaactg agtgcagctg   2160
ggataaactg ggttgagcta agaatagact acctgaattg tgccaaactc ggctgggatc   2220
aattggaaat tatcaggatt tagatgagcc ggactaaact atgctgagct ggactggttg   2280
gatgtgttga actggcctgc tgctgggctg gcatagctga gttgaactta aatgaggaag   2340
gctgagcaag gctagcctgc ttgcatagag ctgaacttta gcctagcctg agctggacca   2400
gcctgagctg agtaggtcta aactgagtta aaaatcaaca gggataattt aacagctaat   2460
ttaacaagcc tgaggtctga gatt                                          2484
```

<210> SEQ ID NO 6
<211> LENGTH: 4515
<212> TYPE: DNA
<213> ORGANISM: Artificial Sequence
<220> FEATURE:
<223> OTHER INFORMATION: 5' homology arm of targetting vector

<400> SEQUENCE: 6
aacctgggca aatgggagct tagcaacaat gtagggggct ggacctagac ttcctacaca 60
tgtgtaacag atgtgcagct tggtcttcat gtgtgtatta ccctaacatt tggagcagga 120
gctgtctctg actctgttgc ctgccattgg atccccttcc cctgcttggg ctgccttgtt 180
tggccttagt aggaaaggat gtgcttagtc ctgctgtgac ttgatgtccc taggcagaat 240
gataccccag gggggctccc catctctgag gagatgggca aagggtaatg gttggaggga 300
cttgtgaggc tgggactggg aggagagaaa ggagacagct gtaactggaa tgatgttaag 360
tgaacaaatg aatggataga ttagatagac agatagacag acagacagac agacagacag 420
acagacagac agacagacag atagaaagat agatagataa ggggaaaaag aaacgtagct 480
gagcaagcca gagagagcaa gccaaataag cagcattcct ccatgacttt tccttcagct 540
cctgcctatg agtctgcctt gacttccctc agtgattggt tgtaagttaa aaggtgaaat 600
aaaccctttc tttgacaagt tgcttttggt tctgattttt atcacagcaa gagaaaatca 660
aactagaaca aacatgtatt tttcctggca catgtccata gtaaggcaga aatgatcttc 720
agacctagac catagatact acagagagca gaagtgtaga taggtggact tactgtatga 780
ttgtaatcca agtaaatcta catagctaga gagctagagg aaaggccaaa gcttcctctg 840
ggaggtcaga tcctgtcgca ctgtagccaa taaggcatat tgcatcacag gaaaggacta 900
agacccaggc tggcaatagt gtctgtatct taactagatc tctctagtga gtgaggaagt 960
aaatttgtga gagcccagac tgtgggctcg gaaggtacct gccatgcccc tgttagtaac 1020
tgagtactac agcaggagca ggtgttctct agaaagcctg agacaactct acttcttctc 1080
tcaagagacc acctaataca ggcctgagag aacagactct ggaaatagat gggacttacg 1140
gagctaagat ctagagctca tctacagagc agaatcccag ccaagagaac aaagaatact 1200
gactctctcc tgttccctac tcctagagtt ctaaaacaca ctatagggaa gggagcctct 1260
agacctccgt ccattcccca tcttgctcat tccatcttcc catgtcccca ggtctccaag 1320
ccacagacac cacctttcct attcacccac ctttctgtgt ccctaggtcc ccaggccata 1380
gtcacctccc cccacacccc gctcaccctg ccccatctat gcccctagat gcttacttac 1440
cagagtcttt tgtctgacgt ggggctacaa gcatctatgc tccctaagca cctactgctg 1500
acctgtagga cccagctctg aaccaactca tataagtaaa tacagactct cccctgtctt 1560
aggatggccc cctgggtcag gaggagacca ctgccaagga accttctctt agagcactga 1620
actcctcccc tgtaccactt aggacagacc tgagacctat tattactgat taccagagct 1680
ctggcagtga ccacggagga gatagatcca ccctggacac aggaaacaca gcaccagaga 1740
tactgcttca tcacaacagt agagtgacac tttagacttt aatttgggtc actttcctgc 1800
tgtagaggtg ggatcagaaa gcaaagagca gtatgagtgc ctgataggca cccaagtaca 1860
ctatagagta ctcatggtga ataaggtacc tccatggctt cccagggagg ggcactgccc 1920
cacccccacc atcacagacc tttctccata gttgataact cagacacaag tgaatgacag 1980
atggacctcc atctgctctt attttaaaaa gaagacaaac cccacaggct cgagaacttt 2040
agcgactgtt ttgagagaaa tcattggtcc ctgactcaag agatgactgg cagattgggg 2100
atcagaatac ccatactctg tggctagtgt gaggtttaag cctcagagtc cctgtggtct 2160
ctgactggtg caaggttttg actaagcgga gcaccacagt gctaactggg accacggtga 2220
cacgtggctc aacaaaaacc ttctgtttgg agctctccag gggcagcctg agctatgagg 2280
aagtagagag gcttgagaaa tctgaggaag aaaagagtag atctgagagg aaaggtagct 2340

-continued

```
ttctggaggt caggagacag tgcagagaag aacgagttac tgtggacagg tcttagatgg   2400
ggaaagaatg agcaaatgca agcatcagaa gggtggatgc aatgtcctgc caaggactta   2460
ccaagaggat ccccggacag agcaggcagg tggagttgac tgagaggaca ggataggtgc   2520
aggtccctct cttgtttcct ttctccttct cctgtttcct tcttctcttg tcacaggtct   2580
cactatgcta gccaaggcta gcctgaaaga ttaccatcct acagatgggc ccatccagtt   2640
gaattaaggt ggagatctct ccaaacatct gagtttctga ggcttggatg ccactgggga   2700
cgccaaggga ctttgggatg ggtttggttg gccccagatg aagggctact tcactgggtc   2760
tataattact ctgatgtcta ggaccagggg gctcaggtca ctcaggtcag gtgagtcctg   2820
catctgggga ctgtggggtt caggtggcct aaggcaggat gtggagagag ttttagtata   2880
ggaacagagg cagaacagag actgtgctac tggtacttcg atgtctgggg cacagggacc   2940
acggtcaccg tctcctcagg taagctggct tttttctttc tgcacattcc attctgaaac   3000
gggaaaagat attctcagat ctccccatgt caggccatct gccacactct gcatgctgca   3060
gaagcttttc tgtaaggata gggtcttcac tcccaggaaa agaggcagtc agaggctagc   3120
tgcctgtgga acagtgacaa tcatggaaaa taggcattta cattgttagg ctacatgggt   3180
agatgggttt ttgtacaccc actaaagggg tctatgatag tgtgactact ttgactactg   3240
gggccaaggc accactctca cagtctcctc aggtgagtcc ttacaacctc tctcttctat   3300
tcagcttaaa tagattttac tgcatttgtt ggggggggaaa tgtgtgtatc tgaatttcag   3360
gtcatgaagg actagggaca ccttgggagt cagaaagggt cattgggagc cctggctgac   3420
gcagacagac atcctcagct cccatacttc atggccagag atttataggg atcctggcca   3480
gcattgccgc taggtccctc tcttctatgc tttctttgtc cctcactggc ctccatctga   3540
gatcatcctg gagccctagc caaggatcat ttattgtcag ggtctaatc attgttgtca   3600
caatgtgcct ggtttgctta ctggggccaa gggactctgg tcactgtctc tgcaggtgag   3660
tcctaacttc tcccattcta aatgcatgtt ggggggattc tgggccttca ggaccaagat   3720
tctctgcaaa cgggaatcaa gattcaaccc ctttgtccca aagttgagac atgggtctgg   3780
gtcagggact ctctgcctgc tggtctgtgg tgacattaga actgaagtat gatgaaggat   3840
ctgccagaac tgaagcttga agtctgaggc agaatcttgt ccagggtcta tcggactctt   3900
gtgagaatta ggggctgaca gttgatggtg acaatttcag ggtcagtgac tgtctggttt   3960
ctctgaggtg aggctggaat ataggtcacc ttgaagacta aagaggggtc caggggcttc   4020
tgcacaggca gggaacagaa tgtggaacaa tgacttgaat ggttgattct tgtgtgacac   4080
caggaattgg cataatgtct gagttgccca ggggtgattc tagtcagact ctggggtttt   4140
tgtcgggtat agaggaaaaa tccactattg tgattactat gctatggact actggggtca   4200
aggaacctca gtcaccgtct cctcaggtaa gaatggcctc tccaggtctt tatttttaac   4260
ctttgttatg gagttttctg agcattgcag actaatcttg gatatttgtc cctgagggag   4320
ccggctgaga gaagttggga aataaactgt ctagggatct cagagccttt aggacagatt   4380
atctccacat ctttgaaaaa ctaagaatct gtgtgatggt gttggtggag tccctggatg   4440
atgggatagg gactttggag gctcatttga agaagatgct aaaacaatcc tatggctgga   4500
gggatagttg gggct                                                   4515
```

<210> SEQ ID NO 7
<211> LENGTH: 25
<212> TYPE: DNA

<213> ORGANISM: Artificial Sequence
<220> FEATURE:
<223> OTHER INFORMATION: Oligonucleotide HV2-5

<400> SEQUENCE: 7
agatcacctt gaaggagtct ggtcc 25

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide HV4-4

<400> SEQUENCE: 8
tggtgaagcc ttcggagacc ctgtc 25

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide HV1-3

<400> SEQUENCE: 9
cactagctat gctatgcatt gggtg 25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide HV1-2

<400> SEQUENCE: 10
atggatcaac cctaacagtg gtggc 25

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide HV6-1

<400> SEQUENCE: 11
ggaaggacat actacaggtc caagt 25

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide C

<400> SEQUENCE: 12
taggtacttg ccccctgtcc tcagt 25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide KV1-9

<400> SEQUENCE: 13
agcccagtgt gttccgtaca gcctg 25

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide KV1-8

<400> SEQUENCE: 14
atcctcattc tctgcatcta cagga 25

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide KV1-6

<400> SEQUENCE: 15
ggtaaggatg gagaacactg gcagt 25

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide KV1-5

<400> SEQUENCE: 16
ttagtagctg gttggcctgg tatca 25

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide Ck

<400> SEQUENCE: 17
ctttgctgtc ctgatcagtc caact 25

<210> SEQ ID NO 18
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(10)
<223> OTHER INFORMATION: Repeated 148 times

<400> SEQUENCE: 18
gagctgagct 10

<210> SEQ ID NO 19
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(10)
<223> OTHER INFORMATION: Repeat 25 times

<400> SEQUENCE: 19
ggggtggggt 10

<210> SEQ ID NO 20
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(5)
<223> OTHER INFORMATION: Repeat 82 times

<400> SEQUENCE: 20
gggctgggct 10

<210> SEQ ID NO 21
<211> LENGTH: 6
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR, RT, or PW

<400> SEQUENCE: 21

Xaa Xaa Thr Phe Gly Gln
1 5

<210> SEQ ID NO 22
<211> LENGTH: 17
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa= PR, RT, or PW

<400> SEQUENCE: 22

Xaa Xaa Thr Phe Gly Gln Gly Thr Lys Val Glu Ile Lys Arg Ala Asp
1 5 10 15

Ala

<210> SEQ ID NO 23
<211> LENGTH: 6
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR or PW

<400> SEQUENCE: 23

Xaa Xaa Thr Phe Gly Gln
1 5

<210> SEQ ID NO 24
<211> LENGTH: 17
<212> TYPE: PRT
<213> ORGANISM: Artificial Sequence
<220> FEATURE:
<223> OTHER INFORMATION: Antibody Sequence
<220> FEATURE:

<221> NAME/KEY: MISC_FEATURE
<222> LOCATION: (1)..(2)
<223> OTHER INFORMATION: Xaa Xaa = PR or PW

<400> SEQUENCE: 24

Xaa Xaa Thr Phe Gly Gln Gly Thr Lys Val Glu Ile Lys Arg Ala Asp
1               5                   10                  15

Ala

<210> SEQ ID NO 25
<211> LENGTH: 24
<212> TYPE: DNA
<213> ORGANISM: Artificial Sequence
<220> FEATURE:
<223> OTHER INFORMATION: Primer E1554

<400> SEQUENCE: 25
atgacttcag tgttgttctg gtag 24

<210> SEQ ID NO 26
<211> LENGTH: 19
<212> TYPE: DNA
<213> ORGANISM: Artificial Sequence
<220> FEATURE:
<223> OTHER INFORMATION: Primer E1555

<400> SEQUENCE: 26
caccagattc ttatcagac 19

<210> SEQ ID NO 27
<211> LENGTH: 35
<212> TYPE: DNA
<213> ORGANISM: Artificial Sequence
<220> FEATURE:
<223> OTHER INFORMATION: ELP1352_Cy1

<400> SEQUENCE: 27
agagcggccg ctgggcaacg ttgcaggtga cggtc 35

<210> SEQ ID NO 28
<211> LENGTH: 34
<212> TYPE: DNA
<213> ORGANISM: Artificial Sequence
<220> FEATURE:
<223> OTHER INFORMATION: ELP1353_Cy2b

<400> SEQUENCE: 28
agagcggccg ctttgtccac cgtggtgctg ctgg 34

<210> SEQ ID NO 29
<211> LENGTH: 33
<212> TYPE: DNA
<213> ORGANISM: Artificial Sequence
<220> FEATURE:
<223> OTHER INFORMATION: ELP1354_Cy2a

<400> SEQUENCE: 29
agagcggccg cacattgcag gtgatggact ggc 33

<210> SEQ ID NO 30
<211> LENGTH: 35
<212> TYPE: DNA
<213> ORGANISM: Artificial Sequence
<220> FEATURE:
<223> OTHER INFORMATION: ELP1356_VH4-4

<400> SEQUENCE: 30
aggacgcgtg aaacacctgt ggttcttcct cctgc 35

<210> SEQ ID NO 31
<211> LENGTH: 33
<212> TYPE: DNA
<213> ORGANISM: Artificial Sequence
<220> FEATURE:
<223> OTHER INFORMATION: ELP1357_VH1-2,3

<400> SEQUENCE: 31
aggacgcgtc accatggact ggacctggag gat 33

<210> SEQ ID NO 32
<211> LENGTH: 34
<212> TYPE: DNA
<213> ORGANISM: Artificial Sequence
<220> FEATURE:
<223> OTHER INFORMATION: ELP1358_VH6-1

<400> SEQUENCE: 32
aggacgcgta tgtctgtctc cttcctcatc ttcc 34

<210> SEQ ID NO 33
<211> LENGTH: 21
<212> TYPE: DNA
<213> ORGANISM: Artificial Sequence
<220> FEATURE:
<223> OTHER INFORMATION: mIgG1_2 rev

<400> SEQUENCE: 33
ggggccagtg gatagacaga t 21

<210> SEQ ID NO 34
<211> LENGTH: 18
<212> TYPE: DNA
<213> ORGANISM: Artificial Sequence
<220> FEATURE:
<223> OTHER INFORMATION: mIgG2b rev

<400> SEQUENCE: 34
cagtggatag actgatgg 18

<210> SEQ ID NO 35
<211> LENGTH: 18
<212> TYPE: DNA
<213> ORGANISM: Artificial Sequence
<220> FEATURE:
<223> OTHER INFORMATION: mIgG2a_2 rev

<400> SEQUENCE: 35
cagtggatag accgatgg 18

<210> SEQ ID NO 36
<211> LENGTH: 20
<212> TYPE: DNA
<213> ORGANISM: Artificial Sequence
<220> FEATURE:
<223> OTHER INFORMATION: mCH1 unirev
<220> FEATURE:
<221> NAME/KEY: misc_feature
<222> LOCATION: (1)..(1)
<223> OTHER INFORMATION: K = G or T

<400> SEQUENCE: 36
kcaggggcca gtggatagac 20

<210> SEQ ID NO 37
<211> LENGTH: 20
<212> TYPE: DNA
<213> ORGANISM: Artificial Sequence
<220> FEATURE:
<223> OTHER INFORMATION: mCH1 unirev_2
<220> FEATURE:
<221> NAME/KEY: misc_feature
<222> LOCATION: (3)..(3)
<223> OTHER INFORMATION: R = A or G
<220> FEATURE:
<221> NAME/KEY: misc_feature
<222> LOCATION: (6)..(6)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 37
tarccyttga cmaggcatcc 20

<210> SEQ ID NO 38
<211> LENGTH: 24
<212> TYPE: PRT
<213> ORGANISM: Artificial Sequence
<220> FEATURE:
<223> OTHER INFORMATION: 16C9

<400> SEQUENCE: 38

Gln Glu Val Ile Asn Tyr Tyr Tyr Tyr Gly Met Asp Val Trp Gly Gln
1 5 10 15

Gly Thr Thr Val Thr Val Ser Ser
20

<210> SEQ ID NO 39
<211> LENGTH: 24
<212> TYPE: PRT
<213> ORGANISM: Artificial Sequence
<220> FEATURE:
<223> OTHER INFORMATION: 20B5

<400> SEQUENCE: 39

Gln Glu Val Ile Asn Tyr Tyr Tyr Tyr Gly Met Asp Val Trp Gly Gln
1 5 10 15

Gly Thr Thr Val Thr Val Ser Ser
20

<210> SEQ ID NO 40
<211> LENGTH: 26
<212> TYPE: PRT
<213> ORGANISM: Artificial Sequence
<220> FEATURE:
<223> OTHER INFORMATION: 19F4

<400> SEQUENCE: 40

Leu Glu Met Ala Thr Ile Asn Tyr Tyr Tyr Tyr Gly Met Asp Val Trp
1 5 10 15

Gly Gln Gly Thr Met Val Thr Val Ser Ser
20 25

<210> SEQ ID NO 41
<211> LENGTH: 24
<212> TYPE: PRT
<213> ORGANISM: Artificial Sequence
<220> FEATURE:

<223> OTHER INFORMATION: 19E1

<400> SEQUENCE: 41

```
Gln Glu Phe Gly Asn Tyr Tyr Tyr Tyr Gly Met Asp Val Trp Gly Gln
1               5                   10                  15

Gly Thr Thr Val Thr Val Ser Ser
            20
```

<210> SEQ ID NO 42
<211> LENGTH: 24
<212> TYPE: PRT
<213> ORGANISM: Artificial Sequence
<220> FEATURE:
<223> OTHER INFORMATION: 19G8

<400> SEQUENCE: 42

```
Gln Glu Asp Gly Asn Pro Tyr Tyr Phe Gly Met Asp Phe Trp Gly Gln
1               5                   10                  15

Gly Thr Thr Val Thr Val Ser Ser
            20
```

<210> SEQ ID NO 43
<211> LENGTH: 22
<212> TYPE: PRT
<213> ORGANISM: Artificial Sequence
<220> FEATURE:
<223> OTHER INFORMATION: 20H10

<400> SEQUENCE: 43

```
Gly Ser Ser Tyr Tyr Tyr Asp Gly Met Asp Val Trp Gly Gln Gly Thr
1               5                   10                  15

Thr Val Thr Val Ser Ser
            20
```

<210> SEQ ID NO 44
<211> LENGTH: 25
<212> TYPE: PRT
<213> ORGANISM: Artificial Sequence
<220> FEATURE:
<223> OTHER INFORMATION: 18D10

<400> SEQUENCE: 44

```
Leu Glu Asn Asp Tyr Gly Tyr Tyr Tyr Tyr Gly Met Asp Val Trp Gly
1               5                   10                  15

Gln Gly Thr Thr Val Thr Val Ser Ser
            20                  25
```

<210> SEQ ID NO 45
<211> LENGTH: 23
<212> TYPE: PRT
<213> ORGANISM: Artificial Sequence
<220> FEATURE:
<223> OTHER INFORMATION: 16F2

<400> SEQUENCE: 45

```
Arg Gly Gly Leu Ser Pro Leu Tyr Gly Met Asp Val Trp Gly Gln Gly
1               5                   10                  15

Thr Thr Val Thr Val Ser Ser
            20
```

<210> SEQ ID NO 46
<211> LENGTH: 15
<212> TYPE: DNA
<213> ORGANISM: Artificial Sequence
<220> FEATURE:
<223> OTHER INFORMATION: Rat Switch

<400> SEQUENCE: 46
gggctgggct gggct 15

<210> SEQ ID NO 47
<211> LENGTH: 20
<212> TYPE: DNA
<213> ORGANISM: Artificial Sequence
<220> FEATURE:
<223> OTHER INFORMATION: Rat Switch

<400> SEQUENCE: 47
gggctgggct gggctgggct 20

<210> SEQ ID NO 48
<211> LENGTH: 25
<212> TYPE: DNA
<213> ORGANISM: Artificial Sequence
<220> FEATURE:
<223> OTHER INFORMATION: Rat Switch

<400> SEQUENCE: 48
gggctgggct gggctgggct gggct 25

<210> SEQ ID NO 49
<211> LENGTH: 30
<212> TYPE: DNA
<213> ORGANISM: Artificial Sequence
<220> FEATURE:
<223> OTHER INFORMATION: Rat Switch

<400> SEQUENCE: 49
gggctgggct gggctgggct gggctgggct 30

<210> SEQ ID NO 50
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(5)
<223> OTHER INFORMATION: Repeat 6 to 81 times

<400> SEQUENCE: 50
gggctgggct 10

<210> SEQ ID NO 51
<211> LENGTH: 6
<212> TYPE: PRT
<213> ORGANISM: Artificial Sequence
<220> FEATURE:
<223> OTHER INFORMATION: IGHV4-4*02 CDR1

<400> SEQUENCE: 51

Ser Ser Asn Trp Trp Ser
1 5

<210> SEQ ID NO 52
<211> LENGTH: 6
<212> TYPE: PRT
<213> ORGANISM: Artificial Sequence
<220> FEATURE:
<223> OTHER INFORMATION: 12D10 CDR1

<400> SEQUENCE: 52

Ser Gly Asn Trp Trp Ser
1 5

<210> SEQ ID NO 53
<211> LENGTH: 6
<212> TYPE: PRT
<213> ORGANISM: Artificial Sequence
<220> FEATURE:
<223> OTHER INFORMATION: 1283 CDR1

<400> SEQUENCE: 53

Arg Ser Asn Trp Trp Ser
1 5

<210> SEQ ID NO 54
<211> LENGTH: 7
<212> TYPE: PRT
<213> ORGANISM: Artificial Sequence
<220> FEATURE:
<223> OTHER INFORMATION: IGHV6-1*01 CDR1

<400> SEQUENCE: 54

Ser Asn Ser Ala Ala Trp Asn
1 5

<210> SEQ ID NO 55
<211> LENGTH: 7
<212> TYPE: PRT
<213> ORGANISM: Artificial Sequence
<220> FEATURE:
<223> OTHER INFORMATION: 4A12 CDR1

<400> SEQUENCE: 55

Ser Asn Ser Ala Ala Trp Asn
1 5

<210> SEQ ID NO 56
<211> LENGTH: 16
<212> TYPE: PRT
<213> ORGANISM: Artificial Sequence
<220> FEATURE:
<223> OTHER INFORMATION: IGHV4-4*02 CDR2

<400> SEQUENCE: 56

Glu Ile Tyr His Ser Gly Ser Thr Asn Tyr Asn Pro Ser Leu Lys Ser
1 5 10 15

<210> SEQ ID NO 57
<211> LENGTH: 16
<212> TYPE: PRT
<213> ORGANISM: Artificial Sequence
<220> FEATURE:
<223> OTHER INFORMATION: 12D10 CDR2

<400> SEQUENCE: 57

Glu Ile Tyr His Ser Gly Asn Thr Asn Tyr Asn Pro Ser Leu Lys Ser
1 5 10 15

<210> SEQ ID NO 58
<211> LENGTH: 16
<212> TYPE: PRT
<213> ORGANISM: Artificial Sequence
<220> FEATURE:
<223> OTHER INFORMATION: 1283 CDR2

<400> SEQUENCE: 58

Glu Ile Tyr His Ser Gly Ser Thr Asn Tyr Asn Pro Ser Leu Lys Ser
1 5 10 15

<210> SEQ ID NO 59
<211> LENGTH: 18
<212> TYPE: PRT
<213> ORGANISM: Artificial Sequence
<220> FEATURE:
<223> OTHER INFORMATION: IGHV6-1*01 CDR2

<400> SEQUENCE: 59

Arg Thr Tyr Tyr Arg Ser Lys Trp Tyr Asn Asp Tyr Ala Val Ser Val
1 5 10 15

Lys Ser

<210> SEQ ID NO 60
<211> LENGTH: 18
<212> TYPE: PRT
<213> ORGANISM: Artificial Sequence
<220> FEATURE:
<223> OTHER INFORMATION: 4A12 CDR2

<400> SEQUENCE: 60

Arg Thr Tyr Tyr Arg Ser Lys Trp Tyr Asn Asp Tyr Lys Val Ser Val
1 5 10 15

Lys Ser

<210> SEQ ID NO 61
<211> LENGTH: 12
<212> TYPE: PRT
<213> ORGANISM: Artificial Sequence
<220> FEATURE:
<223> OTHER INFORMATION: 12D10 CDR3

<400> SEQUENCE: 61

Gly Pro Leu Thr Gly Glu Lys Tyr Tyr Phe Asp Leu
1 5 10

<210> SEQ ID NO 62
<211> LENGTH: 8
<212> TYPE: PRT
<213> ORGANISM: Artificial Sequence
<220> FEATURE:
<223> OTHER INFORMATION: 1283 CDR3

<400> SEQUENCE: 62

Ile Gly Asp Trp Tyr Phe Asp Leu
1 5

<210> SEQ ID NO 63
<211> LENGTH: 16
<212> TYPE: PRT
<213> ORGANISM: Artificial Sequence
<220> FEATURE:
<223> OTHER INFORMATION: 4A12 CDR3

<400> SEQUENCE: 63

Glu Gly Ser His Ser Gly Ser Gly Trp Tyr Leu Asp Ala Phe Asp Ile
1 5 10 15

<210> SEQ ID NO 64
<211> LENGTH: 17
<212> TYPE: PRT
<213> ORGANISM: Artificial Sequence
<220> FEATURE:
<223> OTHER INFORMATION: IGHJ2*01 J-region

<400> SEQUENCE: 64

Tyr Trp Tyr Phe Asp Leu Trp Gly Arg Gly Thr Leu Val Thr Val Ser
1 5 10 15

Ser

<210> SEQ ID NO 65
<211> LENGTH: 16
<212> TYPE: PRT
<213> ORGANISM: Artificial Sequence
<220> FEATURE:
<223> OTHER INFORMATION: 12D10 J-region

<400> SEQUENCE: 65

Tyr Tyr Phe Asp Leu Trp Gly Arg Gly Thr Leu Val Thr Val Ser Ser
1 5 10 15

<210> SEQ ID NO 66
<211> LENGTH: 16
<212> TYPE: PRT
<213> ORGANISM: Artificial Sequence
<220> FEATURE:
<223> OTHER INFORMATION: 1283 J-Region

<400> SEQUENCE: 66

Trp Tyr Phe Asp Leu Trp Gly Arg Gly Thr Leu Val Thr Val Ser Ser
1 5 10 15

<210> SEQ ID NO 67
<211> LENGTH: 16
<212> TYPE: PRT
<213> ORGANISM: Artificial Sequence
<220> FEATURE:
<223> OTHER INFORMATION: IGHJ3*01 J-Region

<400> SEQUENCE: 67

Asp Ala Phe Asp Val Trp Gly Gln Gly Thr Met Val Thr Val Ser Ser
1 5 10 15

<210> SEQ ID NO 68
<211> LENGTH: 16
<212> TYPE: PRT
<213> ORGANISM: Artificial Sequence
<220> FEATURE:
<223> OTHER INFORMATION: 4A12 J-region

<400> SEQUENCE: 68

Asp Ala Phe Asp Ile Trp Gly Gln Gly Thr Lys Val Thr Val Ser Ser
1 5 10 15

TRANSGENIC MOUSE HOMOZYGOUS FOR CHIMERIC IGH LOCUS

CROSS-REFERENCE TO RELATED APPLICATIONS

This application is a divisional of U.S. Ser. No. 13/310,431, filed Dec. 2, 2011, which is a continuation-in-part of PCT/GB2010/051122 filed Jul. 7, 2010, which claims the benefit of U.S. Provisional Application No. 61/223,960 filed Jul. 8, 2009; U.S. Provisional Application No. 61/355,666 filed Jun. 17, 2010; GB Patent Application No.: 0911846.4 filed Jul. 8, 2009; and GB Patent Application No.: 0913102.0 filed Jul. 28, 2009, the entire contents of which are incorporated herein by reference. This application is a continuation-in-part of PCT/GB2011/050019, filed Jan. 7, 2011, which claims the benefit of PCT/GB2010/051122, filed Jul. 7, 2010, the entire contents of which are incorporated herein by reference. This application claims the benefit of U.S. Provisional Application No. 61/223,960 filed Jul. 8, 2009; U.S. Provisional Application No. 61/355,666 filed Jun. 17, 2010; GB Patent Application No.: 0911846.4 filed Jul. 8, 2009; and GB Patent Application No.: 0913102.0 filed Jul. 28, 2009, the entire contents of which are incorporated herein by reference.

BACKGROUND

The present invention relates inter alia to non-human animals and cells that are engineered to contain exogenous DNA, such as human immunoglobulin gene DNA, their use in medicine and the study of disease, methods for production of non-human animals and cells, and antibodies and antibody chains produced by such animals and derivatives thereof.

In order to get around the problems of humanizing antibodies a number of companies set out to generate mice with human immune systems. The strategy used was to knockout the heavy and light chain loci in ES cells and complement these genetic lesions with transgenes designed to express the human heavy and light chain genes. Although fully human antibodies could be generated, these models have several major limitations:

(i) The size of the heavy and light chain loci (each several Mb) made it impossible to introduce the entire loci into these models. As a result the transgenic lines recovered had a very limited repertoire of V-regions, most of the constant regions were missing and important distant enhancer regions were not included in the transgenes.

(ii) The very low efficiency of generating the large insert transgenic lines and the complexity and time required to cross each of these into the heavy and light chain knockout strains and make them homozygous again, restricted the number of transgenic lines which could be analysed for optimal expression.

(iii) Individual antibody affinities rarely reached those which could be obtained from intact (non-transgenic) animals.

WO2007117410 discloses chimaeric constructs for expressing chimaeric antibodies.

WO2010039900 discloses knock in cells and mammals having a genome encoding chimaeric antibodies.

The present invention provides, inter alia, a process for the generation in non-human mammals of antibodies that comprise a human Ig variable region, and further provides non-human animal models for the generation of such antibodies.

SUMMARY OF THE INVENTION

All nucleotide co-ordinates for the mouse are those corresponding to NCBI m37 for the mouse C57BL/6J strain, e.g. April 2007 ENSEMBL Release 55.37h, e.g. NCBI37 July 2007 (NCBI build 37) (e.g. UCSC version mm9 see World Wide Web (www) genome.ucsc.edu and World Wide Web (www) genome.ucsc.edu/FAQ/FAQreleases.html) unless otherwise specified. Human nucleotides coordinates are those corresponding to GRCh37 (e.g. UCSC version hg 19, World Wide Web (www) genome.ucsc.edu/FAQ/FAQreleases.html), February 2009 ENSEMBL Release 55.37, or are those corresponding to NCBI36, Ensemble release 54 unless otherwise specified. Rat nucleotides are those corresponding to RGSC 3.4 Dec. 2004 ENSEMBL release 55.34w, or Baylor College of Medicine HGSC v3.4 Nov. 2004 (e.g., UCSC rn4, see World Wide Web (www) genome.ucsc.edu and World Wide Web (www) genome.ucsc.edu/FAQ/FAQreleases.html) unless otherwise specified.

In the present invention, methods are disclosed for constructing a chimaeric human heavy and light chain loci in a non-human mammal, for example a mouse. Reference to work in mice herein is by way of example only, and reference to mice is taken to include reference to all non-human mammals unless otherwise apparent from the disclosure, with mice being preferred as the non-human mammal.

In one aspect the invention relates to a non-human mammal whose genome comprises:

(a) a plurality of human IgH V regions, one or more human D regions and one or more human J regions upstream of the host non-human mammal constant region; and (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;

wherein the non-human mammal is able to produce a repertoire of chimaeric antibodies, or chimaeric light or heavy chains, having a non-human mammal constant region and a human variable region.

In one aspect the invention relates to non-human mammal whose genome comprises (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and (b) optionally one or more human IgH V regions, one or more human D regions and one or more human J regions upstream of the host non-human mammal constant region;

wherein the non-human mammal is able to produce a repertoire of chimaeric antibodies, or chimaeric light or heavy chains, having a non-human mammal constant region and a human variable region.

In one aspect the invention relates to non-human mammalian cell whose genome comprises (a) a plurality of human IgH V regions, one or more human D regions and one or more human J regions upstream of the host non-human mammal constant region and (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region.

In one aspect the invention relates to a non-human mammalian cell whose genome comprises (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and (b) optionally one or more human IgH V regions, one or more human D regions and one or more human J regions upstream of the host non-human mammal constant region;

In a further aspect the invention relates to a method for producing a non-human cell or mammal comprising inserting into a non-human mammal cell genome, such as an ES cell genome;

(a) a plurality of human IgH V regions, one or more human D regions and one or more human J regions upstream of the host non-human mammal constant region; and (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region; respectively, the insertion being such that the non-human cell or mammal is able to produce a repertoire of chimaeric antibodies having a non-human mammal constant region and a human variable region, wherein steps (a) and (b) can be carried out in either order and each of steps (a) and (b) can be carried out in a stepwise manner or as a single step. Insertion may be by homologous recombination.

In a further aspect the invention relates to a method for producing an antibody or antibody chain specific to a desired antigen the method comprising immunizing a transgenic non-human mammal as disclosed herein with the desired antigen and recovering the antibody or antibody chain.

In a further aspect the invention relates to a method for producing a fully humanised antibody comprising immunizing a transgenic non-human mammal as disclosed herein with the desired antigen, recovering the antibody or cells producing the antibody and then replacing the non-human mammal constant region with a human constant region, for example by protein or DNA engineering.

In a further aspect the invention relates to humanised antibodies and antibody chains produced according to the present invention, both in chimaeric (for example, mouse-human) and fully humanised form, as well as fragments and derivatives of said antibodies and chains, and use of said antibodies, chains and fragments in medicine, including diagnosis.

In a further aspect the invention relates to use of a non-human mammal as described herein as a model for the testing of drugs and vaccines.

In one aspect the invention relates to a non-human mammal whose genome comprises:

(a) a plurality of human IgH V regions, one or more human D regions and one or more human J regions upstream of the host non-human mammal constant region; and (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;

wherein the non-human mammal is able to produce a repertoire of chimaeric antibodies or antibody chains having a non-human mammal constant region and a human variable region.

In a further aspect the invention relates to a non-human mammal whose genome comprises:

(a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and (b) optionally one or more human IgH V regions, one or more human D regions and one or more human J regions upstream of the host non-human mammal constant;

wherein the non-human mammal is able to produce a repertoire of chimaeric antibodies having a non-human mammal constant region and a human variable region.

Optionally the non-human mammal genome is modified to prevent expression of fully host-species specific antibodies.

In one aspect the inserted human DNA comprises at least 50% of the human heavy chain variable (V) genes, such as at least 60%, at least 70%, at least 80%, at least 90%, and in one aspect all of the human V genes.

In one aspect the inserted human DNA comprises at least 50% of the human heavy chain diversity (D) genes, such as at least 60%, at least 70%, at least 80%, at least 90%, and in one aspect all of the human D genes.

In one aspect the inserted human DNA comprises at least 50% of the human heavy chain joining (J) genes, such as at least 60%, at least 70%, at least 80%, at least 90%, and in one aspect all of the human J genes.

In one aspect the inserted human DNA comprises at least 50% of the human light chain Variable (V) genes, such as at least 60%, at least 70%, at least 80%, at least 90%, and in one aspect all of the human light chain V genes.

In one aspect the inserted human DNA comprises at least 50% of the human light chain joining (J) genes, such as at least 60%, at least 70%, at least 80%, at least 90%, and in one aspect all of the human light chain J genes.

The inserted human genes may be derived from the same individual or different individuals, or be synthetic or represent human consensus sequences.

Although the number of V D and J regions is variable between human individuals, in one aspect there are considered to be 51 human V genes, 27 D and 6 J genes on the heavy chain, 40 human V genes and 5 J genes on the kappa light chain and 29 human V genes and 4 J genes on the lambda light chain (Janeway and Travers, Immunobiology, Third edition)

In one aspect the human heavy chain locus inserted into the non-human mammal contains the full repertoire of human V, D and J regions, which in the genome is in functional arrangement with the non-human mammal constant regions such that functional chimaeric antibodies can be produced between the human variable and non-human mammal constant regions. This total inserted human heavy chain genetic material is referred to herein as the human IgH VDJ region, and comprises DNA from a human genome that encodes all the exons encoding human V, D and J portions and suitably also the associated introns. Similarly, reference to the human Ig light chain kappa V and J regions herein refers to human DNA comprising all the exons encoding V and J regions and suitably also the associated introns of the human genome. Reference to the human Ig light chain lambda V and J regions herein refers to human DNA comprising all the exons encoding V and J regions and suitably also the associated introns of the human genome.

Human variable regions are suitably inserted upstream of a non-human mammal constant region, the latter comprising all of the DNA required to encode the full constant region or a sufficient portion of the constant region to allow the formation of an effective chimaeric antibody capable of specifically recognising an antigen.

In one aspect the chimaeric antibodies or antibody chains have a part of a host constant region sufficient to provide one or more effector functions seen in antibodies occurring naturally in a host mammal, for example that they are able interact with Fc receptors, and/or bind to complement.

Reference to a chimaeric antibody or antibody chain having a host non mammal constant region herein therefore is not limited to the complete constant region but also includes chimaeric antibodies or chains which have all of the host constant region, or a part thereof sufficient to provide one or more effector functions. This also applies to non-human mammals and cells and methods of the invention in which human variable region DNA may be inserted into the host genome such that it forms a chimaeric antibody chain with all or part of a host constant region. In one aspect the whole of a host constant region is operably linked to human variable region DNA.

The host non-human mammal constant region herein is preferably the endogenous host wild-type constant region located at the wild type locus, as appropriate for the heavy or light chain. For example, the human heavy chain DNA is suitably inserted on mouse chromosome 12, suitably adjacent the mouse heavy chain constant region.

In one aspect the insertion of the human DNA, such as the human VDJ region is targeted to the region between the J4 exon and the Cμ locus in the mouse genome IgH locus, and in one aspect is inserted between co-ordinates 114,667,090 and 114,665,190, or at co-ordinate 114,667,091, after 114,667,090. In one aspect the insertion of the human DNA, such as the human light chain kappa VJ is targeted into mouse chromosome 6 between co-ordinates 70,673,899 and 70,675,515, suitably at position 70,674,734, or an equivalent position in the lambda mouse locus on chromosome 16.

In one aspect the host non-human mammal constant region for forming the chimaeric antibody may be at a different (non endogenous) chromosomal locus. In this case the inserted human DNA, such as the human variable VDJ or VJ region(s) may then be inserted into the non-human genome at a site which is distinct from that of the naturally occurring heavy or light constant region. The native constant region may be inserted into the genome, or duplicated within the genome, at a different chromosomal locus to the native position, such that it is in a functional arrangement with the human variable region such that chimaeric antibodies of the invention can still be produced.

In one aspect the human DNA is inserted at the endogenous host wild-type constant region located at the wild type locus between the host constant region and the host VDJ region.

Reference to location of the variable region upstream of the non-human mammal constant region means that there is a suitable relative location of the two antibody portions, variable and constant, to allow the variable and constant regions to form a chimaeric antibody or antibody chain in vivo in the mammal. Thus, the inserted human DNA and host constant region are in functional arrangement with one another for antibody or antibody chain production.

In one aspect the inserted human DNA is capable of being expressed with different host constant regions through isotype switching. In one aspect isotype switching does not require or involve trans switching. Insertion of the human variable region DNA on the same chromosome as the relevant host constant region means that there is no need for trans-switching to produce isotype switching.

As explained above, the transgenic loci used for the prior art models were of human origin, thus even in those cases when the transgenes were able to complement the mouse locus so that the mice produced B-cells producing fully human antibodies, individual antibody affinities rarely reached those which could be obtained from intact (non-transgenic) animals. The principal reason for this (in addition to repertoire and expression levels described above) is the fact that the control elements of the locus are human. Thus, the signalling components, for instance to activate hyper-mutation and selection of high affinity antibodies are compromised.

In contrast, in the present invention, host non-human mammal constant regions are maintained and it is preferred that at least one non-human mammal enhancer or other control sequence, such as a switch region, is maintained in functional arrangement with the non-human mammal constant region, such that the effect of the enhancer or other control sequence, as seen in the host mammal, is exerted in whole or in part in the transgenic animal.

This approach above is designed to allow the full diversity of the human locus to be sampled, to allow the same high expression levels that would be achieved by non-human mammal control sequences such as enhancers, and is such that signalling in the B-cell, for example isotype switching using switch recombination sites, would still use non-human mammal sequences.

A mammal having such a genome would produce chimaeric antibodies with human variable and non-human mammal constant regions, but these could be readily humanized, for example in a cloning step. Moreover the in vivo efficacy of these chimaeric antibodies could be assessed in these same animals.

In one aspect the inserted human IgH VDJ region comprises, in germline configuration, all of the V, D and J regions and intervening sequences from a human.

In one aspect 800-1000 kb of the human IgH VDJ region is inserted into the non-human mammal IgH locus, and in one aspect a 940, 950 or 960 kb fragment is inserted. Suitably this includes bases 105,400,051 to 106,368,585 from human chromosome 14.

In one aspect the inserted IgH human fragment consists of bases 105,400,051 to 106,368,585 from chromosome 14. In one aspect the inserted human heavy chain DNA, such as DNA consisting of bases 105,400,051 to 106,368,585 from chromosome 14, is inserted into mouse chromosome 12 between the end of the mouse J4 region and the Eμ region, suitably between co-ordinates 114,667,090 and 114,665, 190, or at co-ordinate 114,667,091, after 114,667,090. In one aspect the insertion is between co-ordinates 114,667,089 and 114,667,090 (co-ordinates refer to NCBI m37, for the mouse C57BL/6J strain), or at equivalent position in another non-human mammal genome.

In one aspect the inserted human kappa VJ region comprises, in germline configuration, all of the V and J regions and intervening sequences from a human. Suitably this includes bases 88,940,356 to 89,857,000 from human chromosome 2, suitably approximately 917 kb. In a further aspect the light chain VJ insert may comprise only the proximal clusters of V segments and J segments. Such an insert would be of approximately 473 kb. In one aspect the human light chain kappa DNA, such as the human IgK fragment of bases 88,940,356 to 89,857,000 from human chromosome 2, is suitably inserted into mouse chromosome 6 between co-ordinates 70,673,899 and 70,675,515, suitably at position 70,674,734. These co-ordinates refer to NCBI36 for the human genome, ENSEMBL Release 54 and NCBIM37 for the mouse genome, relating to mouse strain C57BL/6J.

In one aspect the human lambda VJ region comprises, in germline configuration, all of the V and J regions and intervening sequences from a human.

Suitably this includes analogous bases to those selected for the kappa fragment, from human chromosome 2.

A cell or non-human mammal of the invention, in one embodiment, comprises an insertion of human heavy chain variable region DNA between co-ordinates 114,666,183 and 114,666,725, such as between 114 666 283 and 114 666 625, optionally between co-ordinates 114,666,335 and 114,666, 536, optionally between 114,666,385 and 114,666,486, or between 114,666,425 and 114,666,446, or between 114,666, 435 and 114,666,436 of mouse chromosome 12 with reference to NCBIM37 for the mouse genome, relating to mouse strain C57BL/6J or an equivalent position of mouse chromosome 12 from a different mouse strain or an equivalent position in the genome of another non-human vertebrate, e.g., a rat. The insertion between co-ordinates 114,666,435 and 114,666,436 relating to mouse strain C57BL/6J is equivalent to an insertion between co-ordinates 1207826 and 1207827 on chromosome 12 with reference to the 129/SvJ genomic sequence of the GenBank® access number NT114985.2. An insertion may be made at equivalent position in another genome, such as another mouse genome. In an example of this embodiment, the cell or mammal of the invention comprises a human IgH VDJ region which comprises or consists of nucleotides 106,328,851-107,268,544, such as nucleotides 106,328,901-107,268,494, such as nucleotides 106,328,941-107,268,454, such as nucleotides 106,328,951-107,268,444 of human Chromosome 14, with reference to the GRCH37/hg19 sequence database, or insertion of equivalent nucleotides relating to chromosome 14 from a different human sequence or database. The human insertion may be made between the regions indicated above.

A cell or mammal of the invention, in one embodiment, comprises an insertion of the human kappa VJ region, suitably comprising or consisting of, in germline configuration, all of the V and J regions and intervening sequences from a human, the insertion of the human DNA being made between co-ordinates 70,673,918-70,675,517, such as between co-ordinates 70,674,418 and 70 675,017, such as between co-ordinates 70,674,655-70,674,856, such as between co-ordinates 70,674,705-70,674,906, such as between co-ordinates 70,674,745-70,674,766, such as between co-ordinates 70,674,755 and 70,674,756 of mouse chromosome 6, numbering with reference to NCBIM37 for the mouse genome, relating to mouse strain C57BL/6J, or an insertion at an equivalent position in another genome, such as another mouse genome. In an example of this embodiment, a cell or mammal of the invention comprises an insertion of nucleotides 89,159,079-89,630,437 and/or 89,941,714-90,266,976 of human chromosome 2 with reference to the GRCH37/hg19 sequence database (or equivalent nucleotides relating to chromosome 2 from a different human sequence or database), such as an insertion of these 2 discrete fragments without the intervening sequence, or an insertion of the complete 89,159,079-90,266,976 region.

The insertion may comprise, or consist, of:

(i) nucleotides 89,158,979-89,630,537, such as 89,159, 029-89,630,487, such as 89,159,069-89,630,447, such as 89,159,079-89,630,437, optionally in addition to fragment (ii) below (ii) nucleotides 89,941,614-90,267,076, such as 89,941, 664-90,267,026, such as 89,941,704-90,266,986, such as 89,941,714-90,266,976; optionally in addition to fragment (i)

(iii) nucleotides 89,158,979-90,267,076, such as nucleotides 89,159,079-90,266,976.

The human insertion may be made between the regions indicated above.

In an embodiment, a cell or mammal of the invention comprises an insertion of a human lambda region which comprises at least one human Jλ region (eg, a germline region) and at least one human Cλ region (eg, a germline region), optionally $C_\lambda 6$ and/or $C_\lambda 7$. For example, the cell or mammal comprises a plurality of human Jλ regions, optionally two or more of $J_\lambda 1$, $J_\lambda 2$, $J_\lambda 6$ and $J_\lambda 7$, optionally all of $J_\lambda 1$, $J_\lambda 2$, $J_\lambda 6$ and $J_\lambda 7$. In an example, the cell or mammal comprises at least one human $J_\Lambda$-$C_\Lambda$ cluster, optionally at least $J_\lambda 7$-$C_\lambda 7$.

In one aspect the human JC cluster is inserted 3' of the last endogenous J lambda or is inserted 3' of the last endogenous J kappa region, suitably immediately 3' of these sequences, or substantially immediately 3' of these sequences.

In one aspect the insertion into the mouse lambda locus is made downstream of the endogenous C1 gene segment, for example where there is a 3' J1C1 cluster, suitably immediately 3' of the C1 segment, or substantially immediately 3' of the segment.

In one aspect (e.g. cell or non-human mammal) a human JC cluster is inserted into a kappa locus and any resulting cell or animal is heterozygous at that locus, such that the cell has one chromosome with human lambda DNA inserted into the kappa locus, and another chromosome with human kappa DNA at the endogenous kappa locus.

In an embodiment, a cell or mammal of the invention comprises a human EA enhancer.

A cell or mammal may of the invention comprise an inserted human lambda VJ region, suitably comprising or consisting of, in germline configuration, all of the V and J regions and intervening sequences from a human, the inserted region comprises or consisting of nucleotides 22,375,509-23,327,984, such as nucleotides 22,375,559-23, 327,934, such as nucleotides 22,375,599-23,327,894, such as nucleotides 22,375,609-23,327,884 from human Chromosome 22, with reference to the GRCH37/hg19 sequence database, or equivalent DNA from another human sequence or database. The insertion into the mouse genome may be made between co-ordinates 19,027,763 and 19,061,845, such as between co-ordinates 19,037,763 and 19,051,845, such as between co-ordinates 19,047,451 and 19,047,652, such as between co-ordinates 19,047,491 and 19,047,602, such as between co-ordinates 19,047,541 and 19,047,562, such as between co-ordinates 19,047,551 and 19,047,552 of mouse Chromosome 16 (with reference to NCBIM37 for the mouse genome, relating to mouse strain C57BL/6J, equivalent to co-ordinates 1,293,646-1,293,647 of the 129 SvJ genomic sequence in the sequence file of NT_039630.4), or may be an insertion at an equivalent position in other genome, such as another mouse genome. The insertion of the human lambda nucleic acid into the mouse genome may alternatively be made between co-ordinates 70,673,918 and 70,675,517, such as between co-ordinates 70,674,418 and 70 675,017, such as between co-ordinates 70,674,655 and 70,674,856, such as between co-ordinates 70,674,705 and 70,674,806, such as between co-ordinates 70,674,745 and 70,674,766, such as between co-ordinates 70,674,755 and 70,674,756 of mouse Chromosome 6 (with reference to NCBIM37 for the mouse genome, relating to mouse strain C57BL/6J) or equivalent in another genome. The human insertion may be made between the regions indicated above.

All specific human fragments described above may vary in length, and may for example be longer or shorter than defined as above, such as 500 bases, 1 KB, 2K, 3K, 4K, 5 KB, 10 KB, 20 KB, 30 KB, 40 KB or 50 KB or more, which suitably comprise all or part of the human V(D)J region, whilst preferably retaining the requirement for the final insert to comprise human genetic material encoding the complete heavy chain region and light chain region, as appropriate, as described above.

In one aspect the 5' end of the human insert described above is increased in length. Where the insert is generated in a stepwise fashion then the increase in length is generally in respect of the upstream (5') clone.

In one aspect the 3' end of the last inserted human gene, generally the last human J gene to be inserted is less than 2 kb, preferably less than 1 KB from the human-mouse join region.

In one aspect the non-human mammal comprises some or all of the human light chain kappa VJ region as disclosed herein but not the human light chain lambda VJ region.

In one aspect the cell or non-human mammal comprises a fully human lambda locus (lambda VJC regions from a human), a chimaeric kappa locus (human kappa VJ regions operatively linked to a host kappa constant region) and a chimaeric heavy chain locus, having a human VDJ region operatively linked to a host heavy chain constant region.

In a further aspect the genome comprises an insertion of V, D (heavy chain only) and J genes as described herein at the heavy chain locus and one light chain locus, or at the heavy chain locus and both light chain loci. Preferably the genome is homozygous at one, or both, or all three loci.

In another aspect the genome may be heterozygous at one or more of the loci, such as heterozygous for DNA encoding a chimaeric antibody chain and native (host cell) antibody chain. In one aspect the genome may be heterozygous for DNA capable of encoding 2 different antibody chains of the invention, for example, comprising 2 different chimaeric heavy chains or 2 different chimaeric light chains.

In one aspect the invention relates to a non-human mammal or cell, and methods for producing said mammal or cell, as described herein, wherein the inserted human DNA, such as the human IgH VDJ region and/or light chain V, J regions are found on only one allele and not both alleles in the mammal or cell. In this aspect a mammal or cell has the potential to express both an endogenous host antibody heavy or light chain and a chimaeric heavy or light chain.

In a further aspect of the invention the human VDJ region, or light chain VJ region, is not used in its entirety, but parts of the equivalent human VDJ or VJ region, such as the exons, from other species may be used, such as one or more V, D, or J exons from other species, or regulatory sequences from other species. In one aspect the sequences used in place of the human sequences are not human or mouse. In one aspect the sequences used may be from rodent, or, primate such as chimp. For example, 1, 2, 3, 4, or more, or all of the J regions from a primate other than a human may be used to replace, one, 2, 3, 4, or more or all of the human J exons in the VDJ/VJ region of the cells and animals of the invention.

In a further aspect the inserted human DNA, such as the human IgH VDJ region, and/or light chain VJ regions, may be inserted such that they are operably linked in the genome with a mu constant region from a non-human, non-mouse species, such as a rodent or primate sequence, such as a rat sequence.

Other non-human, non-mouse species from which DNA elements may be used in the present invention include rabbits, lamas, dromedary, alpacas, camels and sharks.

In one aspect the inserted human DNA, such as the human VDJ or VJ region, is not operably linked to the endogenous host mu sequence but rather to a non-host mu sequence.

Operable linkage suitably allows production of an antibody heavy or light chain comprising the human variable region.

In one aspect the inserted human DNA, such as the human IgH VDJ region (and/or light chain VJ regions) may be inserted into the host chromosome together with mu constant region nucleic acid which is not host mu constant region nucleic acid, and preferably is a mu constant region from a non-mouse, non-human species. Suitably the inserted human DNA, such as the human VDJ region (and/or light chain VJ regions) is operably linked to a non-human, non-mouse mu, and is able to form a chimaeric antibody heavy or light chain. In another aspect a non-mouse, non-human mu may be inserted into the host chromosome on a separate genetic element to that of the human variable region, or at a different location in the genome, suitably operably linked to the variable region such that a chimaeric antibody heavy or light can be formed.

In an additional aspect the invention relates to a non-human mammal or a cell whose genome comprises a plurality of human IgH V regions, one or more human D regions and one or more human J regions upstream of a host non-human mammal light chain constant region, arranged such that the cell or mammal is able to express a chimaeric antibody chain. The invention also relates to a non-human mammal or a cell whose genome additionally or alternatively comprises a plurality of human Ig light chain V regions, and one or more human J regions upstream of a host non-human mammal heavy chain constant region, such that the cell or mammal is able to express a chimaeric antibody chain. The cell or mammal may be able to express an antibody having both heavy and light chains, including at least one chimaeric antibody chain, as disclosed above.

The inserted human heavy chain variable regions may be any of those described herein, and may be inserted at the positions described above for insertion 5' of the lambda and kappa constant regions. Likewise the inserted human light chain variable regions may be those described above, and may be inserted at the positions described above for insertion 5' of the heavy chain constant region.

For example, the genome or the cell or non-human mammal of the invention may encode an antibody comprising an antibody chain having a human heavy chain variable region upstream of a mouse light chain constant region, or an antibody chain having a human light chain variable region upstream of a mouse heavy chain constant region, in combination with one of:

a fully human antibody light chain;

a fully human antibody heavy chain;

a non-human vertebrate (e.g., mouse or rat) antibody light chain;

a non-human vertebrate (e.g., mouse or rat) antibody heavy chain;

a chimaeric non-human vertebrate (e.g., mouse or rat)—human antibody chain;

an antibody chain having a human heavy chain variable region upstream of a non-human vertebrate (e.g., mouse or rat) light chain constant region;

an antibody chain having a human light chain variable region upstream of a non-human vertebrate (e.g., mouse or rat) heavy chain constant region.

The invention also relates to a transgene encoding a plurality of human IgH V regions, one or more human D regions and one or more human J regions upstream of a host non-human mammal light chain constant region, optionally comprised within a vector.

The invention also relates to a transgene encoding a plurality of human Ig light chain V regions, and one or more human light chain J regions upstream of a host non-human mammal heavy chain constant region, optionally comprised within a vector.

In one aspect the invention relates to a cell, or non-human mammal, the genome of which comprises: one or more human Ig light chain kappa V regions and one or more human Ig light chain kappa J regions upstream of all or part of the human kappa constant region.

In another aspect the invention relates to a cell, or non-human mammal, the genome of which comprises: one or more human Ig light chain lambda V regions and one or more human Ig light chain lambda J regions upstream of all or part of the human lambda constant region.

Suitably the light chain VJ and C regions are able to form antibody chains in vivo capable of specifically reacting with an antigen.

In one aspect of the invention there is no non-human coding sequence in the inserted light chain region.

In such aspects a human kappa and/or lambda region is inserted into the genome, in combination with insertion of the heavy chain VDJ region or part thereof, upstream of the host heavy chain constant region as disclosed herein.

The cell or non-human mammal of the invention may comprise:

(a) a plurality of human IgH V regions, one or more human D regions and one or more human J regions upstream of the host non-human mammal constant region; and (b) one or more human Ig light chain kappa V regions and one or more human Ig light chain kappa J regions upstream of all or part of the non-human kappa constant region, wherein the non-human mammal is able to produce a repertoire of antibodies having an antibody chain comprising non-human mammal constant region and a human variable region.

The cell or non-human mammal of the invention may comprise (a) a plurality of human IgH V regions, one or more human D regions and one or more human J regions upstream of the host non-human mammal constant region; and one or more human Ig light chain lambda V regions and one or more human Ig light chain lambda J regions upstream of the host non-human mammal lambda constant region;

wherein the non-human mammal is able to produce a repertoire of antibodies having an antibody chain comprising a non-human mammal constant region and a human variable region.

Suitably the insertion of the human VJC light chain DNA, or part thereof as disclosed above, is made at the equivalent mouse locus. In one aspect the human light chain kappa VJC DNA, or part thereof, is inserted immediately upstream or downstream of the mouse kappa VJC region. In one aspect, the human light chain lambda VJC region or part thereof is inserted immediately upstream or downstream of the mouse lambda VJC region. In one aspect only the human kappa VJC locus is inserted and not the human lambda VJC locus. In one aspect only the human lambda VJC locus is inserted and not the human kappa VJC locus. Insertions may be made using the techniques disclosed herein, and suitably do not remove the host sequences from the genome. In one aspect the non-human mammal host VJC sequences may be inactivated in some way, by mutation, or inversion, or by insertion of the human variable region DNA, or by any other means. In one aspect the cell or non-human mammal of the invention may comprise an insertion of the complete VJC human region.

The human kappa variable region DNA might be inserted into the genome in functional arrangement with a lambda constant region, for example inserted upstream of a lambda constant region. Alternatively human lambda region variable DNA might be inserted in functional arrangement with a kappa constant region, for example inserted upstream of a kappa constant region.

In one aspect one or more non-human mammal control sequences such as the enhancer sequence(s) is maintained upstream of the nonhuman mammal Mu constant region, suitably in its native position with respect to the distance from the constant region.

In one aspect one or more non-human mammal control sequences such as an enhancer sequence(s) are maintained downstream of the nonhuman mammal Mu constant region, suitably in its native position with respect to the distance from the constant region.

In one aspect a non-human mammal switch sequence, suitably the endogenous switch sequence, is maintained upstream of the non-human mammal Mu constant region, suitably in its native position with respect to distance from the constant region.

In such location the host enhancer or switch sequences are operative in vivo with the host constant region sequence(s).

In one aspect a switch sequence is neither human, nor native in the non-human mammal, for example in one aspect a non-human mammal switch sequence is not a mouse or human switch sequence. The switch sequence may be, for example, a rodent or primate sequence, or a synthetic sequence. In particular the switch sequence may be a rat sequence where the non-human mammal is a mouse. By way of example, a mouse or human constant mu sequence may be placed under the control of a switch sequence from a rat, or chimp, or other switch sequence, suitably capable of allowing isotype switching to occur in vivo.

In one aspect the switch sequence of the invention is a switch sequence comprising 3, 4, 5, 6 or more (up to 82) contiguous repeats of the repeat sequence GGGCT (SEQ ID no 46-50), such as a rat switch sequence. By "rat switch" herein it is meant that the switch is a wild-type switch corresponding to a switch from a rat genome or derived from such a switch.

In one aspect the switch sequence of the invention is a rat switch sequence comprising the following repeats: GAGCT (296 repeats; SEQ ID No 18), GGGGT (50 repeats; SEQ ID No 19), and GGGCT (83 repeats; SEQ ID No 20).

In one example the rat switch sequence comprises or consists of the sequence of SEQ ID no 1.

In these embodiments, and where the non-human mammal is a mouse or the cell is a mouse cell, the switch is optionally a rat switch as described herein.

Alternatively, the switch sequence present in cells or mammal of the invention is a mouse switch, eg, is from a mouse such as a mouse 129 strain or mouse C57 strain, or from a strain derived therefrom, optionally comprising or consisting of the sequence of SEQ ID no 4 or 5. By "mouse switch" herein it is meant that the switch is a wild-type switch corresponding to a switch from a mouse genome or derived from such a switch. In this embodiment, and where the non-human mammal is a mouse or the cell is a mouse cell, the mouse switch sequence is optionally the endogenous switch or is a mouse switch from another mouse strain.

The cell or mammal of the invention may therefore comprise a human or non-human mammal switch sequence and a human or non-human mammal enhancer region or regions. They may be upstream of a human or non-human mammal constant region. Preferably the control sequences are able to direct expression or otherwise control the production of antibodies comprising a constant region with which they are associated. One combination envisaged is a rat switch with mouse enhancer sequences and mouse constant regions in a mouse cell.

In one aspect the invention relates to a cell, preferably a non-human cell, or non-human mammal comprising an immunoglobulin heavy chain or light chain locus having DNA from 3 or more species. For example, the cell or animal may comprise host cell constant region DNA, one or more human V, D or J coding sequences and one or more non-human, non-host DNA regions that are able to control a region of the immunoglobulin locus, such as a switch sequence, promoter or enhancer which are able to control expression or isotype switching in vivo of the Ig DNA. In one aspect the cell or animal is a mouse and comprises additionally human DNA from the human Ig locus and additionally a non-mouse DNA sequence, such as a rat DNA sequence, capable of regulation of the mouse or human DNA.

In another aspect the invention relates to a cell, preferably non-human cell, or non-human mammal comprising an immunoglobulin heavy chain or light chain locus having DNA from 2 or more different human genomes. For example, it could comprise heavy chain V(D)J sequences from more than one human genome within a heavy or light chain, or heavy chain VDJ DNA from one genome and light chain VJ sequences from a different genome.

In one aspect the invention relates to a DNA fragment or cell or non-human mammal comprising an immunoglobulin heavy chain or light chain locus, or part thereof, having DNA from 2 or more species, where one species contributes a non-coding region such as a regulatory region, and the other species coding regions such as V, D, J or constant regions.

In one aspect the human promoter and/or other control elements that are associated with the different human V, D or J regions are maintained after insertion of the human VDJ into the mouse genome.

In a further aspect one or more of the promoter elements, or other control elements, of the human regions, such as the human V regions, are optimised to interact with the transcriptional machinery of a non-human mammal.

Suitably a human coding sequence may be placed under the control of an appropriate non-human mammal promoter, which allows the human DNA to be transcribed efficiently in the appropriate non-human animal cell. In one aspect the human region is a human V region coding sequence, and a human V region is placed under the control of a non-human mammal promoter.

The functional replacement of human promoter or other control regions by non-human mammal promoter or control regions may be carried out by use of recombineering, or other recombinant DNA technologies, to insert a part of the human Ig region (such as a human V region) into a vector (such as a BAC) containing a non-human Ig region. The recombineering/recombinant technique suitably replaces a portion of the non-human (e.g. mouse) DNA with the human Ig region, and thus places the human Ig region under control of the non-human mammal promoter or other control region. Suitably the human coding region for a human V region replaces a mouse V region coding sequence. Suitably the human coding region for a human D region replaces a mouse D region coding sequence. Suitably the human coding region for a human J region replaces a mouse J region coding sequence. In this way human V, D or J regions may be placed under the control of a non-human mammal promoter, such as a mouse promoter.

In one aspect the only human DNA inserted into the non-human mammalian cell or animal are V, D or J coding regions, and these are placed under control of the host regulatory sequences or other (non-human, non-host) sequences, In one aspect reference to human coding regions includes both human introns and exons, or in another aspect simply exons and no introns, which may be in the form of cDNA.

It is also possible to use recombineering, or other recombinant DNA technologies, to insert a non-human-mammal (e.g. mouse) promoter or other control region, such as a promoter for a V region, into a BAC containing a human Ig region. A recombineering step then places a portion of human DNA under control of the mouse promoter or other control region.

The approaches described herein may also be used to insert some or all of the V, D and J regions from the human heavy chain upstream of a light chain constant region, rather than upstream of the heavy chain constant region. Likewise some or all of the human light chain V and J regions may be inserted upstream of the heavy chain constant region. Insertion may be at the endogenous constant region locus, for example between the endogenous constant and J region, and may be of some, or all, of the V, D or J genes alone, excluding promoter or enhancer sequences, or may be of some, or all, of the V, D or J genes with one or more or all respective promoter or enhancer sequences. In one aspect the full repertoire of V, D or J fragments in germline orientation may be inserted upstream and in functional arrangement with a host constant region.

Thus the present invention allows V and/or D and/or J regions from a human, or any species, to be inserted into a chromosome of a cell from a different species that comprises a constant region, allowing a chimaeric antibody chain to be expressed.

In one aspect the invention requires only that some human variable region DNA is inserted into the genome of a non-human mammal in operable arrangement with some, or all, of the human heavy chain constant region at the region of the endogenous heavy chain constant region locus such that an antibody chain can be produced. In this aspect of the invention and where human light chain DNA is additionally inserted, the light chain DNA insertion can be in the form of a completely human construct, having both human variable DNA and human constant region DNA, or have human variable region DNA and constant region DNA from a non-human, non-host species. Other variations are also possible, such as insertion of both of the light chain human variable region and host genome constant region. In addition the insertion of said light chain transgenes need not be at the equivalent endogenous locus, but may be anywhere in the genome. In such a scenario the cell or mammal may produce chimaeric heavy chains (comprising human variable region DNA and mouse constant region DNA) and light chains comprising human variable and human constant region DNA. Thus in one aspect of the invention the lambda and or kappa human variable region DNA can be inserted upstream of the endogenous locus, or downstream, or indeed on a different chromosome to the endogenous locus, and inserted with or without constant region DNA.

As well insertion of human light chain DNA upstream of the host non-human mammal constant region, a further aspect of the invention relates to insertion of one or both light chain human variable regions downstream of the equivalent endogenous locus constant region, or elsewhere in the genome.

Generally, insertion of human variable region DNA at or close to the equivalent endogenous locus in the recipient genome is preferred, for example within 1, 2, 3, 4, 5, 6, 7, 8, 9, or 10 kb of the boundary (upstream or downstream) of a host immunoglobulin locus.

Thus in one aspect the invention can relate to a cell or non-human mammal whose genome comprises:

(a) a plurality of human IgH V regions, one or more human D regions and one or more human J regions upstream of the host non-human mammal constant region; and (b) one or more human Ig light chain kappa V regions and one or more human Ig light chain kappa J regions, and/or, one or more human Ig light chain lambda V regions and one or more human Ig light chain lambda J regions;

wherein the non-human mammal is able to produce a repertoire of chimaeric antibodies, or chimaeric light or heavy chains, having a non-human mammal constant region and a human variable region.

In one particular aspect the genome of the cell or non-human mammal comprises:

a plurality of human IgH V regions, one or more human D regions and one or more human J regions upstream of the host non-human mammal constant region;

one or more human Ig light chain kappa V regions and one or more human Ig light chain kappa J regions upstream of the host non-human mammal kappa constant region, and one or more human Ig light chain lambda V regions and one or more human Ig light chain lambda J regions downstream of the host non-human mammal lambda constant region, optionally in which the human lambda variable region may be inserted upstream or downstream of the endogenous host lambda locus in operable linkage with a human lambda constant region, such that the non-human mammal or cell can produce fully human antibody light chains and chimaeric heavy chains.

In a further, different, aspect of the invention, the use of the methods of the invention allows a locus to be built up in a stepwise manner by sequential insertions, and thus allows for the insertion of human variable DNA together with human or non-human constant region DNA at any suitable location in the genome of a non-human host cell. For example, methods of the invention can be used to insert human immunoglobulin variable region DNA together with constant region DNA from the host genome anywhere in the genome of a non-human host cell, allowing a chimaeric antibody chain to be produced from a site other than the endogenous heavy region. Any human heavy chain or light chain DNA construct contemplated above can be inserted into any desired position into the genome of a non-human host cell using the techniques described herein. The present invention thus also relates to cells and mammals having genomes comprising such insertions.

The invention also relates to a vector, such as a BAC, comprising a human V, D or J region in a functional arrangement with a non-human mammal promoter, or other control sequence, such that the expression of the human V, D or J region is under the control of the non-human mammal promoter in a cell of the non-human mammal, such as an ES cell, in particular once inserted into the genome of that cell.

The invention also relates to cells and non-human mammals containing said cells, which cells or mammals have a human V, D or J region in a functional arrangement with a non-human mammal promoter, or other control sequence, such that the expression of the human V, D or J region is under the control of the non-human mammal promoter in the cells or mammal.

Generally, one aspect of the invention thus relates to a non-human mammal host cell capable of expression of a human V, D or J coding sequence under the control of a host promoter or control region, the expression capable of producing a humanised antibody having a human variable domain and non-human mammal constant region.

In one aspect the invention relates to a cell, such as a non mammalian cell, such as an ES cell, the genome of which comprises (a) a plurality of human IgH V regions, one or more human D regions and one or more human J regions upstream of the host non-human mammal constant region; and (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;

In another aspect the invention relates to a cell, such as a non-human mammal cells, such as ES cells whose genome comprises (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and (b) optionally one or more human IgH V regions, one or more human D regions and one or more human J regions upstream of the host non-human mammal constant region In one aspect the cell is an ES cell is capable of developing into a non-human mammal able to produce a repertoire of antibodies which are chimaeric, said chimaeric antibodies having a non-human mammal constant region and a human variable region. Optionally the genome of the cell is modified to prevent expression of fully host-species specific antibodies.

In one aspect the cell is an induced pluripotent stem cell (iPS cell).

In one aspect cells are isolated non-human mammalian cells.

In one aspect a cell as disclosed herein is preferably a non-human mammalian cell.

In one aspect the cell is a cell from a mouse strain selected from C57BL/6, M129 such as 129/SV, BALB/c, and any hybrid of C57BL/6, M129 such as 129/SV, or BALB/c.

The invention also relates to a cell line which is grown from or otherwise derived from cells as described herein, including an immortalised cell line. The cell line may comprise inserted human V, D or J genes as described herein, either in germline configuration or after rearrangement following in vivo maturation. The cell may be immortalised by fusion (eg, electrofusion or using PEG according to standard procedures.) to a tumour cell (eg, P3X63-Ag8.653 (obtainable from LGC Standards; CRL-1580), SP2/0-Ag14 (obtainable from ECACC), NSI or NS0), to provide an antibody producing cell and cell line, or be made by direct cellular immortalisation.

The present invention also relates to vectors for use in the invention. In one aspect such vectors are BACs (bacterial artificial chromosomes). It will be appreciated that other cloning vectors may be used in the invention, and therefore reference to BACs herein may be taken to refer generally to any suitable vector.

In one aspect BACs used for generation of human DNA to be inserted, such as the VDJ or VJ regions are trimmed so that in the final human VDJ or VJ region or part thereof in the non-human mammal, no sequence is duplicated or lost when compared to the original human genomic sequence.

In one aspect the invention relates to a vector comprising an insert, preferably comprising a region of human DNA from some of the human VDJ or VJ locus, flanked by DNA which is not from that locus. The flanking DNA may comprise one or more selectable markers or one or more site specific recombination sites. In one aspect the vector comprises 2 or more, such as 3, heterospecific and incompatible site specific recombination sites. In one aspect the site specific recombination sites may be loxP sites, or variants thereof, or FRT sites or variants thereof. In one aspect the vector comprises one or more transposon ITR (inverted terminal repeat) sequences.

In one aspect the non-human animals of the invention suitably do not produce any fully humanised antibodies. In one aspect this is because there is no DNA inserted from the human constant region. Alternatively there is no human constant region DNA in the genome capable of forming an antibody in conjunction with the inserted human variable region DNA component, for example due to mutation within any human constant region DNA or distance from any constant region human DNA and human variable region DNA.

In one aspect human light chain constant region DNA may be included in the cell genome, such that a fully human lambda or kappa human antibody chain might be generated, but this would only be able to form an antibody with a chimaeric heavy chain, and not produce a fully human antibody having human variable and constant regions.

In one aspect the non-human mammal genome is modified to prevent expression of fully host-species specific antibodies. Fully host species specific antibodies are antibodies that have both variable and constant regions from the host organism. In this context the term 'specific' is not intended to relate to the binding of the antibodies produced by the cells or animals of the invention but rather to the origin of the DNA which encodes those antibodies.

In one aspect the non-human mammal genome is modified to prevent expression of the native (fully host species specific) antibodies in the mammal by inactivation of all or a part of the host non-human mammal Ig loci. In this context, inactivation or prevention of endogenous antibody or gene segment usage (using any inactivation technique described herein) is, for example, substantially complete inactivation or prevention (substantially 100%, ie, essentially none (eg, less than 10, 5, 4, 3, 2, 1 or 0.5%) of the endogenous antibody chain (eg, no endogenous heavy chains) is expressed). This can be determined, for example, at the antibody chain (protein) level by assessing the antibody repertoire produced by the non-human vertebrate, mammal or at the nucleotide level by assessing mRNA transcripts of antibody chain loci, eg, using RACE. In an embodiment, inactivation is more than 50% (ie, 50% or less of the antibodies or transcripts are of an endogenous antibody chain), 60%, 70%, 80%, 85%, 90%, 95%, 96%, 97%, 98% or 99%. For example, in an embodiment, endogenous heavy chain expression is substantially inactivated such that no more than 85%, 90%, 95%, 96%, 97%, 98% or 99% of the heavy chain repertoire of the vertebrate (mammal) is provided by endogenous heavy chains. For example, endogenous heavy chain expression is substantially inactivated such that substantially none of the heavy chain repertoire of the vertebrate (mammal) is provided by endogenous heavy chains. For example, in an embodiment, endogenous heavy chain expression is substantially inactivated such that no more than 85%, 90%, 95%, 96%, 97%, 98% or 99% of the kappa chain repertoire of the vertebrate (mammal) is provided by endogenous kappa chains. For example, endogenous kappa chain expression is substantially inactivated such that substantially none of the kappa chain repertoire of the vertebrate (mammal) is provided by endogenous kappa chains. For example, in an embodiment, endogenous heavy chain expression is substantially inactivated such that no more than 85%, 90%, 95%, 96%, 97%, 98% or 99% of the lambda chain repertoire of the vertebrate (mammal) is provided by endogenous lambda chains. For example, endogenous lambda chain expression is substantially inactivated such that substantially none of the lambda chain repertoire of the vertebrate (mammal) is provided by endogenous lambda chains.

In one aspect this is achieved by inversion of all or part of the non-human mammal VDJ region, or VJ region, optionally by insertion of one or more site specific recombinase sites into the genome and then use of these sites in recombinase-mediated excision or inversion of all or a part of the non-human mammal Ig locus. In one aspect a double inversion, may be employed, the first to move the V(D)Js away from the endogenous locus and then a more local inversion which puts them in the correct orientation. In one aspect a single loxP site is used to invert the non-human mammal VDJ region to a centromeric locus or telomeric locus.

In one example, a mouse or mouse cell of the invention comprises inverted endogenous heavy chain gene segments (eg, VH, D and JH, such as the entire endogenous heavy chain VDJ region) that are immediately 3' of position 119753123, 119659458 or 120918606 on an endogenous mouse chromosome 12. Optionally, the genome of the mouse or cell is homozygous for said chromosome 12.

The invention also provides: —

A cassette for inversion and inactivation of endogenous non-human vertebrate (eg, mouse or rat) antibody chain gene segments, the segments being part of an antibody chain locus sequence on a chromosome of a non-human vertebrate (eg, mouse or rat) cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the cell genome on a different chromosome or on said chromosome at least 10, 15, 20, 25, 30, 35, 40, 45 or 50 mb away from the endogenous gene segments.

The invention also provides: —

A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the mouse cell genome on a different chromosome or on chromosome 12 at least 10, 15, 20, 25, 30, 35, 40, 45 or 50 mb away from the endogenous gene segments.

The invention provides: —

A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein (i) the 5' homology arm is mouse chromosome 12 DNA from coordinate 119753124 to coordinate 119757104 and the 3' homology arm is mouse chromosome 12 DNA from coordinate 119749288 to 119753123; or (ii) the 5' homology arm is mouse chromosome 12 DNA from coordinate 119659459 to coordinate 119663126 and the 3' homology arm is mouse chromosome 12 DNA from coordinate 119656536 to 119659458; or (iii) the 5' homology arm is mouse chromosome 12 DNA from coordinate 120918607 to coordinate 120921930 and the 3' homology arm is mouse chromosome 12 DNA from coordinate 120915475 to 120918606.

Embodiment (i) results in an inversion of mouse chromosome 12 from coordinate 119753123 to coordinate 114666436.

Embodiment (ii) results in an inversion of mouse chromosome 12 from coordinate 119659458 to coordinate 114666436

Embodiment (iii) results in an inversion of mouse chromosome 12 from coordinate 12091806 to coordinate 114666436.

Thus, the invention provides a mouse or mouse cell whose genome comprises an inversion of a chromosome 12, wherein the inversion comprises inverted endogenous heavy chain gene segments (eg, VH, D and JH, such as the entire endogenous heavy chain VDJ region); wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments; and wherein the inversion is (i) an inversion of mouse chromosome 12 from coordinate 119753123 to coordinate 114666436; (ii) an inversion of mouse chromosome 12 from coordinate 119659458 to coordinate 114666436; or (iii) an inversion of mouse chromosome 12 from coordinate 12091806 to coordinate 114666436.

In one embodiment, the endogenous gene segments are from a 129-derived mouse cell (eg, segments from an AB2.1 cell) and the homology arms are isogenic DNA (ie, identical to 129-derived endogenous sequences demarcated by the respective coordinates stated in (i) to (iii) above). Thus, no new sequence is created by homologous recombination using these homology arms. In another embodiment, the arms are from a mouse strain that is different from the endogenous strain. The site-specific recombination sites are mutually compatible and mutually inverted such that, on expression of an associated recombinase enzyme (eg, Cre, Dre or Flp), recombination between the site in the inserted inversion cassette and the site flanking the endogenous gene segments is carried out, thereby inverting and moving the endogenous gene segments far upstream (5') of their original location in the heavy chain locus. This inactivates endogenous heavy chain expression. Similarly, light chain inactivation can be performed by choosing the homology arms of the inversion cassette with reference to a chromosomal region spaced at least 10, 15, 20, 25, 30, 35, 40, 45 or 50 mb away from the endogenous light chain locus, the latter comprising a site-specific recombination site that is compatible with the site in the inversion cassette.

In one embodiment, the expressible label is a fluorescent label, eg, GFP or a variant thereof (eg, YFP, CFP or RFP). Thus, a label is used instead of a selection marker, such as one that confers resistance to allow for selection of transformants.

The invention provides a method of inactivating gene segments of an endogenous antibody locus, the method comprising (i) Providing a non-human vertebrate cell (eg, an ES cell, eg, a mouse ES cell) whose genome comprises an antibody chain locus comprising endogenous variable region gene segments;

(ii) Targeting a site-specific recombination site to flank the 3' of the 3'-most of said endogenous gene segments;

(iii) Targeting a second site-specific recombination site at least 10 mb away from said endogenous gene segments, the second site being compatible with the first site inverted with respect to the first site;

(iv) Expressing a recombinase compatible with said sites to effect site-specific recombination between said sites, thereby inverting and moving said gene segments away from said locus, wherein the endogenous gene segments are inactivated; and (v) Optionally developing the cell into a progeny cell or vertebrate (eg, mouse or rat) whose genome is homozygous for the inversion.

The genome of the progeny cell or vertebrate can comprise transgenic heavy and/or light chain loci, each capable of expressing antibody chains comprising human variable regions. Optionally, endogenous heavy and kappa light chain expression is inactivated by inverting endogenous heavy and kappa variable region gene segments according to the method of the invention. Optionally, endogenous lambda chain expression is also inactivated in this way.

In an alternative to the method and inversion cassettes of the invention, instead of inverting and moving variable region gene segments only, other parts of the endogenous locus can alternatively or additionally be inverted and moved to effect inactivation. For example, one or more endogenous regulatory elements (eg, Smu and/or Emu) and/or one or more endogenous constant regions (eg, Cmu and/or Cgamma) can be inverted and moved.

Sites that "flank" in the above contexts of the invention can be provided such that a site-specific recombination site immediately flanks the endogenous sequence or is spaced therefrom, eg, by no more than 250, 200, 250, 100, 50 or 20 kb in the 3' direction.

In one aspect the non-human mammal genome into which human DNA is inserted comprises endogenous V, (D) and J regions, and the endogenous sequences have not been deleted.

The invention comprises a method for insertion of multiple DNA fragments into a DNA target, suitably to form a contiguous insertion in which the inserted fragments are joined together directly without intervening sequences. The method is especially applicable to the insertion of a large DNA fragment into a host chromosome which can be carried out in a stepwise fashion.

In one aspect the method comprises insertion of a first DNA sequence into a target, the sequence having a DNA vector portion and a first sequence of interest (X1); insertion of a second DNA sequence into the vector portion of the first sequence, the second DNA sequence having a second sequence of interest (X2) and a second vector portion; and then excising any vector sequence DNA separating X1 and X2 to provide a contiguous X1X2, or X2X1 sequence within the target. There is optionally insertion of a further one or more DNA sequences, each DNA sequence having a further sequence of interest (X3, . . . ) and a further vector portion, into the vector portion of the preceding DNA sequence, to build up a contiguous DNA fragment in the target.

The DNA target for insertion of the first DNA sequence may be a specific site or any point in the genome of a particular cell.

The general method is described herein in relation to the insertion of elements of the human VDJ region, but is applicable to insertion of any DNA region, from any organism, and in particular insertion of large DNA fragments of >100 kB, such as 100-250 kb, or even larger, such as that of the TCR or HLA. Features and approaches described herein in respect of the VDJ insertion may be equally applied to the any of the methods disclosed In one aspect the inserted DNA is human DNA, such as the human VDJ or VJ region, is built up in the genome of a cell, such as an ES cell, in a stepwise manner using 2, 3, 4, 5, 6, 7, 8, 9, 10, 11, 12, 13, 14, 15, 20 or more separate insertions for each heavy chain or light chain region. Fragments are suitably inserted at the same or substantially the same cell locus, e.g. ES cell locus, one after another, to form the complete VDJ or VJ region, or part thereof. The present invention also relates to cells and non-human animals comprising intermediates in the process whose genomes may comprise only a partial VDJ region, such as only human variable region DNA.

In a further aspect the method for producing a transgenic non-human mammal comprises the insertion of human VDJ or VJ regions upstream of the host non-human mammal constant region by step-wise insertion of multiple fragments by homologous recombination, preferably using an iterative process. Suitably fragments of approximately 100 KB from the human VDJ and VJ locus are inserted, suitably to form part of, or a complete, VDJ or VJ region after the final iteration of the insertion process, as disclosed herein.

In one aspect the insertion process commences at a site where an initiation cassette has been inserted into the genome of a cell, such as an ES cell, providing a unique targeting region. In one aspect the initiation cassette is inserted in the non-human mammal heavy chain locus, for use in insertion of human heavy chain DNA. Similarly an initiation cassette may be inserted in the non-human mammal light chain locus, for use in insertion of human light chain VJ DNA The initiation cassette suitably comprises a vector backbone sequence with which a vector having a human DNA fragment in the same backbone sequence can recombine to insert the human DNA into the cell (e.g. ES) cell genome, and suitably a selection marker, such as a negative selection marker. Suitably the vector backbone sequence is that of a BAC library, to allow BACs to be used in the construction of the ES cells and mammals. The vector backbone sequence may however be any sequence which serves as a target site into which a homologous sequence can insert, for example by homologous recombination, for example RMCE, and is preferably not DNA encoding any of the VDJ or constant region.

In one aspect the insertion of the first DNA fragment into an initiation cassette is followed by insertion of a second DNA fragment into a portion of the first DNA fragment, suitably a part of the vector backbone of the second DNA fragment. In one aspect an inserted DNA fragment comprises a part of the human VDJ region flanked by 5' and/or 3' sequences that are not from the human VDJ region. In one aspect the 5' and/or 3' flanking sequences may each contain one or more selectable markers, or be capable of creating a selectable system once inserted into the genome. In one aspect one or both flanking sequences may be removed from the genome in vitro, or in vivo, following insertion. In one aspect the method comprises insertion of a DNA fragment followed by selection of both 5' and 3' ends of the inserted fragment flanking the human VDJ DNA. In one aspect the iterative insertion is made by insertion of DNA fragments at the 5' end of the previous inserted fragment, and in this aspect there may be deletion in vivo of the vector DNA which separates the inserted human DNA sequences, to provide a contiguous human DNA sequence.

In one aspect insertion of human VDJ DNA into a genome may be achieved without leaving any flanking DNA in the genome, for example by transposase mediate DNA excision. One suitable transposase is the Piggybac transposase.

In one aspect the first human variable region fragment is inserted by homologous recombination at the initiation cassette backbone sequence and then the DNA of any negative selection marker and initiation cassette are subsequently removed by recombination between recombinase target sequences, such as FRT using in this example, FLPase expression. Generally repeated targeted insertions at the (e.g. BAC) backbone initiation sequence and subsequent removal by rearrangement between recombinase target sequences are repeated to build up the entire human VDJ region upstream of the host non-mammal constant region.

In one aspect a selectable marker or system may be used in the method. The marker may be generated upon insertion of a DNA fragment into a genome, for example forming a selectable marker in conjunction with a DNA element already present in the genome.

In one aspect the cell (e.g. ES) cell genome does not contain 2 identical selectable markers at the same time during the process. It can be seen that the iterative process of insertion and selection can be carried out using only 2 different selection markers, as disclosed in the examples herein, and for example the third selectable marker may be identical to the first marker, as by the time of insertion of the third vector fragment the first vector fragment and the first marker has been removed.

In one aspect a correct insertion event, is confirmed before moving to the next step of any multistep cloning process, for example by confirmation of BAC structure using high density genomic arrays to screen ES cells to identify those with intact BAC insertions, sequencing and PCR verification.

Initiation Cassette (Also Called a "Landing Pad")

The invention also relates to a polynucleotide 'landing pad' sequence, the polynucleotide comprising nucleic acid regions homologous to regions of a target chromosome to allow for insertion by homologous recombination into the target chromosome, and comprising a nucleic acid site which permits recombinase-driven insertion of nucleic acid into the landing pad. The invention also relates to vectors, cells and mammals of the invention comprising a landing pad as disclosed herein inserted into the genome of the cell.

The landing pad optionally comprises a non-endogenous S-mu, e.g. a rat S-mu switch The landing pad optionally comprises (in 5' to 3' orientation) a mouse Eμ sequence, a non-human, non-mouse (e.g. rat) Switch μ and at least a portion of a mouse Cμ or the entire mouse Cμ.

The rat switch sequence optionally comprises or consists of SEQ ID NO 1.

The landing pad optionally comprises the 5' homology arm of SEQ ID NO 6.

The landing pad optionally has the sequence of SEQ ID 2 or SEQ ID NO 3.

In one embodiment, the landing pad comprises an expressible label. For example the label is a fluorescent label, eg, GFP or a variant thereof (eg, YFP, CFP or RFP). Thus, a label is used instead of a selection marker (such as one that confers resistance to allow for selection of transformants).

In an embodiment, the landing pad comprises 5' and 3' homology arms for insertion into the cell genome using homologous recombination. The homology arms can be isogenic DNA (eg, identical to 129-derived endogenous sequences of when a 129-derived ES cell is used). Thus, no new sequence is created by homologous recombination using these homology arms. In another embodiment, the arms are from a mouse strain that is different from the endogenous strain (ES cell strain).

The methods of the invention include methods wherein the landing pad sequence comprises any of the configurations or sequences as disclosed herein.

Another method of the invention comprises the step of insertion of the landing pad into a mouse chromosome by homologous recombination between mouse J1-4 and mouse C mu sequences.

Another method of the invention comprises the step of insertion of the landing pad into the mouse chromosome 12 by homologous recombination between mouse J1-4 and E mu.

In one aspect the method uses site specific recombination for insertion of one or more vectors into the genome of a cell, such as an ES cell. Site specific recombinase systems are well known in the art and may include Cre-lox, and FLP/FRT or combinations thereof, in which recombination occurs between 2 sites having sequence homology.

Additionally or alternatively to any particular Cre/Lox or FLP/FRT system described herein, other recombinases and sites that may be used in the present invention include Dre recombinase, rox sites, and PhiC31 recombinase.

Suitable BACs are available from the Sanger centre, see "A genome-wide, end-sequenced 129Sv BAC library resource for targeting vector construction". Adams D J, Quail M A, Cox T, van der Weyden L, Gorick B D, Su Q, Chan W I, Davies R, Bonfield J K, Law F, Humphray S, Plumb B, Liu P, Rogers J, Bradley A. Genomics. 2005 December; 86(6):753-8. Epub 2005 Oct. 27. The Wellcome Trust Sanger Institute, Hinxton, Cambridgeshire CB10 1SA, UK. BACs containing human DNA are also available from, for example, Invitrogen™. A suitable library is described in Osoegawa K et al, Genome Research 2001. 11: 483-496.

In one aspect a method of the invention specifically comprises:

(1) insertion of a first DNA fragment into a non-human ES cell, the fragment containing a first portion of human VDJ or VJ region DNA and a first vector portion containing a first selectable marker;

(2) optionally deletion of the a part of the first vector portion;

(3) insertion of a second DNA fragment into a non-human ES cell containing the first DNA fragment, the insertion occurring within the first vector portion, the second DNA fragment containing a second portion of the human VDJ or VJ region and a second vector portion containing a second selectable marker, (4) deletion of the first selectable marker and first vector portion, preferably by a recombinase enzyme action;

(5) insertion of a third DNA fragment into a non-human ES cell containing the second DNA fragment, the insertion occurring within the second vector portion, the third DNA fragment containing a third portion of the human VDJ or VJ region and a third vector portion containing third selectable marker, (6) deletion of the second selectable marker and second vector portion; and (7) iteration of the steps of insertion and deletion, as necessary, for fourth and further fragments of the human VDJ or VJ human regions, as necessary, to produce an ES cell with a part or all of the human VDJ or VJ region inserted as disclosed herein, and suitably to remove all the vector portions within the ES cell genome.

In another aspect the invention comprises (1) insertion of DNA forming an initiation cassette into the genome of a cell;

(2) insertion of a first DNA fragment into the initiation cassette, the first DNA fragment comprising a first portion of a human DNA and a first vector portion containing a first selectable marker or generating a selectable marker upon insertion;

(3) optionally removal of part of the vector DNA (4) insertion of a second DNA fragment into the vector portion of the first DNA fragment, the second DNA fragment containing a second portion of human DNA and a second vector portion, the second vector portion containing a second selectable marker, or generating a second selectable marker upon insertion;

(5) optionally, removal of any vector DNA to allow the first and second human DNA fragments to form a contiguous sequence; and (6) iteration of the steps of insertion of human VDJ DNA and vector DNA removal, as necessary, to produce a cell with all or part of the human VDJ or VJ region sufficient to be capable of generating a chimaeric antibody in conjunction with a host constant region, wherein the insertion of one, or more, or all of the DNA fragments uses site specific recombination.

In one aspect the non-human mammal is able to generate a diversity of at least $1\times10^6$ different functional chimaeric immunoglobulin sequence combinations.

In one aspect the targeting is carried out in ES cells derived from the mouse C57BL/6N, C57BL/6J, 129S5 or 129Sv strain.

In one aspect non-human animals, such as mice, are generated in a RAG-1-deficient or a RAG-2-deficient background, or other suitable genetic background which prevents the production of mature host B and T lymphocytes.

In one aspect the non-human mammal is a rodent, suitably a mouse, and cells of the invention, are rodent cells or ES cells, suitably mouse ES cells.

The ES cells of the present invention can be used to generate animals using techniques well known in the art, which comprise injection of the ES cell into a blastocyst followed by implantation of chimaeric blastocystys into females to produce offspring which can be bred and selected for homozygous recombinants having the required insertion. In one aspect the invention relates to a chimeric animal comprised of ES cell-derived tissue and host embryo derived tissue. In one aspect the invention relates to genetically-altered subsequent generation animals, which include animals having a homozygous recombinants for the VDJ and/or VJ regions.

In a further aspect the invention relates to a method for producing an antibody specific to a desired antigen the method comprising immunizing a transgenic non-human mammal as above with the desired antigen and recovering the antibody (see e.g. Harlow, E. & Lane, D. 1998, 5th edition, Antibodies: A Laboratory Manual, Cold Spring Harbor Lab. Press, Plainview, N.Y.; and Pasqualini and Arap, Proceedings of the National Academy of Sciences (2004) 101:257-259). Suitably an immunogenic amount of the antigen is delivered. The invention also relates to a method for detecting a target antigen comprising detecting an antibody produced as above with a secondary detection agent which recognises a portion of that antibody.

In a further aspect the invention relates to a method for producing a fully humanised antibody comprising immunizing a transgenic non-human mammal as above with the desired antigen, recovering the antibody or cells expressing the antibody, and then replacing the non-human mammal constant region with a human constant region. This can be done by standard cloning techniques at the DNA level to replace the non-human mammal constant region with an appropriate human constant region DNA sequence—see e.g. Sambrook, J and Russell, D. (2001, 3'd edition) Molecular Cloning: A Laboratory Manual (Cold Spring Harbor Lab. Press, Plainview, N.Y.).

In a further aspect the invention relates to humanised antibodies and antibody chains produced according to the present invention, both in chimaeric and fully humanised form, and use of said antibodies in medicine. The invention also relates to a pharmaceutical composition comprising such an antibodies and a pharmaceutically acceptable carrier or other excipient.

Antibody chains containing human sequences, such as chimaeric human—non-human antibody chains, are considered humanised herein by virtue of the presence of the human protein coding regions region. Fully humanised antibodies may be produced starting from DNA encoding a chimaeric antibody chain of the invention using standard techniques.

Methods for the generation of both monoclonal and polyclonal antibodies are well known in the art, and the present invention relates to both polyclonal and monoclonal antibodies of chimaeric or fully humanised antibodies produced in response to antigen challenge in non-human mammals of the present invention.

In a yet further aspect, chimaeric antibodies or antibody chains generated in the present invention may be manipulated, suitably at the DNA level, to generate molecules with antibody-like properties or structure, such as a human variable region from a heavy or light chain absent a constant region, for example a domain antibody; or a human variable region with any constant region from either heavy or light chain from the same or different species; or a human variable region with a non-naturally occurring constant region; or human variable region together with any other fusion partner. The invention relates to all such chimaeric antibody derivatives derived from chimaeric antibodies identified according to the present invention.

In a further aspect, the invention relates to use of animals of the present invention in the analysis of the likely effects of drugs and vaccines in the context of a quasi-human antibody repertoire.

The invention also relates to a method for identification or validation of a drug or vaccine, the method comprising delivering the vaccine or drug to a mammal of the invention and monitoring one or more of: the immune response, the safety profile; the effect on disease.

The invention also relates to a kit comprising an antibody or antibody derivative as disclosed herein and either instructions for use of such antibody or a suitable laboratory reagent, such as a buffer, antibody detection reagent.

The invention also relates to a method for making an antibody, or part thereof, the method comprising providing:

(i) a nucleic acid encoding an antibody, or a part thereof, obtained according to the present invention; or (ii) sequence information from which a nucleic acid encoding an antibody obtained according to the present invention, or part thereof, can be expressed to allow an antibody to be produced.

The present invention also relates to a chimaeric antibody comprising a human variable region and a non-human vertebrate or mammal (optionally a rat or mouse) constant region (optionally a C gamma or C mu), wherein the antibody is encoded by a nucleotide sequence corresponding to the nucleotide sequence of a chimaeric heavy chain locus of a cell (optionally a B-cell, ES cell or hybridoma), the locus comprising a non-human vertebrate constant region nucleotide sequence and a rearranged VDJ nucleotide sequence produced by the in vivo rearrangement of a human V region, a human D region and a human J region, the V region being selected from one of a V1-3 region, V2-5 region, V4-4 region, V1-2 region or V6-1 region, and optionally a V1-3 or V6-1 segment. Optionally, the J region is any of JH1, JH2, JH3, JH4, JH5 or JH6, and in one aspect is JH4 or JH6. The D region is, in one aspect, any D3-9, D3-10, D6-13 or D6-19. In one example, rearranged VDJ nucleotide sequence is produced by the in vivo rearrangement of human V1-3 and JH4 (optionally with D3-9, D3-10, D6-13 or D-19); or V1-3 and JH6 (optionally with D3-9, D3-10, D6-13 or D-19); or V6-1 and JH4 (optionally with D3-9, D3-10, D6-13 or D-19); or V6-1 and JH6 (optionally with D3-9, D3-10, D6-13 or D-19). In one example the rearranged VDJ nucleotide sequence is produced by the in vivo rearrangement of human V6-1 DH3-10, V1-3 DH3-10, V1-3 DH6-19, V1-3 Dh3-9 or V6-1 DH6-19. In one aspect the antibody comprises any combination exemplified in the Examples and Figures herein. Optionally, the in vivo rearrangement is in a cell (eg, B cell or ES cell) derived from the same non-human vertebrate species as the constant region sequence (eg, a mouse B cell or ES cell). The invention also relates to a non-human vertebrate or mammal cell (eg, a B-cell or ES cell or hybridoma) whose genome comprises a chimaeric heavy chain locus as described above in this paragraph. The invention also relates to a non-human vertebrate or mammal (eg, a mouse or rat) whose genome comprises a chimaeric heavy chain locus as described above in this paragraph.

The present invention also relates to a non-human vertebrate or mammal having a genome encoding a chimaeric antibody, the chimaeric antibody comprising a human variable region and a non-human vertebrate or mammal (optionally a rat or mouse) constant region (optionally a C gamma or C mu), the mammal:

- expressing more V1-3 antibodies than V2-5, V4-4, V1-2 or V6-1 antibodies; and/or
- expressing more V1-3 JH4 or V1-3 JH6 antibodies than any of, individually, V1-3 JH1, V1-3 JH2, V1-3 JH3 or V1-3 JH5 antibodies, and/or
- expressing more V6-1 JH4 or V6-1 JH6 antibodies than any of, individually, V6-1 JH1, V6-1 JH2, V6-1 JH3 or V6-1 JH5 antibodies and/or
- expressing a greater number of V1-3 DH3-10 antibodies than antibodies V1-3 with any other D region. Expression of antibodies can be assessed by methods readily available to the skilled person and as conventional in the art. For example, expression can be assessed at the mRNA level as shown in the examples below.

The invention also relates to a chimaeric antibody comprising a human variable region and a non-human vertebrate or mammal (optionally a rat or mouse) constant region (optionally a light chain constant region), wherein the antibody is obtainable from a mammal (optionally a rat or mouse) whose genome comprises an antibody chain locus comprising a germline human kappa V1-8 and germline human kappa J1 sequence, and wherein the antibody is obtainable by in vivo recombination in said mammal of the V1-8 and J1 sequences and wherein the antibody has a variable region sequence which is different from that which is encoded by germline human kappa V1-8 and germline human kappa J1sequences. Thus, in this aspect of the invention the human germline sequences are able to undergo productive rearrangement to form a coding sequence which, in conjunction with the non-human constant region sequence, can be expressed as a chimaeric antibody chain having at least a complete human variable region and a non-human constant region. This is in contrast (as the examples show below) to the combination of the germline human kappa V1-8 and germline human kappa J1sequendces per se, which do not provide for an antibody coding sequence (due to the inclusion of stop codons). In one aspect the rearranged sequence of the chimaeric antibody is a result of somatic hypermutation. In one aspect the antibody is a kappa antibody; in another aspect the antibody comprises a non-human heavy chain constant region (eg, a rat or mouse C gamma or C mu). The antibody sequence optionally comprises a $X_1X_2$ TFGQ, where $X_1X_2$=PR, RT, or PW (SEQ ID No 21); optionally a $X_1X_2$ TFGQGTKVEIKRADA (SEQ ID No 22) motif. Such motifs are not found in the equivalent position in the germline sequence as shown in the examples. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human vertebrate or mammal (optionally a rat or mouse) constant region (optionally a light chain constant region), wherein the antibody is obtainable from a mammal (optionally a rat or mouse) whose genome comprises an antibody chain locus comprising a germline human kappa V1-6 and germline human kappa J1 sequence, and wherein the antibody is obtainable by in vivo recombination in said mammal of the V1-6 and J1 sequences and wherein the antibody has a variable region sequence which is different from that which is encoded by germline human kappa V1-6 and germline human kappa J1sequences. Thus, in this aspect of the invention the human germline sequences are able to undergo productive rearrangement to form a coding sequence which, in conjunction with the non-human constant region sequence, can be expressed as a chimaeric antibody chain having at least a complete human variable region and a non-human constant region. This is in contrast (as the examples show below) to the combination of the germline human kappa V1-6 and germline human kappa J1sequendces per se, which do not provide for an antibody coding sequence (due to the inclusion of stop codons). In one aspect the rearranged sequence of the chimaeric antibody is a result of somatic hypermutation. In one aspect the antibody is a kappa antibody; in another aspect the antibody comprises a non-human heavy chain constant region (eg, a rat or mouse C gamma or C mu). The antibody sequence optionally comprises a $X_3X_4$TFGQ, where $X_3X_4$=PR or PW (SEQ ID No 23); optionally a $X_3X_4$TFGQGTKVEIKRADA (SEQ ID No 24) motif. Such motifs are not found in the equivalent position in the germline sequence as shown in the examples. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human (optionally a rat or mouse) constant region (optionally a C gamma or C mu or a C kappa), wherein the antibody is obtainable from a mammal (optionally a rat or mouse) whose genome comprises an antibody chain locus comprising a germline human kappa V1-5 and germline human kappa J1 sequence, and wherein the antibody is obtainable by in vivo recombination in said mammal of the V1-5 and J1 sequences. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human (optionally a rat or mouse) constant region (optionally a C gamma or C mu or a C kappa), wherein the antibody is obtainable from a mammal (optionally a rat or mouse) whose genome comprises an antibody chain locus comprising a germline human kappa V1-5 and germline human kappa J4 sequence, and wherein the antibody is obtainable by in vivo recombination in said mammal of the V1-5 and J4 sequences. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

Antibodies of the invention may be isolated, in one aspect being isolated from the cell or organism in which they are expressed.

A non-human mammal whose genome comprises:

(a) the human IgH VDJ region upstream of the host non-human mammal constant region; and (b) the human Ig light chain kappa V and J regions upstream of the host non-human mammal kappa constant region and/or the human Ig light chain lambda V and J regions upstream of the host non-human mammal lambda constant region;

wherein the non-human mammal is able to produce a repertoire of chimaeric antibodies having a non-human mammal constant region and a human variable region, and optionally wherein the non-human mammal genome is modified to prevent expression of fully host-species specific antibodies.

A non-human mammal ES cell whose genome comprises:

(a) the human IgH V, D and J region upstream of a non-human mammal constant region; and (b) the human Ig locus light chain kappa V and J regions upstream of the host non-human mammal kappa constant region, and/or the human Ig locus light chain lambda V and J regions upstream of the host non-human mammal lambda constant region wherein the ES cell is capable of developing into a non-human mammal, being able to produce a repertoire of antibodies which are chimaeric, having a non-human mammal constant region and a human variable region.

A method for producing a transgenic non-human mammal able to produce a repertoire of chimaeric antibodies, the antibodies having a non-human mammal constant region and a human variable region, the method comprising inserting by homologous recombination into a non-human mammal ES cell genome (a) the human IgH VDJ region upstream of the host non-human mammal heavy chain constant region, and (b) the human IgL VJ region for lambda or kappa chains upstream of the host non-human mammal lambda or kappa chain constant region, respectively such that the non-human mammal is able to produce a repertoire of chimaeric antibodies having a non-human mammal constant region and a human variable region, wherein steps (a) and (b) can be carried out in either order and each of steps (a) and (b) can be carried out in a stepwise manner or as a single step.

In one aspect the insertion of human VDJ or VJ regions upstream of the host non-human mammal constant region is accomplished by step-wise insertion of multiple fragments by homologous recombination.

In one aspect the step-wise insertions commence at a site where an initiation cassette has been inserted into the genome of an ES cell providing a unique targeting region consisting of a BAC backbone sequence and a negative selection marker.

In one aspect the first human variable region fragment is inserted by homologous recombination at the initiation cassette BAC backbone sequence and said negative selection marker and initiation cassette are subsequently removed by recombination between recombinase target sequences.

In one aspect repeated targeted insertions at the BAC backbone initiation sequence and subsequent removal of the backbone by rearrangement between recombinase target sequences is repeated to build up the entire human VDJ region upstream of the host non-mammal constant region.

Insertion of Human Variable Region Gene Segments Precisely within the Endogenous Mouse JH4-Cmu Intron There is further provided a cell or non human mammal according to the invention wherein the mammal is a mouse or the cell is a mouse cell and wherein the insertion of the human heavy chain DNA is made in a mouse genome between coordinates 114,667,091 and 114,665,190 of mouse chromosome 12.

There is further provided a cell or non human mammal according to the invention wherein the insertion of the human heavy chain DNA is made at coordinate 114,667,091.

There is further provided a cell or non human mammal according to the invention wherein the human IgH VDJ region comprises nucleotides 105,400,051 to 106,368,585 from human chromosome 14 (coordinates refer to NCBI36 for the human genome).

There is further provided a method, cell or non human mammal according to the invention wherein a human coding region DNA sequence is in a functional arrangement with a non-human mammal control sequence, such that transcription of the human DNA is controlled by the non-human mammal control sequence. In one example, the initiation cassette is inserted between the mouse J4 and C alpha exons. There is further provided an initiation cassette suitable for use in the method comprising a vector backbone sequence and a selection marker.

The invention provides the following aspects (starting at aspect number 103): —

103. A cell or non human mammal according to any one of the above configurations, examples, embodiments or aspects, wherein the mammal is a mouse or the cell is a mouse cell and wherein the insertion of the human heavy chain DNA is made in a mouse genome between coordinates 114,667,091 and 114,665,190 of mouse chromosome 12.

104. A cell or non human mammal according to any one of the above configurations, examples, embodiments or aspects, wherein the insertion of the human heavy chain DNA is made at coordinate 114,667,091.

105. A cell or mammal according to any one of the above configurations, examples, embodiments or aspects, wherein the human IgH VDJ region comprises nucleotides 105,400,051 to 106,368,585 from human chromosome 14 (coordinates refer to NCBI36 for the human genome).

106. A method, cell or mammal according to any one of the above configurations, examples, embodiments or aspects, wherein a human coding region DNA sequence is in a functional arrangement with a non-human mammal control sequence, such that transcription of the human DNA is controlled by the non-human mammal control sequence.

107. A method according to aspect 106 wherein the initiation cassette is inserted between the mouse J4 and C alpha exons.

108. An initiation cassette suitable for use in the method of aspect 107 comprising a vector backbone sequence and a selection marker.

Inactivation of Endogenous Antibody Chain Expression by Insertion of Human Antibody Variable Region Gene Segments 109. A non-human vertebrate (optionally a mouse or rat) or non-human vertebrate cell (optionally a mouse or rat cell) having a genome that
 (i) comprises a transgenic antibody chain locus capable of expressing an antibody chain comprising a human variable region (optionally following antibody gene rearrangement); and
 (ii) is inactivated for endogenous non-human vertebrate antibody chain expression; wherein the transgenic locus comprises
 (iii) a DNA sequence comprising a plurality of human antibody variable region gene segments inserted between endogenous antibody variable region gene segments and an endogenous antibody constant region, whereby endogenous antibody chain expression is inactivated.

The transgenic locus is a heavy chain or light chain locus.

Inactivation of endogenous heavy chain expression in non-human vertebrates such as mice and rats has involved the deletion of all or part of the endogenous heavy chain VDJ region (including sequences between gene segments). The ADAM6 genes are present in the endogenous mouse VDJ region. In mouse, there are two copies of ADAM6 (ADAM6a, ADAM6b) located between the VH and D gene segments in the IgH locus of chromosome 12 (in the intervening region between mouse VH5-1 and D1-1 gene segments). These two adjacent intronless ADAM6 genes have 95% nucleotide sequence identity and 90% amino acid identity. In human and rat, there is only one ADAM6 gene. Expression pattern analysis of mouse ADAM6 shows that it is exclusively expressed in testis [1]. Although ADAM6 transcripts can be detected in lymphocytes, it is restricted to the nucleus, suggesting that the transcription of ADAM6 gene in particular was due to transcriptional read-through from the D region rather than active messenger RNA production[2]. In rat, ADAM6 is on chromosome 6.

Mature ADAM6 protein is located on the acrosome and the posterior regions of sperm head. Notably, ADAM6 forms a complex with ADAM2 and ADAM3, which is required for fertilization in mice [3]. Reference [4] implicates ADAM6 in a model where this protein interacts with ADAM3 after ADAM6 is sulphated by TPST2, sulphation of ADAM6 being critical for stability and/or complex formation involving ADAM6 and ADAM3, and thus ADAM6 and ADAM3 are lost from Tpst2-null sperm. The study observes that Tpst2-deficient mice have male infertility, sperm mobility defects and possible abnormalities in sperm-egg membrane interactions.

Thus, the maintenance of ADAM6 expression in sperm is crucial for fertility. Thus, it is thought that transgenic male mice and rats in which ADAM6 genes have been deleted are not viably fertile. This hampers breeding of colonies and hampers the utility of such mice as transgenic antibody-generating platforms. It would be desirable to provide improved non-human transgenic antibody-generating vertebrates that are fertile.

[1]. Choi I, et. al., Characterization and comparative genomic analysis of intronless Adams with testicular gene expression. Genomics. 2004 April; 83(4):636-46.

[2]. Featherstone K, Wood A L, Bowen A J, Corcoran A E. The mouse immunoglobulin heavy chain V-D intergenic sequence contains insulators that may regulate ordered V(D)J recombination. J Biol Chem. 2010 Mar. 26; 285 (13):9327-38. Epub 2010 Jan. 25.

[3]. Han C, et. al., Comprehensive analysis of reproductive ADAMs: relationship of ADAM4 and ADAM6 with an ADAM complex required for fertilization in mice. Biol Reprod. 2009 May; 80(5):1001-8. Epub 2009 Jan. 7.

[4]. Marcello et al, Lack of tyrosylprotein sulfotransferase-2 activity results in altered sperm-egg interactions and loss of ADAM3 and ADAM6 in epididymal sperm, J Biol Chem. 2011 Apr. 15; 286(15):13060-70. Epub 2011 Feb. 21.

According to aspect 109 of the invention, inactivation does not involve deletion of the VDJ region or part thereof including endogenous ADAM6, but instead inactivation by insertion allows for the preservation of endogenous ADAM6 and thus does not risk infertility problems.

The final mouse resulting from the method (or a mouse derived from a cell produced by the method) is in one embodiment a male, so that the invention improves upon the prior art male transgenic mice that are infertile as a result of genomic manipulation. Fertile mice produce sperm that can fertilise eggs from a female mouse. Fertility is readily determined, for example, by successfully breeding to produce an embryo or child mouse. In another embodiment, the method of the invention makes a final female mouse. Such females are, of course, useful for breeding to create male progeny carrying ADAM6 and which are fertile.

In one embodiment of aspect 109, the genome is homozygous for the transgenic locus. For example, the genome is homozygous for endogenous ADAM6 genes.

In one embodiment of the vertebrate of aspect 109, the genome is inactivated for expression of endogenous heavy and kappa (and optionally also lambda) chains.

In one embodiment, in part (iii) of aspect 109 said DNA comprises human VH, D and JH gene segments or human VL and JL gene segments (eg, Vκ and Jκ gene segments). In an example, the DNA comprises a landing pad having a selectable marker, eg, a HPRT gene, neomycin resistance gene or a puromycin resistance gene; and/or a promoter.

In one embodiment, in part (iii) of aspect 109 the endogenous gene segments are the entire endogenous VDJ region of a heavy chain locus and/or the endogenous constant region is a Cmu or Cgamma.

In one embodiment, in part (iii) of aspect 109 the endogenous gene segments are the entire endogenous VJ region of a kappa chain locus and/or the endogenous constant region is a Ckappa In one embodiment, in part (iii) of aspect 109 the endogenous gene segments are the entire endogenous VJ region of a lambda chain locus and/or the endogenous constant region is a Clambda.

The non-human vertebrate cell can be a hybridoma, B-cell, ES cell or an IPS cell. When the cell is an ES cell or IPS cell, the endogenous antibody chain expression is inactivated following differentiation of the cell into a progeny B-cell (eg, in a B-cell in a non-human vertebrate).

The invention further provides: —

110. The vertebrate or cell according to aspect 109, wherein said plurality of human antibody gene segments comprises at least 11 human V segments and/or at least 6 human J segments, eg at least 11 human VH gene segments and at least 6 human JH segments and optionally also at least 27 human D segments; optionally with the human inter-gene segment intervening sequences. In an embodiment, the human antibody gene segments are provided by a stretch of DNA sequence of human chromosome 14, comprising the gene segments and intervening sequences in germline configuration.

111. The vertebrate or cell according to aspect 109 or 110, wherein said inserted DNA sequence comprises a human nucleotide sequence comprising said antibody gene segments, wherein the nucleotide sequence is at least 110, 130, 150, 170, 190, 210, 230, 250, 270 or 290 kb. In an embodiment, the nucleotide sequence corresponds to a stretch of DNA sequence of human chromosome 14, comprising the gene segments and intervening sequences in germline configuration, eg, at least a sequence corresponding to the nucleotide sequence from coordinate 106328951 to coordinate 106601551 of a human chromosome 14, eg, a sequence in the GRCH37/hg19 sequence database.

112. The vertebrate or cell according to aspect 109, wherein the transgenic locus is a light chain kappa locus and the human antibody gene segments are between the 3'-most endogenous Jk gene segment and endogenous Ck; optionally wherein the human antibody gene segments comprise five functional human Jλ-Cλ clusters and at least one human Vλ gene segment, eg, at least a sequence corresponding to the nucleotide sequence from coordinate 23217291 to 23327884 of a lambda locus found on a human chromosome 22.

113. The vertebrate or cell according to any one of aspects 109 to 112, wherein the transgenic locus is a heavy chain locus and the human antibody gene segments are between the 3'-most endogenous JH gene segment (eg, JH4 in a mouse genome) and endogenous Cmu.

114. The vertebrate or cell according to any one of aspects 109 to 113, wherein the genome is homozygous for said transgenic locus.

115. A mouse or mouse cell or a rat or rat cell according to any one of aspects 109 to 114.

116. A method of making a non-human vertebrate cell (optionally a mouse or rat cell), the method comprising (a) providing a non-human ES cell whose genome comprises an endogenous antibody chain locus comprising endogenous antibody variable region gene segments and an endogenous antibody constant region; and (b) making a transgenic antibody chain locus by inserting into said endogenous locus a DNA sequences comprising a plurality of human antibody variable region gene segments between said endogenous antibody variable region gene segments and said endogenous constant region, so that the human antibody variable region gene segments are operably connected upstream of the endogenous constant region, whereby a non-human vertebrate ES cell is produced that is capable of giving rise to a progeny cell in which endogenous antibody expression is inactivated and wherein the progeny is capable of expressing antibodies comprising human variable regions; and (c) optionally differentiating said ES cell into said progeny cell or a non-human vertebrate (eg, mouse or rat) comprising said progeny cell.

117. The method according to aspect 116, wherein said plurality of human antibody gene segments comprises at least 11 human V segments.

118. The method according to aspect 116 or 117, wherein said plurality of human antibody gene segments comprises at least 6 human J segments.

119. The method according to aspect 116, 117 or 118, wherein a human nucleotide sequence is inserted in step (b), the nucleotide sequence comprising said antibody gene segments, wherein the nucleotide sequence is at least 110 kb.

120. The method according to any one of aspects 110 to 113, wherein the endogenous locus is a heavy chain locus and the human antibody gene segments are between the 3'-most endogenous JH gene segment and endogenous Cmu.

121. The method according to any one of aspects 116 to 120, wherein the progeny cell is homozygous for said transgenic locus.

In one embodiment of the method of aspect 116, the method comprises inactivating the genome for expression of endogenous heavy and kappa (and optionally also lambda) chains.

In one embodiment of the method of aspect 116, in part (b) said DNA sequence comprises human VH, D and JH gene segments or human VL and JL gene segments (eg, Vκ and Jκ gene segments). In an example, the DNA comprises a landing pad having a selectable marker, eg, a HPRT gene, neomycin resistance gene or a puromycin resistance gene; and/or a promoter.

In one embodiment, in part (b) of aspect 116 the endogenous gene segments are the entire endogenous VDJ region of a heavy chain locus and/or the endogenous constant region is a Cmu or Cgamma.

In one embodiment, in part (b) of aspect 116 the endogenous gene segments are the entire endogenous VJ region of a kappa chain locus and/or the endogenous constant region is a Ckappa In one embodiment, in part (b) of aspect 116 the endogenous gene segments are the entire endogenous VJ region of a lambda chain locus and/or the endogenous constant region is a Clambda.

The non-human vertebrate cell can be a hybridoma, B-cell, ES cell or an IPS cell. When the cell is an ES cell or IPS cell, the endogenous antibody chain expression is inactivated following differentiation of the cell into a progeny B-cell (eg, in a B-cell in a non-human vertebrate).

The invention further provides: —

The method according to aspect 116, wherein said inserted DNA sequence comprises a human nucleotide sequence comprising said human antibody gene segments, wherein the nucleotide sequence is at least 110, 130, 150, 170, 190, 210, 230, 250, 270 or 290 kb. In an embodiment, the nucleotide sequence corresponds to a stretch of DNA sequence of human chromosome 14, comprising the gene segments and intervening sequences in germline configuration, eg, at least a sequence corresponding to the nucleotide sequence from coordinate 106328951 to coordinate 106601551 of a human chromosome 14, eg, a sequence in the GRCH37/hg19 sequence database.

The method according to aspect 116, wherein the transgenic locus is a light chain kappa locus and the human antibody gene segments are between the 3'-most endogenous Jk gene segment and endogenous Ck; optionally wherein the human antibody gene segments comprise five functional human Jλ-Cλ clusters and at least one human Vλ gene segment, eg, at least a sequence corresponding to the nucleotide sequence from coordinate 23217291 to 23327884 of a lambda locus found on a human chromosome 22.

The method according to aspect 116, wherein, wherein the transgenic locus is a heavy chain locus and the human antibody gene segments are inserted between the 3'-most endogenous JH gene segment (eg, JH4 in a mouse genome) and endogenous Cmu.

122. The method according to any one of aspects 116 to 121, comprising making the genome of the progeny homozygous for said transgenic locus.

Isolating Antibodies from Transgenic Non-Human Vertebrates of the Invention & Useful Antigen-Specific Antibodies of Therapeutically-Relevant Affinities 123. A method of isolating an antibody that binds a predetermined antigen, the method comprising
    (a) providing a vertebrate (optionally a mammal; optionally a mouse or rat according to any one of the above configurations, examples, embodiments or aspects;
    (b) immunising said vertebrate with said antigen (optionally wherein the antigen is an antigen of an infectious disease pathogen);
    (c) removing B lymphocytes from the vertebrate and selecting one or more B lymphocytes expressing antibodies that bind to the antigen;
    (d) optionally immortalising said selected B lymphocytes or progeny thereof, optionally by producing hybridomas therefrom; and
    (e) isolating an antibody (eg, and IgG-type antibody) expressed by the B lymphocytes.

124. The method of aspect 123, comprising the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

125. The method of aspect 123 or 124, further comprising making a mutant or derivative of the antibody produced by the method of aspect 122 or 123.

As demonstrated by the examples below, the non-human vertebrates of the invention are able to produce antigen-specific antibodies of sub-50 nM affinity with human sequences in their CDR3 regions. Thus, the invention further provides: —

126. An antibody or fragment (eg, a Fab or $Fab_2$) thereof comprising variable regions that specifically bind a predetermined antigen with a sub-50 nM affinity (optionally sub-40, 30, 20, 10, 1, 0.1 or 0.01 nM) as determined by surface plasmon resonance, wherein the antibody is isolated from a non-human vertebrate (optionally a mammal; optionally a mouse or rat) according to any one of the above configurations, examples, embodiments or aspects and comprises heavy chain CDR3s (as defined by Kabat) encoded by a rearranged VDJ of said vertebrate, wherein the VDJ is the product of rearrangement in vivo of a human JH gene segment of a heavy chain locus of said vertebrate with D (optionally a human D gene segment of said locus) and VH gene segments.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antibody is determined using SPR by
1. Coupling anti-mouse (or other relevant non-human vertebrate) IgG (eg, Biacore BR-1008-38) to a biosensor chip (eg, GLM chip) such as by primary amine coupling;
2. Exposing the anti-mouse IgG (non-human vertebrate antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

The invention also relates to an scFv, diabody or other antibody fragment comprising a VH and VL domain from an antibody or fragment of aspect 126 (optionally following affinity maturation, eg, by phage display).

In one embodiment, the antigen is a serpin, eg, ovalbumin, antithrombin or antitrypsin. Serpins are a group of proteins with similar structures that were first identified as a set of proteins able to inhibit proteases. The acronym serpin was originally coined because many serpins inhibit chymotrypsin-like serine proteases (serine protease inhibitors). The first members of the serpin superfamily to be extensively studied were the human plasma proteins antithrombin and antitrypsin, which play key roles in controlling blood coagulation and inflammation, respectively. Initially, research focused upon their role in human disease: antithrombin deficiency results in thrombosis and antitrypsin deficiency causes emphysema. In 1980 Hunt and Dayhoff made the surprising discovery that both these molecules share significant amino acid sequence similarity to the major protein in chicken egg white, ovalbumin, and they proposed a new protein superfamily.

127. An antibody or fragment that is identical to an antibody of aspect 126 or a derivative thereof (optionally a derivative whose constant regions are human and/or an affinity matured derivative) that specifically binds said antigen with a sub-50 nM affinity as determined by surface plasmon resonance.

128. A pharmaceutical composition comprising an antibody or fragment of aspect 126 or 127 and a pharmaceutically-acceptable diluent, excipient or carrier.
129. A nucleotide sequence encoding a heavy chain variable region of an antibody or fragment of aspect 126 or 127, optionally as part of a vector (eg, an expression vector).
130. The nucleotide sequence of aspect 129, wherein the sequence is a cDNA derived from a B-cell of the vertebrate from which the antibody of aspect 126 is isolated, or is identical to such a cDNA.
131. An isolated host cell (eg, a hybridoma or a CHO cell or a HEK293 cell) comprising a nucleotide sequence according to aspect 129 or 130.
132. A method of isolating an antibody that binds a predetermined antigen, the method comprising
(a) providing a vertebrate (optionally a mammal; optionally a mouse or rat according to any one of the above configurations, examples, embodiments or aspects;
(b) immunising said vertebrate with said antigen;
(c) removing B lymphocytes from the vertebrate and selecting a B lymphocyte expressing an antibody that binds to the antigen with sub-nM affinity, wherein the antibody is according to aspect 126;
(d) optionally immortalising said selected B lymphocyte or progeny thereof, optionally by producing hybridomas therefrom; and
(e) isolating an antibody (eg, and IgG-type antibody) expressed by the B lymphocyte.
133. The method of aspect 132, comprising the step of isolating from said B lymphocyte nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.
134. The method of aspect 132 or 133, further comprising making a mutant or derivative of the antibody produced by the method of aspect 132 or 133.

Inactivation by Inversion of Endogenous VDJ to Genome Desert Regions

135. A mouse or mouse cell comprising inverted endogenous heavy chain gene segments (eg, VH, D and JH, such as the entire endogenous heavy chain VDJ region) that are immediately 3' of position 119753123, 119659458 or 120918606 on an endogenous mouse chromosome 12, wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments.
136. The mouse or cell of aspect 135, wherein the genome of the mouse or cell is homozygous for said chromosome 12.
137. A cassette for inversion and inactivation of endogenous non-human vertebrate (eg, mouse or rat) antibody chain gene segments, the segments being part of an antibody chain locus sequence on a chromosome of a non-human vertebrate (eg, mouse or rat) cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the cell genome on a different chromosome or on said chromosome at least 10 mb away from the endogenous gene segments.
138. A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein (i) the 5' homology arm is mouse chromosome 12 DNA from coordinate 119753124 to coordinate 119757104 and the 3' homology arm is mouse chromosome 12 DNA from coordinate 119749288 to 119753123; (ii) the 5' homology arm is mouse chromosome 12 DNA from coordinate 119659459 to coordinate 119663126 and the 3' homology arm is mouse chromosome 12 DNA from coordinate 119656536 to 119659458; or (iii) the 5' homology arm is mouse chromosome 12 DNA from coordinate 120918607 to coordinate 120921930 and the 3' homology arm is mouse chromosome 12 DNA from coordinate 120915475 to 120918606.
139. A method of inactivating gene segments of an endogenous antibody locus, the method comprising
(i) Providing a non-human vertebrate cell (eg, an ES cell, eg, a mouse ES cell) whose genome comprises an antibody chain locus comprising endogenous variable region gene segments;
(ii) Targeting a site-specific recombination site to flank the 3' of the 3'-most of said endogenous gene segments;
(iii) Targeting a second site-specific recombination site at least 10 mb away from said endogenous gene segments, the second site being compatible with the first site inverted with respect to the first site;
(iv) Expressing a recombinase compatible with said sites to effect site-specific recombination between said sites, thereby inverting and moving said gene segments away from said locus, wherein the endogenous gene segments are inactivated; and
(v) Optionally developing the cell into a progeny cell or vertebrate (eg, mouse or rat) whose genome is homozygous for the inversion.
140. A mouse or mouse cell whose genome comprises an inversion of a chromosome 12, wherein the inversion comprises inverted endogenous heavy chain gene segments (eg, VH, D and JH, such as the entire endogenous heavy chain VDJ region); wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments; and wherein the inversion is (i) an inversion of mouse chromosome 12 from coordinate 119753123 to coordinate 114666436; (ii) an inversion of mouse chromosome 12 from coordinate 119659458 to coordinate 114666436; or (iii) an inversion of mouse chromosome 12 from coordinate 12091806 to coordinate 114666436.

Other aspects include:

A method for producing an antibody specific to a desired antigen the method comprising immunizing a non-human mammal as disclosed herein with the desired antigen and recovering the antibody or a cell producing the antibody.

A method for producing a fully humanised antibody comprising immunizing a non-human mammal as disclosed herein and then replacing the non-human mammal constant region of an antibody specifically reactive with the antigen with a human constant region, suitably by engineering of the nucleic acid encoding the antibody.

A method, cell or mammal as disclosed herein wherein a human coding region DNA sequence is in a functional arrangement with a non-human mammal control sequence, such that transcription of the DNA is controlled by the non-human mammal control sequence. In one aspect the human coding region V, D or J region is in a functional arrangement with a mouse promoter sequence.

The invention also relates to a humanised antibody produced according to any methods disclosed herein and use of a humanised antibody so produced in medicine.

BRIEF DESCRIPTION OF THE FIGURES

FIG. 31 illustrates sequential RMCE—Integration into Landing Pad FIG. 38 illustrates the distribution of nucleotide numbers of deletion and insertion in IGH-VDI or IGK-VJ junctions FIG. 39 illustrates Distribution of JH Usage Within Each VHs FIG. 40 illustrates Distribution of DH Usage Within Each VHs FIG. 43 illustrates Joint Diversity Produces Functional CDS

SEQUENCES

Figure 1:
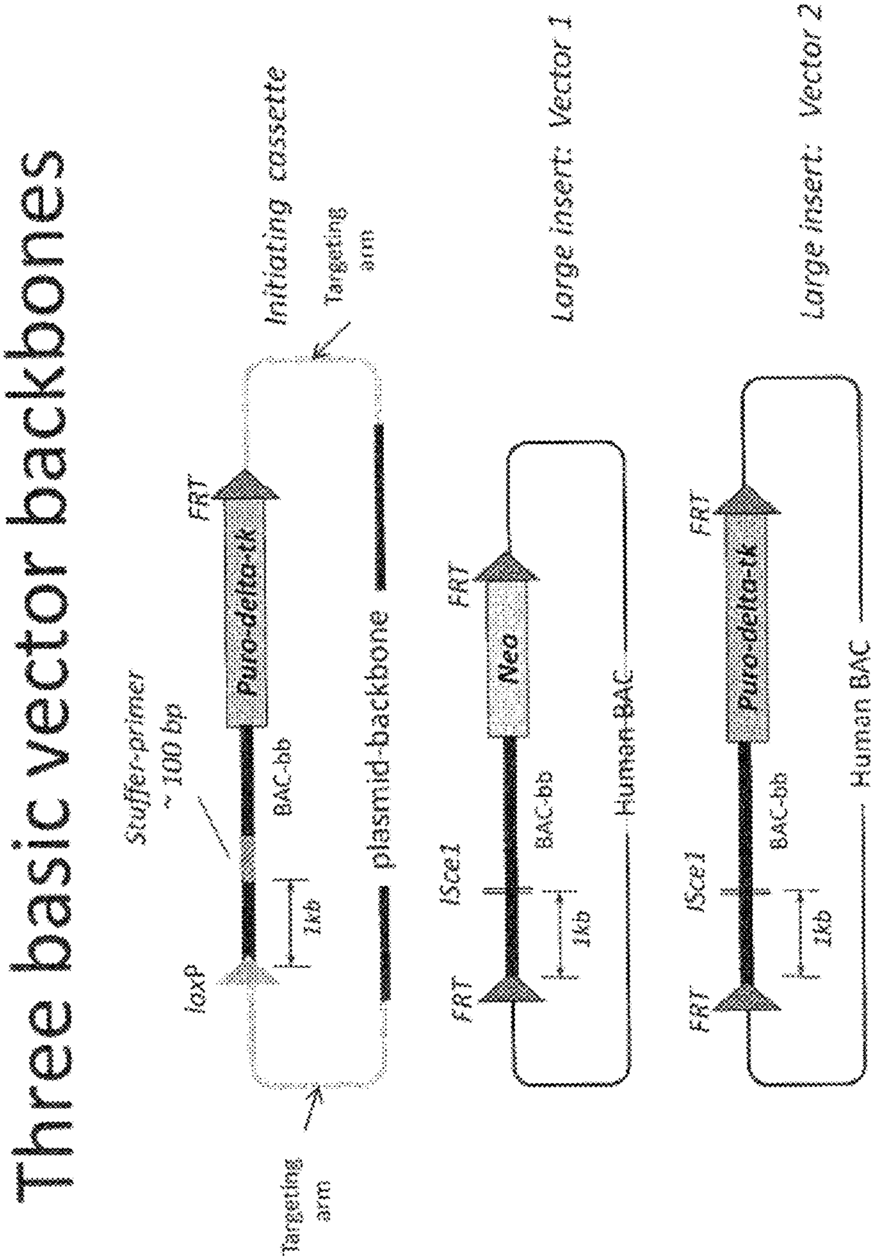
FIGS. 1-8 show an iterative process for insertion of a series of human BACs into a mouse Ig locus

SEQ ID No 1 is a Rat switch sequence

SEQ ID No 2 is a landing pad targeting vector (long version)

SEQ ID No 3 is a landing pad targeting vector (shorter version)

SEQ ID No 4 is the mouse strain 129 switch

SEQ ID No 5 is the mouse strain C57 switch

SEQ ID No 6 is the 5' homology arm of a landing pad

SEQ ID No 7 is oligo HV2-5

SEQ ID No 8 is oligo HV4-4

SEQ ID No 9 is oligo HV1-3

SEQ ID No 10 is oligo HV1-2

SEQ ID No 11 is oligo HV6-1

SEQ ID No 12 is oligo Cμ

SEQ ID No 13 is oligo KV1-9

SEQ ID No 14 is oligo KV1-8

SEQ ID No 15 is oligo KV1-6

SEQ ID No 16 is oligo KV1-5

SEQ ID No 17 is oligo OK

SEQ ID Nos 18-20 are rat switch sequences

SEQ ID No 21 is $X_1X_2$ TFGQ, where $X_1X_2$=PR, RT, or PW

SEQ ID No 22 is $X_1X_2$TFGQGTKVEIKRADA, where $X_1X_2$=PR, RT, or PW;

SEQ ID No 23 is $X_3X_4$ TFGQ, where $X_3X_4$=PR or PW

SEQ ID No 24 is $X_3X_4$TFGQGTKVEIKRADA, where $X_3X_4$=PR or PW

SEQ ID No 25 is Primer E1554

SEQ ID No 26 is Primer E1555

SEQ ID No 27 is Primer ELP1352_Cγ1

SEQ ID No 28 is Primer ELP1353_Cγ2b

SEQ ID No 29 is Primer ELP1354_Cγ2a

SEQ ID No 30 is Primer ELP1356_VH4-4

SEQ ID No 31 is Primer ELP1357_VH1-2,3

SEQ ID No 32 is Primer ELP1358_VH6-1

SEQ ID No 33 is Primer mIgG1_2 rev

SEQ ID No 34 is Primer mIgG2b rev

SEQ ID No 35 is Primer mIgG2a_2 rev

SEQ ID No 36 is Primer mCH1 unirev

SEQ ID No 37 is Primer mCH1 unirev_2

SEQ ID Nos 38-45 are CDRH3 sequences

SEQ ID Nos 46-50 is 3, 4, 5, 6 or more (up to 82) repeats of GGGCT

SEQ ID NOs 51-55 are heavy chain CDR1 sequences against CTB (cloned and reference)

SEQ ID NOs 56-60 are heavy chain CDR2 sequences against CTB (cloned and reference)

SEQ ID NOs 61-63 are heavy chain CDR3 sequences against CTB (cloned and reference)

SEQ ID NOs 64-68 are J Region sequences against CTB (cloned and reference)

DETAILED DESCRIPTION OF THE INVENTION

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As a source of antibody gene segment sequences, the skilled person will also be aware of the following available databases and resources (including updates thereof) the contents of which are incorporated herein by reference:

The Kabat Database (G. Johnson and T. T. Wu, 2002; World Wide Web (www) kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment, sequence subgroup classification, and the generation of variability plots. See also Kabat, E. A., Wu, T. T., Perry, H., Gottesman, K., and Foeller, C. (1991) *Sequences of Proteins of Immunological Interest*, 5th ed., NIH Publication No. 91-3242, Bethesda, Md., which is incorporated herein by reference, in particular with reference to human gene segments for use in the present invention.

KabatMan (A. C. R. Martin, 2002; World Wide Web (www) bioinf.org.uk/abs/simkab.html). This is a web interface to make simple queries to the Kabat sequence database.

IMGT (the International ImMunoGeneTics Information System®; M.-P. Lefranc, 2002; World Wide Web (www) imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

V-BASE (I. M. Tomlinson, 2002; World Wide Web (www) mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

Antibodies—Structure and Sequence (A. C. R. Martin, 2002; World Wide Web (www) bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

AAAAA (A Ho's Amazing Atlas of Antibody Anatomy; A. Honegger, 2001; World Wide Web (www) unizh.ch/~antibody). This resource includes tools for structural analysis, modeling, and engineering. It adopts a unifying scheme for comprehensive structural alignment of antibody and T-cell-receptor sequences, and includes Excel macros for antibody analysis and graphical representation.

WAM (Web Antibody Modeling; N. Whitelegg and A. R. Rees, 2001; World Wide Web (www) antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

Mike's Immunoglobulin Structure/Function Page (M. R. Clark, 2001; World Wide Web (www) path.cam.ac.uk/-mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

The Antibody Resource Page (The Antibody Resource Page, 2000; World Wide Web (www) antibody-resource.com). This site describes itself as the "complete guide to antibody research and suppliers." Links to amino acid sequencing tools, nucleotide antibody sequencing tools, and hybridoma/cell-culture databases are provided.

Humanization by Design (J. Saldanha, 2000; World Wide Web (www) people.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, Methods in Molecular Biology™, Human Press. Also at World Wide Web (www) blogsua.com/pdf/antibody-engineering-methods-and-protocolsantibody-engineering-methods-and-protocols.pdf Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The following examples are put forth so as to provide those of ordinary skill in the art with a complete disclosure and description of how to make and use the invention, and are not intended to limit the scope of what the inventors regard as their invention.

EXAMPLES

Example 1

BAC Recombineering

Overall Strategy:

A mouse model of the invention can be achieved by inserting ~960 kb of the human heavy chain locus containing all the V, D and J-regions upstream of the mouse constant region and 473 kb of the human kappa region upstream of the mouse constant region. Alternatively, or in tandem, the human lambda region is inserted upstream of the mouse constant region. This insertion is achieved by gene targeting in ES cells using techniques well known in the art.

High fidelity insertion of intact V-D-J regions into each locus in their native (wild-type) configuration is suitably achieved by insertion of human bacterial artificial chromosomes (BACs) into the locus. Suitably the BACs are trimmed so that in the final locus no sequence is duplicated or lost compared to the original. Such trimming can be carried out by recombineering.

The relevant human BACs, suitably trimmed covering these loci are on average 90 kb in size.

In one approach the full complement of human D and J-elements as well as seven or eight human V-regions are covered by the first BACs to be inserted in the experimental insertion scheme described below. The first BACs to be inserted in the IgH and IgK loci may contain the following V-regions. IgH:V6-1, VII-1-1, V1-2, VIII-2-1, V1-3, V4-4, V2-5 and IgK: V4-1, V5-2, V7-3, V2-4, V1-5, V1-6, V3-7, V1-8.

Suitably the performance of each locus is assessed after the first BAC insertion using chimaeric mice and also after each subsequent BAC addition. See below for detailed description of this performance test.

Nine additional BAC insertions will be required for the IgH locus and five for IgK to provide the full complement of human V-regions covering all 0.96 Mb and 0.473 Mb of the IgH and IgK loci, respectively.

Not all BACs retain their wild-type configuration when inserted into the ES cell genome. Thus, high density genomic arrays were deployed to screen ES cells to identify those with intact BAC insertions (Barrett, M. T., Scheffer, A., Ben-Dor, A., Sampas, N., Lipson, D., Kincaid, R., Tsang, P., Curry, B., Baird, K., Meltzer, P. S., et al. (2004). Comparative genomic hybridization using oligonucleotide microarrays and total genomic DNA. Proceedings of the National Academy of Sciences of the United States of America 101, 17765-17770.). This screen also enables one to identify and select against ES clones in which the ES cell genome is compromised and thus not able to populate the germ line of chimeric animals. Other suitable genomic tools to facilitate this assessment include sequencing and PCR verification.

Thus in one aspect the correct BAC structure is confirmed before moving to the next step.

It is implicit from the description above that in order to completely engineer the loci with 90 kb BACs, it is necessary to perform a minimum of 10 targeting steps for IgH and 5 steps for the IgK. Mice with an IgL locus can be generated in a similar manner to the IgK locus. Additional steps are required to remove the selection markers required to support gene targeting. Since these manipulations are being performed in ES cells in a step-wise manner, in one aspect germ line transmission capacity is retained throughout this process.

Maintaining the performance of the ES cell clones through multiple rounds of manipulation without the need to test the germ line potential of the ES cell line at every step may be important in the present invention. The cell lines currently in use for the KOMP and EUCOMM global knockout projects have been modified twice prior to their use for this project and their germ line transmission rates are unchanged from the parental cells (these lines are publicly available, see World Wide Web (www) komp.org and World Wide Web (www) eucomm.org). This cell line, called JM8, can generate 100% ES cell-derived mice under published culture conditions (Pettitt, S. J., Liang, Q., Rairdan, X. Y., Moran, J. L., Prosser, H. M., Beier, D. R., Lloyd, K. C., Bradley, A., and Skarnes, W. C. (2009). Agouti C57BL/6N embryonic stem cells for mouse genetic resources. Nature Methods.). These cells have demonstrated ability to reproducibly contribute to somatic and germ line tissue of chimaeric animals using standard mouse ES cell culture conditions. This capability can be found with cells cultured on a standard feeder cell line (SNL) and even feeder-free, grown only on gelatine-coated tissue culture plates. One particular sub-line, JM8A3, maintained the ability to populate the germ line of chimeras after several serial rounds of sub-cloning. Extensive genetic manipulation via, for example, homologous recombination—as would be the case in the present invention—cannot compromise the pluripotency of the cells. The ability to generate chimeras with such high percentage of ES cell-derived tissue has other advantages. First, high levels of chimerism correlates with germ line transmission potential and provide a surrogate assay for germ line transmission while only taking 5 to 6 weeks. Second, since these mice are 100% ES cell derived the engineered loci can be directly tested, removing the delay caused by breeding. Testing the integrity of the new Ig loci is possible in the chimera since the host embryo will be derived from animals that are mutant for the RAG-1 gene as described in the next section.

Another cell line that may be used is an HPRT-ve cell line, such as AB2.1, as disclosed in Ramirez-Solis R, Liu P and Bradley A, "Chromosome engineering in mice," Nature, 1995; 378; 6558; 720-4.

RAG-1 Complementation:

While many clones will generate 100% ES derived mice some will not. Thus, at every step mice are generated in a RAG-1-deficient background. This provides mice with 100% ES-derived B- and T-cells which can be used directly for immunization and antibody production. Cells having a RAG-2 deficient background, or a combined RAG-1/RAG-2 deficient background may be used, or equivalent mutations in which mice produce only ES cell-derived B cells and/or T cells.

In order that only the human-mouse IgH or IgK loci are active in these mice, the human-mouse IgH and IgK loci can be engineered in a cell line in which one allele of the IgH or IgK locus has already been inactivated. Alternatively the inactivation of the host Ig locus, such as the IgH or IgK locus, can be carried out after insertion.

Figure 19:
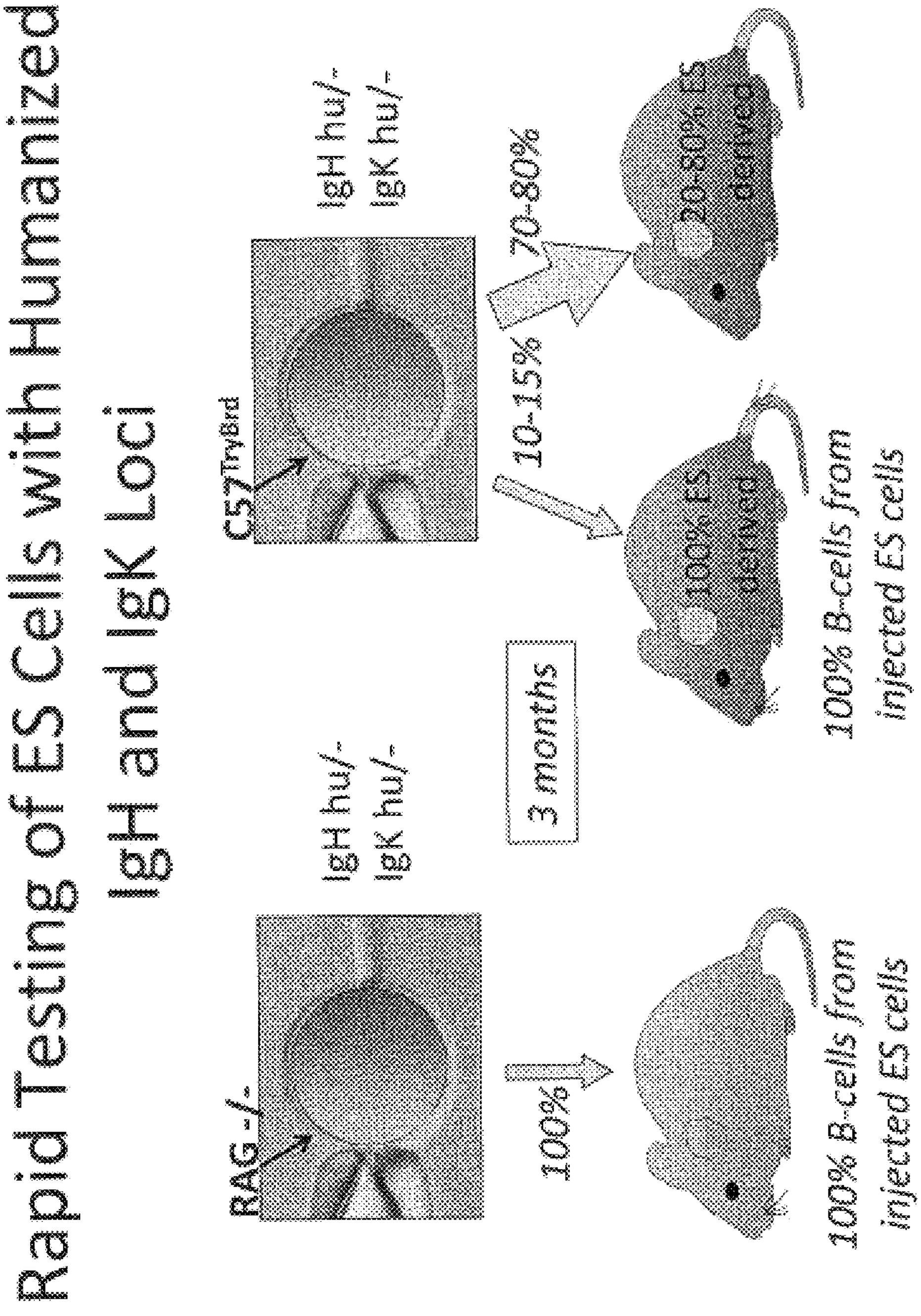
FIGS. 19 and 20 show the principles behind antibody generation in chimaeric mice
Figure 20:
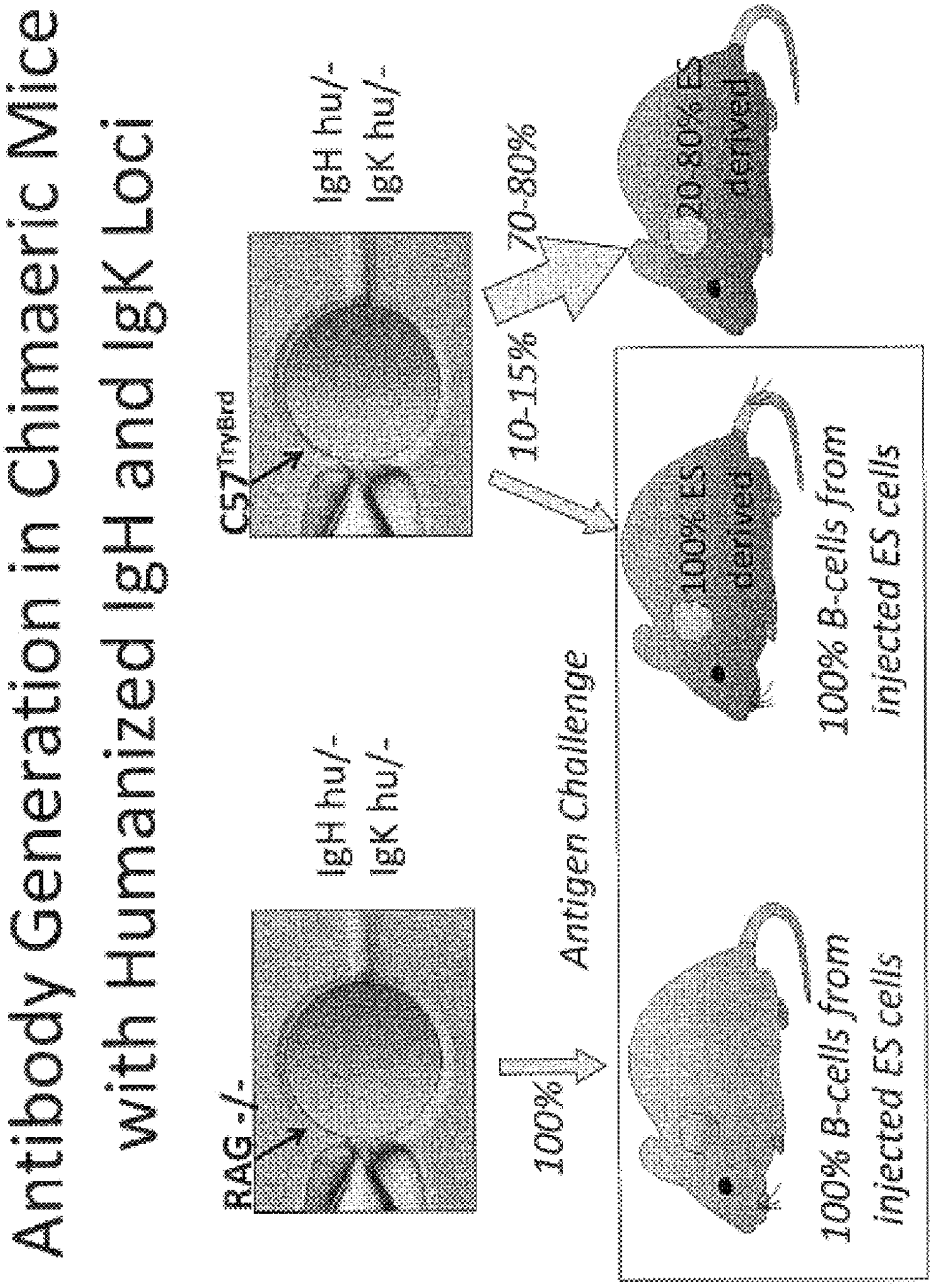
Figure 21:
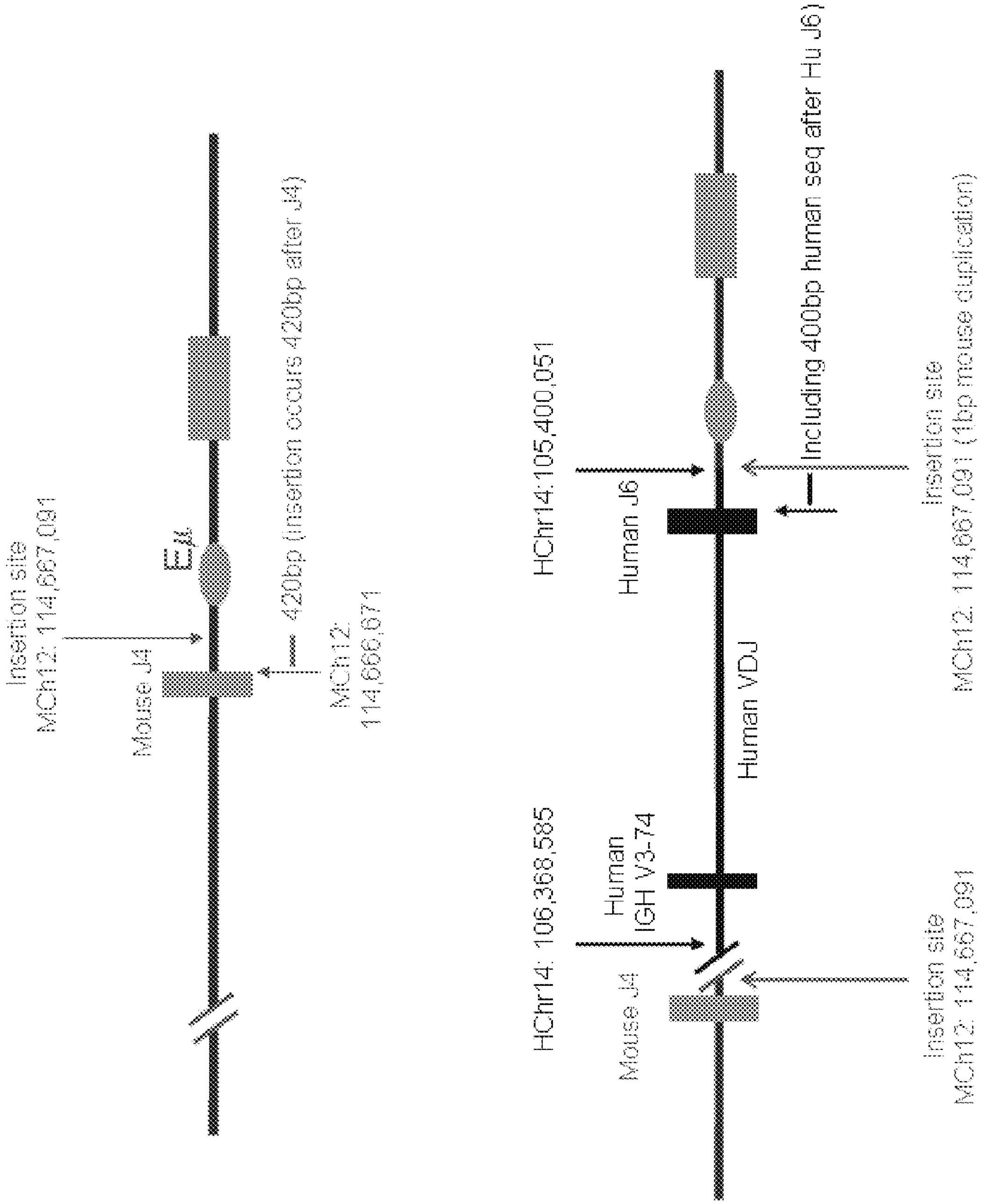
FIG. 21 shows a possible insertion site for the human DNA in a mouse chromosome FIGS. 22-26 disclose an alternative iterative process for insertion of a series of human BACs into a mouse Ig locus

Mouse strains that have the RAG-1 gene mutated are immunodeficient as they have no mature B- or T-lymphocytes (U.S. Pat. No. 5,859,307). T- and B-lymphocytes only differentiate if proper V(D)J recombination occurs. Since RAG-1 is an enzyme that is crucial for this recombination, mice lacking RAG-1 are immunodeficient. If host embryos are genetically RAG-1 homozygous mutant, a chimera produced by injecting such an embryo will not be able to produce antibodies if the animal's lymphoid tissues are derived from the host embryo. However, JM8 cells and AB2.1 cells, for example, generally contribute in excess of 80% of the somatic tissues of the chimeric animal and would therefore usually populate the lymphoid tissue. JM8 cells have wild-type RAG-1 activity and therefore antibodies produced in the chimeric animal would be encoded by the engineered JM8 ES cell genome only. Therefore, the chimeric animal can be challenged with an antigen by immunization and subsequently produce antibodies to that antigen. This allows one skilled in the art to test the performance of the engineered human/mouse IgH and IgK loci as described in the present invention. See FIGS. 19 and 20.

One skilled in the art would use the chimeric animal as described to determine the extent of antibody diversity (see e.g. Harlow, E. & Lane, D. 1998, $5^{th}$ edition, *Antibodies: A Laboratory Manual*, Cold Spring Harbor Lab. Press, Plainview, N.Y.). For example, the existence in the chimeric animal's serum of certain antibody epitopes could be ascertained by binding to specific anti-idiotype antiserum, for example, in an ELISA assay. One skilled in the art could also sequence the genomes of B-cell clones derived from the chimeric animal and compare said sequence to wild-type sequence to ascertain the level of hypermutation, such hypermutation indicative of normal antibody maturation.

One skilled in the art would also use said chimeric animal to examine antibody function wherein said antibodies are encoded from the engineered Ig loci (see e.g. Harlow, E. & Lane, D. 1998, $5^{th}$ edition, Antibodies: A Laboratory Manual, Cold Spring Harbor Lab. Press, Plainview, N.Y.). For example, antisera could be tested for binding an antigen, said antigen used to immunize the chimeric animal. Such a measurement could be made by an ELISA assay. Alternatively, one skilled in the art could test for neutralization of the antigen by addition of the antisera collected from the appropriately immunized chimeric animal.

It is well known to those skilled in the art that positive outcomes for any of these tests demonstrate the ability of the engineered Ig loci, the subject of the instant invention, to encode antibodies with human variable regions and mouse constant regions, said antibodies capable of functioning in the manner of wild-type antibodies.

Experimental Techniques:

Recombineering for the production of vectors for use in homologous recombination in ES cells is disclosed in, for example, WO9929837 and WO0104288, and the techniques are well known in the art. In one aspect the recombineering of the human DNA takes place using BACs as a source of said human DNA. Human BAC DNA will be isolated using QIAGEN®, BAC purification kit. The backbone of each human BAC will be modified using recombineering to the exact same or similar configuration as the BAC already inserted into the mouse IgH region. The genomic insert of each human BAC will be trimmed using recombineering so that once the BACs are inserted, a seamless contiguous part of the human V(D)J genomic region will form at the mouse IgH or IgK locus. BAC DNA transfection by electroporation and genotyping will be performed accordingly to standard protocols (Prosser, H. M., Rzadzinska, A. K., Steel, K. P., and Bradley, A. (2008). "Mosaic complementation demonstrates a regulatory role for myosin Vila in actin dynamics of stereocilia." Molecular and Cellular Biology 28, 1702-1712; Ramirez-Solis, R., Davis, A. C., and Bradley, A. (1993). "Gene targeting in embryonic stem cells." Methods in Enzymology 225, 855-878.). Recombineering will be performed using the procedures and reagents developed by Pentao Liu and Don Court's laboratories (Chan, W., Costantino, N., Li, R., Lee, S. C., Su, Q., Melvin, D., Court, D. L., and Liu, P. (2007). "A recombineering based approach for high-throughput conditional knockout targeting vector construction." Nucleic Acids Research 35, e64).

These and other techniques for gene targeting and recombination of BAC-derived chromosomal fragments into a non-human mammal genome, such as a mouse are well-known in the art and are disclosed in, for example, in World Wide Web (www) eucomm.org/information/targeting and World Wide Web (www) eucomm.org/information/publications.

Cell culture of C57BL/6N-derived cell lines, such as the JM8 male ES cells will follow standard techniques. The JM8 ES cells have been shown to be competent in extensively contributing to somatic tissues and to the germline, and are being used for large mouse mutagenesis programs at the Sanger Institute such as EUCOMM and KOMP (Pettitt, S. J., Liang, Q., Rairdan, X. Y., Moran, J. L., Prosser, H. M., Beier, D. R., Lloyd, K. C., Bradley, A., and Skarnes, W. C. (2009). "Agouti C57BL/6N embryonic stem cells for mouse genetic resources." Nature Methods.). JM8 ES cells ($1.0\times10^7$) will be electroporated (500 μf, 230V; Bio-Rad®) with 10 μg I-SceI linearized human BAC DNA. The transfectants will be selected with either Puromycin (3 μg/ml) or G418 (150 μg/ml). The selection will begin either 24 hours (with G418) or 48 hours (with Puromycin) post electroporation and proceed for 5 days. 10 μg linearized human BAC DNA can yield up to 500 Puromycin or G418 resistant ES cell colonies. The antibiotic resistant ES cell colonies will be picked into 96-well cell culture plates for genotyping to identify the targeted clones.

Once targeted mouse ES cell clones are identified, they will be analyzed by array Comparative Genomic Hybridization (CGH) for total genome integrity (Chung, Y. J., Jonkers, J., Kitson, H., Fiegler, H., Humphray, S., Scott, C., Hunt, S., Yu, Y., Nishijima, I., Velds, A., et al. (2004). "A whole-genome mouse BAC microarray with 1-Mb resolution for analysis of DNA copy number changes by array comparative genomic hybridization." Genome research 14, 188-196. and Liang, Q., Conte, N., Skarnes, W. C., and Bradley, A. (2008). "Extensive genomic copy number variation in embryonic stem cells." Proceedings of the National Academy of Sciences of the United States of America 105, 17453-17456.). ES cells that have abnormal genomes do not contribute to the germline of the chimeric mice efficiently. BAC integrity will be examined by PCR-amplifying each known functional V gene in the BAC. For example, in one approach the first human BAC chosen for the IgH locus has 6 functional V genes. To confirm the integrity of this BAC for the presence of these 6 IGH V genes, at least 14 pairs of PCR primers will be designed and used to PCR-amplify genomic DNA from the targeted ES cells. The human wild-type size and sequence of these fragments will ensure that the inserted BAC has not been rearranged.

More detailed CGH will also confirm the integrity of the inserted BACs. For example, one skilled in the art could use an oligo aCGH platform, which is developed by Agilent Technologies, Inc. This platform not only enables one to study genome-wide DNA copy number variation at high resolution (Barrett, M. T., Scheffer, A., Ben-Dor, A., Sampas, N., Lipson, D., Kincaid, R., Tsang, P., Curry, B., Baird, K., Meltzer, P. S., et al. (2004). "Comparative genomic hybridization using oligonucleotide microarrays and total genomic DNA." Proceedings of the National Academy of Sciences of the United States of America 101, 17765-17770.), but permit examination of a specific genome region using custom designed arrays. Comparing the traditional aCGH techniques which rely on cDNA probes or whole BAC probes, the 60-mer oligonucleotides probes can ensure specific hybridization and high sensitivity and precision that is needed in order to detect the engineered chromosome alterations that were made. For example, oligos designed to hybridize at regular intervals along the entire length of the inserted BAC would detect even quite short deletions, insertions or other rearrangements. Also, this platform provides the greatest flexibility for customized microarray designs. The targeted ES cell genomic DNA and normal human individual genomic DNA will be labelled separately with dyes and hybridized to the array. Arrays slides will be scanned using an Aglient Technologies DNA microarray scanner. Reciprocal fluorescence intensities of dye Cy5 and dye Cy3 on each array image and the log 2 ratio values will be extracted by using Bluefuse software (Bluegnome). Spots with inconsistent fluorescence patterns ("confidence"<0.29 or "quality"=0) will be excluded before normalizing all log 2 ratio values. Within an experiment, Log 2 ratio between −0.29 and +0.29 for the signal from any oligo probe are regarded as no copy number change. The log 2 ratio threshold for "Duplication" is usually >0.29999, and for deletion is <0.29999.

Once the first human BAC is inserted into the mouse IgH locus and confirmed to be in its intact, native configuration, the FRT-flanked BAC backbone will be excised by using Flp site-specific recombinase. If regular Flp-catalyzed FRT recombination is not high enough, one can use Flo, an improved version of Flpo recombinase which in certain tests is 3-4 times more efficient than the original Flp in ES cells. After the BAC backbone is excised, ES cells will become sensitive to Puromycin (or G418) and resistant to FIAU (for loss of the TK cassette). The excision events will be further characterized by PCR amplification of the junction fragment using human genomic DNA primers. These FRT-flanked BAC backbone-free ES cells will be used for the next round of human BAC insertion and for blastocyst injection.

Targeting of the genome of an ES cell to produce a transgenic mouse may be carried out using a protocol as explained by reference to the attached FIGS. 1-18.

FIG. 1 illustrates three basic backbone vectors; an initiating cassette and 2 large insert vectors 1 and 2 respectively. The initiating cassette comprises sequences homologous to the desired site of insertion into the mouse genome, those sites flanking a selectable marker and stuffer primer sequence for PCR based genotyping to confirm correct insertion of BACs. The Stuffer-primer sequence provides the basis for genotyping each BAC addition step. This sequence is considered to provide a robust well validated sequence template for PCR primer and may be located at the ISceI site, ideally ~1 kb from the BAC insert.

The large insert vectors comprise human DNA on plasmids with selectable markers and a unique restriction site for linearisation of the plasmid to aid in homologous recombination into the genome of the ES cell.

Figure 2:
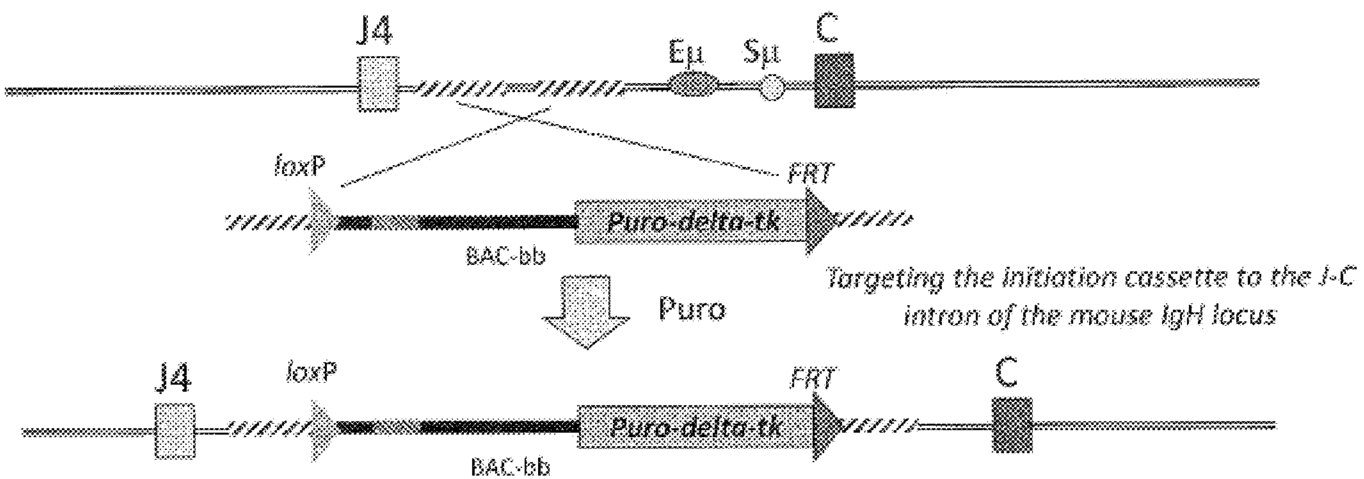

FIG. 2 illustrates insertion of an initiating cassette into the mouse genome by Homologous recombination between the mouse J4 and C alpha exons. Puromycin selection allows identification of ES cells with insertion of the cassette. pu(Delta)tk is a bifunctional fusion protein between puromycin N-acetyltransferase (Puro) and a truncated version of herpes simplex virus type 1 thymidine kinase (DeltaTk). Murine embryonic stem (ES) cells transfected with pu(Delta)tk become resistant to puromycin and sensitive to 1-(-2-deoxy-2-fluoro-1-beta-D-arabino-furanosyl)-5-iodouracil (FIAU). Unlike other HSV1 tk transgenes, puDeltatk is readily transmitted through the male germ line. Thus pu(Delta)tk is a convenient positive/negative selectable marker that can be widely used in many ES cell applications.

Figure 3:
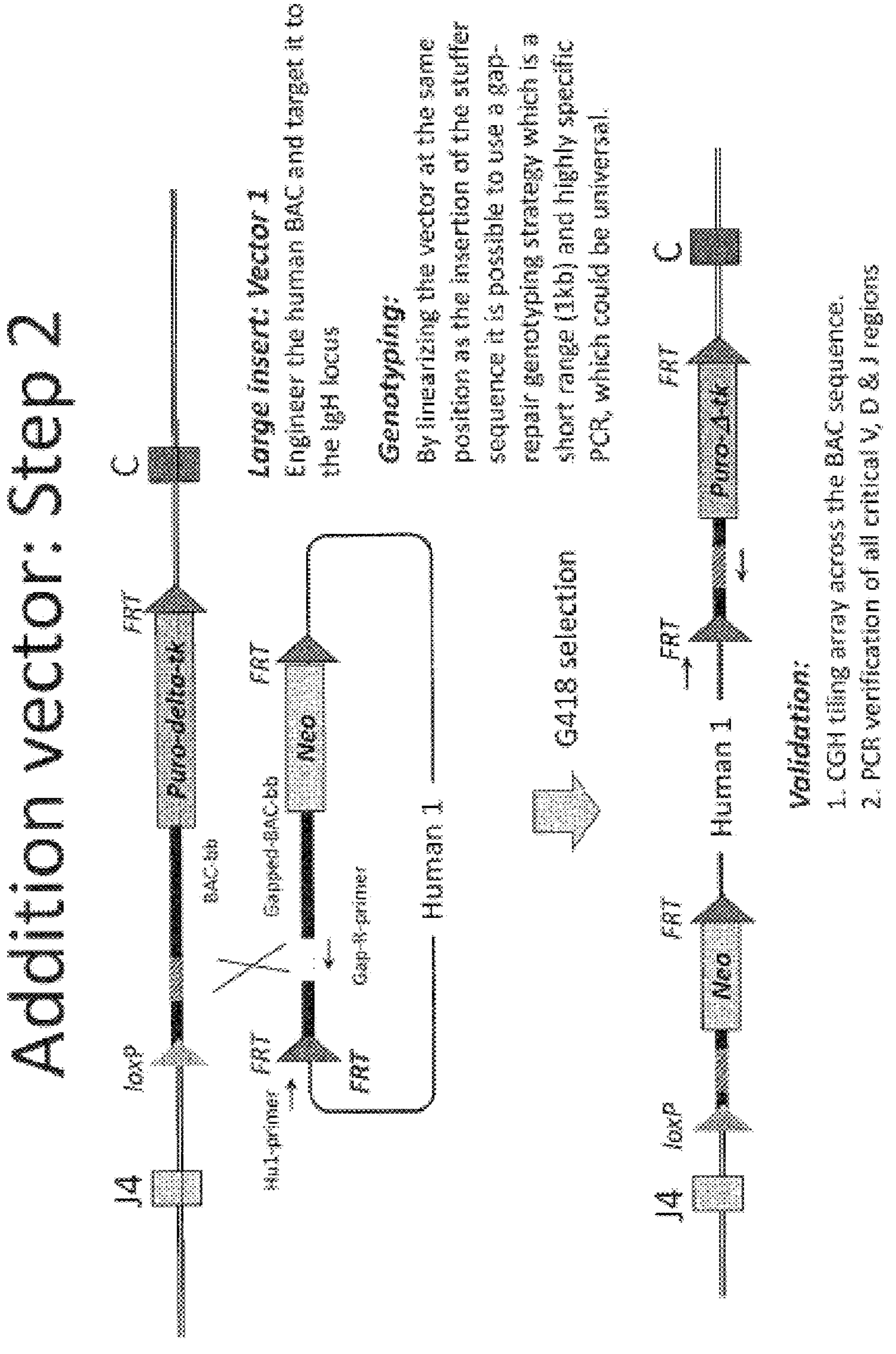

FIG. 3 illustrates targeting of the large insert vector 1 to the mouse ES cell genome. Linearisation of the vector is made at the same position as the stuffer primer sequence which allows for a gap repair genotyping strategy, well known in the art—see Zheng et al NAR 1999, Vol 27, 11, 2354-2360. In essence, random insertion of the targeting vector into the genome will not 'repair' the gap whereas a homologous recombination event will repair the gap. Juxtaposition of appropriate PCR primer sequences allows colonies to be screened individually for a positive PCR fragment indicating proper insertion. Positive selection using G418 allows for identification of mouse ES cells containing the neo selection marker. PCR verification can be made of all critical V, D and J regions. Array comparative genomic hybridization can be used to validate the BAC structure.

Figure 4:
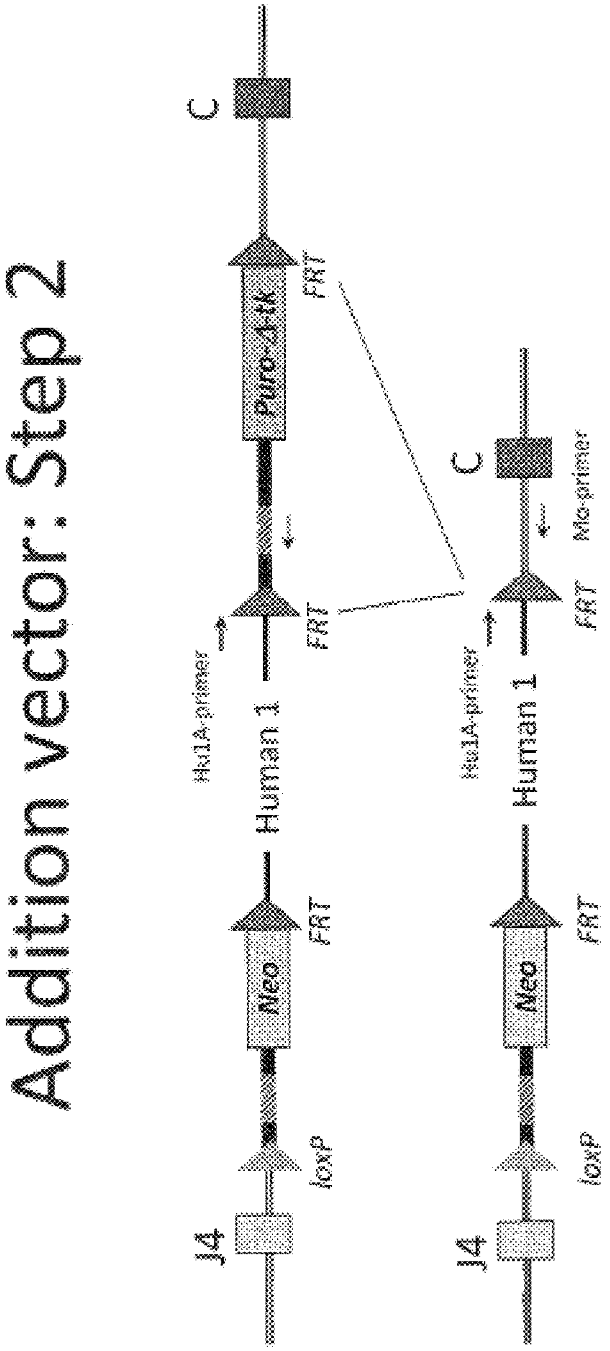

FIG. 4 illustrates the puro-delta-tk cassette and the BAC plasmid backbone is deleted using Flpe and select in FIAU. Since Flpe works inefficiently in mouse ES cells (5% deletion with transient Flpe expression), it is expected that in most cases, the recombination occurs between the two FRT sites flanking the BAC backbone. Flpo can also be tested to find out the recombination efficiency between two FRT sites that are 10 kb away.

Given that the FRT deletion step is selectable it is possible to pool FIAU resistant clones and proceed immediately to the next step in parallel with clonal analysis. Alternatively it may be desirable to show by short range PCR that the human sequences are now adjacent to those of the mouse as shown (Hu-primer 1 and Mo-primer)

Figure 5:
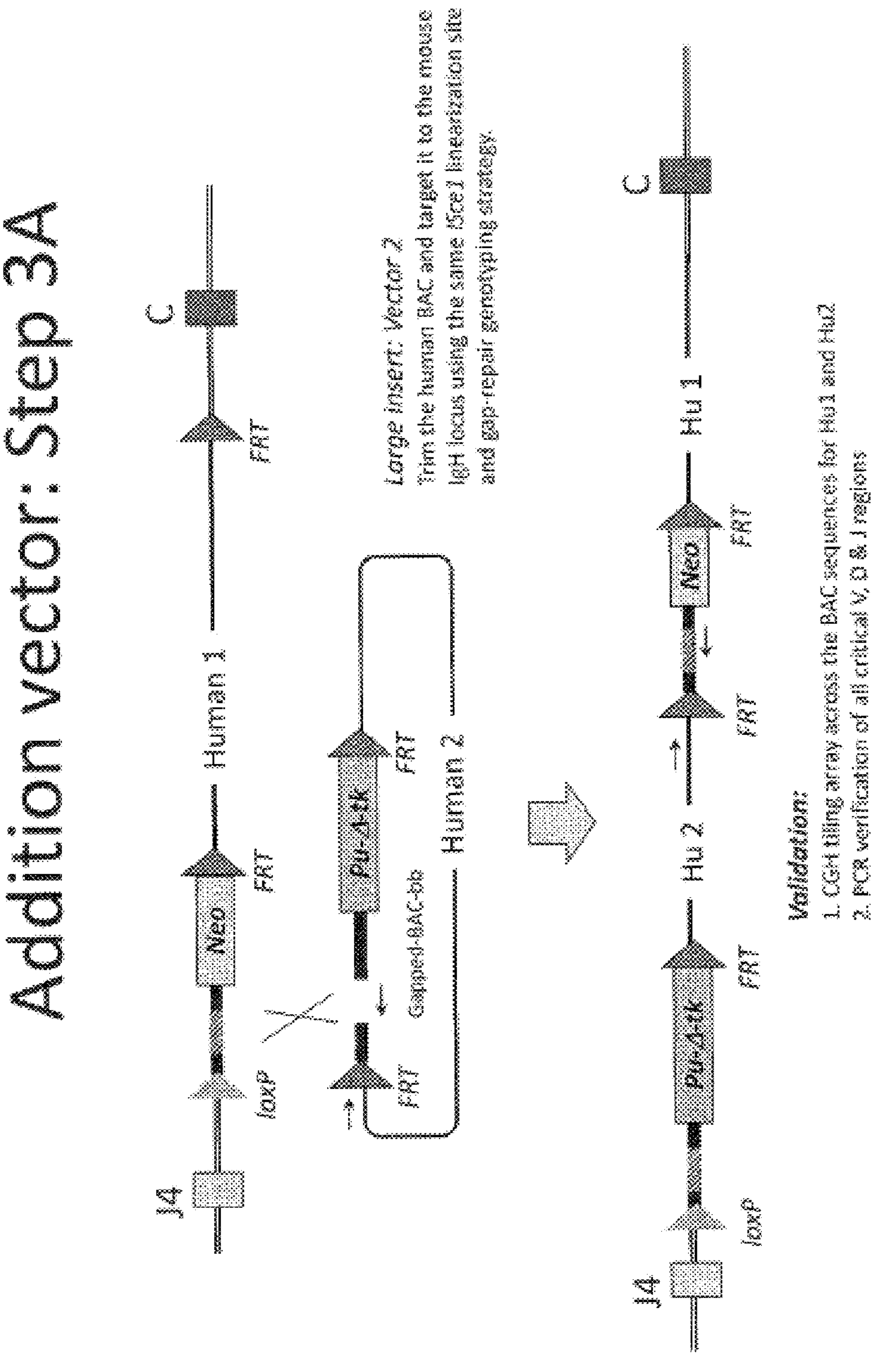

At this stage a 200 kb human locus will have been inserted,

FIG. 5 illustrates a second large insert vector is targeted into the ES cell chromosome. The human BAC is targeted to the mouse IgH locus using the same initiation cassette insertion followed by IScel BAC linearization, BAC targeting to the initiation cassette and gap-repair genotyping strategy. Verification of the BAC insertion is carried out as before.

Figure 6:
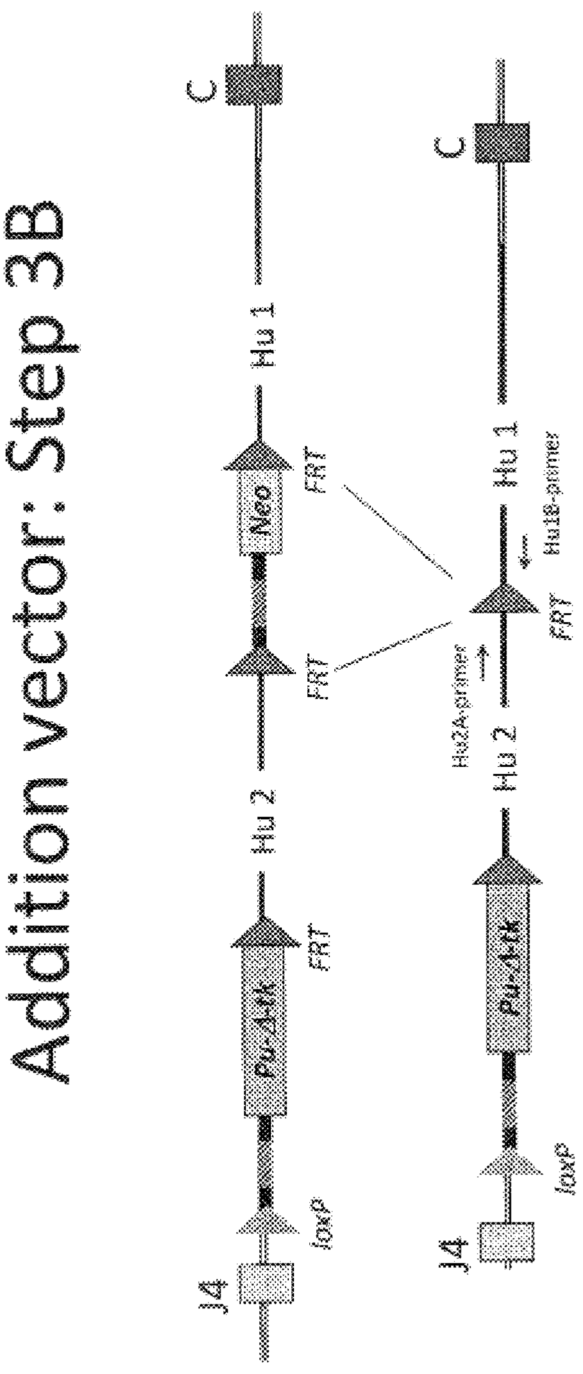

FIG. 6 illustrates the FRTY flanked BAC backbone of large insert vector 2 and the neo marker are deleted via Flpo. Note that this is not selectable, thus it will be necessary for clonal analysis at this point. This will enable confirmation of the juxtaposition of the human 2 insert with human 1 and other validation efforts.

At this stage a ~200 kb human locus will have been inserted.

Figure 7:
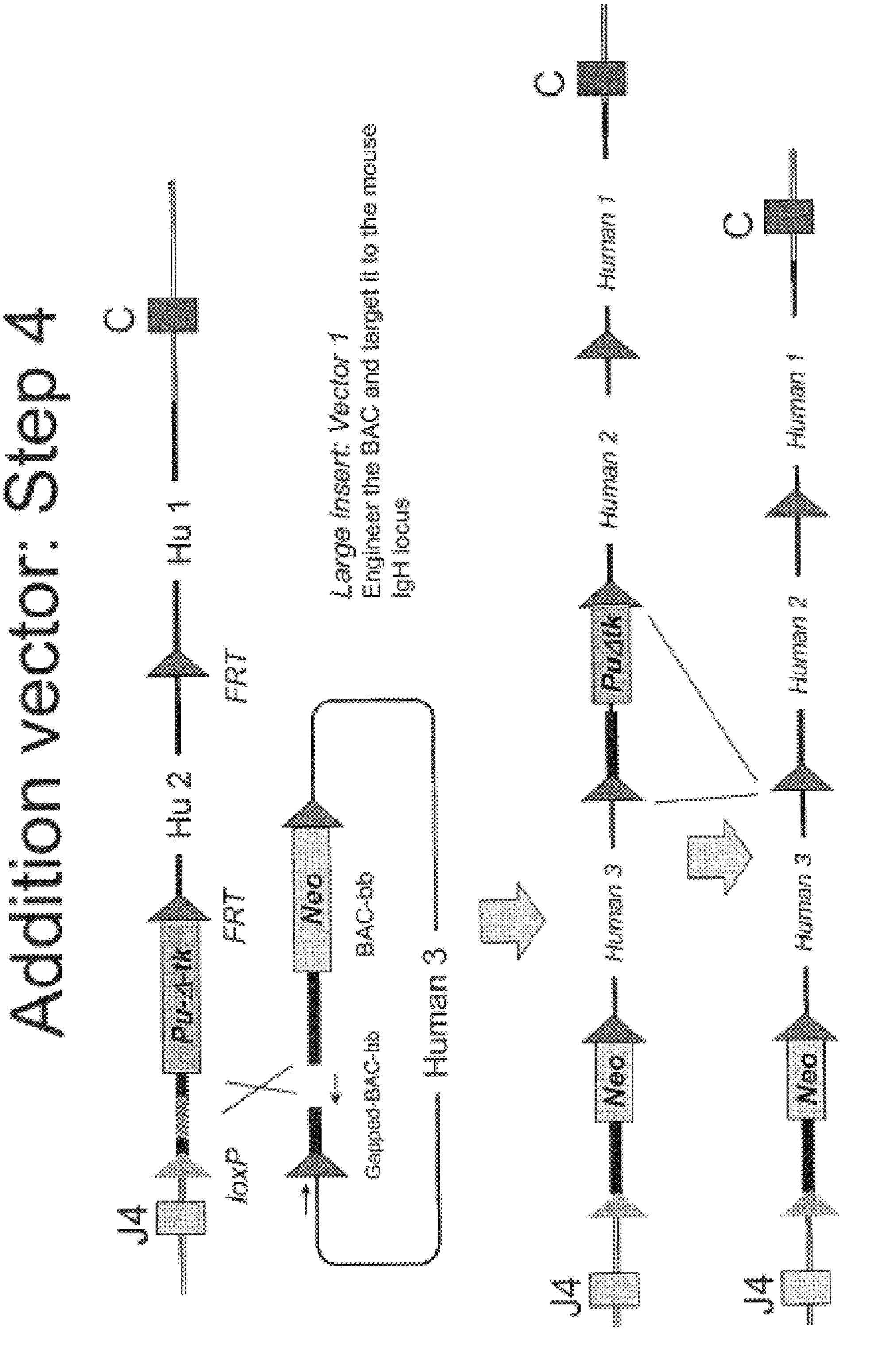

FIG. 7 illustrates the next large insert vector targeted to the mouse IgH locus. The pu-delta TK cassette is then removed, as for FIG. 4. The process can be repeated to incorporate other BACs.

Figure 8:
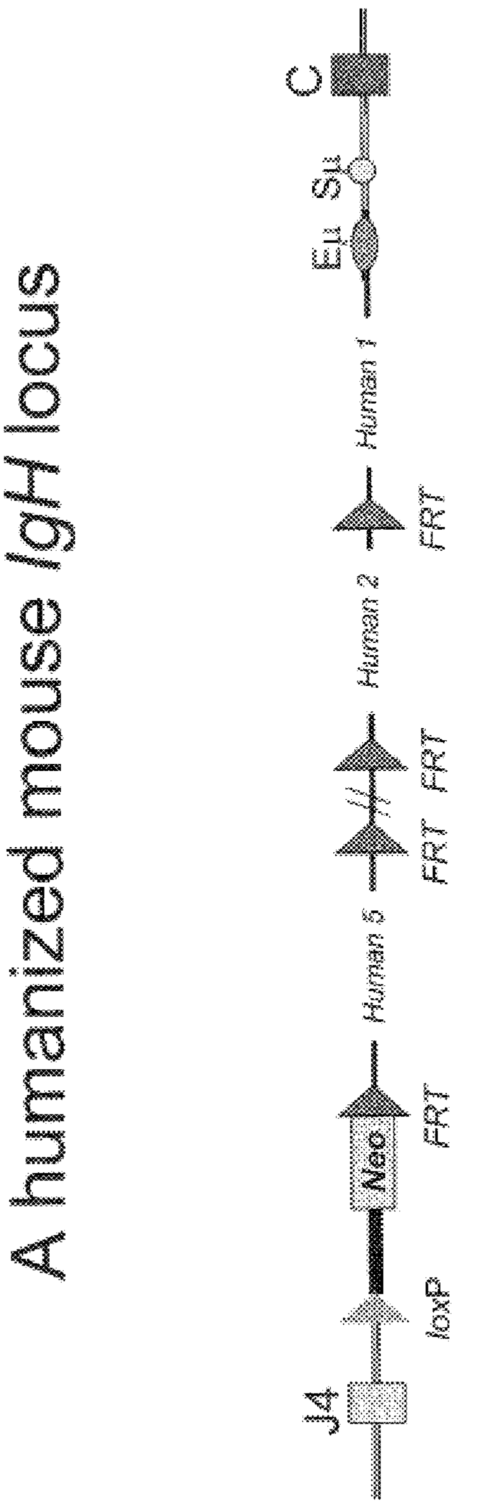
Figure 9:
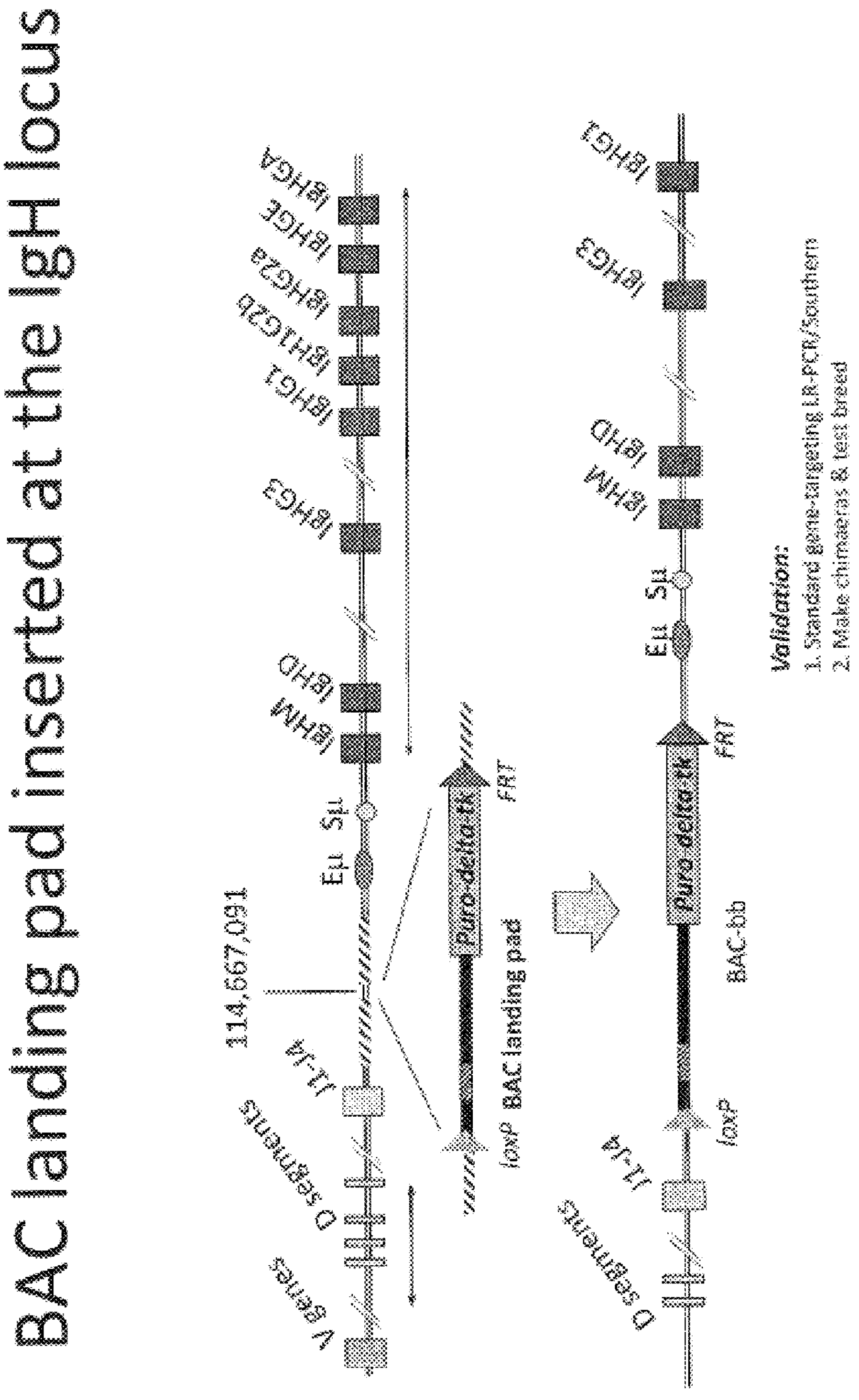
FIGS. 9-18 show in more detail the process of FIGS. 1-8 for the IgH and kappa locus
Figure 10:
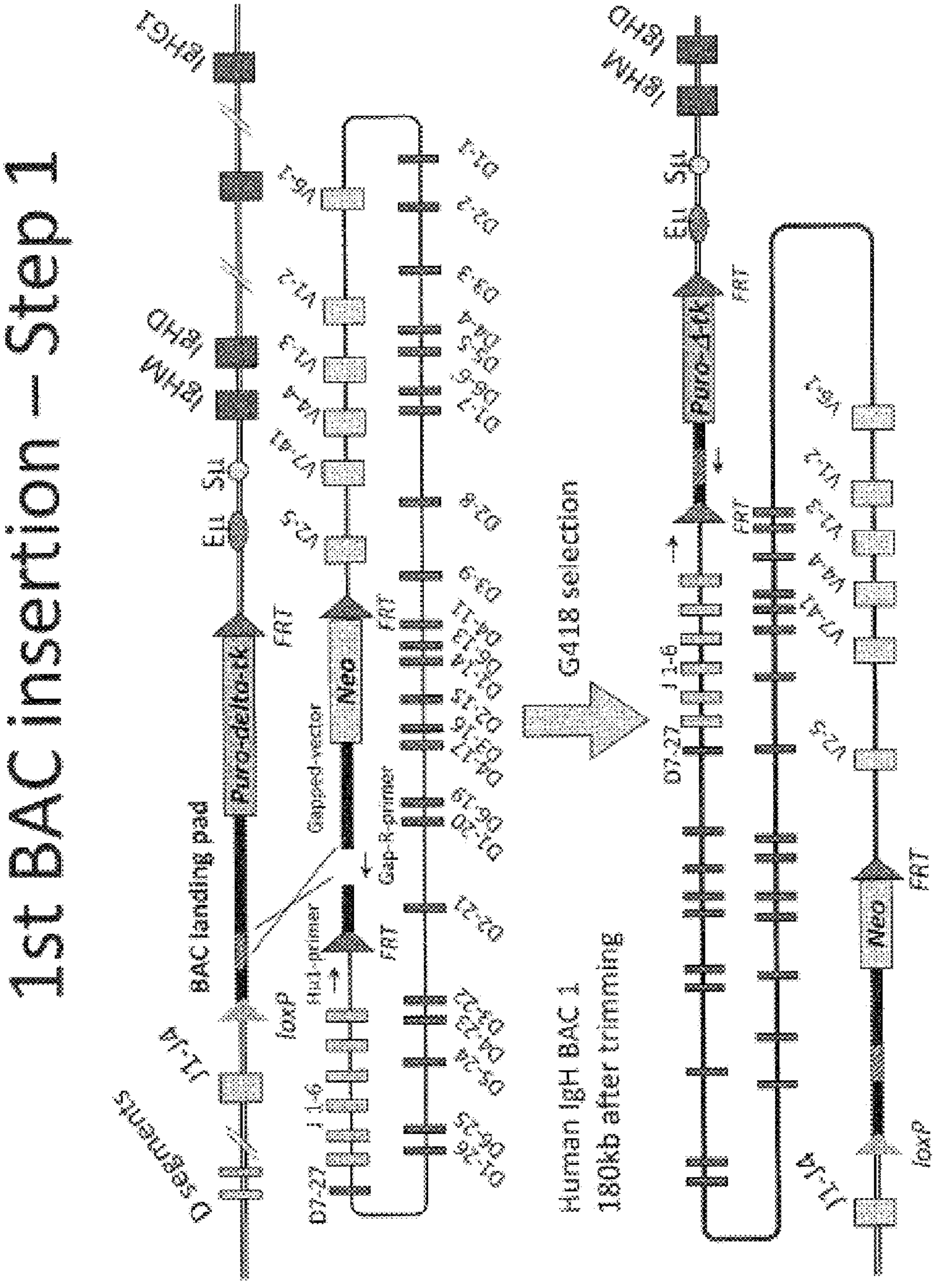
Figure 11:
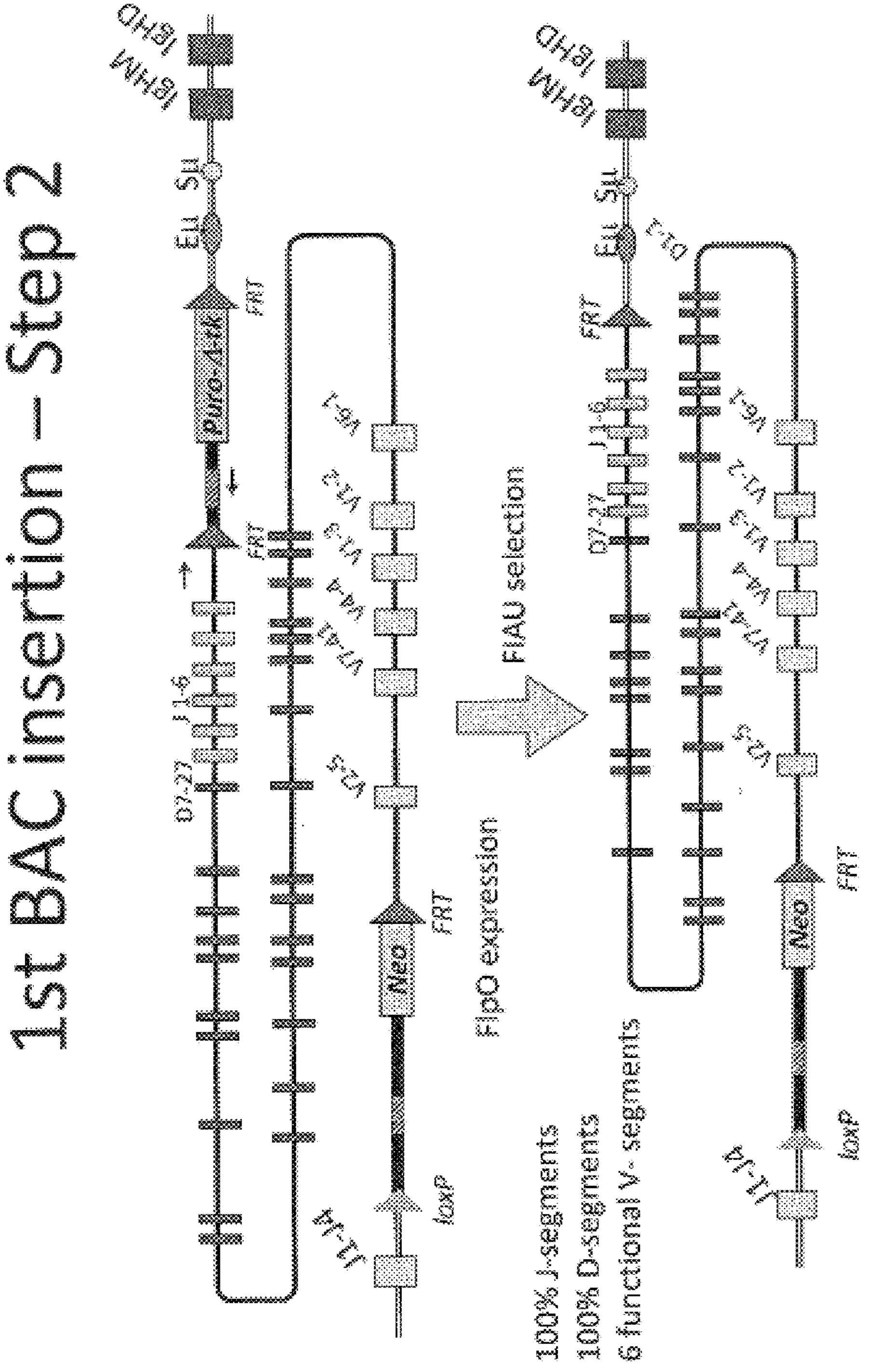
Figure 12:
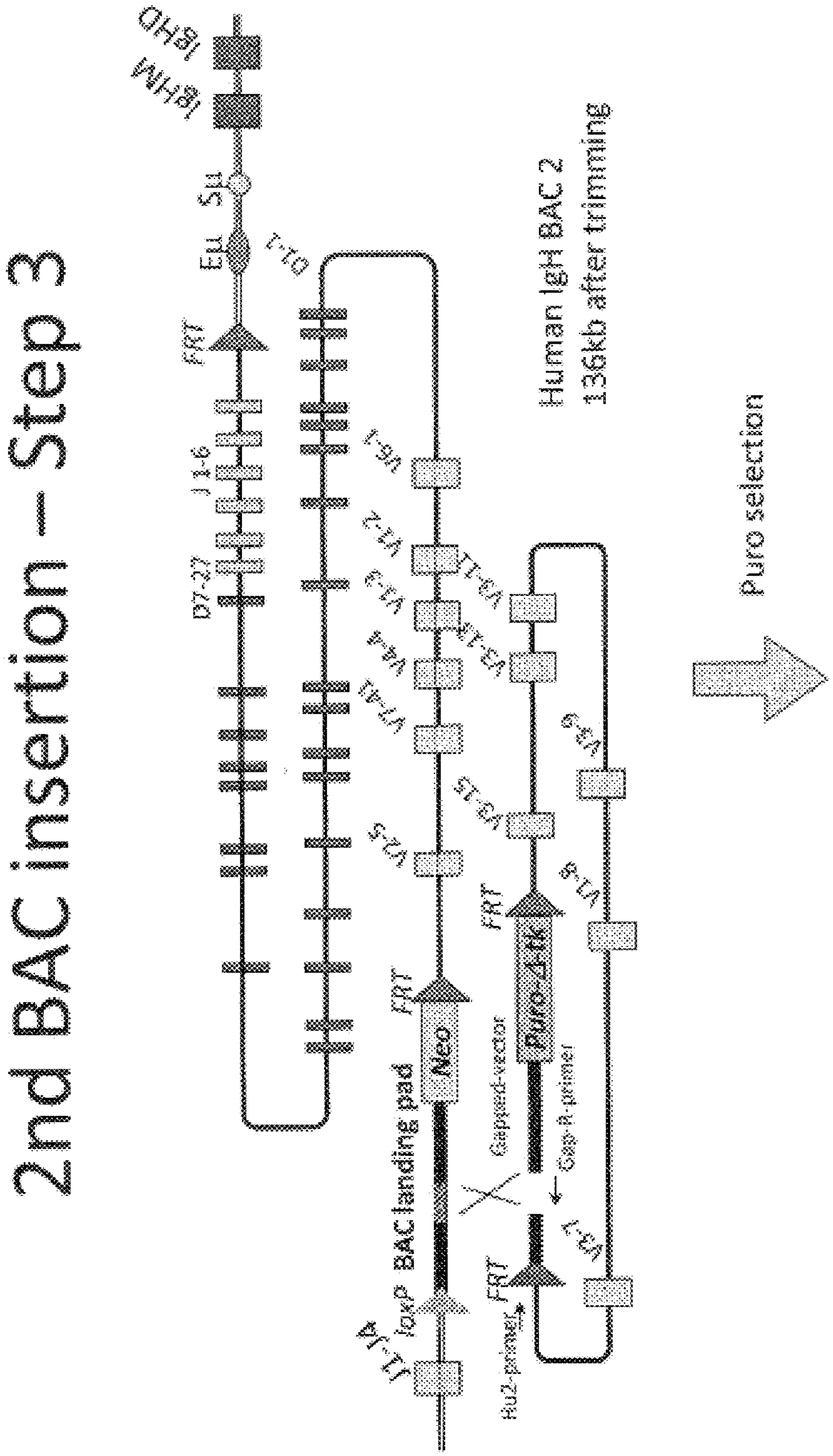
Figure 13:
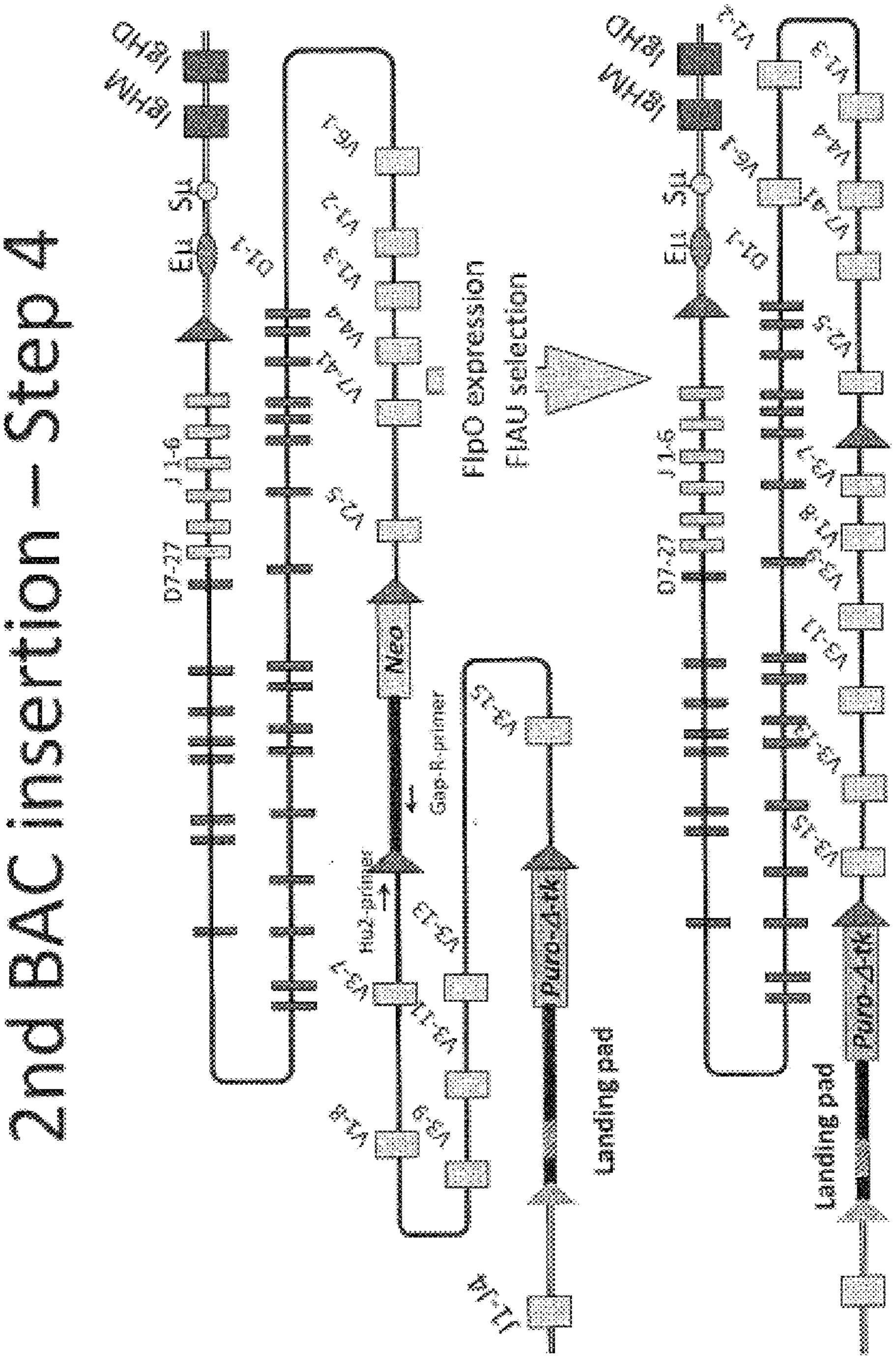
Figure 14:
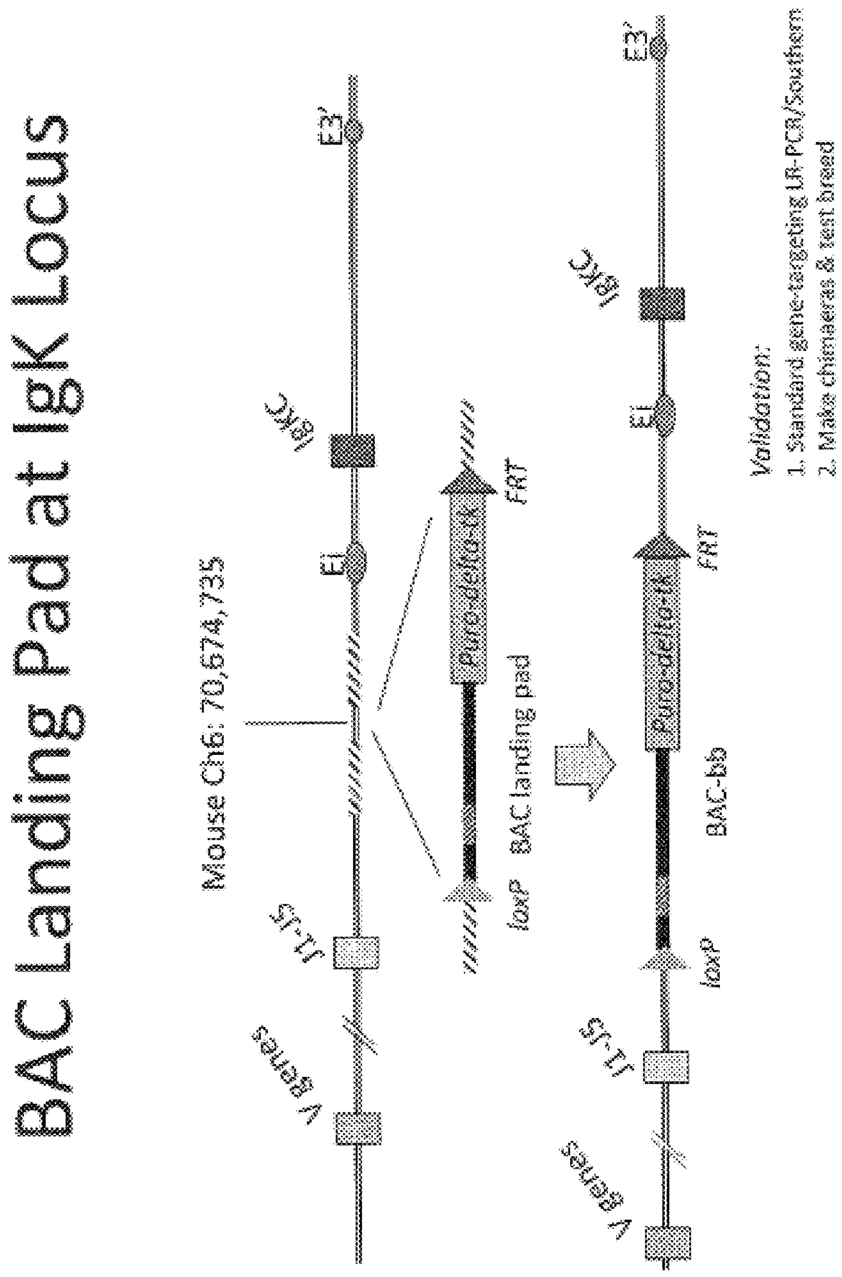
Figure 15:
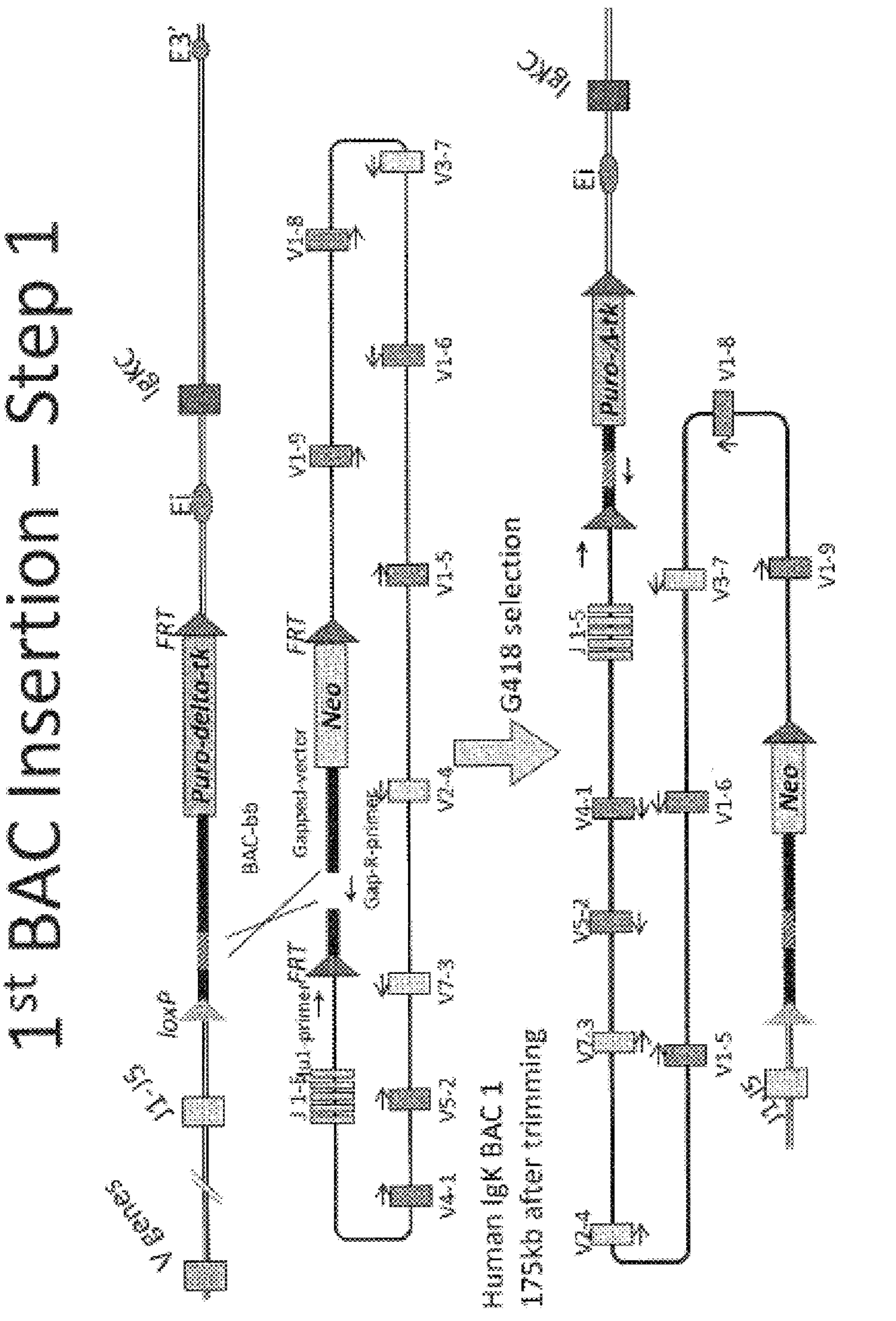
Figure 16:
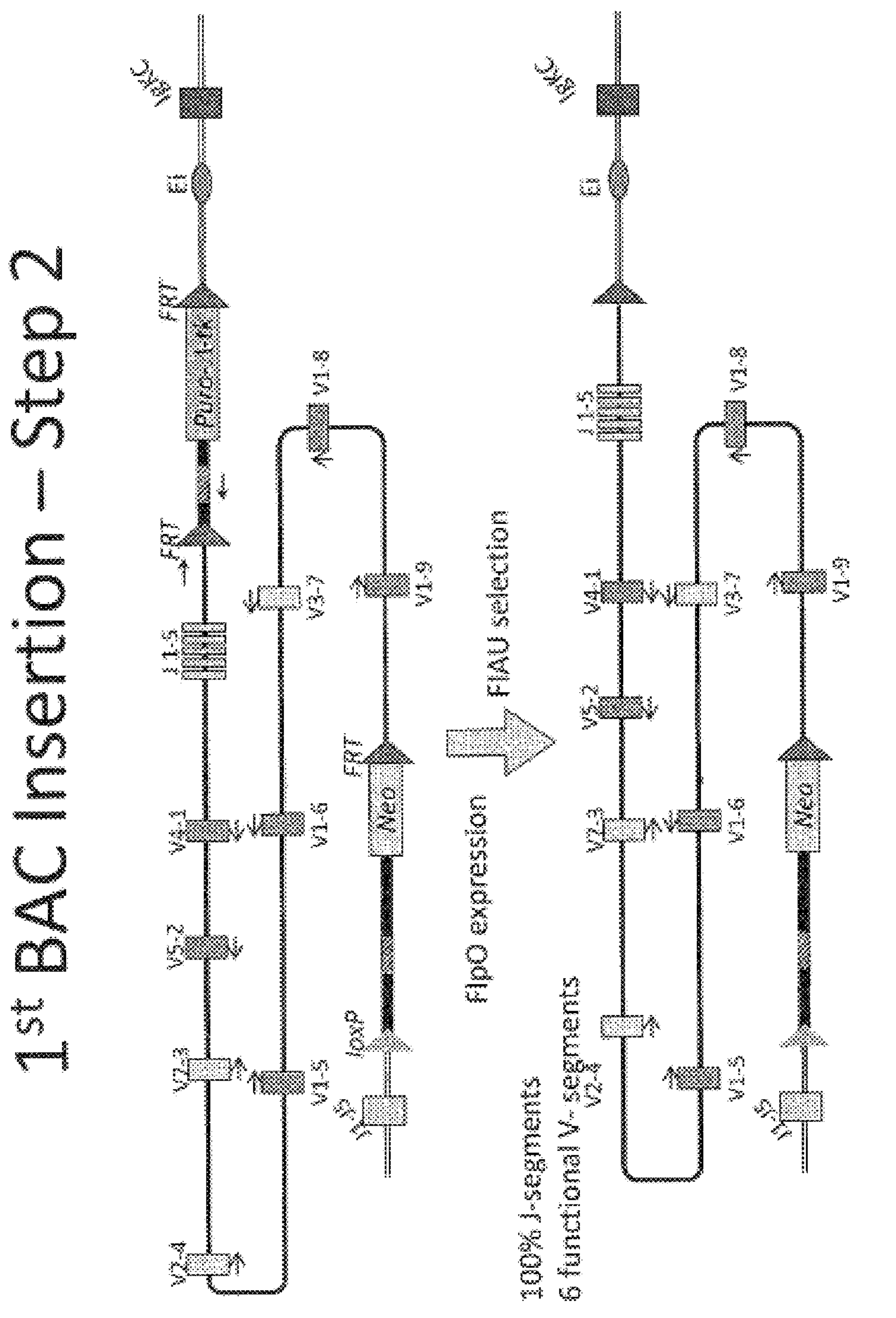
Figure 17:
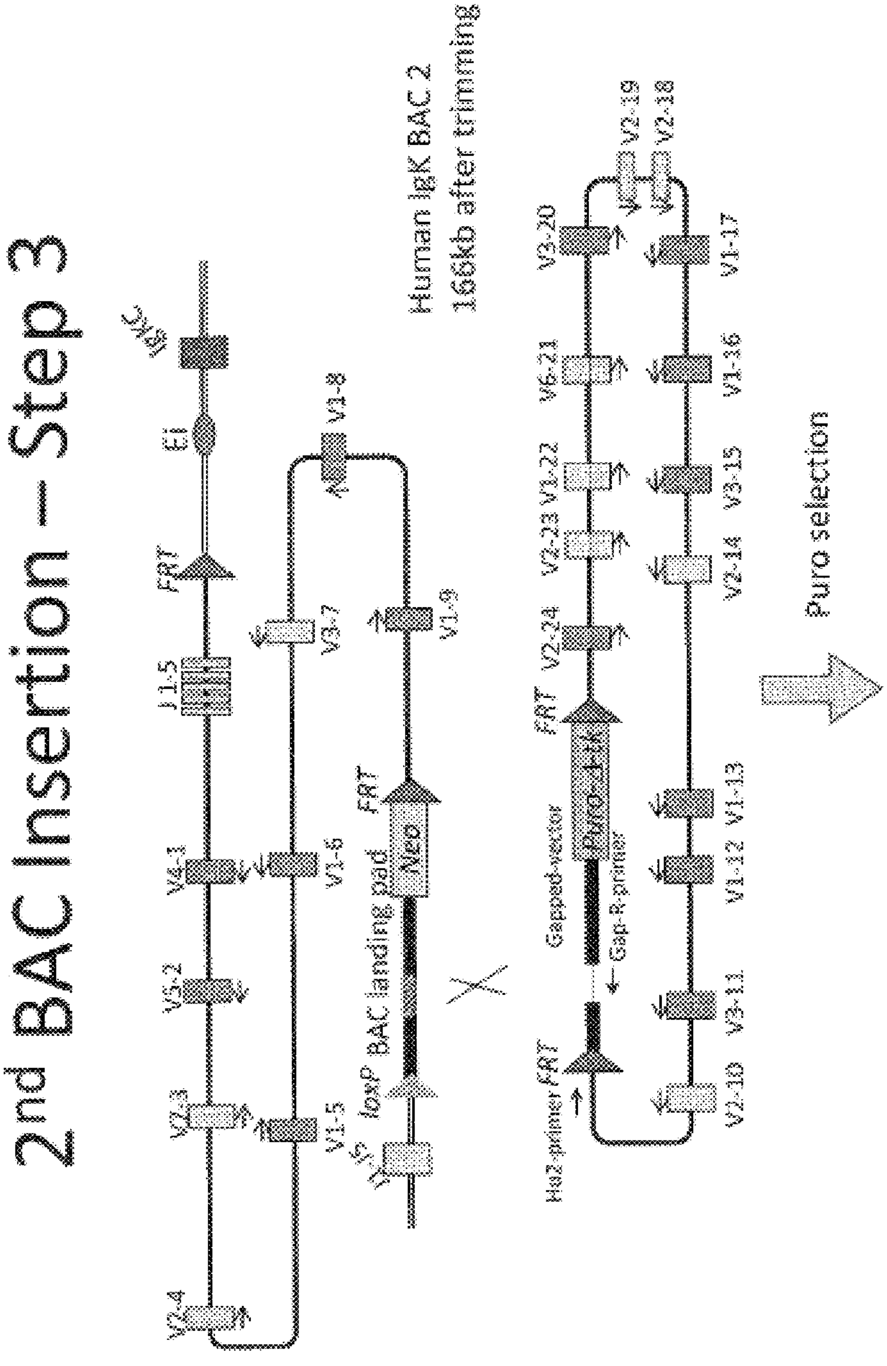
Figure 18:
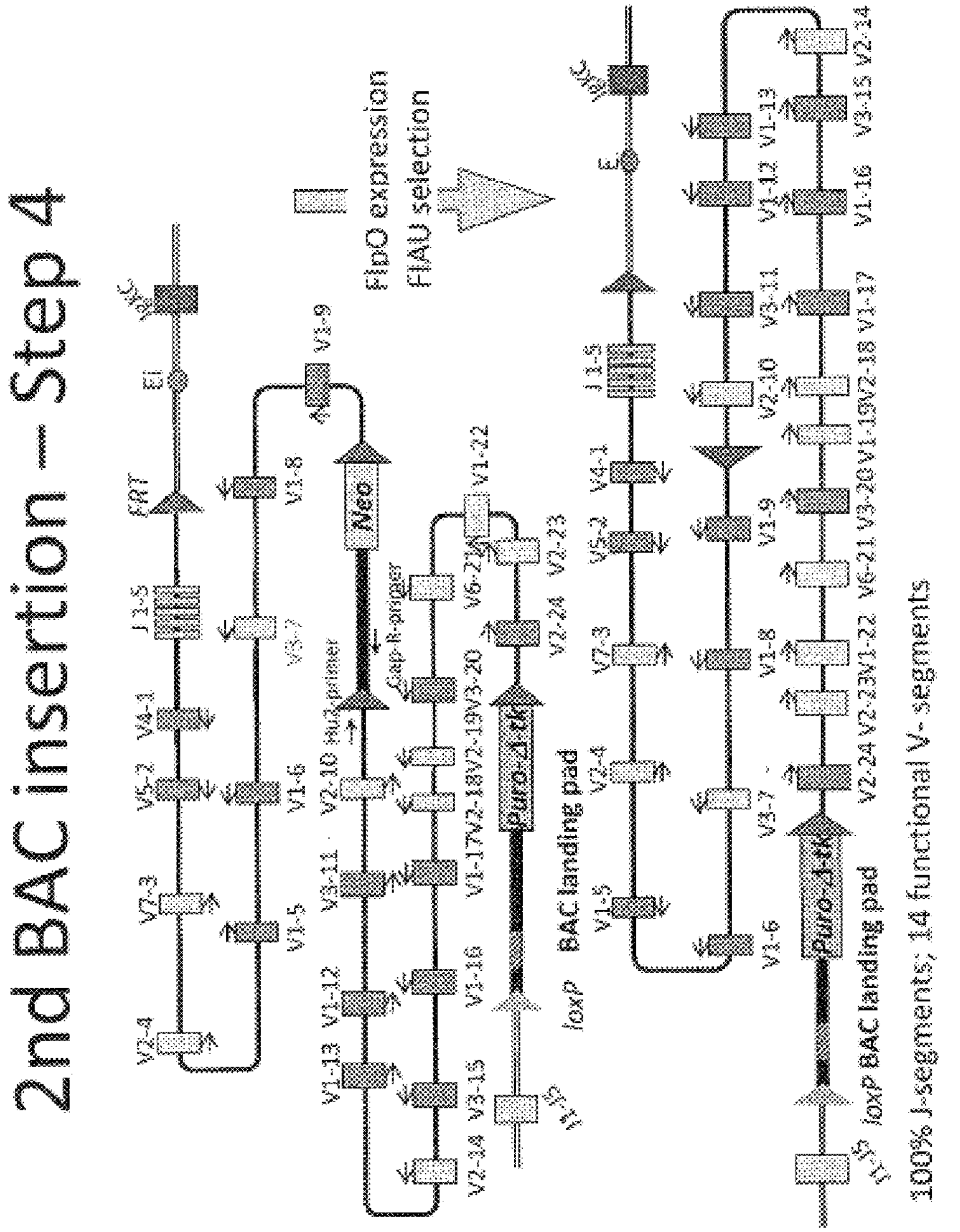

FIG. 8 illustrates the final predicted ES cell construct.

FIGS. 9-18 provide a further level of detail of this process.

Example 2

Site-Specific Recombination

In a further method of the invention site specific recombination can also be employed. Site-specific recombination (SSR) has been widely used in the last 20-years for the integration of transgenes into defined chromosomal loci. SSR involves recombination between homologous DNA sequences.

The first generation of SSR-based chromosomal targeting involved recombination between (i) a single recombination target site (RT) such as loxP or FRT in a transfected plasmid with (ii) a chromosomal RT site provided by a previous integration. A major problem with this approach is that insertion events are rare since excision is always more efficient than insertion. A second generation of SSR called RMCE (recombinase-mediated cassette exchange) was introduced by Schlake and Bode in 1994 (Schlake, T.; J. Bode (1994). "Use of mutated FLP-recognition-target-(FRT-)sites for the exchange of expression cassettes at defined chromosomal loci". Biochemistry 33: 12746-12751). Their method is based on using two heterospecific and incompatible RTs in the transfected plasmid which can recombine with compatible RT sites on the chromosome resulting in the swap of one piece of DNA for another—or a cassette exchange. This approach has been successfully exploited in a variety of efficient chromosomal targeting, including integration of BAC inserts of greater than 50 kb (Wallace, H. A. C. et al. (2007). "Manipulating the mouse genome to engineering precise functional syntenic replacements with human sequence". Cell 128: 197-209; Prosser, H. M. et al. (2008). "Mosaic complementation demonstrates a regulatory role for myosin Vila in actin dynamics of Stereocilia". Mol. Cell. Biol. 28: 1702-12).

The largest insert size of a BAC is about 300-kb and therefore this places an upper limit on cassette size for RMCE.

In the present invention a new SSR-based technique called sequential RMCE (SRMCE) was used, which allows continuous insertion of BAC inserts into the same locus.

The method comprises the steps of 1 insertion of DNA forming an initiation cassette (also called a landing pad herein) into the genome of a cell;

2 insertion of a first DNA fragment into the insertion site, the first DNA fragment comprising a first portion of a human DNA and a first vector portion containing a first selectable marker or generating a selectable marker upon insertion;

3 removal of part of the vector DNA;

4 insertion of a second DNA fragment into the vector portion of the first DNA fragment, the second DNA fragment containing a second portion of human DNA and a second vector portion, the second vector portion containing a second selectable marker, or generating a second selectable marker upon insertion;

5 removal of any vector DNA to allow the first and second human DNA fragments to form a contiguous sequence; and 6 iteration of the steps of insertion of a part of the human V(D)J DNA and vector DNA removal, as necessary, to produce a cell with all or part of the human VDJ or VJ region sufficient to be capable of generating a chimaeric antibody in conjunction with a host constant region, wherein the insertion of at least one DNA fragment uses site specific recombination.

Figure 22:
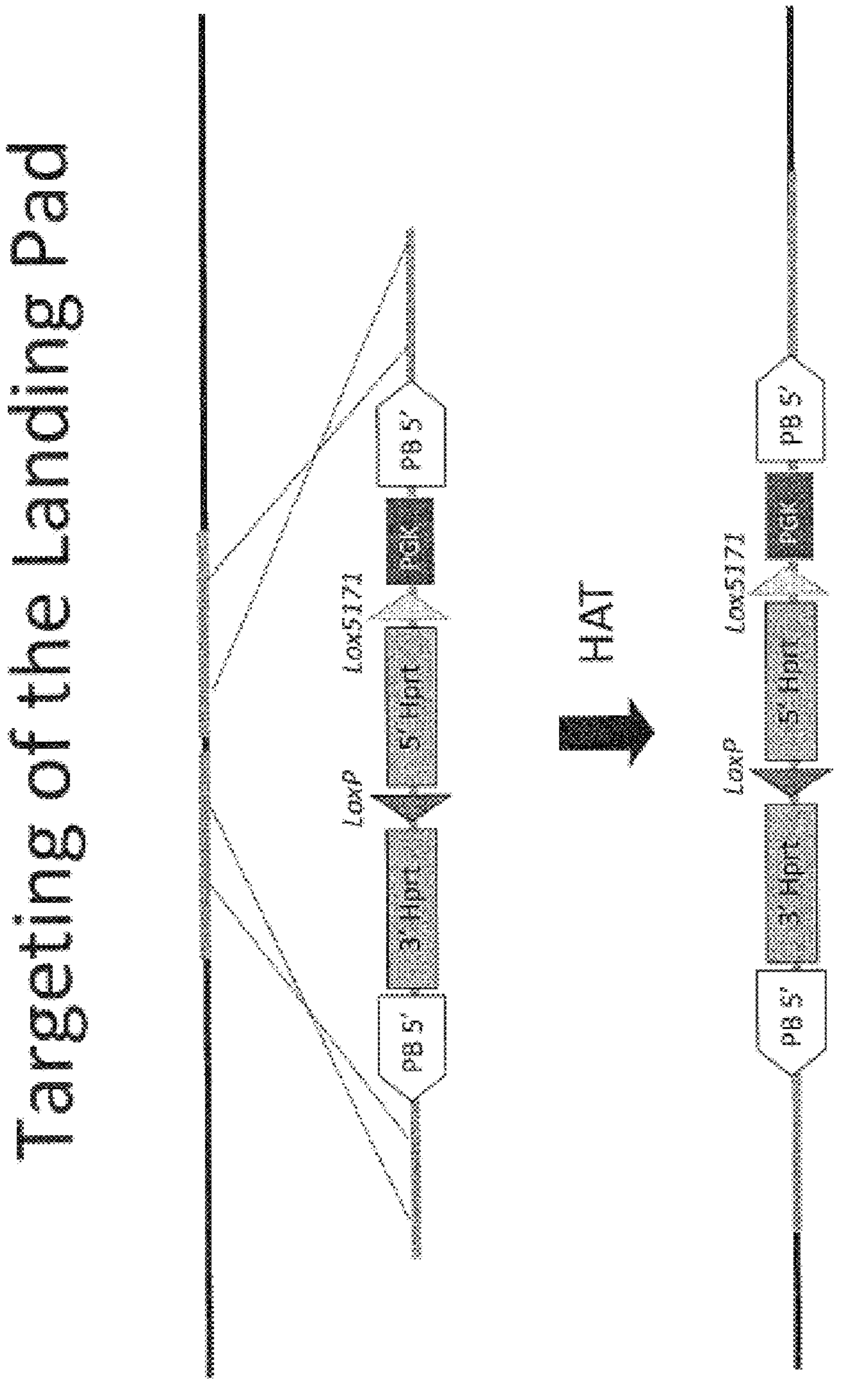

In one specific aspect the approach utilizes three heterospecific and incompatible loxP sites. The method is comprised of the steps as follows, and illustrated in FIGS. 22-26:

1. Targeting a landing pad into the defined locus. An entry vector containing an HPRT mini-gene flanked by inverted piggyBac (PB) ITRs is targeted into defined region (for example: a region between IGHJ and Eμ or IGKJ and Eκ or IGLC1 and EA3-1) to serve as a landing pad for BAC targeting. The HPRT mini-gene is comprised of two synthetic exons and associated intron. The 5' HPRT exon is flanked by two heterospecific and incompatible loxP sites (one wild-type and the other a mutated site, lox5171) in inverted orientation to each other (FIG. 22). These two loxP sites provide recombination sites for the BAC insertion through RMCE.

Figure 23:
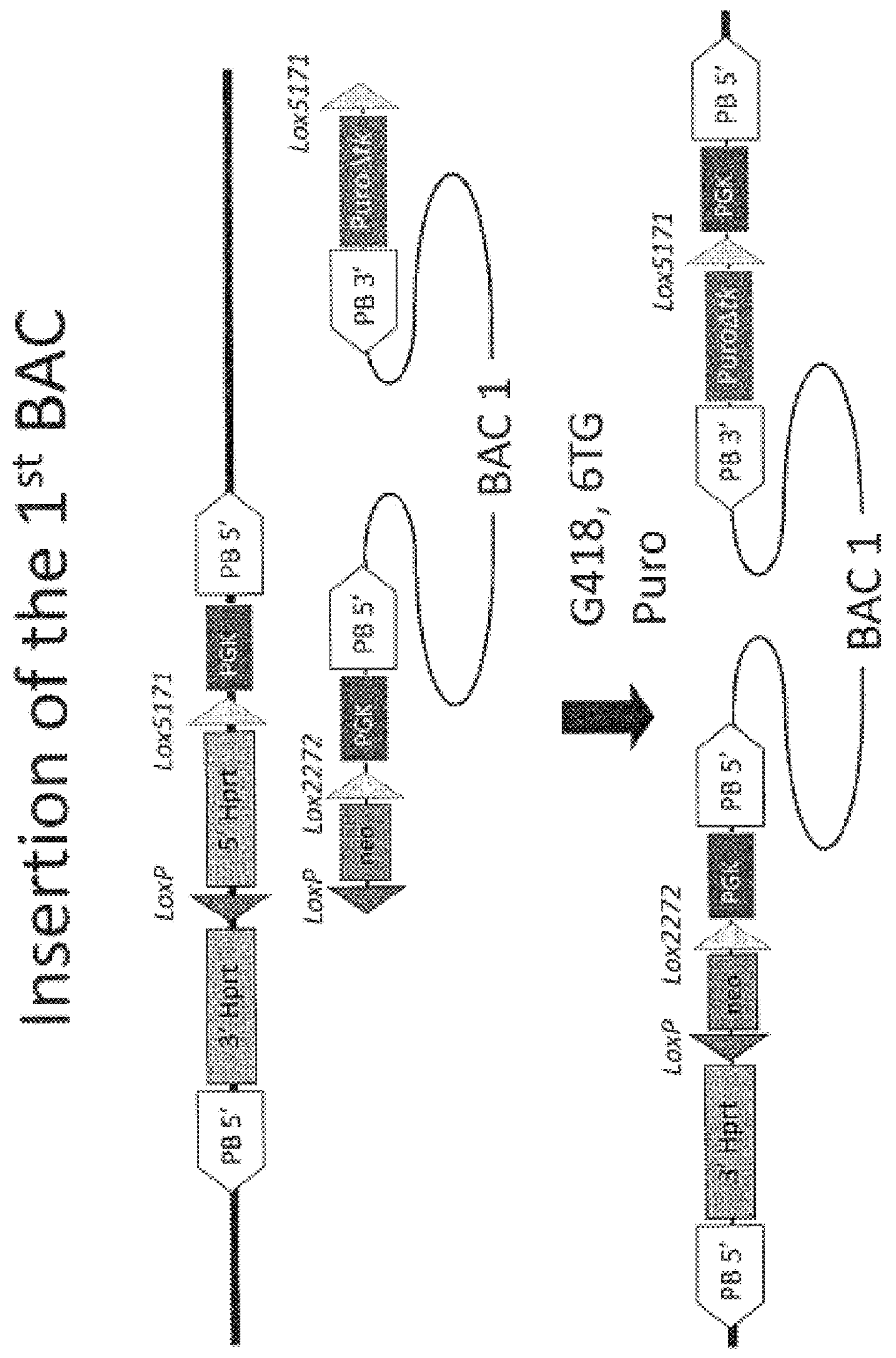

2. Insertion of the $1^{st}$ modified BAC into the targeted landing pad. The $1^{st}$ BAC has a length of DNA to be inserted into the genome flanked by engineered modifications. The 5' modification (loxP—neo gene—lox2272—PGK promoter—PB 5'LTR) and 3' modification (PB3'LTR—purotTK gene—lox5171) is depicted in FIG. 23 along with the relative orientations of the lox sites and PB LTRs. With transient CRE expression from a co-electroporated vector, the DNA sequence would be inserted into the defined locus through RMCE. The cells in which a correct insertion has occurred can be selected as follows: (i) Puromycin-resistance (the purotTK gene has acquired a promoter—"PGK"—from the landing pad), (ii) 6TG-resistance (the HPRT mini-gene has been disrupted), and (iii) G418-resistance (selects for any insertion via the 5' region PGK-neo arrangement). Any combination of these selection regimes can be used. G418- and 6TG-resistance select for correct events on the 5' end while puro-resistance selects for correct events on the 3' end.
3. Curing (removing) the 3' modification of the $1^{st}$ insertion. A properly inserted $1^{st}$ BAC results the 3' end having a purotTK gene flanked by inverted PB LTRs (FIG. 24)—essentially a proper transposon structure. This transposon can then be removed by the transient expression of the piggyBac transposase (from an electroporated vector). Cells with the correct excision event can be selected by FIAU resistance—ie, no thymidine kinase activity from the purotTK gene. This completely removes the 3' modification leaving no trace nucleotides.
4. Insertion of a $2^{nd}$ modified BAC into the 5' end of $1^{st}$ insertion. The $2^{nd}$ BAC has a length of DNA to be inserted into the genome (usually intended to be contiguous with the DNA inserted with the $1^{st}$ BAC) flanked by engineered modifications. The 5' modification (loxP—HPRT mini gene 5' portion—lox5171—PGK promoter—PB5'LTR) and 3' modification (PB3'LTR—purotTK—lox2272) is depicted in FIG. 25 along with the relative orientations of the lox sites and PB LTRs. With transient CRE expression from a co-electroporated vector, the DNA sequence would be inserted into the defined locus through RMCE. The cells in which a correct insertion has occurred can be selected as follows: (i) HAT-resistance (the HPRT mini-gene is reconstituted by a correct insertion event, ie: the 5' and 3' exon structures are brought together), and (ii) puromycin-resistance (purotTK gene has acquired a promoter—"PGK"—from the landing pad).
5. Curing (removing) the 3' modification of the $2^{nd}$ insertion. A properly inserted $2^{nd}$ BAC results the 3' end having a purotTK gene flanked by inverted PB LTRs (FIG. 26)—essentially a proper transposon structure, exactly analogous to the consequence of a successful $1^{st}$ BAC insertion. And therefore this transposon can likewise be removed by the transient expression of the piggyBac transposase (from an electroporated vector). Cells with the correct excision event can be selected by FIAU resistance—ie, no thymidine kinase activity from the purotTK gene. This completely removes the 3' modification leaving no trace nucleotides.
6. After curing of the 3' modification of the $2^{nd}$ BAC insertion, the landing pad becomes identical to the original. This entire process, steps 2 through 5, can be repeated multiple times to build up a large insertion into the genome. When complete, there are no residual nucleotides remaining other than the desired insertion.

Figure 27:
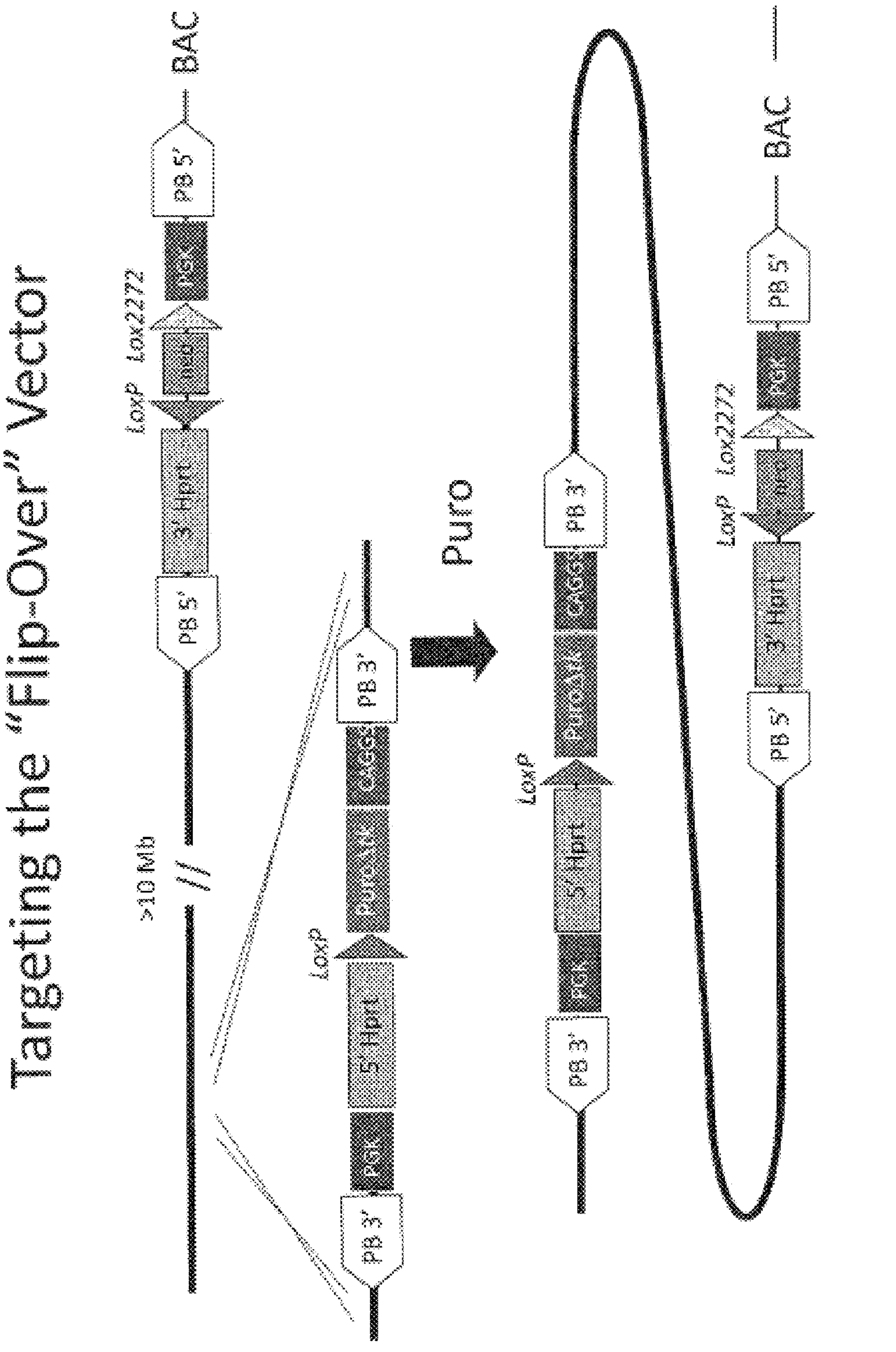
FIGS. 27-29 illustrate a mechanism for inversion of the host VDJ region
Figure 28:
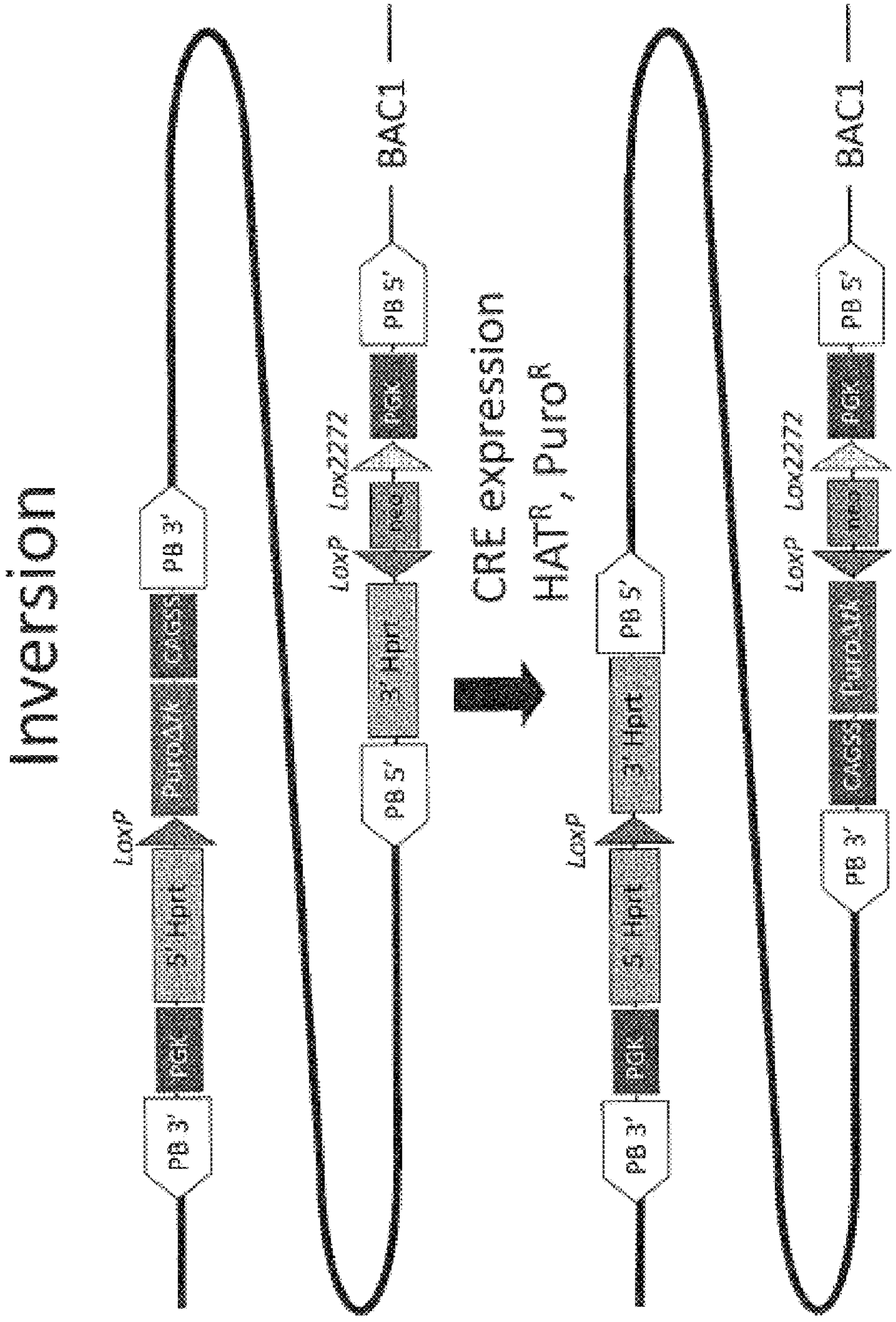
Figure 29:
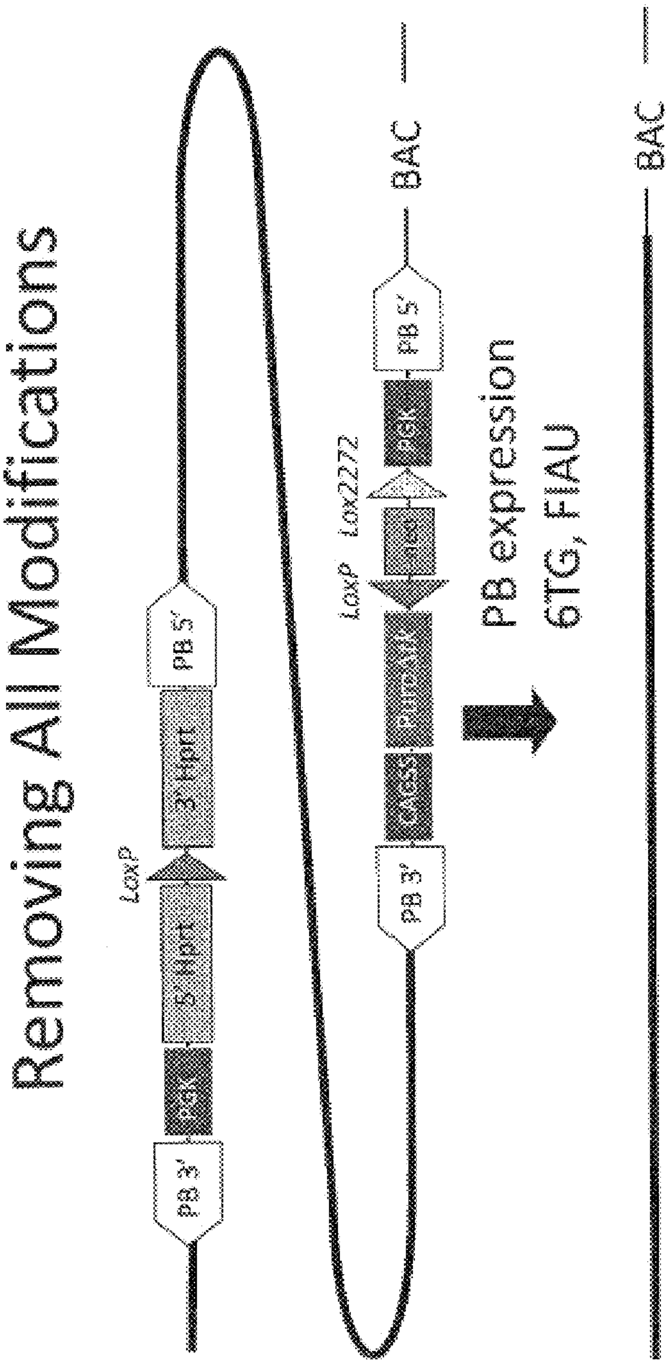

With the insertion of an odd number of BACs into the Ig loci, the endogenous VDJ or VJ sequences can be inactivated through an inversion via chromosomal engineering as follows (see FIGS. 27-29):

1. Targeting a "flip-over" cassette into a 5' region 10 to 40 megabases away from the endogenous VDJ or VJ. The flip-over vector (PB3'LTR—PGK promoter—HPRT mini gene 5' portion—loxP—purotTK—CAGGS promoter—PB3'LTR) is depicted in FIG. 27 along with the relative orientations of the lox sites and PB LTRs.
2. Transient CRE expression will result in recombination between the loxP site in the "flip-over" cassette and the loxP site in the 5' modification. This 5' modification is as described in Steps 2 and 3 above—essentially the modification resulting from insertion of an odd number of BACs, after the 3' modification has been cured. The loxP sites are inverted relative to one another and therefore the described recombination event results in an inversion as depicted in FIG. 28. Cells with the correct inversion will be HAT-resistance since the HPRT mini-gene is reconstituted by a correct inversion.
3. A correct inversion also leaves two transposon structures flanking the "flip-over" cassette and the 5' modification. Both can be excised with transient piggyBAC transposase expression, leaving no remnant of either modification (FIG. 29). Cells with the correct excisions can be selected as follows: (i) 6TG-resistance (the HPRT mini-gene is deleted) and (ii) FIAU-resistance (the purotTK gene is deleted). An inversion as described in the Ig loci would move the endogenous IGH-VDJ or IGK-VJ region away from the Eμ or Eκ enhancer region, respectively, and lead to inactivation of the endogenous IGH-VDJ or IGK-VJ regions.

The methods of insertion of the invention suitably provide one or more of:

- Selection at both 5' and 3' ends of the inserted DNA fragment;
- Efficient curing of the 3' modification, preferably by transposase mediated DNA excision;
- Inactivation of endogenous IGH or IGK activity through an inversion; and
- Excision of modifications, leaving no nucleotide traces remaining in the chromosome.

Example 3

Insertion of a Test Vector into the Genome at a Defined Location

Figure 30:
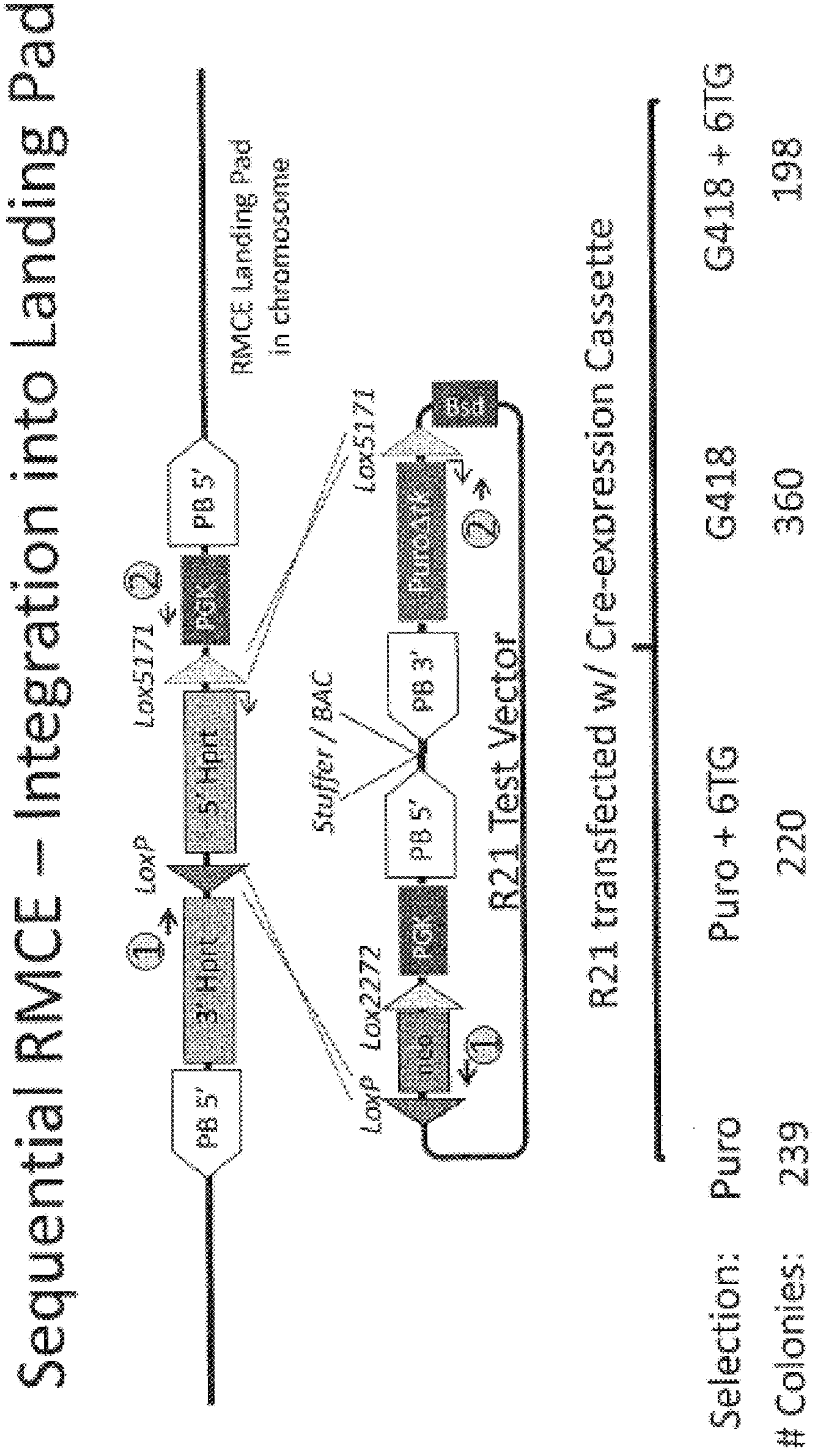
FIG. 30 illustrates proof of principle for insertion of a plasmid using an RMCE approach

Proof of concept of the approach is disclosed in FIG. 30. In FIG. 30 a landing pad as shown in FIG. 22 was inserted into the genome of a mouse by homologous recombination, followed by insertion of the R21 plasmid into that landing pad via cre-mediated site specific recombination. The insertion event generated a number of general insertion events, 360 G418 resistant colonies, of which ~220 were inserted into the desired locus, as demonstrated by disruption of the HRPT minilocus.

The R21 vector mimicks the $1^{st}$ BAC insertion vector at the 5' and 3' ends, including all selection elements and recombinase target sites. In place of BAC sequences, there is a small 'stuffer' sequence. This vector will both test all the principals designed in the invention and allow easy testing of the results in that PCR across the stuffer is feasible and therefore allows both ends of the insertion to be easily tested. R21 was co-electroporated with a cre-expressing vector into the ES cells harbouring the landing pad in the IGH locus. Four sets of transformed cells were transfected in parallel and then placed under different selection regimes as indicated in FIG. 30. G418 selection (neo gene expression) resulted in the largest number of colonies due to there being no requirement for specific landing-pad integration. Any integration of R21 into the genome will provide neo expression leading to G418-resistance. Puro selection resulted in a similar colony number to Puro+6TG or G418+6TG, suggesting that the stringency of Puro selection is due to the PurotTK lacking a promoter in the vector. Puro expression is only acquired when an integration occurs near a promoter element—in this design most likely specifically in the landing pad. These conclusions are supported by the results from junction PCR which is shown in FIG. 31.

Figure 32:
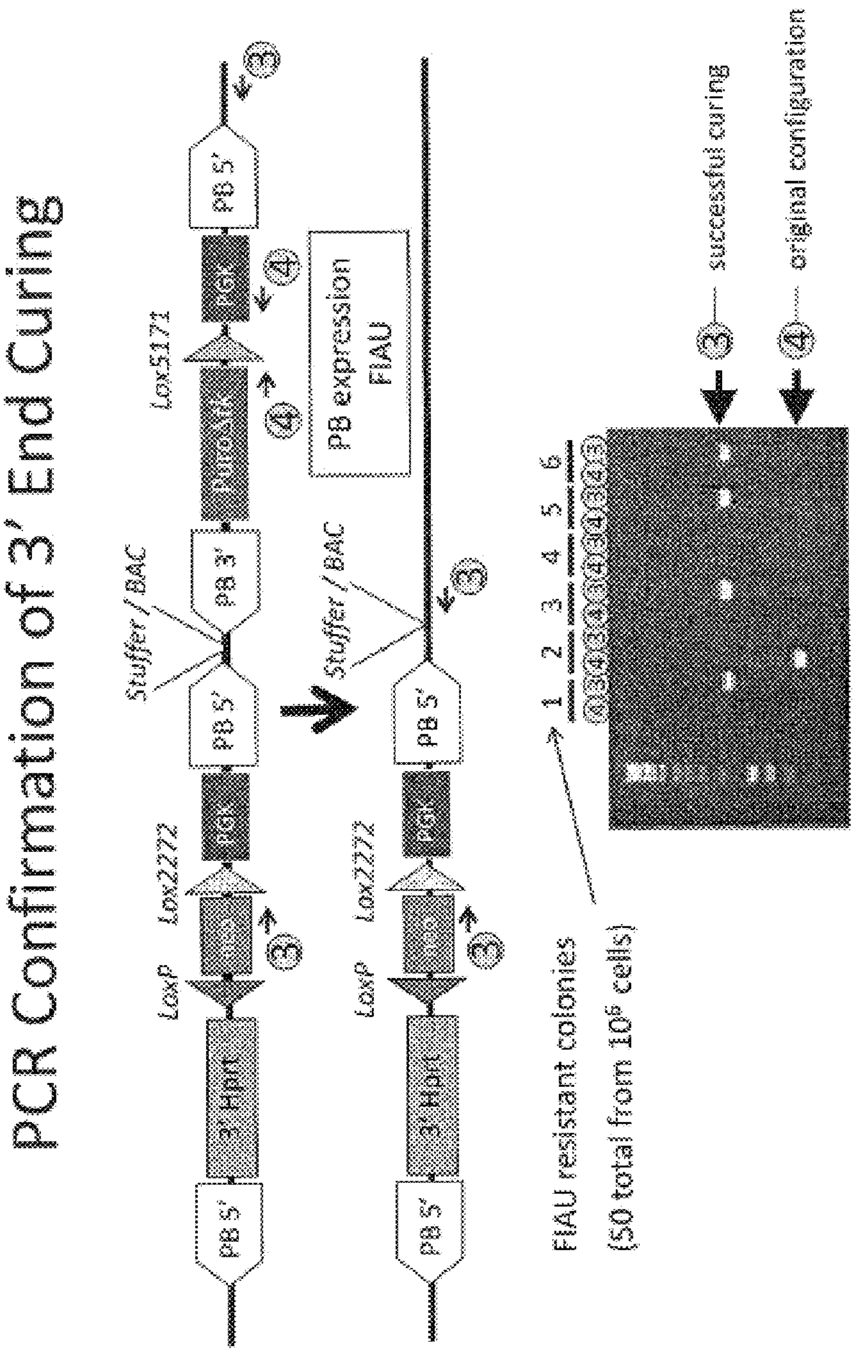
FIG. 32 illustrates confirmation of Successful Insertion into Landing Pad

The next step in the invention is to 'cure' the 3' end of the integrated BAC vector, leaving a seamless transition between the insertion and the flanking genome. This curing was demonstrated by expanding an individual clone from above (R21 inserted into the landing pad) and expressing piggyBac recombinase in this clone via transfection of an expressing plasmid. FIAU was used to select colonies in which the 3' modification was excised—ie, through loss of the 'PGK-puroΔTK' element between the piggyBac terminal repeats. Fifty such clones resulted from a transfection of $10^6$ cells; of these six were tested for the expected genomic structure. Successful curing resulted in positive PCR between the primer set labelled "3" in FIG. 32. Of the 6 clones, 4 had correct excisions, 1 clone remained in the original configuration and 1 other had a deletion.

These data demonstrate iterative insertion of DNA into a landing pad at a defined genomic locus using the approaches outlined above.

Example 4

Insertion of Large Parts of the Human IG Loci into Defined Positions in the Mouse Genome Example 3 demonstrated that the design of the claimed invention was capable of providing for the insertion of a test vector into the genome at a defined location, in this case the R21 vector into the mouse IGH locus. The use of the appropriate selection media and the expression of cre-recombinase resulted in a genomic alteration with the predicted structure.

The same design elements described in this invention were built into the 5' and 3' ends of a BAC insert. Said insert comprised human sequences from the IGH locus and was approximately 166-kb. This engineered BAC was electroporated along with a cre-expressing plasmid DNA into mouse ES cells harbouring the landing pad at the mouse IGH locus. The transfected cell population was grown in puro-containing media to select for appropriate insertion events.

Figure 33:
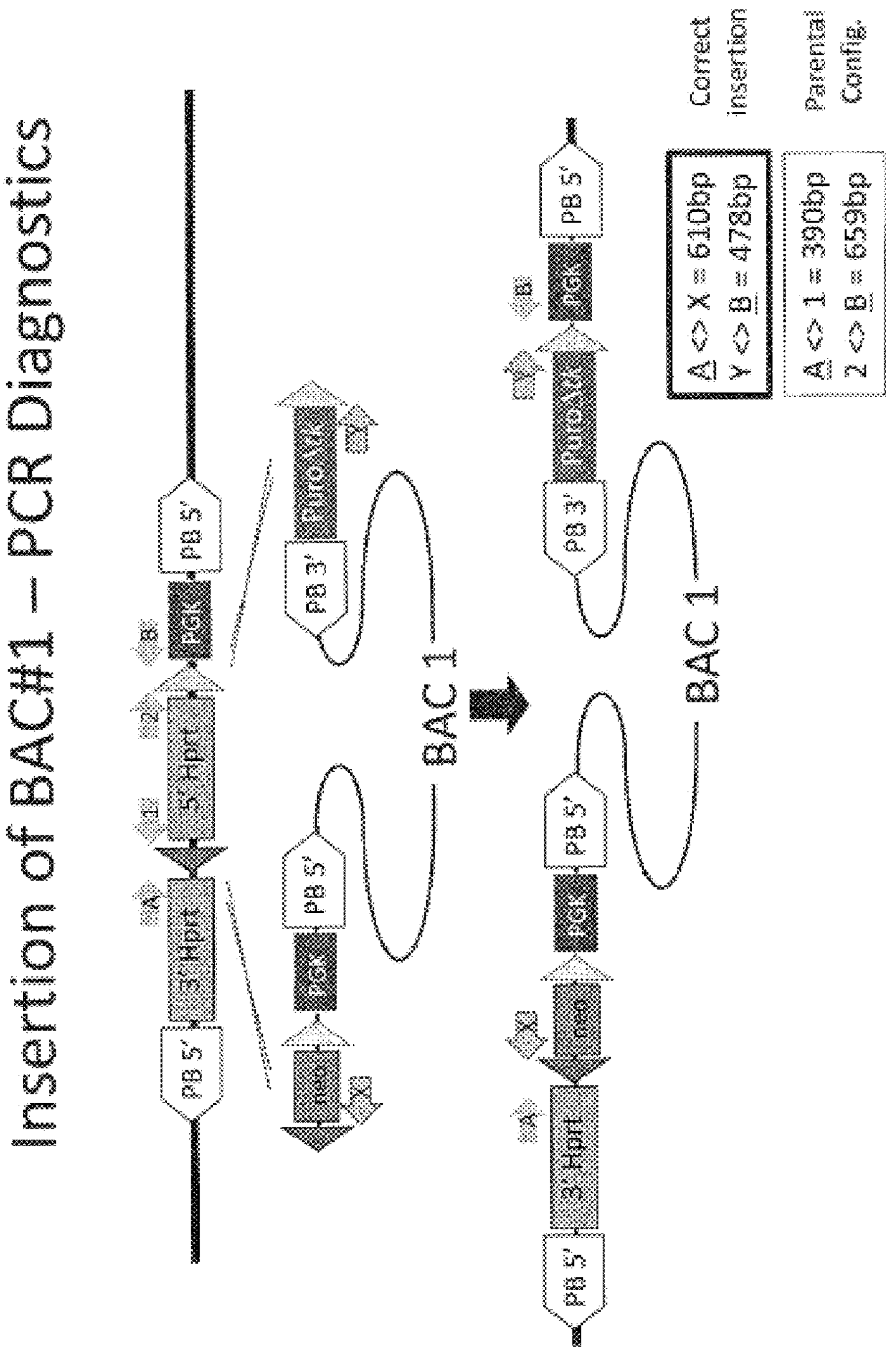
FIG. 33 illustrates PCR Confirmation of 3' End Curing
Figure 34:
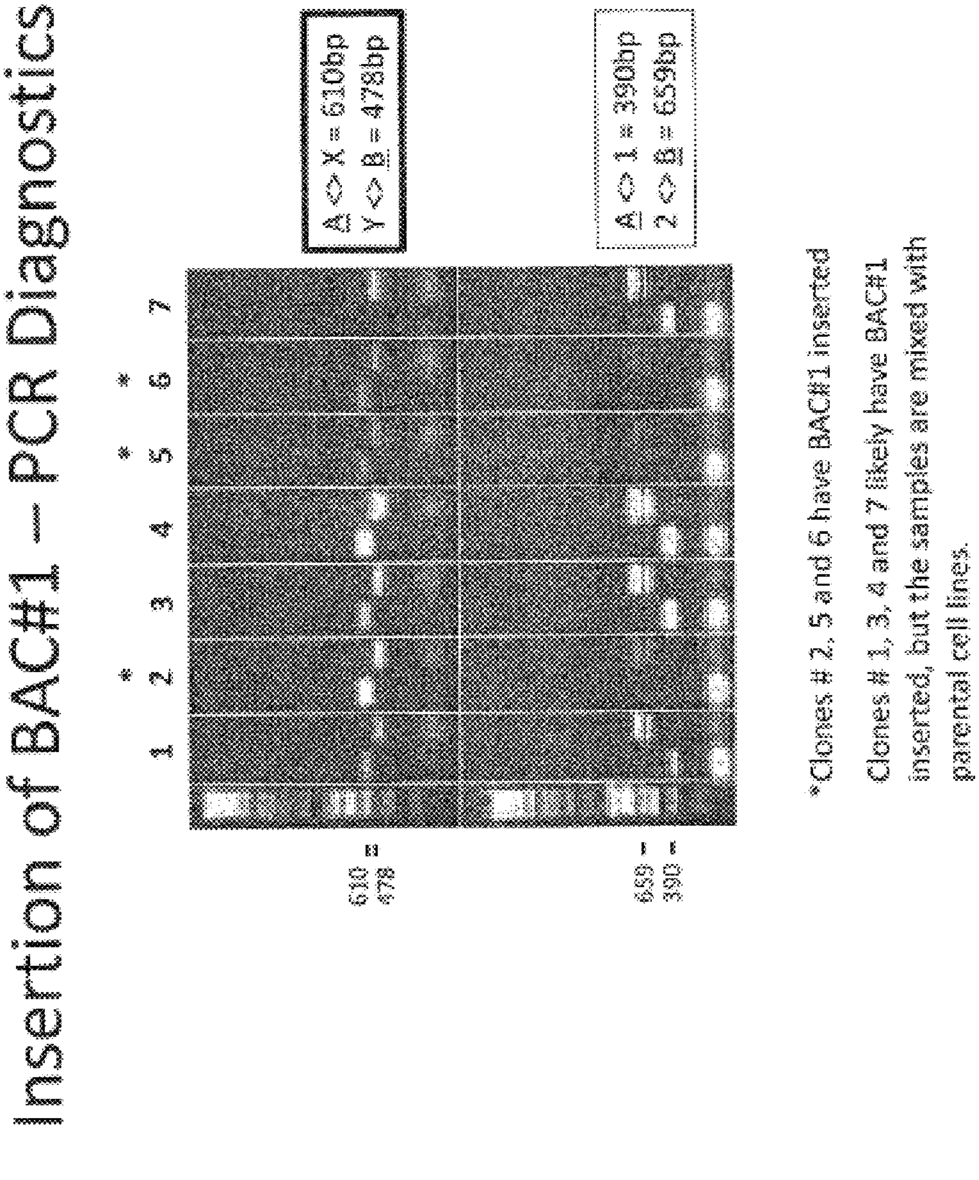
FIG. 34 illustrates insertion of BAC#1 and PCR Diagnostics

Seven resulting clones were isolated and further analysed. The expected recombination event and resulting structure are depicted in FIG. 33. Based upon data from the R21 experiment outlined in Example 3, a stringent selection for correct clones was expected when the transfected population was selected in puro-containing media. This is because the puro-coding region requires a promoter element and this is preferentially supplied by the landing pad after recombination. Accordingly, the majority of the 7 isolated clones had inserted correctly into the genome at the landing pad as determined by the diagnostic PCR. The primers for diagnosing a correct insertion are depicted in FIG. 33. Correct junctions are present in the genome if a 610-bp fragment is amplified between primers 'A' and 'X' and a 478-bp fragment is amplified between primers 'Y' and 'B' (FIGS. 33 and 34). Note that there are amplified fragments between 'A' and '1' primers and '2' and 'B' primers indicating the presence of parental genome (that is, the landing pad alone). These result from parental cells present internally in the cell colonies under puro-selection that escape the selection due to the geometry of a colony. After passaging the colony through puro-containing media, these parental junction fragments disappear indicating that the parental cells are removed from the population. In addition, all the clones were shown to be resistant to 6-TG as expected if the HPRT gene is inactivated by the correct insertion event.

These data indicate that the disclosed strategy for inserting large parts of the human IG loci into defined positions in the mouse genome will enable the construction of a mouse with a plurality of the variable regions of human IG regions upstream of the mouse constant regions as described.

Example 5

Inserted Loci are Functional in Terms of Gene Rearrangement, Junctional Diversity as Well as Expression Bacterial artificial chromosomes (BACs) were created, wherein the BACs had inserts of human Ig gene segments (human V, D and/or J gene segments). Using methods described herein, landing pads were used in a method to construct chimaeric Ig loci in mouse embryonic stem cells (ES cells), such that chimaeric IgH and IgK loci were provided in which human gene segments are functionally inserted upstream of endogenous constant regions. To test if the human IgH-VDJ or IgK-VJ gene segments in the chimaera mice derived from human BAC-inserted ES cell clones appropriately rearrange and express, RT-PCR was performed for the RNA samples of white blood cells from those mice with the primer pairs of human variable (V) region and mouse constant (C) region. The sequences of oligos are shown as follows (Table 1). Each V oligo is paired with C oligo (HV with Cμ; KV with Cκ) for PCR reaction.

TABLE 1

| Oligo | Sequence |
|---|---|
| HV2-5 | AGATCACCTTGAAGGAGTCTGGTCC (SEQ ID NO 7) |
| HV4-4 | TGGTGAAGCCTTCGGAGACCCTGTC (SEQ ID NO 8) |
| HV1-3 | CACTAGCTATGCTATGCATTGGGTG (SEQ ID NO 9) |
| HV1-2 | ATGGATCAACCCTAACAGTGGTGGC (SEQ ID NO 10) |
| HV6-1 | GGAAGGACATACTACAGGTCCAAGT (SEQ ID NO 11) |
| Cμ | TAGGTACTTGCCCCCTGTCCTCAGT (SEQ ID NO 12) |
| KV1-9 | AGCCCAGTGTGTTCCGTACAGCCTG (SEQ ID NO 13) |
| KV1-8 | ATCCTCATTCTCTGCATCTACAGGA (SEQ ID NO 14) |
| KV1-6 | GGTAAGGATGGAGAACACTGGCAGT (SEQ ID NO 15) |
| KV1-5 | TTAGTAGCTGGTTGGCCTGGTATCA (SEQ ID NO 16) |
| Cκ | CTTTGCTGTCCTGATCAGTCCAACT (SEQ ID NO 17) |

Using the one-step formulation of SuperScript™ III One-Step RT-PCR System with Platinum® Taq High Fidelity (Invitrogen™; World Wide Web (www) invitrogen.com/site/us/en/home/References/protocols/nucleic-acid-amplification-and-expression-profiling/per-protocol/superscript-3-one-step-rt-per-system-with-platinum-taq-high-fidelity.html#prot3), both cDNA synthesis and PCR amplification were achieved in a single tube using gene-specific primers and target RNAs.

The RT-PCR results showed most of the human IGH-VDJ or IGK-VJ gene segments appropriately rearrange and express in the chimaera mice. To investigate the details about the diversity generated from VDJ/VJ rearrangement, those specific RT-PCR fragments were cloned into a common vector for sequencing.

Figure 35:
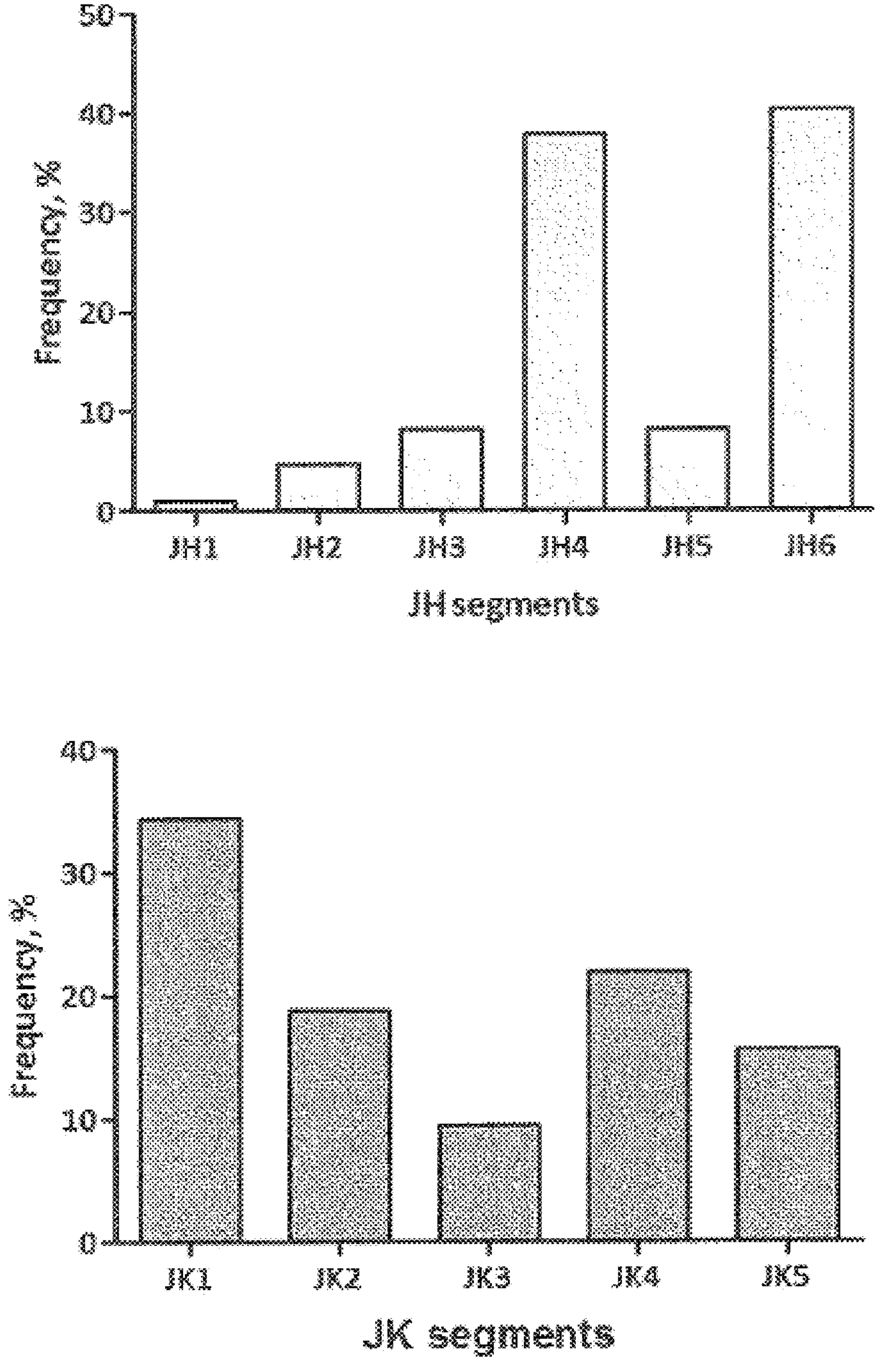
FIG. 35 illustrates JH and JK usage
Figure 36:
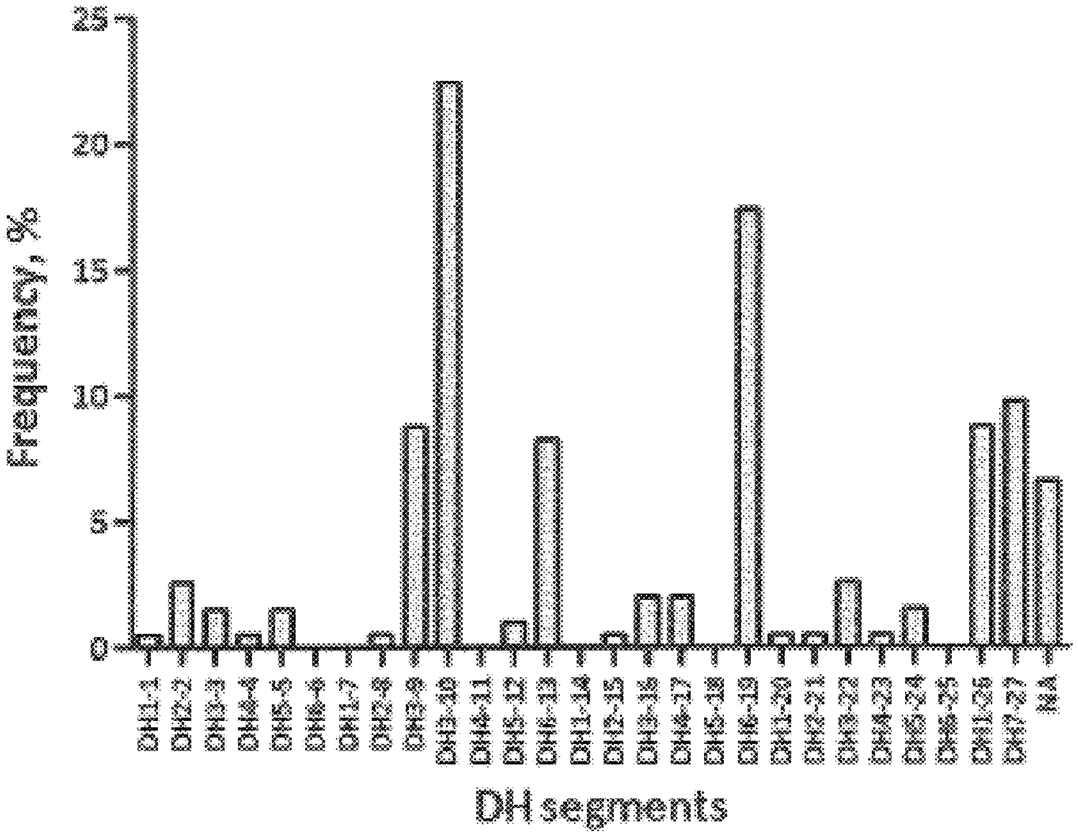
FIG. 36 illustrates DH usage
Figure 37:
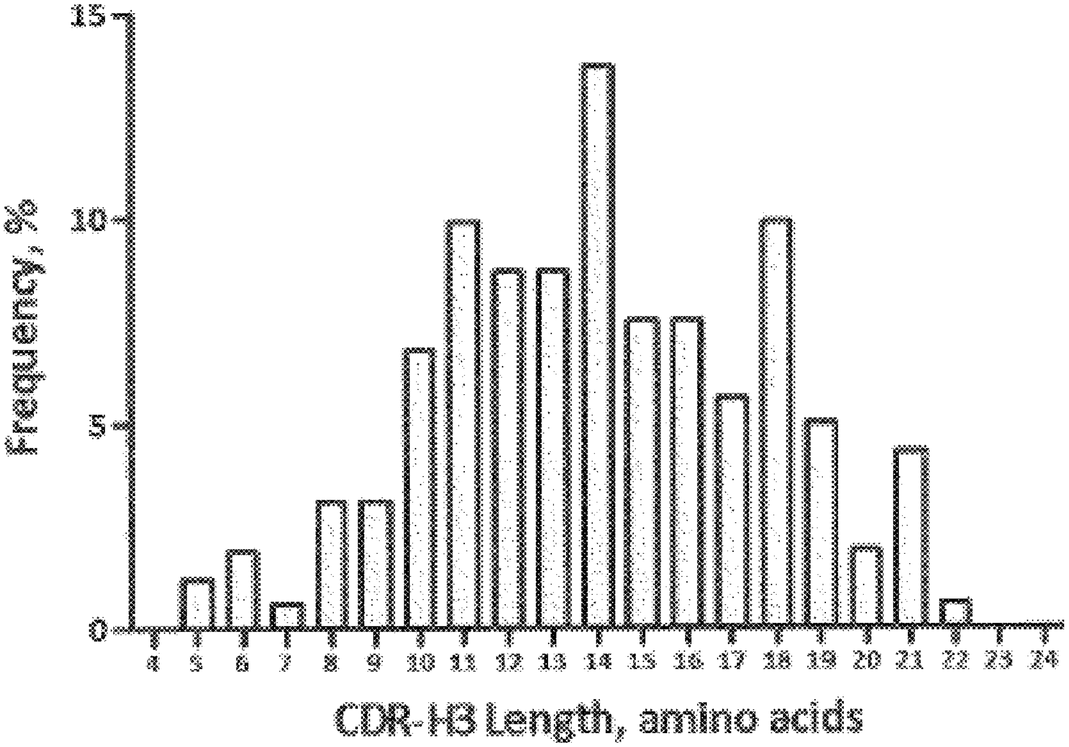
FIG. 37 illustrates the distribution of CDR-H3 length in human VDJCμ transcripts from chimera mice

Sequencing results indicate that JH, DH, and JK usages (FIG. 35 and FIG. 36) are similar to human results. In addition, the results from the IGH-VDJCμ transcripts show that the range and mean of CDR-H3 length (FIG. 37) are similar to that observed in human. The junctional diversity generated from exonuclease and nucleotide addition activities (FIG. 38) was also observed. The IGH rearrangement possessed a higher frequency of these activities compared to the IGK one. These data suggest that the inserted loci are functional in terms of gene rearrangement, junctional diversity as well as expression.

Example 6

Productive VJ Rearrangement and Somatic Hypermutation can be Obtained

Figure 41:
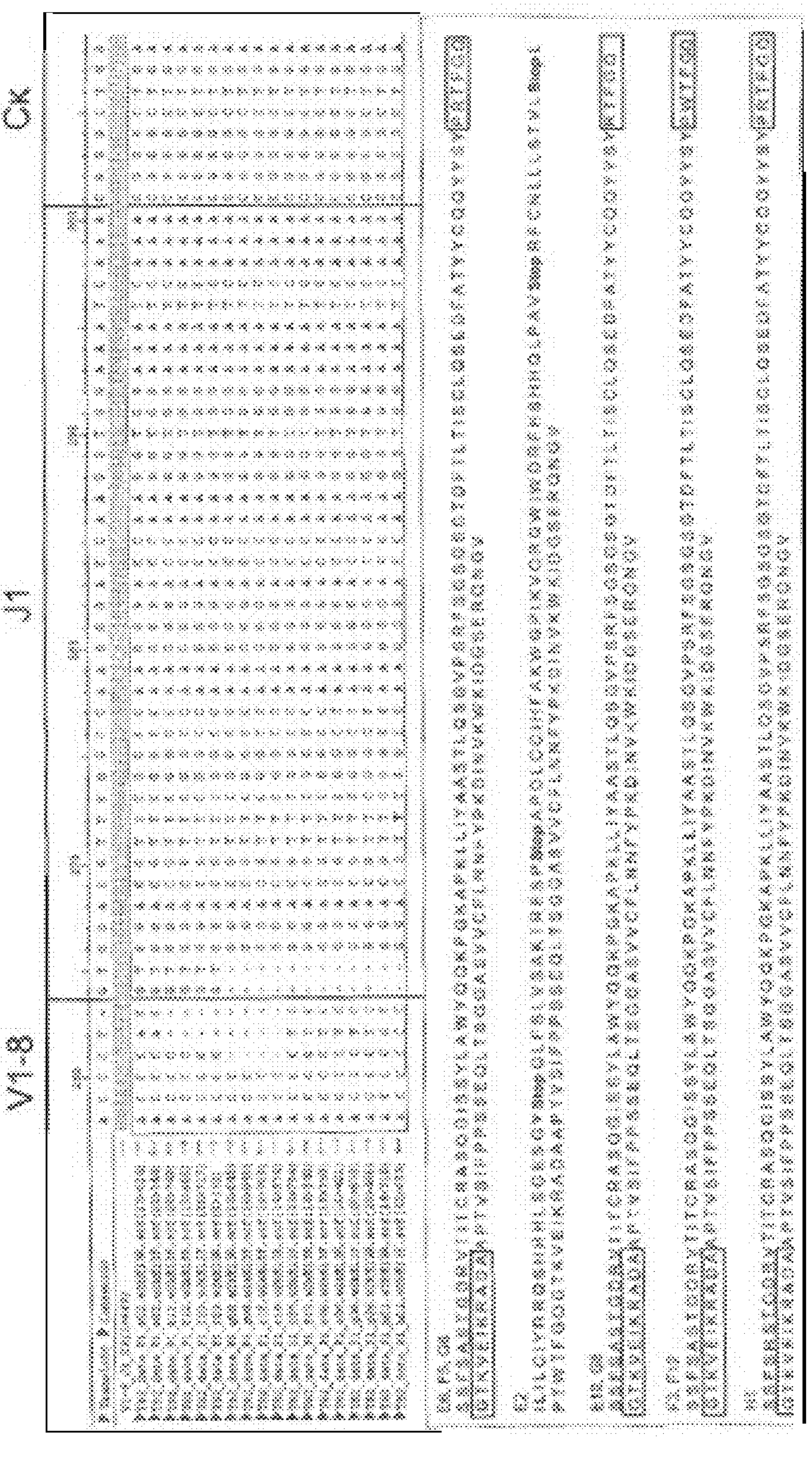
FIG. 41 illustrates Nucleotide Gain or Loss at VJ Joints Generates IGK Variants
Figure 42:
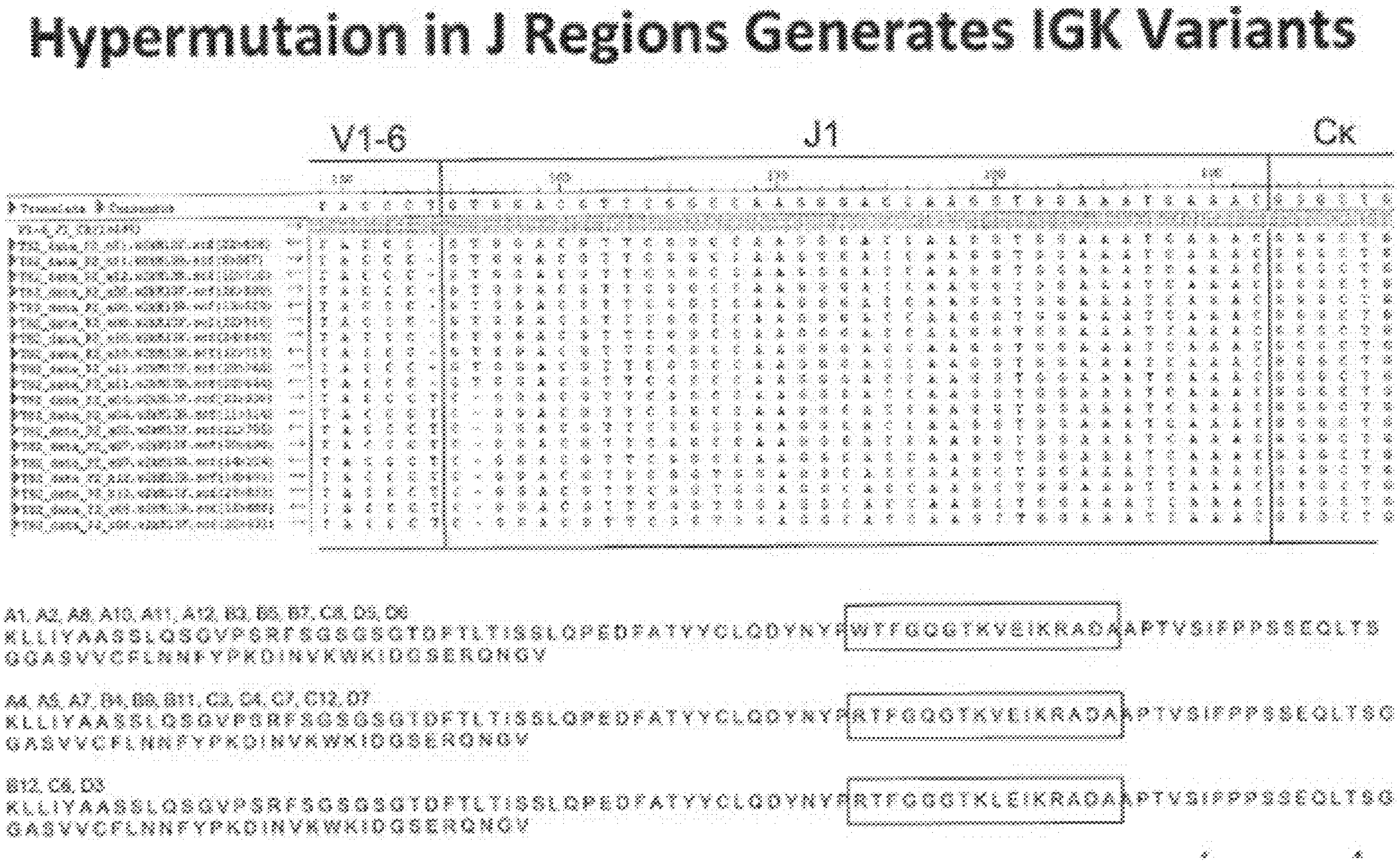
FIG. 42 illustrates Hypermutaion in J Regions Generates IGK Variants

FIG. 41 shows an analysis of kappa mRNA from mice B-cells bearing rearranged VJ, the VJ having been rearranged from human germline kappa V1-8 and J1, and demonstrates that both that productive VJ rearrangement and somatic hypermutation can be obtained, the latter as seen from the changes in antibodies encoded by mRNA with respect to the germline sequences. The same is displayed for V1-6 and J1 in FIG. 42. Importantly, the recombination eliminates stop codons that are encoded by the combination of (unmutated) human germline gene segments, thereby allowing for antibody-encoding mRNA sequences. FIG. 43 demonstrates that inserted human kappa V1-5 J1 and V1-5 J4 can produce functional coding sequences in vivo and junctional diversity.

Example 7

Figure 44:
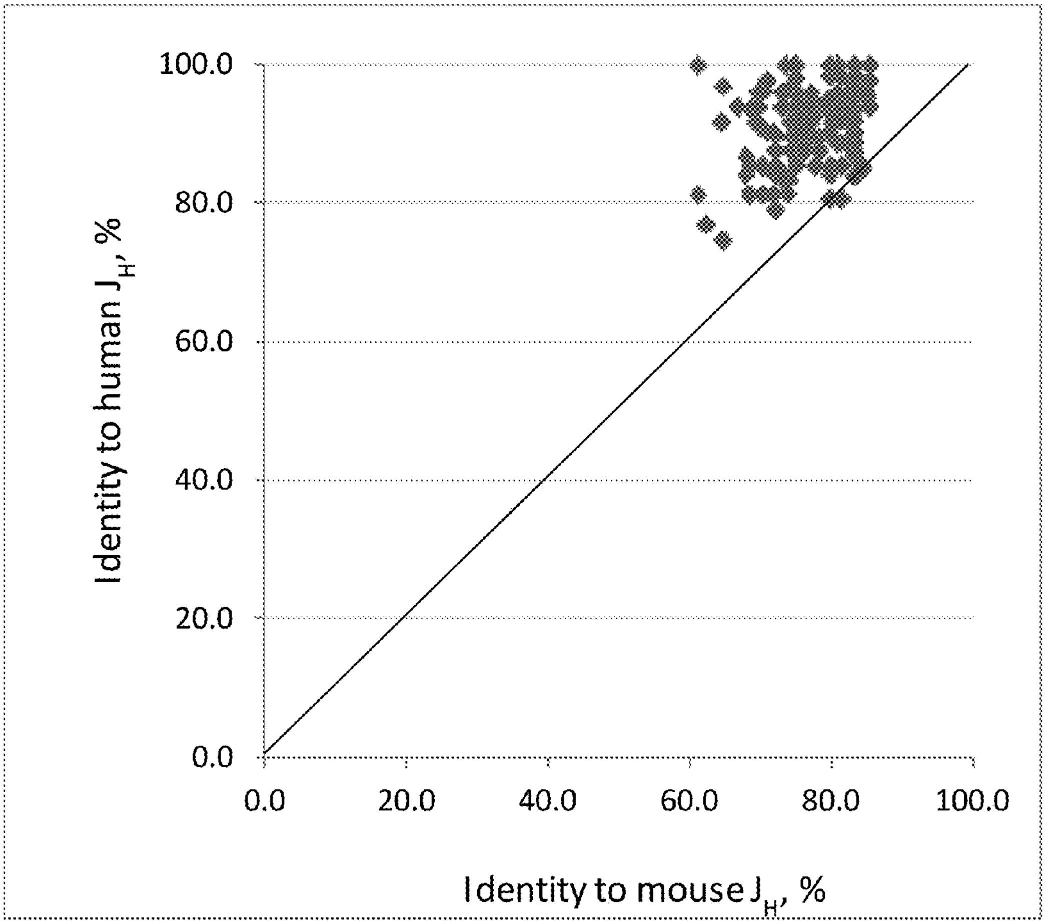
FIG. 44 illustrates a plot of identity of $J_H$ gene segment use a 5'-RACE Cγ-specific library generated from the splenic B lymphocytes of transgenic mice according to the invention in which endogenous gene segment use has been inactivated by inversion

Inactivation of Use of Endogenous IGHV Gene Segments for Expressed Rearranged Heavy Chain by Inversion Introduction A 5'-RACE Cμ-specific library was generated from the splenic B lymphocytes of transgenic mice, denoted S1 mice. These mice comprise transgenic heavy chain loci, each locus containing the six most 3' functional human $V_H$ gene segments ($V_H$2-5, 7-4-1, 4-4, 1-3, 1-2, 6-1), and all the human D and $J_H$ gene segments inserted into the endogenous heavy chain locus between endogenous IGHJ4 and Eμ (mouse chromosome 12: between coordinates 114666435 and 114666436). The human DNA was obtained from a bacterial artificial chromosome (BAC) containing the sequence of human chromosome 14 from coordinate 106328951 to coordinate 106494908. Further details on the construction of transgenic antibody loci using sRMCE is given elsewhere herein and in WO2011004192 (which is incorporated herein by reference). 4×96-well plates of clones were randomly picked for sequencing to determine the usage of the gene segments. All detected immunoglobulin heavy chains were rearranged from mouse $V_H$ or human $V_H$ with human D-$J_H$. No mouse D and $J_H$ segments were detected in rearranged products (FIG. 44).

This result indicates that insertion of human $V_H$-D-$J_H$ gene segments into an endogenous locus between the last endogenous J region (in this case, $J_H$4) and the Eμ enhancer effectively inactivates the use of endogenous D and $J_H$ gene segments for expressed rearranged immunoglobulin heavy chains.

Figure 45:
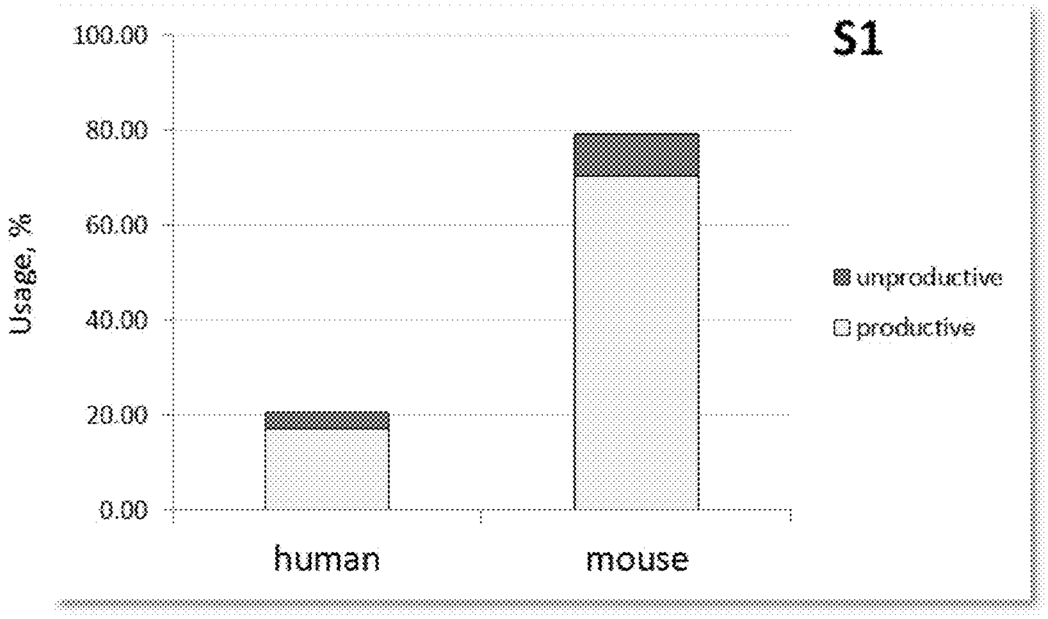
FIG. 45 illustrates the ratio of mouse $V_H$ to human $V_H$ usage as determined from antibody sequences from splenic B lymphocytes of transgenic mice according to the invention in which endogenous gene segment use has been inactivated by inversion

The ratio of mouse $V_H$ to human $V_H$ usage was around 3 to 1 (FIG. 45). To completely eliminate mouse $V_H$ use for antibody generation, the endogenous mouse $V_H$-D-$J_H$ was inverted and moved to a distant region of the same chromosome. The rearrangement of mouse $V_H$S to human D-$J_H$ segments was totally blocked by effects of inversion and distance from the heavy chain locus.

Figure 46:
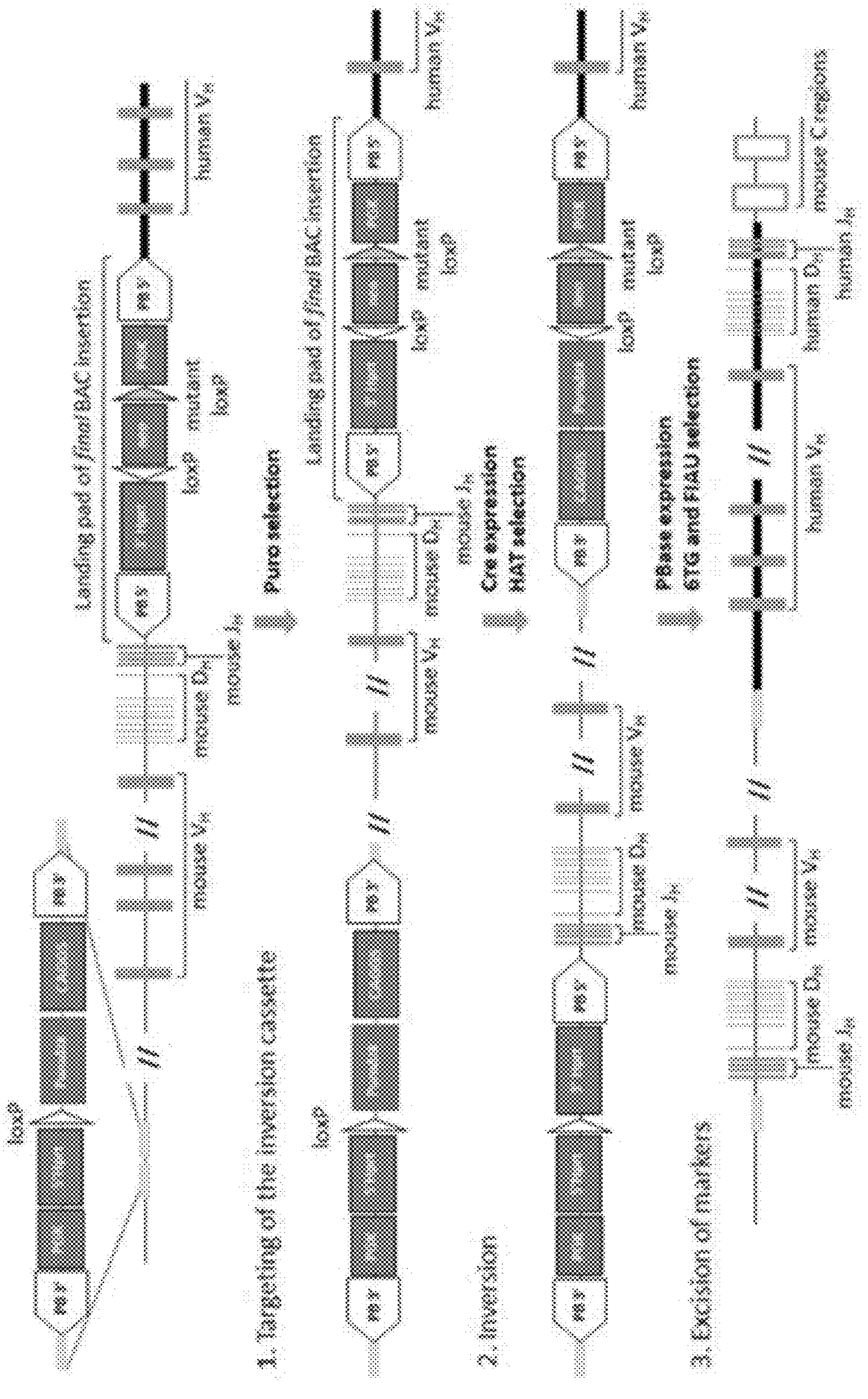
FIG. 46 illustrates inversion strategy schematic

The inversion strategy included three steps: (a) targeting of an inversion cassette, (b) inversion of endogenous VDJ and (c) excision of markers (FIG. 46).

(a) Targeting of the Inversion Cassette:

The inversion cassette consists of four components: a CAGGS promoter-driven puromycin-resistant-delta-thymidine kinase (puroΔtk) gene, a 5' HPRT gene segment under the PGK promoter control, a loxP site between them and inversely oriented to another loxP site already in the heavy chain locus, and two flanking piggyback LTRs (PB3'LTRs). The inversion targeting cassette was inserted to a region that is 5' and distant to the endogenous IGH locus at chromosome 12 as shown in FIG. 46. The targeted ES clones were identified and confirmed by PCR.

(b) Inversion:

Following the insertion, transient expression of cre from a transfected plasmid resulted in inversion of a section of chromosome 12 fragment including the endogenous $V_H$-D-$J_H$ locus and intervening sequences through recombination of two inverted loxP sites, ie, those in the inversion cassette and the landing pad for the BAC insertion respectively. The invertants were selected by HAT and confirmed by junction PCRs cross the two recombined loxP sites.

(c) Excision of Markers:

The inversion rearranged the relative orientation of the PB3'LTRs from the inversion cassette and PB5'LTR from the landing pad to generate two piggyBac transposon structures flanking the inverted region. With transient expression of piggyBac transposase (PBase), these two transposons were excised from the chromosome (and thus the mouse cell genome). The cured ES clones were selected by 1+2-deoxy-2-fluoro-1-b-D-arabinofuranosyl)-5-iodouracil (FIAU) and 6TG, and confirmed by junction PCRs cross the excised regions.

Methods

Tissue Culture:

The procedures for ES cell culture, electroporation and drug selection have been described previously (Ramirez-Solis, R., A. C. Davis, and A. Bradley. 1993. Gene targeting in mouse embryonic stem cells. Methods Enzymol. 225: 855-878).

Figure 47:
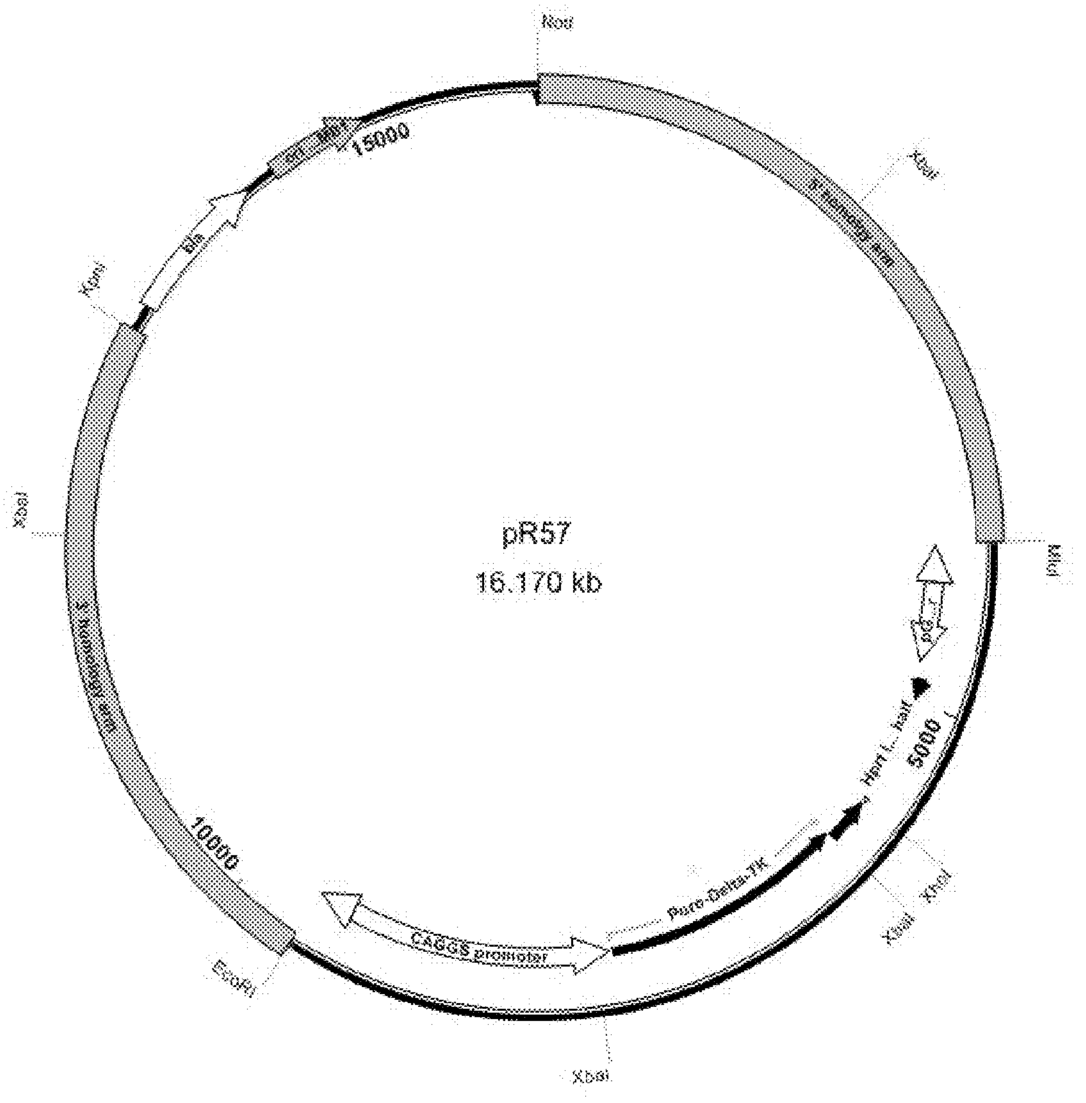
FIG. 47 illustrates targeting construct R57 for inversion

Targeting of the Locus for Inversion:

Briefly, 51 cell line (S1.11.1) was cultured in M15 medium (Knockout™ DMEM supplemented with 15% fetal bovine serum, 2 mM glutamine, antibiotics, and 0.1 mM 2-mercaptoethonal). Targeting construct R57 (FIG. 47) was linearized outside the region of homology by NotI. A total of 20 µg of the linearized construct was electroporated into 51 cell lines (AB2.1-derived) with a Bio-Rad® Gene Pulser™, and 107 cells were plated onto three 90-mm-diameter SNL76/7 feeder plates containing M15 medium. At 24 h after electroporation, M15 containing puromycin (3 µg of the active ingredient per ml) was added to each 90-mm-diameter plate, and the cells were maintained under selection for 9 days. 96 puromycin-resistant clones were then picked and expanded in 96-well plates. The targeting events were identified by long-range PCR.

Cre-loxP Mediated Inversion:

12 positive clones were pooled together and cultured in a 6-well tissue culture plate with M15 medium. The cells were transfected with 10 µg of pCAGGS-Cre plasmid for the inversion of mouse endogenous locus and then plated onto three 90-mm-diameter SNL76/7 feeder plates containing M15 medium. At 24 h after electroporation, M15 containing 1×HAT (hypoxanthine-aminopterin-thymidine) was added to each 90-mm-diameter plate, and the cells were maintained under selection for 7 days and then treated with 1×HT (hypoxanthine-thymidine) for 2 days. 48 HAT resistant colonies were picked and genotyped by PCR amplification of the junctions after Cre-loxP mediated inversion.

HyPBase-Mediated Marker Excision:

12 positive clones were pooled together and cultured in 6-well tissue culture plate using M15 medium. The cells were transfected with 5 µg of HyPBase plasmid to activate the PB transposon LTRs flanking two selection markers (Hprt-mini gene and PGK-puroΔtk gene) and plated onto one 90-mm-diameter SNL76/7 feeder plates containing M15 medium. At 72 h after electroporation, a serial dilution of the cells was then plated onto three 90-mm-diameter SNL76/7 feeder plates containing M15 supplemented with 1-(-2-deoxy-2-fluoro-1-b-D-arabinofuranosyl)-5-iodouracil (FIAU). Cells were maintained under selection for 10 days, and FIAU-resistant colonies were counted, picked, and expanded in 96-well plates. Positive clones were identified by PCR amplification of the junctions after excision of the selection markers. Positive clones were then expanded for blastocyst microinjection.

Generation of Chimera and Breeding:

Mouse chimaeras were generated by microinjection of ES cells into C57/BL6 blastocysts and transferred into pseudopregnant recipients. Male chimaeras were test-crossed with C57/BL6 mice. Agouti F1 offspring were genotyped by 51 3' junction PCR. Test-cross positive heterozygotes were further intercrossed to generate homozygotes.

Determination of VH-D-JH Usage by Rapid Amplification of 5'-cDNA Ends (5' RACE) PCR:

Total RNA was extracted from the spleen of S1inv1 mouse (KMSF30.1d) with TRIzol® Reagent (Invitrogen™, Life Technologies Ltd™) and treated with DNase I. Rapid amplification of 5'-cDNA ends (5' RACE) PCR was performed using 573' RACE kit (2nd Generation, Roche) following the protocol supplied by the manufacturer. The first-strand cDNA was synthesised using primer E1554 (5'-ATGACTTCAGTGTTGTTCTGGTAG-3'; SEQ ID No 25) which is located at the mouse endogenous Cµ region. The synthesised first cDNA strand was purified using High Pure PCR Product Purification Kit (Roche). Poly(A) tail was added following the protocol supplied with the 573' RACE kit (2nd Generation, Roche). The 5' end of the $V_H$-D-$J_H$ rearranged transcript was amplified by nested PCR with forward primers Oligo dT, which is included in the kit, and nested Cµ-specific reverse primers E1555 (5'-CACCAGAT-TCTTATCAGAC-3'; SEQ ID No 26). Following reaction, the 5' RACE PCR product was checked on a 1% agarose gel and purified using QiAquick® Gel Extraction Kit (QIAGEN) as the protocol supplied with the kit, then cloned into pDrive vector using QIAGEN PCR Cloning Kit (QIAGEN) for sequencing analysis.

Results

Figure 48:
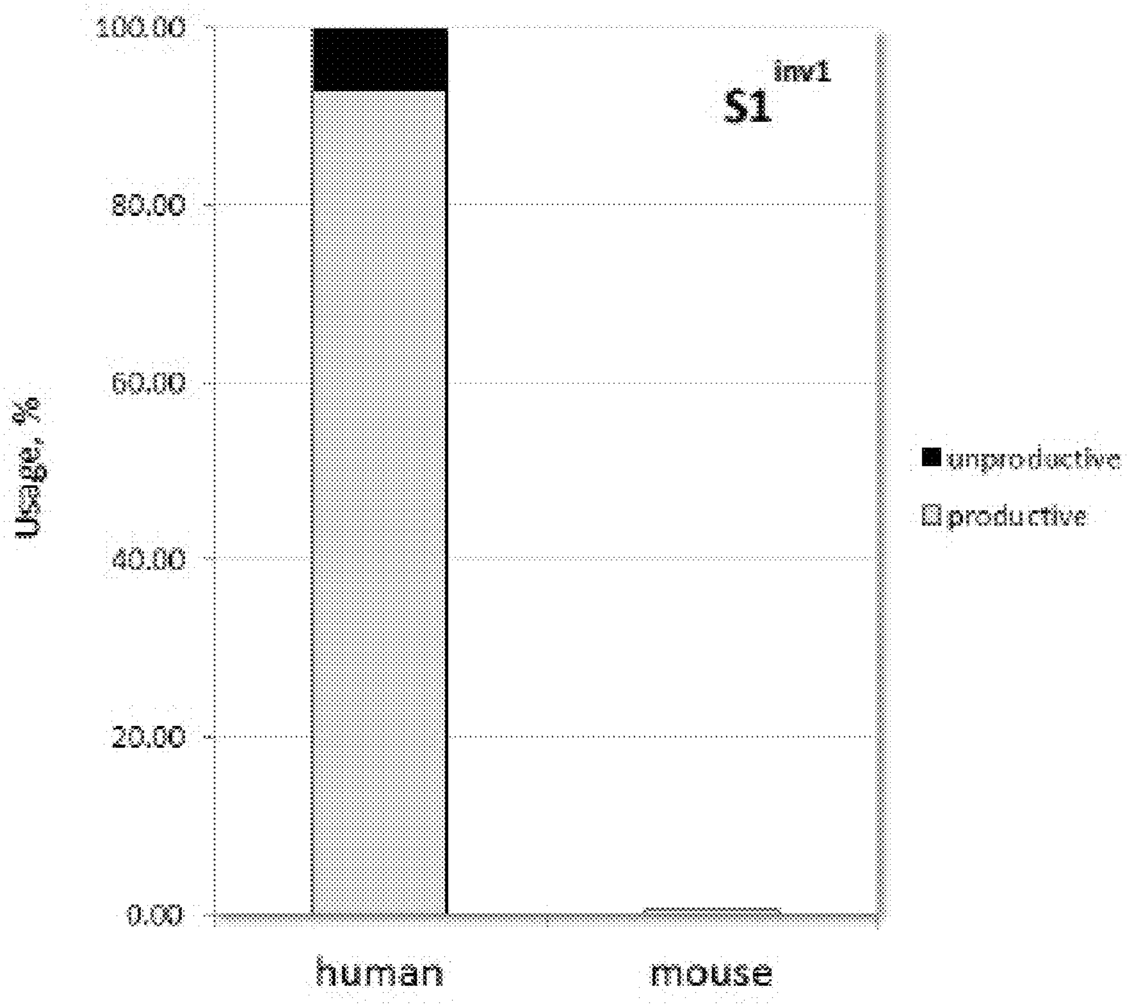
FIG. 48 illustrates sequence analysis from a Cμ-specific 5'-RACE library of splenic B lymphocytes of $S1^{inv1}$ (one human IGH BAC (ie, multiple human VH, all functional human D and JH) with an inverted endogenous IGH locus) mouse shows that practically all the transcripts came from rearranged human $V_H$-D-$J_H$ gene segments

The sequence analysis from a Cµ-specific 5'-RACE library of splenic B lymphocytes of S1$^{inv1}$ (one human IGH BAC (ie, multiple human VH, all functional human D and JH) with an inverted endogenous IGH locus version 1) mouse shows that practically all the transcripts came from rearranged human $V_H$-D-$J_H$ gene segments (FIG. 48). Mouse $V_H$ usage was rarely detected (0.4%), and no mouse D and $J_H$ usage was detected. Human $V_H$ usage was 99.6% and only human D and $J_H$ were used; it was hypothesized that the rare mouse $V_H$ usage was due to trans-switching with another chromosome and not due to use of moue $V_H$ from the inverted sequences. The inversion resulted in complete inactivation of the endogenous $V_H$ use.

This Result Indicates that Inversion is an Effective Way to Inactivate the Rearrangement of Endogenous $V_H$ Gene Segments.

Figure 49:
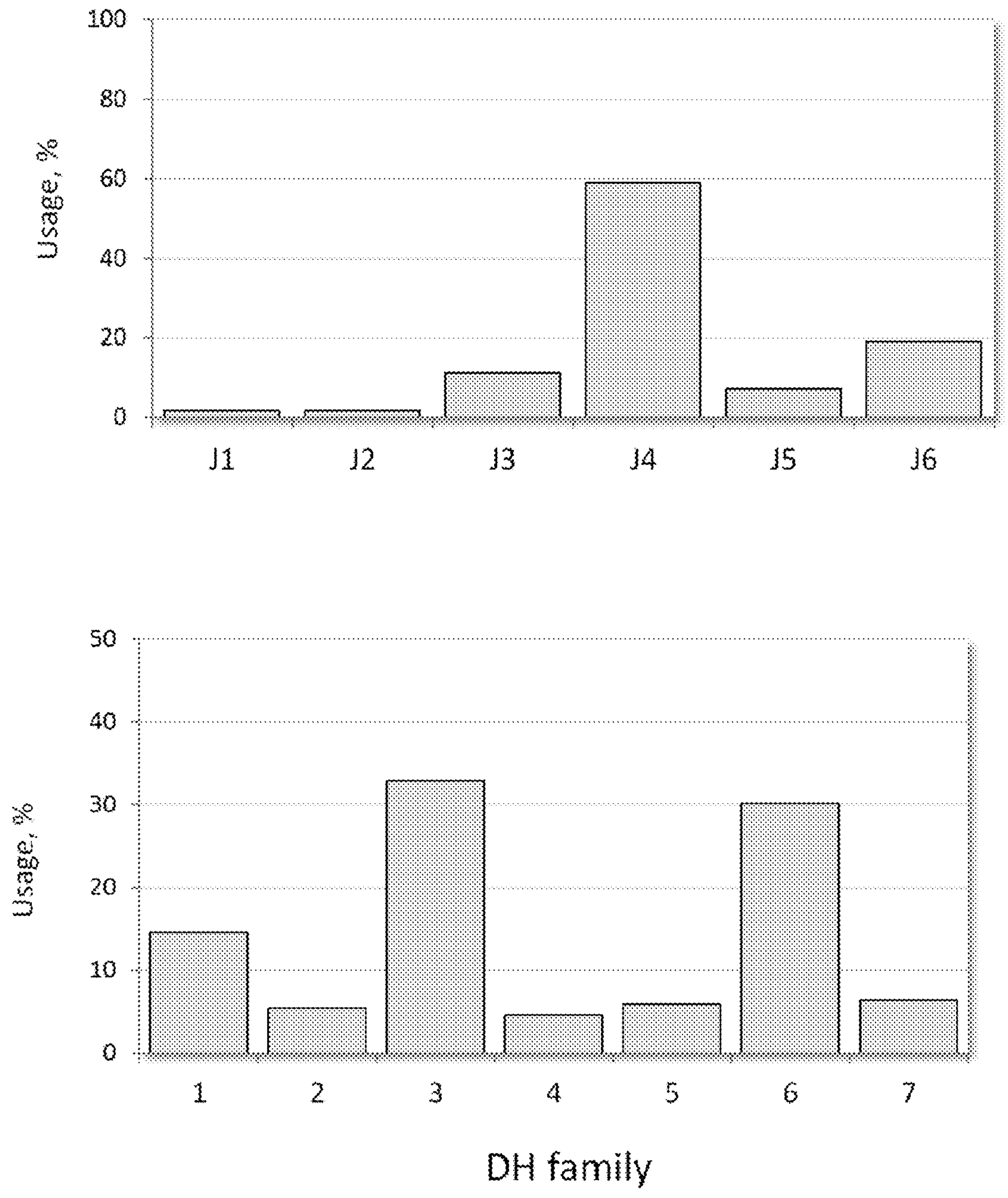
FIG. 49 illustrates that the $S1^{inv1}$ mouse shows a similar usage of both D and $J_H$ gene segments to human

The S1$^{inv1}$ mouse also shows a similar usage of both D and $J_H$ gene segments to human (FIG. 49) (Link, J M et al. Mol. Immunol. 2005. 42, 943-955). Thus, a mouse was produced that comprises a transgenic heavy chain locus that expresses heavy chains comprising human variable regions, but no mouse variable regions, and furthermore the human variable regions demonstrated a normal, human sequence distribution corresponding to human D and J usage observed in humans.

Example 8

Inactivation of Use of Endogenous IGHV Gene Segments for Expressed Rearranged Heavy Chain by Insertion of Human IgH Genomic DNA Introduction Insertion of human BACs with $V_H$-D-$J_H$ gene segments into an endogenous mouse heavy chain locus between $J_H$4 and Eli in chromosome 12 allows human $V_H$-D-$J_H$ gene segments to effectively use mouse Eµ and 3' enhancers and rearrange to generate chimeric antibody with human variable region and mouse constant region. Meanwhile, the endogenous $V_H$-D-$J_H$ gene segments are pushed away from endogenous enhancers and constant regions. This distance effect results in inactivation of mouse D and $J_H$ use for expressed rearranged antibody products. As the distance increases by stepwise BAC insertion, it is expected that the mouse VH usage would be significantly reduced.

Results

Insertion of human DNA from a 1$^{st}$ human BAC (BAC comprising a the sequence of mouse Chromosome 14 from coordinate 106328951 to coordinate 106494908; containing six most 3' functional $V_H$ gene segments ($V_H$2-5, 7-4-1, 4-4, 1-3, 1-2, 6-1), and all the human D and $J_H$ gene segments) into the heavy chain endogenous locus of a AB2.1 ES cell genome between endogenous IGHJ4 and Eµ (at mouse chromosome 12: between coordinates 114666435 and 114666436) effectively inactivates the use of endogenous D and $J_H$ gene segments for expressed rearranged immunoglobulin heavy chain (FIG. 44). The rearranged transcripts with mouse $V_H$ gene segments are reduced in the resulting 51 mouse. The proportion of transcripts using mouse $V_H$ is around 75% of all observed sequences (FIG. 45).

Figure 24:
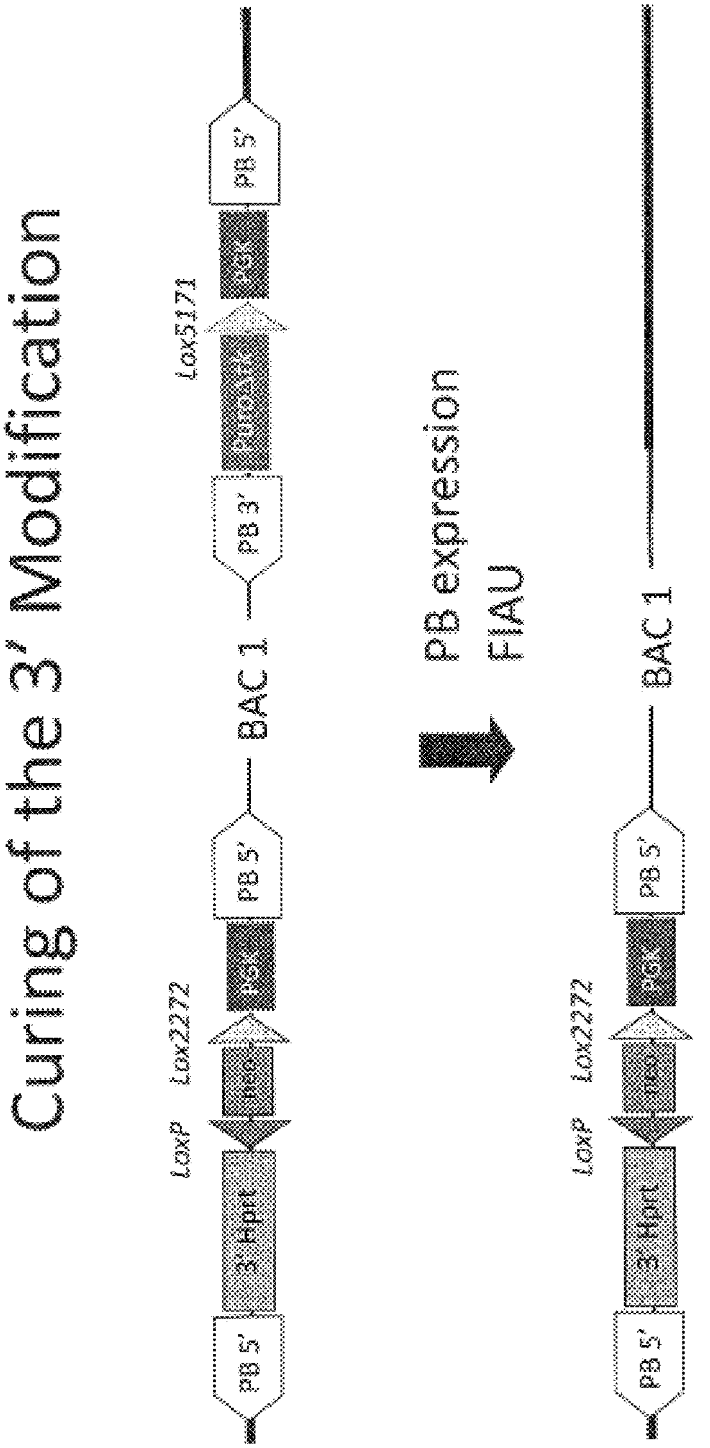
Figure 25:
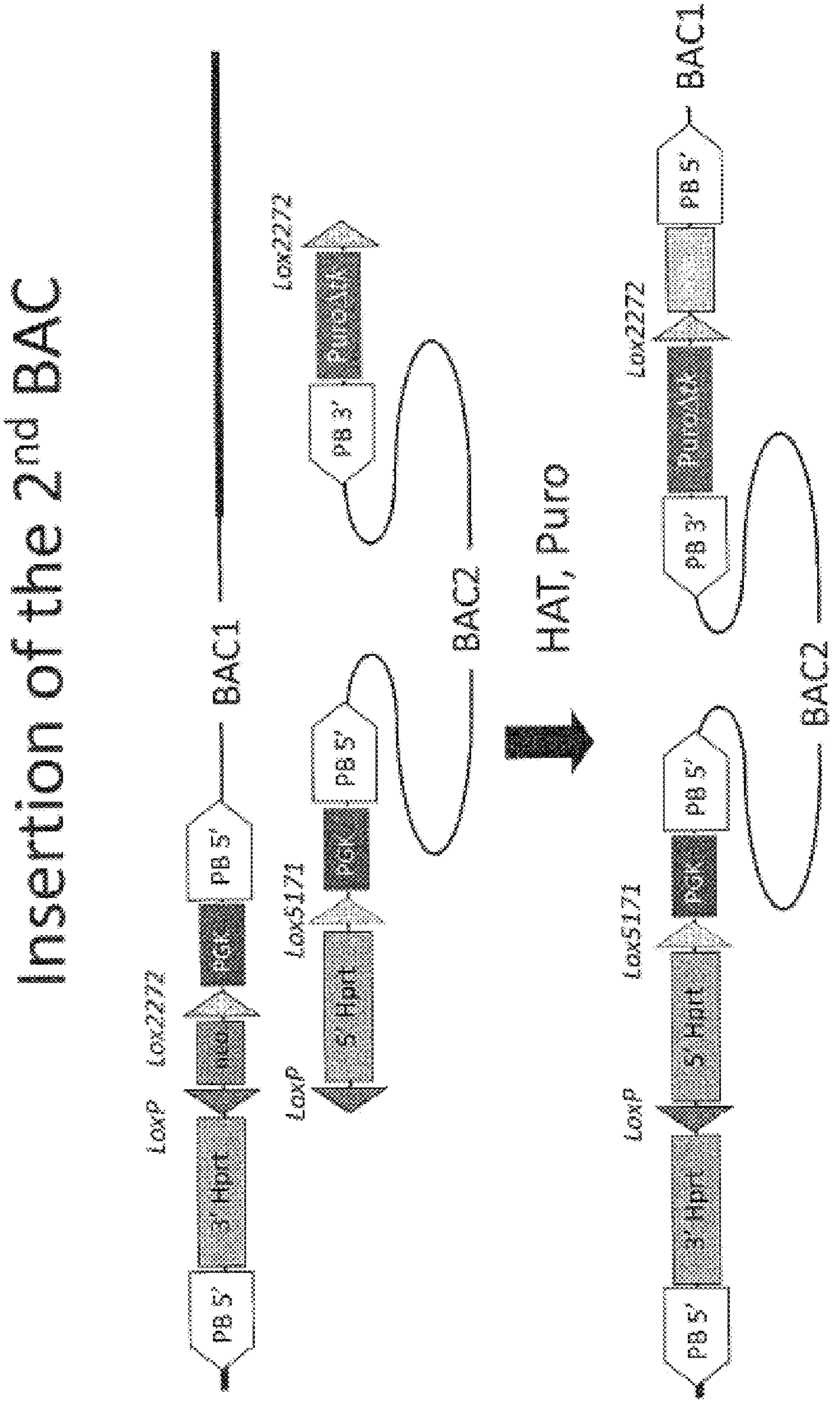
Figure 26:
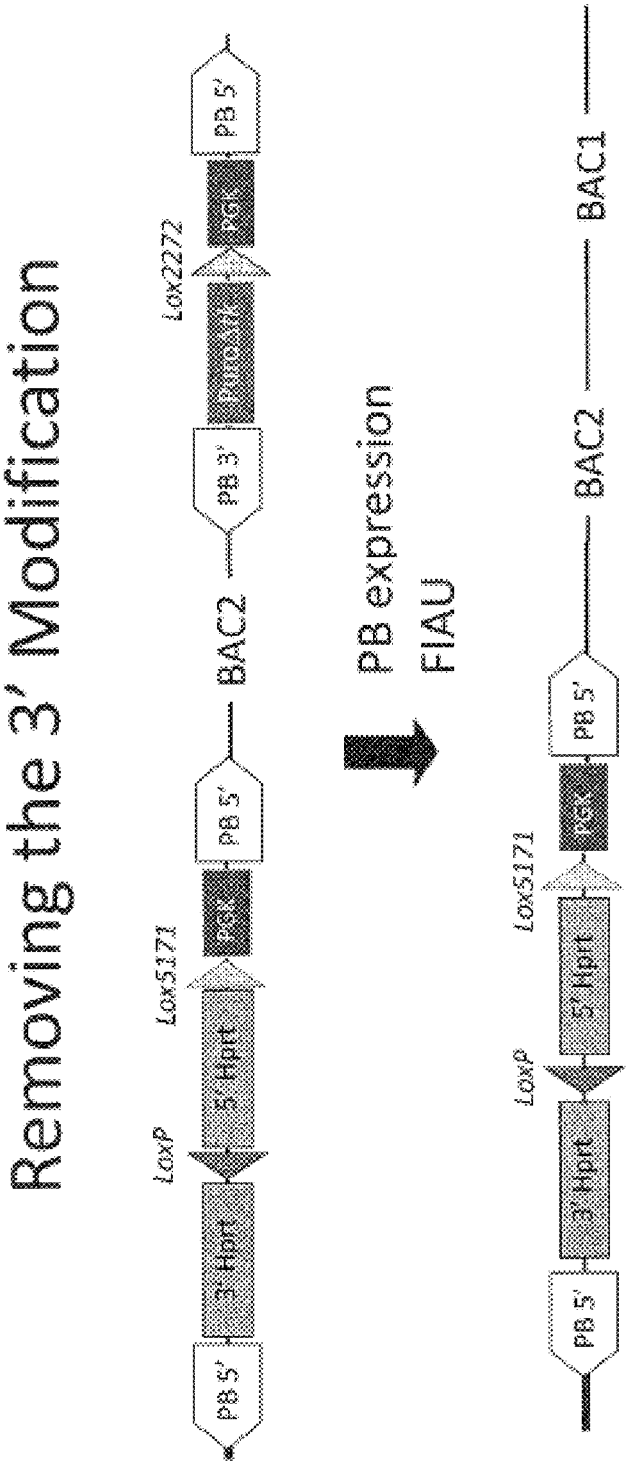
Figure 50:
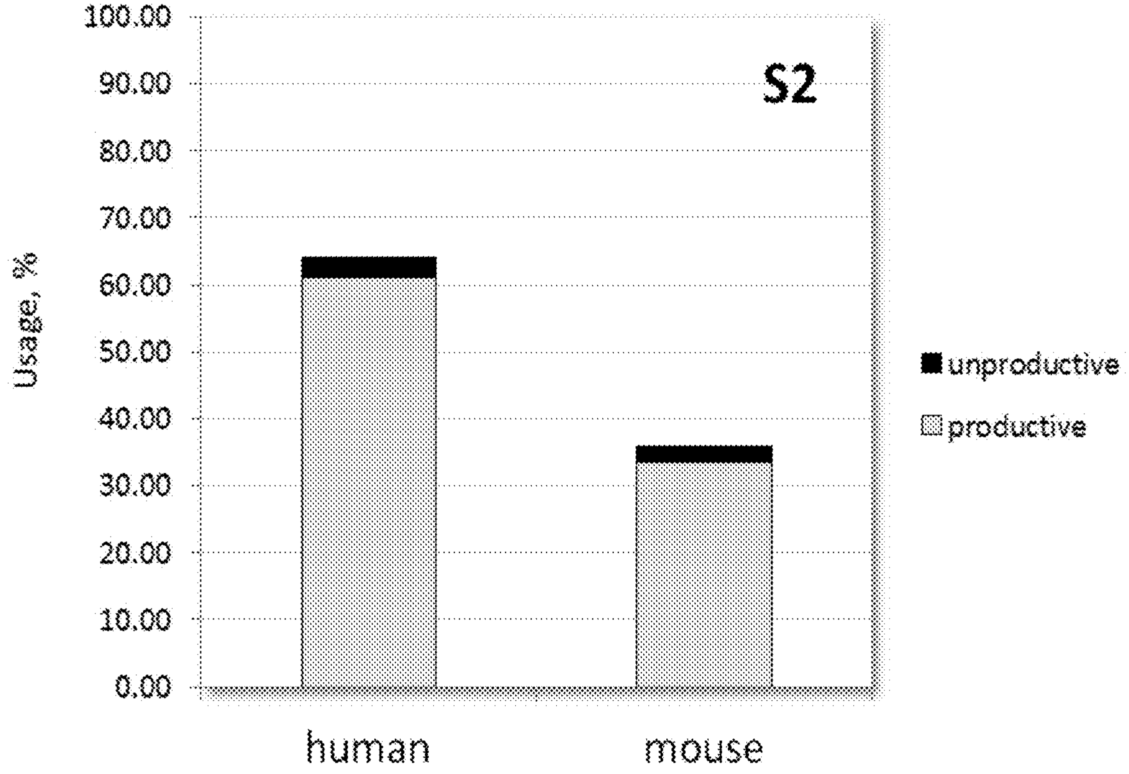
FIG. 50 illustrates that mouse $V_H$ usage is further significantly reduced following insertion of the $2^{nd}$ human BAC into the endogenous heavy chain locus

Following the 1$^{st}$ BAC DNA insertion, human DNA from a 2$^{nd}$ human BAC (Chr14: 106494909-106601551) (BAC comprising a the sequence of mouse Chromosome 14 from coordinate 106494909 to coordinate 106601551; containing 5 more functional VH gene segments ($V_H$3-13, 3-11, 3-9, 1-8, 3-7)) was inserted into the landing pad left behind after curing following the 1st BAC insertion (see, eg, FIG. 24). The mouse $V_H$ usage is further significantly reduced following this insertion of the 2nd BAC into the locus. The proportion of transcripts using mouse VH was further reduced to 35% of all observed sequences (FIG. 50).

This result indicate that the endogenous $V_H$-D-$J_H$ gene segments could be inactivated (ie, not used for expressed rearranged heavy chains) through insertion of human VDJ sequences from one or more BACs. As the distance increases by stepwise BAC insertion, it is expected that the mouse VH usage would be significantly reduced.

Example 9

Normal Class Switch and Hypermutation in Transgenic Mice of the Invention

Introduction

The B cell arm of the immune system has evolved to produce high affinity, antigen-specific antibodies in response to antigenic challenge. Antibodies are generated in B lymphocytes by a process of gene rearrangement in which variable (V), diversity (D; for the IGH locus) and joining (J) gene segments are recombined, transcribed and spliced to a Cμ (for IGH) or a Cκ or Cλ (for IGL) constant region gene segment to form an IgM antibody. Depending on the stage of B cell development, IgM is either located on the cell surface or secreted. The recombination process generates a primary antibody repertoire with sufficient germ line diversity to bind a wide range of antigens. However, it is usually not large enough to provide the high affinity antibodies that are required for an effective immune response to an antigen such as an infectious agent. Therefore, the immune system adopts a two-stage diversification process to increase diversity further. When challenged with antigens, B cells undergo selection and maturation by a process called somatic mutation. B cells expressing antibodies which bind to antigen undergo multiple rounds of diversification, clonal expansion and antigen selection in the germinal centres (GCs) of the secondary lymphoid organs. During this process, the rearranged variable regions of the immunoglobulin genes acquire somatic hypermutation through nucleotide substitution, addition or deletion. This stepwise process creates a secondary repertoire from the weak binders selected originally from the primary repertoire and combines rapid proliferation of antigen-reactive B cells with intense selection for quality of binding, eventually giving rise to high affinity antibodies with broad epitope coverage. During this process, antibodies undergo class switching in which the Cμ constant region is replaced by Cγ, Cα or Cϵ to produce respectively IgG, A or E classes of antibody with different effector functions.

Insertion of 1st human BAC (Chr14: 106328951-106494908) containing six most 3' functional $V_H$ gene segments ($V_H$2-5, 7-4-1, 4-4, 1-3, 1-2, 6-1), and all the D and $J_H$ gene segments into the locus between endogenous IGHJ4 and Eμ (Chr12: 114666435 and 114666436) produces transgenic mice that generate chimeric immunoglobulin heavy chains containing human variable and mouse constant regions. This result demonstrates that human immunoglobulin gene segments are able to be rearranged and expressed in mice. Here, RT-PCR experiments and sequence analysis were performed to further demonstrate that immunized transgenic mice have proper class switch and hypermutation for generated antibodies.

Methods

RT-PCR and Sequence Analysis:

Wild type or S1 chimera mice at 6-8 weeks of age were primed by intraperitoneal injection of $10^6$ sheep RBCs suspended in phosphate buffer saline (PBS). The immunized mice were boosted twice with the same amount of sheep RBCs two and four weeks after priming. Four days after the last boost, peripheral blood cells were collected from the immunized mice. Total RNA was isolated from peripheral blood cells with TRIzol® reagent (Invitrogen™) and treated with DNase I. Reverse transcription polymerase chain reaction (RT-PCR) was performed using SuperScript® III First-Strand Synthesis System (Invitrogen™) following the protocol supplied by the manufacturer. The 1st strand cDNA was synthesized with the specific Cγ primers (Cγ1, Cγ2a, Cγ2b), following by PCR with specific human V primers (VH1-2,3, VH4-4, VH6-1) and Cγ primers (Table 2). Following reaction, the RT-PCR product was checked on a 1% agarose gel and purified using QiAquick® Gel Extraction Kit (QIAGEN) as the protocol supplied with the kit, then cloned into pDrive vector using QIAGEN PCR Cloning Kit (QIAGEN) for sequencing analysis.

TABLE 2

| | | |
|---|---|---|
| ELP1352_Cγ1 | 5'-AGAGCGGCCGCTGGGCAACGTTGCAGGTGACGGTC-3' | SEQ ID No 27 |
| ELP1353_Cγ2b | 5'-AGAGCGGCCGCTTTGTCCACCGTGGTGCTGCTGG-3' | SEQ ID No 28 |
| ELP1354_Cγ2a | 5'-AGAGCGGCCGCACATTGCAGGTGATGGACTGGC-3' | SEQ ID No 29 |
| ELP1356_VH4-4 | 5'-AGGACGCGTGAAACACCTGTGGTTCTTCCTCCTGC-3' | SEQ ID No 30 |
| ELP1357_VH1-2,3 | 5'-AGGACGCGTCACCATGGACTGGACCTGGAGGAT-3' | SEQ ID No 31 |
| ELP1358_VH6-1 | 5'-AGGACGCGTATGTCTGTCTCCTTCCTCATCTTCC-3' | SEQ ID No 32 |

Results

Figure 51:
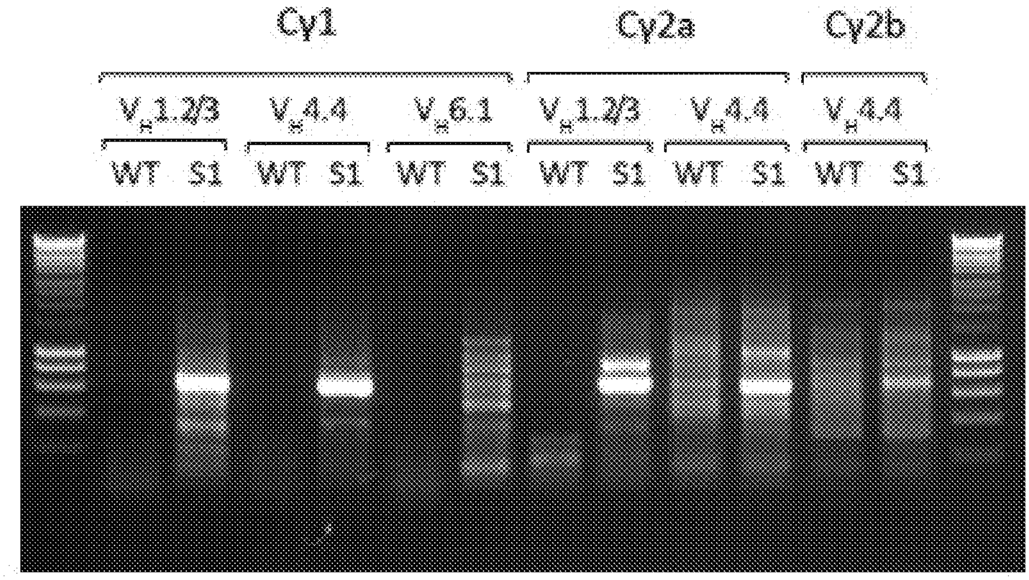
FIG. 51 illustrates a gel showing that normal class-switching (to IgG-type) was observed in transcripts from mice of the invention. The rearranged transcripts were detected using RT-PCR with human VH-specific and mouse Cγ-specific primers for amplification from peripheral blood cells of immunized transgenic mice
Figure 52:
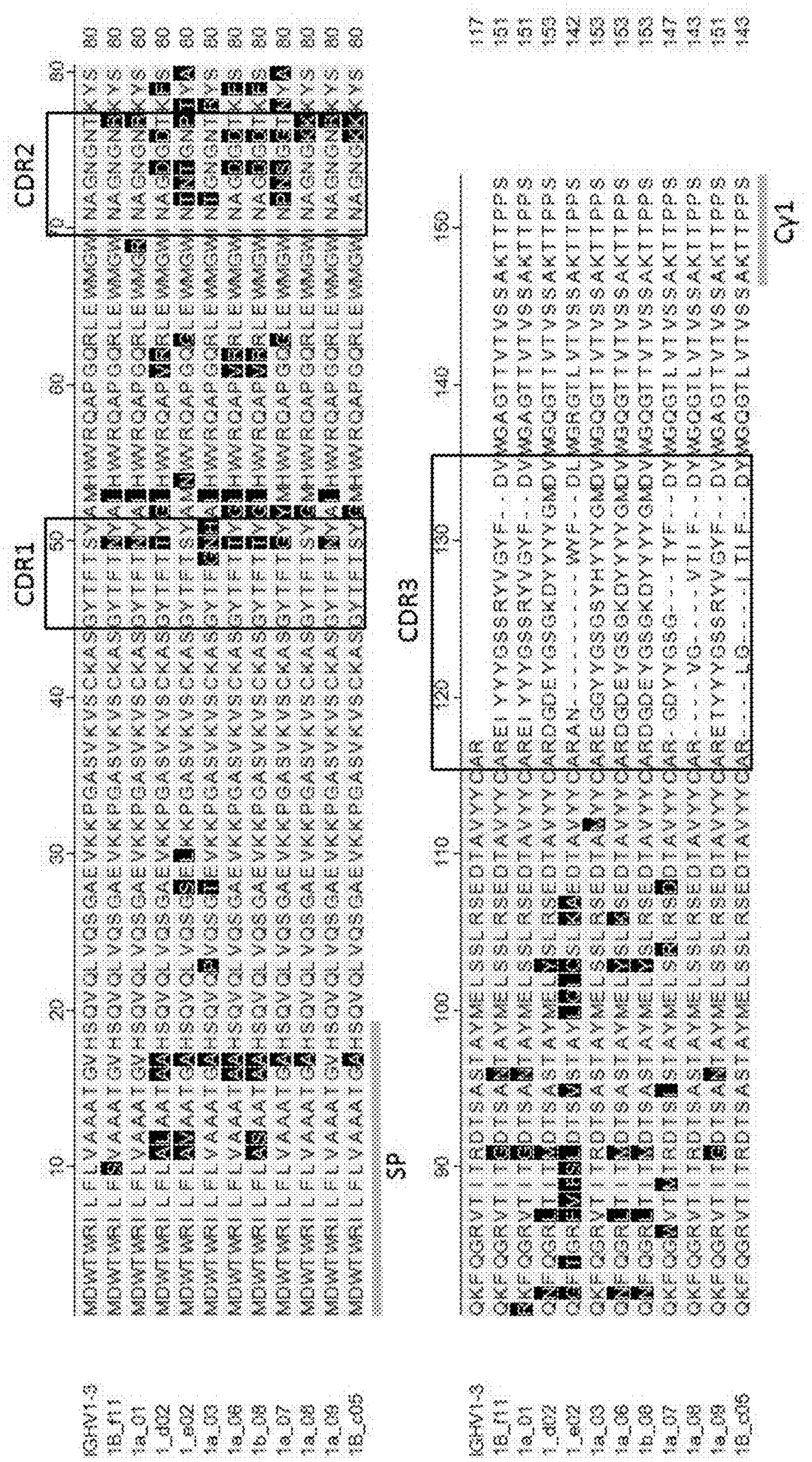
FIG. 52 illustrates sequence analysis amplified fragments demonstrate hypermutation occurred within the human variable regions of these IGγ chains from mice of the invention

The rearranged transcripts were detected using RT-PCR with human VH-specific and mouse Cγ-specific primers for amplification from peripheral blood cells of immunized transgenic mice (FIG. 51). Further sequence analysis of these amplified fragments demonstrated hypermutation happened within the human variable regions of these IGγ chains (FIG. 52). These results indicate that loci of the invention comprising insertion of human IGH BAC containing $V_H$, D and $J_H$ gene segments into the locus between endogenous IGHJ4 and Eμ regions has normal class switching and hypermutation functionality (IgM to IgG) following antigen challenge.

Example 10

Normal B Cell Compartments in Transgenic Mice of the Invention

Introduction

In mice, about $2\times10^7$ bone marrow immature B cells are produced daily. Among them, only 10-20% of these cells survive to exit the bone marrow and enter the spleen. The immature splenic B cell population is divided into two distinct subsets: transitional 1 (T1) and transitional 2 (T2) B cells. In vivo experiments indicate that T1 cells give rise to T2 cells, whereas T2 cells can further differentiate into mature (M) B cells. In contrast to immature B cells (3-4 days old), mature B cells are long-lived (15-20 weeks old) and are ready to respond to antigens (Pillai S et al; Immunol. Reviews. 2004. 197: 206-218). Thus, the component of mature B cell population is directly linked to the efficiency of humoral immune response.

The T1, T2 and M cell populations can be categorized by their cell surface IgM and IgD levels. A normal phenotype of splenic B cell compartment is required to mount a robust immune response.

Methods

Flow Cytometric Analysis of Mature B Lymphocytes:

To obtain a single cell suspension from spleen, the spleens of mice listed below were gently passaged through a 30 μm cell strainer. Single cells were resuspended in PBS supplemented with 3% heat inactivated foetal calf serum (FCS; Gibco®). The following antibodies were used for staining:

Antibody against B220/CD45R conjugated with allophycocyanin (APC) (eBioscience, clone RA3-6B2), antibody against IgD receptor conjugated with phycoerythrin (PE) (eBioscience, clone 11-26) and IgM receptor conjugated with fluorescein isothiocyanate (FITC) (eBioscience, clone 11/41).

$5\times10^6$ cells were used for each staining. To each vial containing splenocytes a cocktail of antibodies was added consisting of: IgD (PE) (eBioscience, clone 11-26), IgM (FITC) and B220/CD45R (APC). Cells were incubated at 6° C. for 15 minutes, washed to remove excess of unbound antibodies and analysed using a fluorescence-activated cell sorting (FACS) analyser from Miltenyi Biotech. B-cells were gated as $B220^+IgM^+IgD^-$ for T1 population, $B220^+IgM^+IgD^+$ for T2 population and $B220^+IgM^-IgD^+$ for M population. Percentage of cells was calculated using gating system.

Results

Four different genotypes of mice were generated: —

Wild type (WT);

A transgenic mouse homozygous for a heavy chain transgene comprising insertion of the $1^{st}$ BAC human DNA noted above in which there are 6 human VH, all functional human D and JH gene segments (S1/S1);

A transgenic mouse homozygous for a heavy chain transgene comprising insertion of a human VH, all functional human D and JH gene segments (H1/H1); and A transgenic mouse homozygous for a kappa chain transgene comprising insertion of 6 functional human Vκ and 5 functional Jκ gene segments (K1/K1).

Figure 53:
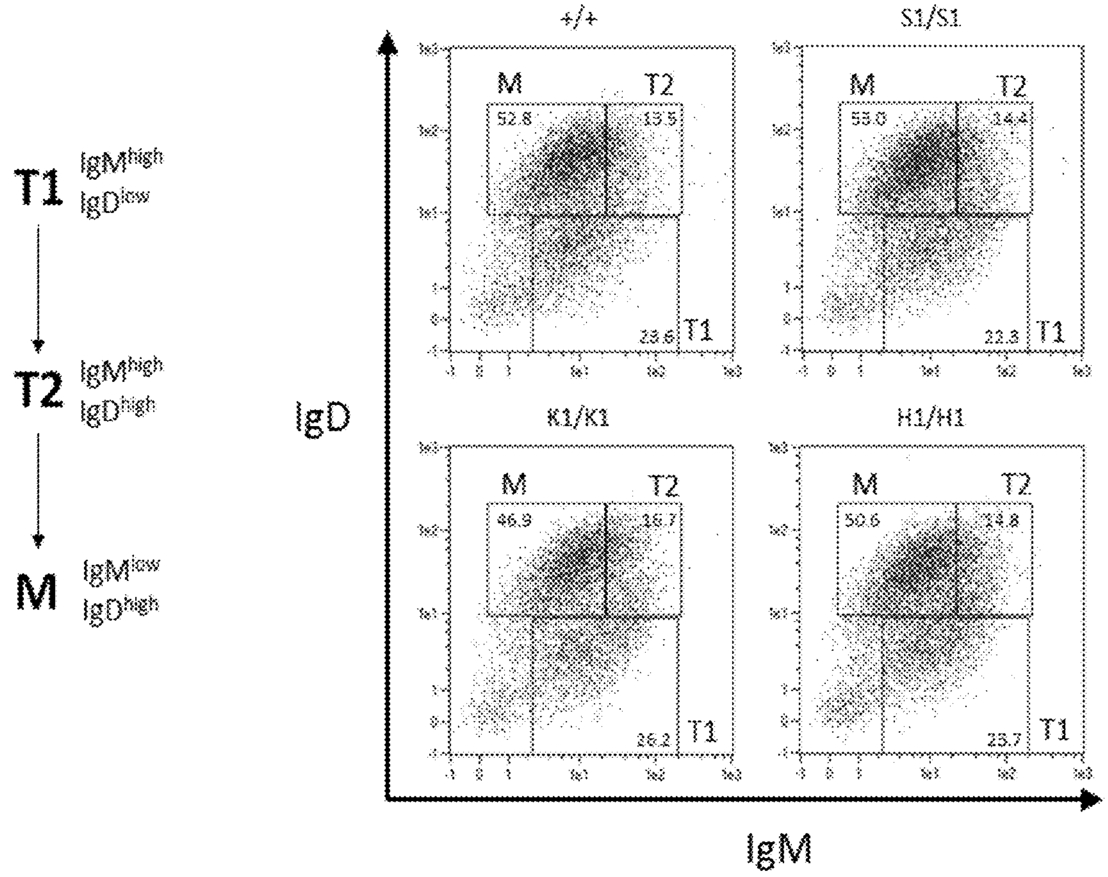
FIG. 53 illustrates Flow cytometric analysis showing normal B-cell compartments in transgenic mice of the invention FIG. 54A. illustrate normal IgH isotypes in transgenic mice (H1) immunised with 100 μg Cholera Toxin B subunit.

Spleens from these naïve mice were collected and analysed for their B cell compartments. The number and percentages of T1, T2 and M cells among those mice are similar (FIG. 53), indicating that genetic manipulation of endogenous IG loci in transgenic mice according to the invention do not compromise their B cell development. These data help to establish that animals according to the invention provide a robust platform for antibody discovery.

Example 11

Normal IgH Isotypes & Serum Levels in Transgenic Animals of the Invention

Figure 54A:
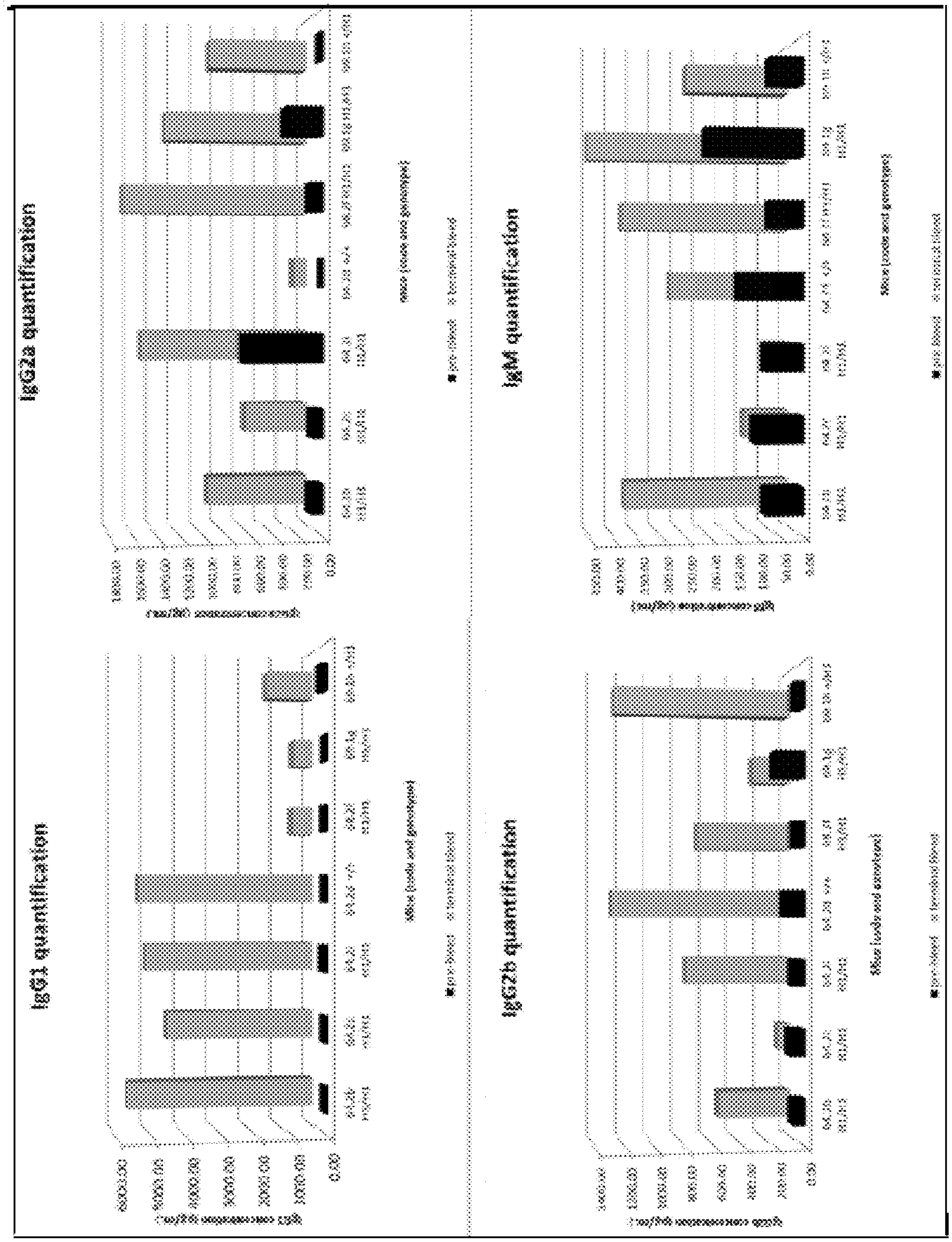
FIGS. 54B. illustrate normal IgH isotypes in transgenic mice (S1) immunised with 100 μg Cholera Toxin B subunit.
Figure 54B:
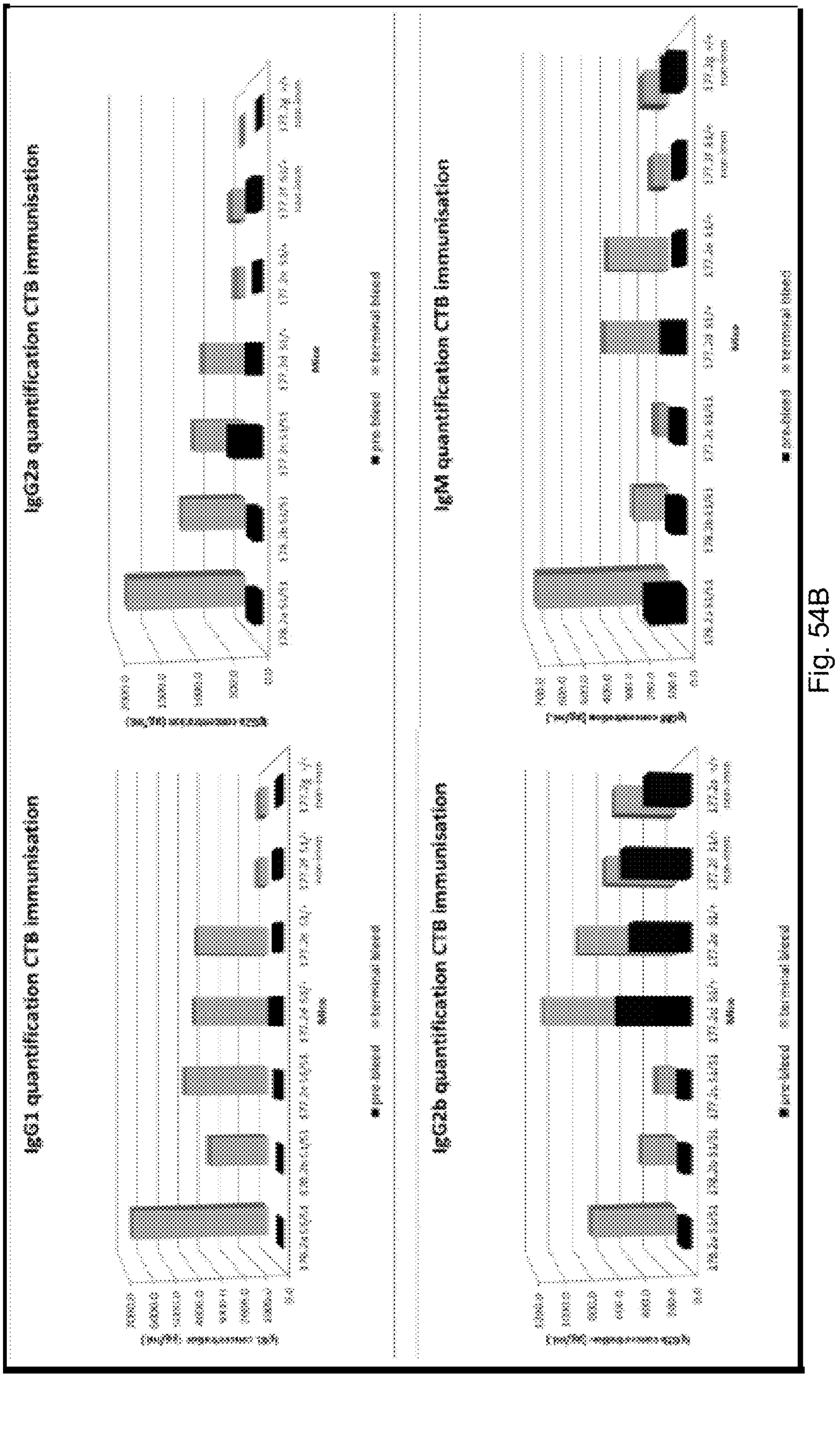
Figure 55A:
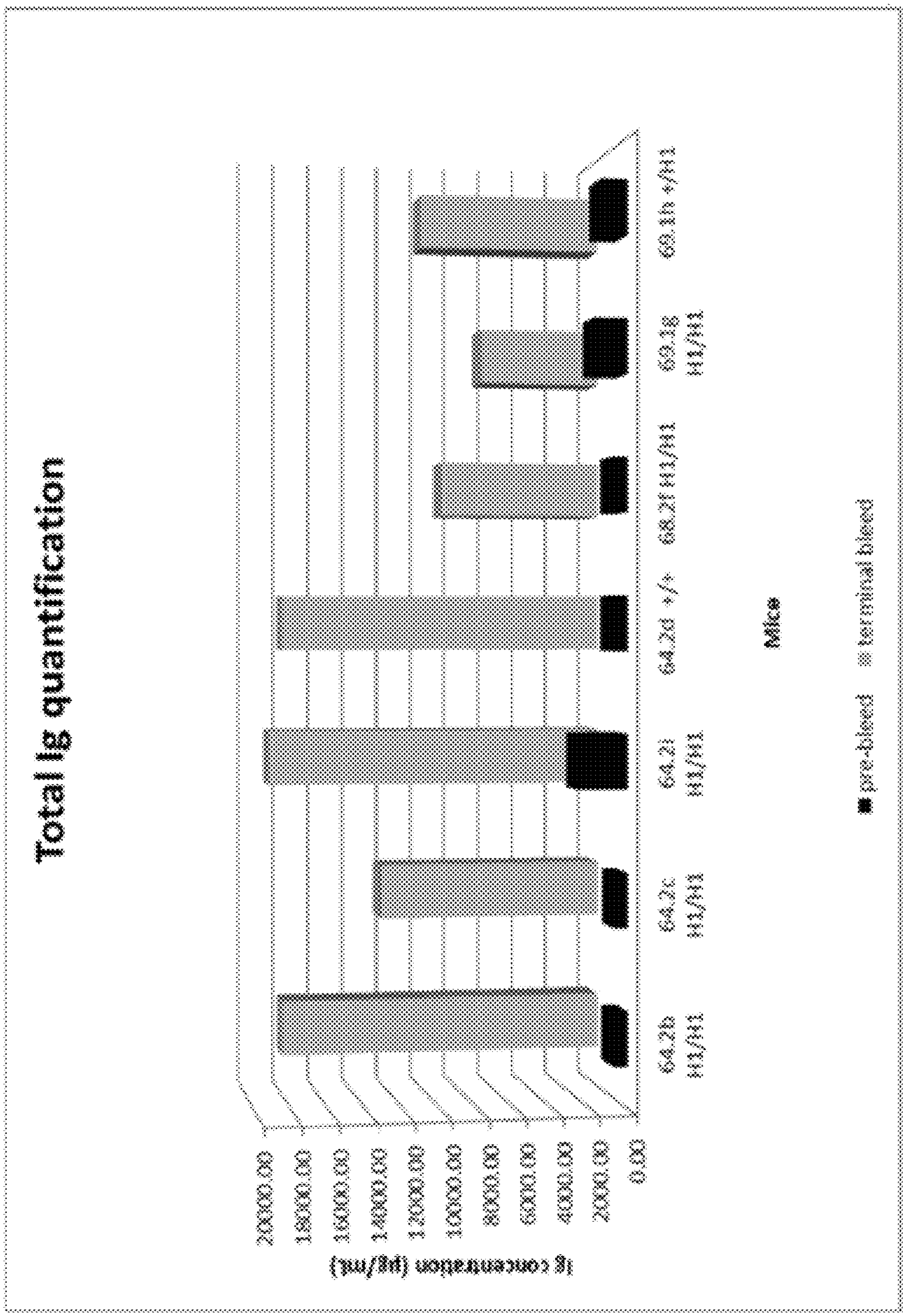
FIGS. 55A and 55B illustrate normal IgH isotypes and serum levels are obtained in transgenic H1 and S1 animals, respectively, of the invention following immunisation with antigens.
Figure 55B:
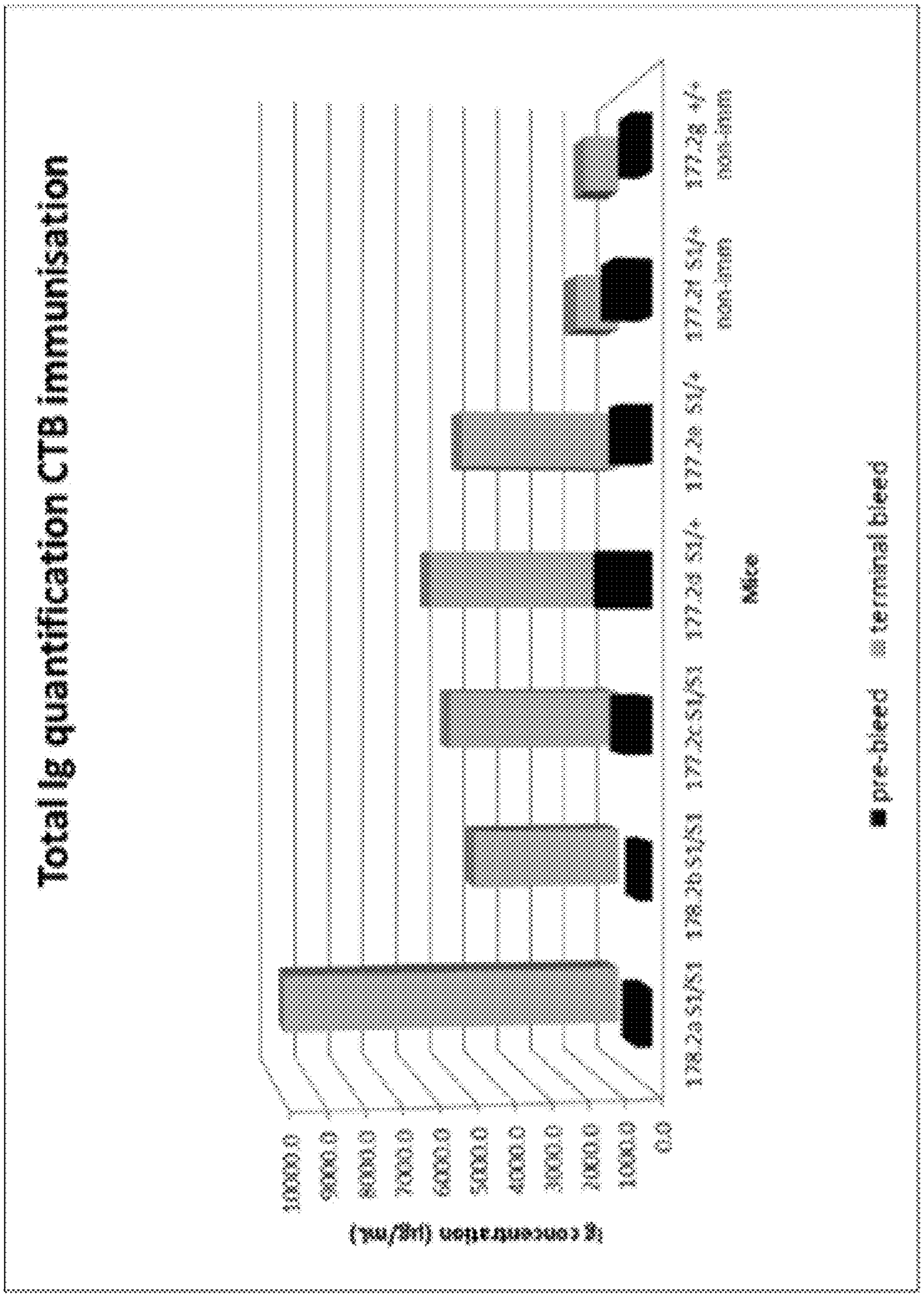

Transgenic mice (H1) carrying all human JH, all human DH and human Vh2-5 under control of a rat switch region or mice (S1) carrying all human JH, all human DH and human Vh2-5, Vh7-41, Vh4-4, Vh1-3, Vh1-2 and Vh6-1 under control of a mouse switch region were immunised with 100 μg Cholera Toxin B subunit (CTB; Sigma-Aldrich® C9903) emulsified in Complete Freund's Adjuvant CFA; Sigma-Aldrich® F 5881). At least three animals were injected sc or ip and then boosted with 25 μg antigen in Incomplete Freund's Adjuvant (IFA; Sigma-Aldrich® F 5506) at (i) 14 days and 21 days or (ii) 28 days after priming. Blood was taken before priming at day "−1" (pre-bleeds) and on the day the spleens were taken (usually 4d after last boost). Serum was analysed by ELISA using an antigen independent assessment of Ig isotypes. This assay detects total serum antibodies of all species. Specific detection for mouse IgG1, IgG2a, IgG2b and IgM was used ((Anti-mouse IgG1 HRP AbD Serotec STAR132P, Anti-mouse IgG2a HRP AbD Serotec STAR133P, Anti-mouse IgG2b HRP AbD Serotec STAR134P, Anti-mouse IgM HRP Abcam® ab97230) and concentrations were read off a standard curve produced for each isotype using polyclonal isotype controls (IgG1, Kappa murine myeloma Sigma-Aldrich® M9269, IgG2a, Kappa murine myeloma Sigma-Aldrich® M9144, IgG2b, Kappa from murine myeloma Sigma-Aldrich® M8894, IgM, Kappa from murine myeloma Sigma-Aldrich® M3795). Results (FIGS. 54 & 55 for H1 homozygous and S1 homozygous and heterozygous mice) showed that even with these relatively short immunisation regimes mice showed an increase in overall IgG levels after immunisation over pre-bleeds. In cases where control mice (+/+) not carrying any human immunoglobulin genes were included and immunised, these mice showed comparable changes in total observed Ig levels (FIG. 54). Individual isotype levels were more variable between animals possibly showing various stages of class switching. IgM levels never exceeded 800 μg/ml whereas IgG levels reached more than 6 mg/ml in some animals. Non-immunised controls showed no such increases in switched isotype Ig levels.

These results demonstrate that mice comprising multiple human VDJ gene segments under the control of a rat Sμ rat or mouse switch are able to undergo productive recombination and class switching in response to antigen challenge and that the mice produce antibody levels that are broadly comparable to unmodified mice The transgenic mice are able to produce antibodies of each of the IgG1, IgG2a, IgG2b and IgM isotypes after immunisation. Titers for CTB-specific Ig in pre-bleeds and terminal bleeds were determined and all immunised animals showed at CTB-specific titres of at least 1/100 000.

Example 12

Generation of Anti-Ovalbumin Antibodies with Sub-50 nm Affinities from Animals of the Invention Transgenic mice carrying all human JH, all human DH and human Vh2-5 under control of a rat Sp switch region were immunised with 25 μg ovalbumin (OVA; Sigma- Aldrich® A7641) in Sigma-Aldrich® adjuvant (Sigma Adjuvant System® S6322) ip and then boosted with the same amount of OVA in adjuvant at day 14 and day 21. Spleenocytes were taken 4 days later and fused using 1 ml polyethyleneglycol (PEG Average MW1450; Sigma-Aldrich® P7306) with a myeloma line. Fused hybridoma cells were plated on 5 96-well plates and after selection with hypoxanthine-aminopterin-thymidine (HAT) wells tested for expression of OVA-specific antibodies by ELISA. Clones positive by ELISA were re-tested by surface plasmon resonance (SPR) and binding kinetics determined using the ProteOn™ XPR36 (Bio-Rad®). Briefly, anti-mouse IgG (GE Biacore™ BR-1008-38) was coupled to a GLM biosensor chip by primary amine coupling, this was used to capture the antibodies to be tested directly from tissue culture supernatants. Ovalbumin was used as the analyte and passed over the captured antibody surface at 1024 nM, 256 nM, 64 nM, 16 nM, 4 nM with a 0 nM (i.e. buffer alone) used to double reference the binding data. Regeneration of the anti-mouse IgG capture surface was by 10 mM glycine pH1.7, this removed the captured antibody and allowed the surface to be used for another interaction. The binding data was fitted to 1:1 model inherent to the ProteOn™ XPR36 analysis software. The run was carried out 1×HBS-EP (10 mM Hepes, 150 mM NaCl, 3 mM EDTA, 0.05% polysorbate, pH7.6 (Teknova H8022)) used as running buffer and carried out at 25° C.

For 8 positive clones, heavy chain V-regions were recovered by RT-PCR (Access RT-PCR System, A1250, Promega) using forward primers specific for Ig signal sequences (Wardemann et al Science 301, 1374 (2003)) and the following reverse primers for the constant regions of mouse IgG (Table 3):

TABLE 3

| Primer Name | Sequence | bp | |
|---|---|---|---|
| mIgG1_2 rev | GGGGCCAGTGGATAGACAGAT | 21 | SEQ ID No 33 |
| mIgG2b rev | CAGTGGATAGACTGATGG | 18 | SEQ ID No 34 |
| mIgG2a_2 rev | CAGTGGATAGACCGATGG | 21 | SEQ ID No 35 |
| mCH1 unirev | KCAGGGGCCAGTGGATAGAC | 20 | SEQ ID No 36 |
| mCH1 unirev_2 | TARCCYTTGACMAGGCATCC | 20 | SEQ ID No 37 |

RT-PCR products were either directly sequenced using the same primer pairs or cloned in to TA plasmids (TOPO® TA Cloning® Kit for Sequencing, K4595-40, Invitrogen™) and submitted for plasmid sequencing. Results (Table 4, below) show that CDRH3 sequences had variable CDRs except for two identical clones (16C9 and 20B5) that also had near identical KD kinetic values. The determined equilibrium binding constant KD ranged from 0.38 nM to 40.60 nM, as determined by SPR at 25° C.

These results demonstrate that mice comprising multiple human VDJ gene segments under the control of a rat Cμ switch are able to undergo productive recombination and produce high affinity antigen-specific antibodies whose CDR3 regions have sequences encoded by human gene segments (human JH was separately identified by V-Quest, IMGT).

TABLE 4

| KD [nM] | clone code | CDR3 and FR4 (underlined) according to Kabat definition | |
|---|---|---|---|
| 0.38 | 16C9 | QEVINYYYYGMDV<u>WGQGTTVTVSS</u> | SEQ ID No 38 |
| 0.52 | 20B5 | QEVINYYYYGMDV<u>WGQGTTVTVSS</u> | SEQ ID No 39 |
| 5.89 | 19F4 | LEMATINYYYYGMDV<u>WGQGTMVTVSS</u> | SEQ ID No 40 |
| 39.70 | 19E1 | QEFGNYYYYGMDV<u>WGQGTTVTVSS</u> | SEQ ID No 41 |
| 3.10 | 19G8 | QEDGNPYYFGMDF<u>WGQGTTVTVSS</u> | SEQ ID No 42 |
| 8.95 | 20H10 | GSSYYYDGMDV<u>WGQGTTVTVSS</u> | SEQ ID No 43 |
| 4.46 | 18D10 | LENDYGYYYYGMDV<u>WGQGTTVTVSS</u> | SEQ ID No 44 |
| 40.60 | 16F2 | RGGLSPLYGMDV<u>WGQGTTVTVSS</u> | SEQ ID No 45 |

Example 13

Generation of Anti-Cholera Toxin B Antibodies with Human Vh Regions from Animals of the Invention Transgenic mice carrying all human JH, all human DH and human Vh2-5, Vh7-41, Vh4-4, Vh1-3, Vh1-2 and Vh6-1 under control of a mouse Sp switch region were immunised and fused as described in Example 11. Fused hybridoma cells were plated on 5 96-well plates and after selection with hypoxanthine-aminopterin-thymidine (HAT) or G418 (Gibco® Cat No 10131-027, Lot 503317) and wells tested for expression of CTB-specific antibodies by ELISA. Clones positive by ELISA were re-tested by surface plasmon resonance SPR and binding kinetics determined using the ProteOn XPR36™ (Bio-Rad®).

Briefly, anti-mouse IgG (GE Biacore™ BR-1008-38) was coupled to a GLM biosensor chip by primary amine coupling, this was used to capture the antibodies to be tested directly from tissue culture supernatants. Cholera toxin B was used as analyte and passed over the captured antibody surface at 256 nM, 64 nM, 16 nM, 4 nM and 1 nM, with a 0 nM (i.e. buffer alone) used to double reference the binding data. Regeneration of the anti-mouse IgG capture surface was by 10 mM glycine pH1.7, this removed the captured antibody and allowed the surface to be used for another interaction. The binding data was fitted to 1:1 model inherent to the ProteOn XPR36™ analysis software. The run was carried out 1×HBS-EP (10 mM Hepes, 150 mM NaCl, 3 mM EDTA, 0.05% polysorbate, pH7.6 (Teknova H8022)) used as running buffer and carried out at 37° C.

From the clones initially identified by ELISA, binding to CTB was confirmed by SPR. However, due to the pentameric nature of the cholera toxin B, the majority of fits to the 1:1 model were poor and the equilibrium binding constant KDs could not be accurately determined. Where fits were acceptable, equilibrium binding constant KDs determined ranged from 0.21 nM to 309 nM but due to the pentameric nature of cholera toxin B these are likely to be the result of multimeric interactions and therefore apparent affinities with possible avidity components.

Clones identified by SPR for binding to CTB were subjected to RT-PCR as described in Example 12 to recover the Vh regions. RT-PCR products were directly sequenced using the same primer pairs. Results were obtained for only 14 clones presumably because the human primers described in Wardemann et al were not designed to amplify mouse Vh regions and therefore may have failed to amplify certain mouse Vh classes. Results showed that 3 of the 14 CTB-specific recovered heavy chain V-region sequences were human V, D and J regions as identified by V-Quest, IMGT (Table 5).

TABLE 5

Alignment of heavy chain CDRs and J-region of 3 clones identified as binding to CTB and preferentially matching with human reference sequences from IMGT database; note that the KD values given here are apparent values due to the avidity of the CTB- antibody interaction

| Vh region | Clone Name | Sequence (Kabat definitions) CDR1 | CDR2 | CDR3 | J-regions | | KD [nM] |
|---|---|---|---|---|---|---|---|
| IGHV4-4*02 | — | **SSNWWS** (SEQ ID NO 51) | **EIYHSGSTNYNPSLKS** (SEQ ID NO 56) | n/a | IGHJ2*01 | **YWYFTLWGRGTLVTVSS** (SEQ ID NO 64) | — |
| | 12D10 | SGNWWS (SEQ ID NO 52) | EIYHSGNTNYNPSLKS (SEQ ID NO 57) | GPLTGEKYYFDL (SEQ ID NO 61) | | -YYFDLWGRGTLVTVSS (SEQ ID NO 65) | 0.27 |
| | 1283 | RSNWWS (SEQ ID NO 53) | EIYHSGSTNYNPSLKS (SEQ ID NO 58) | IGDWYFDL (SEQ ID NO 62) | | -WYFDLWGRGTLVTVSS (SEQ ID NO 66) | 0.85 |
| IGHV6-1*01 | — | **SNSAAWN** (SEQ ID NO 54) | **RTYYRSKWYNDYAVSVKS** (SEQ ID NO 59) | n/a | IGHJ3*01 | **DAFDVWGQGTMVTVSS** (SEQ ID NO 67) | — |
| | 4A12 | SNSAAWN (SEQ ID NO 55) | RTYYRSKWYNDYKVSVKS (SEQ ID NO 60) | EGSHSGSGWYLDAFDI (SEQ ID NO 63) | | DAFDIWGQGTKVTVSS (SEQ ID NO 68) | 1.61 |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference

The invention claimed is:

1. A transgenic mouse whose genome comprises a homozygous chimeric immunoglobulin heavy chain (IgH) locus comprising unrearranged human IgH variable region gene segments at an endogenous mouse heavy chain IgH locus upstream of an enhancer and a constant (C) region comprising an endogenous CH gene segment;

wherein said human variable region gene segments in said chimeric IgH locus are operably linked to said C region at a human/mouse chimeric junction within the JC intron of said chimeric IgH locus;

wherein said homozygous chimeric IgH locus comprises in 5' to 3' transcriptional orientation:

(i) unrearranged human immunoglobulin heavy chain (IgH) variable region (VH) DNA comprising human IgH V gene segments, human D gene segments DH and human JH gene segments comprising a human 3'JH gene segment, (ii) a chimeric J/C intron comprising human DNA downstream of and naturally contiguous with said human 3' JH gene segment, which is contiguous with mouse JC intronic DNA, and (iii) said enhancer and said C region, wherein said human 3'JH is less than 1 kb upstream of said chimeric junction, wherein DNA between said chimeric junction and said enhancer comprises mouse 129 strain JC intronic DNA;

wherein said enhancer is a mouse 129 strain μ enhancer;

wherein said transgenic mouse is functional to form rearranged human VH, DH and JH gene segments and to express chimeric immunoglobulin heavy chain polypeptide comprising a human VH region and a mouse C region, and wherein said transgenic mouse is capable, upon stimulation with antigen, of producing an antibody comprising a chimeric Ig heavy chain comprising a human IgH variable region and said C region; and wherein the genome of said transgenic mouse comprises all or part of the endogenous mouse IgH variable region, and is capable of breeding to produce subsequent generation mice having in their germline an IgH locus comprising unrearranged human IgH variable region gene segments positioned upstream of an IgH constant (C) region comprising an endogenous C gene segment of an IgH locus.

2. The mouse of claim 1, wherein said C region comprises a mouse Cμ gene segment.

3. The mouse of claim 1, said mouse 129 strain DNA being mouse 129Sv DNA.

4. The mouse of claim 1, wherein said human DNA contiguous with said human 3'JH gene segment comprises 400 base pairs of human JC intron DNA.

5. The mouse of claim 2, wherein said mouse Cμ gene segment comprise mouse 129 strain DNA.

6. The mouse of claim 1, wherein said all or part of the endogenous IgH variable region of said transgenic mouse is inverted.

* * * * *